US012747445B2

(12) United States Patent
Manjunath et al.

(10) Patent No.: US 12,747,445 B2

(45) **Date of Patent: *Sep. 29, 2026**

(54) METHODS AND COMPOSITIONS FOR INCREASING HARVESTABLE YIELD VIA EDITING GA20 OXIDASE GENES TO GENERATE SHORT STATURE PLANTS

(71) Applicant: MONSANTO TECHNOLOGY LLC, St. Louis, MO (US)

(72) Inventors: Sivalinganna Manjunath, Chesterfield, MO (US); Linda A. Rymarquis, High Ridge, MO (US); Thomas L. Slewinski, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/967,072

(22) PCT Filed: Feb. 15, 2019

(86) PCT No.: PCT/US2019/018131

§ 371 (c)(1),
(2) Date: Aug. 3, 2020

(87) PCT Pub. No.: WO2019/161147

PCT Pub. Date: Aug. 22, 2019

(65) Prior Publication Data

US 2021/0032646 A1 Feb. 4, 2021

Related U.S. Application Data

(60) Provisional application No. 62/710,302, filed on Feb. 16, 2018, provisional application No. 62/631,412, filed on Feb. 15, 2018.

(51) Int. Cl.
*C12N 15/82* (2006.01)
*A01H 5/10* (2018.01)
*A01H 6/46* (2018.01)

(52) U.S. Cl.
CPC .......... *C12N 15/8213* (2013.01); *A01H 5/10* (2013.01); *A01H 6/4684* (2018.05); *C12N 15/8261* (2013.01)

(58) Field of Classification Search
None
See application file for complete search history.

(56) References Cited

U.S. PATENT DOCUMENTS 7,138,567 B2 11/2006 Okawa et al.
10,724,047 B2 * 7/2020 Allen ................ C12N 15/8273
11,319,550 B2 * 5/2022 Allen ................ C12N 15/8261
11,414,670 B2 * 8/2022 Allen ................ C12N 15/8297
11,441,153 B2 * 9/2022 Dietrich ............ C12N 15/8218
11,472,852 B2 * 10/2022 Alves-Junior ......... C12N 15/52
11,702,670 B2 * 7/2023 Dietrich .............. A01H 6/4684 800/278
12,024,711 B2 * 7/2024 Manjunath ...... C12Y 114/11012
2004/0250315 A1 12/2004 Okawa et al.
2011/0145940 A1 6/2011 Voytas et al.
2011/0301073 A1 12/2011 Gregory et al.
2013/0117869 A1 5/2013 Duchateau et al.
2016/0208272 A1 * 7/2016 Cigan ............... C12N 15/8216
2016/0230183 A1 8/2016 Abad et al.
2017/0114356 A1 4/2017 Li et al.
2022/0298527 A1 9/2022 Dietrich et al.

OTHER PUBLICATIONS

Song et al 2011 (Gene 482: p. 34-42) (Year: 2011).*
Ashikari et al 2002 (Breeding Science 52: p. 143-150) (Year: 2002).*
Dhananjay Mani 2008 (Master's Thesis Texas A&M University) (Year: 2008).*
Petti et al 2015 (Plant Physiology p. 705-716) (Year: 2015).*
Altschul et al., "Basic local alignment search tool," *J. Mol. Biol.*, 215:403-410 (1990).
Beurdeley et al., "Compact designer TALENs for efficient genome engineering," *Nature Communications*, 4:1762 (2013).
Cermak et al., "Efficient design and assembly of custom TALEN and other TAL effector-based constructs for DNA targeting," *Nucleic Acids Research*, 39(12):e82 (2011).
Chen et al., "The Maize DWARF1 Encodes a Gibberellin 3-Oxidase and Is Dual Localized to the Nucleus and Cytosol," *Plant Physiology*, 166:2028-2039 (2014).
Chenna et al., "Multiple sequence alignment with the Clustal series of programs," *Nucleic Acids Research*, 31: 3497-3500 (2003).
Colbert et al., "High-Throughput Screening for Induced Point Mutations," *Plant Physiol*, 126:480-484 (2001).
Doyle et al., "TAL Effector-Nucleotide Targeter (TALE-NT) 2.0: tools for TAL effector design and target prediction," *Nucleic Acids Research*, 40:W117-122 (2012).
Gabsalilow et al., "Site- and strand-specific nicking of DNA by fusion proteins derived from MutH and I-SceI or TALE repeats," *Nucleic Acids Research*, 41(7):e83 (2013).
Gaj et al., "ZFN, TALEN and CRISPR/Cas-based methods for genome engineering," Trends Biotechnol., 31(7):397-405 (2013).
International Search Report and Written Opinion dated Jun. 17, 2019, in International Application No. PCT/US2019/018131 (19 pgs.).

(Continued)

*Primary Examiner* — Matthew R Keogh
(74) *Attorney, Agent, or Firm* — Morrison & Foerster LLP

(57) ABSTRACT

The present disclosure provides compositions and methods for the editing or mutating of specific subtypes of GA20 oxidase genes and specific zygosity combinations of those edits or mutations. Modified plants, and plant parts and cells thereof, having mutations reducing the expression or activity of GA20 oxidase genes are further provided with improved characteristics, such as reduced plant height and increased lodging resistance, but without off-types. Methods are further provided for making modified plants, and plant parts and cells thereof, having one or more mutations in specific subtypes of GA20 oxidase genes.

25 Claims, 1 Drawing Sheet

Specification includes a Sequence Listing.

(56) References Cited

OTHER PUBLICATIONS

Larkin et al., "Clustal W and Clustal X version 2.0," *Bioinformatics*, 23:2947-48 (2007).
McCallum et al., "Targeted screening for induced mutations," *Nature Biotechnology*, 18:455-457 (2000).
Plackett et al., "Analysis of the Developmental Roles of the *Arabidopsis gibberellin* 20-Oxidases Demonstrates That GA20ox1, -2, and -3 are the Dominant Paralogs," *The Plant Cell*, 24(3):941-960 (2012).
Song et al., "Genome-wide identification of gibberellins metabolic enzyme genes and expression profiling analysis during seed germination in maize," *Gene*, 482(1-2):34-42 (2011).
Thompson et al., "Clustal W: Improving the sensitivity of progressive multiple sequence alignment through sequence weighting, position-specific gap penalties and weight matrix choice," *Nucleic Acids Research*, 22:4673-4680 (1994).
Wu et al., "Target specificity of the CRISPR-Cas9 system," *Quant Biol.*, 2(2):59-70 (2014).
Yanik et al., "TALE-Pvull Fusion Proteins—Novel Tools for Gene Targeting," *PLoS One*, 8:e82539 (2013).
Coles, J. P. et al. (1999). "Modification of Gibberellin Production and Plant Development in *Arabidopsis* by Sense and Antisense Expression of Gibberellin 20-Oxidase Genes," The Plant Journal, 17(5): 547-556.
Depalma, A. (Feb. 13, 2018) "Reaping Better Crops with Plant Genome Editing. Biocompare: The Buyer's Guide for Life Scientists" retrieved from the internet: URL:https://www.biocompare.com/Editorial-Articles/346955-Reaping-Better-Crops-with-Plant-Genome-Editing/ [retrieved on Dec. 17, 2021].
GenBank Accession No. AC191666, last updated Sep. 24, 2013, located at https://www.ncbi.nlm.nih.gov/nuccore/AC191666, last visited on Jun. 10, 2022, forty four pages.
GenBank Accession No. AC209074, last updated Sep. 13, 2014, located at https://www.ncbi.nlm.nih.gov/nuccore/AC209074, last visited on Jun. 10, 2022, forty one pages.
GenBank Accession No. BT068785, last updated Jun. 15, 2012 located at https://www.ncbi.nlm.nih.gov/nuccore/BT068785.2/, last visited on Jun. 10, 2022, two pages.
GenBank Accession No. EF030816, last updated Sep. 28, 2006 located at https://www.ncbi.nlm.nih.gov/nuccore/EF030816.1/, last visited on Jun. 13, 2022, two pages.
GenBank Accession No. EF030817, last updated Sep. 28, 2006 located at https://www.ncbi.nlm.nih.gov/nuccore/EF030817.1/, last visited on Jun. 13, 2022, two pages.
Helliwell , C. et al. (Aug. 2003). "Constructs and Methods for High-Throughput Gene Silencing in Plants" Methods in Enzymology 30(4): 289-295.
International Search Report mailed on Jul. 16, 2019, for PCT Patent Application No. PCT/US2019/018133 filed on Feb. 15, 2019, eighteen pages.
International Search Report mailed on Jun. 25, 2019, for PCT Patent Application No. PCT/US2019/018128 filed on Feb. 15, 2019, twelve pages.
Qiao, F. et al. (Jun. 19, 2013). "Alteration of Rice Growth and Development via Antisense Expression of OsGA20ox2 gene," African Journal of Biotechnology. 12(25): 3898-3904.
Spielmeyer, W. et al. (2002) "Semidwarf (sd-1), 'Green Revolution' Rice, Contains a Defective Gibberellin 20-oxidase Gene," PNAS, 99(13):9043-9048.
Tomita, M. (2012), Combining Two Semidwarfing Genes d60 and sd1 for Reduced Height in 'Minihikari', a New Rice Germplasm in the 'Koshihikari' Genetic Background, Genetics Research 94: 235-244.
Uniprot Accession No. A0A1D6N5E5, last updated Nov. 30, 2016 located at https://www.uniprot.org/uniprot/A0A1D6N5E5, last visited Jun. 13, 2022, 6 pages.
Uniprot Accession No. A0A3L6FA55, last updated Feb. 13, 2019 located at https://www.uniprot.org/uniprot/A0A3L6FA55, last visited Jun. 13, 2022, 5 pages.
Uniprot Accession No. COHFM9, last updated May 9, 2009 located at https://www.uniprot.org/uniprot/C0HFM9, last visited Jun. 13, 2022, 4 pages.
Uniprot Accession No. K7VMU4, last updated Feb. 6, 2013 located at https://www.uniprot.org/uniprot/K7VMU4, ast visited Jun. 13, 2022, 6 pages.
Chiang, H.-H. et al. (Feb. 1995). "Isolation of the Arabidopsis GA4 Locus," The Plant Cell 7:195-201.
Unterseer, S. et al. (Jan. 27, 2017). "European Flint Reference Sequences Complement the Maize Pan-genome," BioRxiv 103747, 3 pages.
Williams, J. et al. (1998). "Function and Substrate Specificity of the Gibberellin 3beta-Hydroxylase Encoded by the *Arabidopsis* GA4 Gene," Plant Physiology 117:559-563.
Xu, Y.-L. et al. (Jul. 3, 1995). "The GA5 Locus of *Arabidopsis thaliana* Encodes a Multifunctional Gibberellin 20-oxidase: Molecular Cloning and Functional Expression," Proc Natl Acad Sci USA 92(14):6640-6644.
Bunton-Stasyshyn, R. K. A. et al. (Feb. 1, 2019, e-pub. Jan. 2, 2019). "Prominent Role of Forebrain Excitatory Neurons in SCN8A Encephalopathy," Brain 142(2):362-375.
Guerrero-Mendez, C. et al. (2024, e-pub. Nov. 15, 2023). "Factors Specifying Sex Determination in Maize," Plant Reproduction 37:171-178.
Kusaba, M. et al. (Apr. 2004). "RNA Interference in Crop Plants," Curr Opin Biotechnol. 15(2):139-143.
Schnable, J. A. et al. (Mar. 8, 2011, e-pub. Feb. 22, 2011). "Differentiation of the Maize Subgenomes by Genome Dominance and Both Ancient and Ongoing Gene Loss," Proc Natl Acad Sci U S A. 108(10):4069-4074.
Slewinski, T. L. et al. (Nov. 2012, e-pub. Aug. 29, 2012). "Tie-dyed2 Encodes a Callose Synthase That Functions in Vein Development and Affects Symplastic Trafficking within the Phloem of Maize Leaves," Plant Physiology 160(3):1540-1550.
Small, I. (Apr. 2007, e-pub. Feb. 6, 2007). "RNAi for Revealing and Engineering Plant Gene Functions," Current Opinion in Biotechnology 18:148-153.
Unniyampurath, U. et al. (Feb. 26, 2016). "RNA Interference in the Age of CRISPR: Will CRISPR Interfere with RNAi?" Int. J. Mol. Sci. 17(3):291, 15 pages.
Arora, L. et al. (Nov. 8, 2017). "Gene Editing and Crop Improvement Using CRISPR-Caas 9 System," Frontiers in Plant Science 8:1-21.
Izawa, T. et al. (Mar. 1996). "Becoming a Model Plant: The Importance of Rice to Plant Science," Trends in Plant Science 1(3):95-99.

* cited by examiner

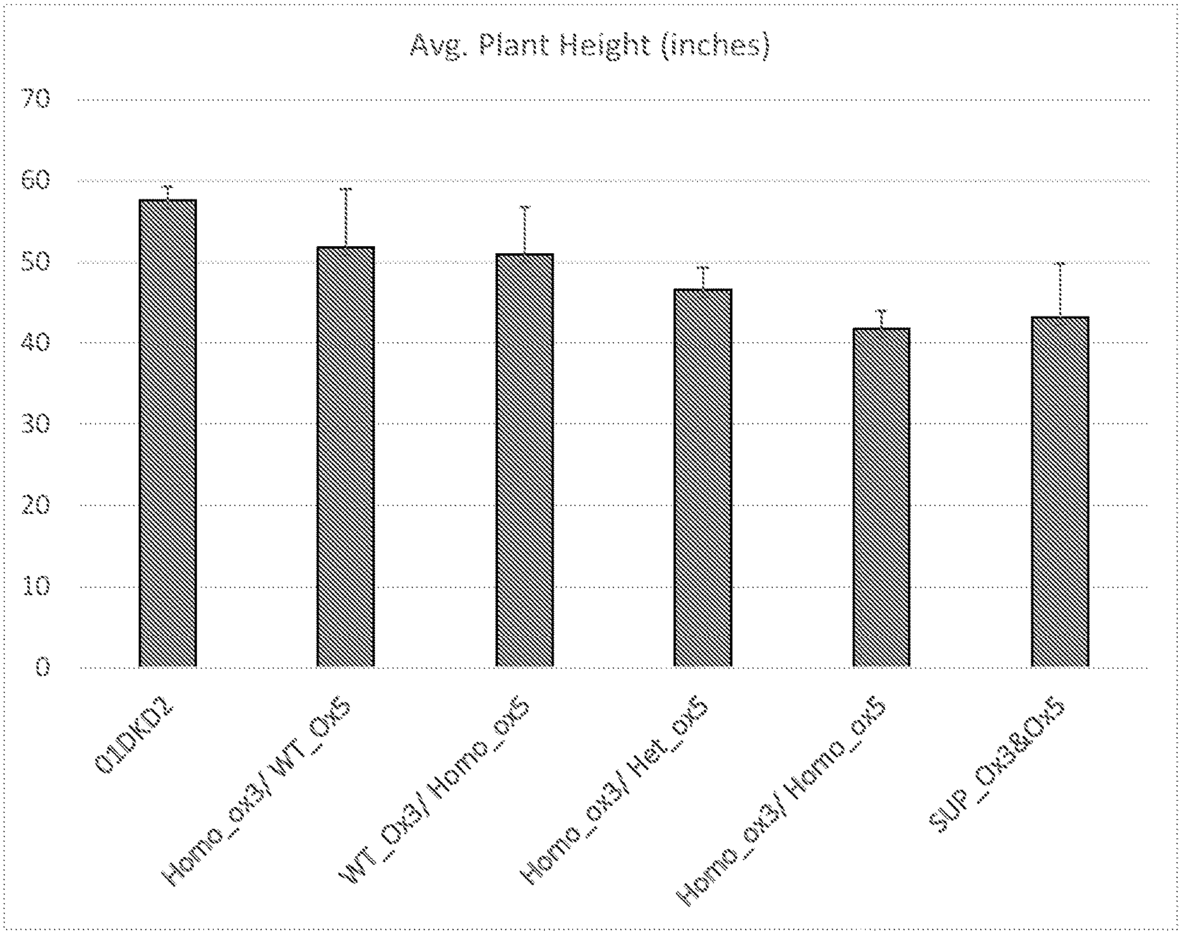
Avg. Plant Height (inches)
70
60
50
40
30
20
10
0
01DKD2
Homo_ox3/ WT_Ox5
WT_Ox3/ Homo_ox5
Homo_ox3/ Het_ox5
Homo_ox3/ Homo_ox5
SUP_Ox3&Ox5

SEQUENCE LISTING

<160> NUMBER OF SEQ ID NOS: 261

<210> SEQ ID NO 1
<211> LENGTH: 1741

<212> TYPE: DNA
<213> ORGANISM: Zea mays

<400> SEQUENCE: 1
gacggtagtt ttcatctaaa gtttattctt cgtcacatgg gatggccgtt tgcttgtttg 60
ttgcttccgg gaggcggtgg tgaattgaag cagatcgaca agcatggctg cccactggtc 120
tcgatcgatc ggcctgccat gccatgccat gccactagag tccgtcctga ctggccgccc 180 gttccccccgt ataaaaaggc aggcaggcag gcagagcggg gacgagcaag caagcagttg 240
cagttgcagc ggcctcctcc tctgcttcct ccctcctcct cctcaccatg gtgctggctg 300
cgcacgatcc ccctcccctt gtgttcgacg ctgcccgcct gagcggcctc tccgacatcc 360
cgcagcagtt catctggccg gcggacgaga gccccacccc ggactccgcc gaggagctgg 420
ccgtgccgct catcgacctc tccggggacg ccgccgaggt ggtccggcag gtccggcgcg 480
cctgcgacct gcacggcttc ttccaggtgg tggggcacgg catcgacgcg gcgctgacgg 540
cggaggccca ccgctgcatg gacgccttct tcacgctgcc gctcccggac aagcagcgcg 600
cgcagcgccg ccagggggac agctgcggct acgccagcag cttcacgggc cggttcgcgt 660
ccaagctgcc ctggaaggag acgctgtcgt tccgctacac cgacgacgac gacggcgaca 720
agtccaagga cgtcgtggcg tcctacttcg tggacaagct gggcgagggg taccggcacc 780
acggggaggt gtacgggcgc tactgctctg agatgagccg tctgtcgctg gagctcatgg 840
aggtgctagg cgagagcctg ggcgtgggcc ggcgccactt ccggcgcttc ttccagggga 900
acgactccat catgcgcctc aactactacc cgccgtgcca gcggccctac gacacgctgg 960
gcacggggcc gcattgcgac ccccacgtcgc tcaccatcct gcaccaggac gacgtgggcg 1020
gactccaggt gttcgacgcc gccacgctcg cgtggcgctc catcaggccc cgcccgggcg 1080
ccttcgtcgt caacatcggc gacaccttca tggcgctctc caacgggcgc tacaggagct 1140
gcctccaccg cgccgtcgtc aacagccggg tggcacgccg ctcgctcgcc ttcttcctgt 1200
gcccggagat ggacaaggtg gtcaggccgc ccaaggagct ggtggacgac gccaacccga 1260
gggcgtaccc ggacttcacg tggaggacgc tgctggactt caccatgagg cactacaggt 1320
cggacatgag gacgctcgag gccttctcca actggctcag caccagtagc aatggcggac 1380
agcacctgct ggagaagaag taggcatgct atttgggtat ggaagatggt ggatgtaagc 1440
aaacaaagcc aaattaagca gagtaggtta attaaggttg gctgatgatc catttaggga 1500
aggagctgat ctccctgact ccctcctcca attttctcaa ccaaatttat atagtataat 1560
aataataata aaatagcaag taatagttgt atcgtattat tattaattaa tttattagct 1620
ggtaggcaag tagtattaaa taccatttgt agtacgatgg gcgtatttct attttggcgt 1680
tttgctctgt gttttttgac gtttcctttg gatttggggg gacctcagat cagctcggcc 1740
t 1741

<210> SEQ ID NO 2
<211> LENGTH: 1116
<212> TYPE: DNA
<213> ORGANISM: Zea mays

<400> SEQUENCE: 2
atggtgctgg ctgcgcacga tccccctccc cttgtgttcg acgctgcccg cctgagcggc 60
ctctccgaca tcccgcagca gttcatctgg ccggcggacg agagccccac cccggactcc 120
gccgaggagc tggccgtgcc gctcatcgac ctctccgggg acgccgccga ggtggtccgg 180

```
caggtccggc gcgcctgcga cctgcacggc ttcttccagg tggtggggca cggcatcgac    240

gcggcgctga cggcggaggc ccaccgctgc atggacgcct tcttcacgct gccgctcccg    300

gacaagcagc gcgcgcagcg ccgccagggg gacagctgcg gctacgccag cagcttcacg    360

ggccggttcg cgtccaagct gccctggaag gagacgctgt cgttccgcta caccgacgac    420

gacgacggcg acaagtccaa ggacgtcgtg gcgtcctact tcgtggacaa gctgggcgag    480

gggtaccggc accacgggga ggtgtacggg cgctactgct ctgagatgag ccgtctgtcg    540

ctggagctca tggaggtgct aggcgagagc ctgggcgtgg gccggcgcca cttccggcgc    600

ttcttccagg ggaacgactc catcatgcgc ctcaactact acccgccgtg ccagcggccc    660

tacgacacgc tgggcacggg gccgcattgc gaccccacgt cgctcaccat cctgcaccag    720

gacgacgtgg gcggactcca ggtgttcgac gccgccacgc tcgcgtggcg ctccatcagg    780

ccccgcccgg gcgccttcgt cgtcaacatc ggcgacacct tcatggcgct ctccaacggg    840

cgctacagga gctgcctcca ccgcgccgtc gtcaacagcc gggtggcacg ccgctcgctc    900

gccttcttcc tgtgcccgga gatggacaag gtggtcaggc cgcccaagga gctggtggac    960

gacgccaacc cgagggcgta cccggacttc acgtggagga cgctgctgga cttcaccatg   1020

aggcactaca ggtcggacat gaggacgctc gaggccttct ccaactggct cagcaccagt   1080

agcaatggcg gacagcacct gctggagaag aagtag                             1116


<210> SEQ ID NO 3
<211> LENGTH: 371
<212> TYPE: PRT
<213> ORGANISM: Zea mays

<400> SEQUENCE: 3

Met Val Leu Ala Ala His Asp Pro Pro Pro Leu Val Phe Asp Ala Ala
1               5                   10                  15

Arg Leu Ser Gly Leu Ser Asp Ile Pro Gln Gln Phe Ile Trp Pro Ala
            20                  25                  30

Asp Glu Ser Pro Thr Pro Asp Ser Ala Glu Glu Leu Ala Val Pro Leu
        35                  40                  45

Ile Asp Leu Ser Gly Asp Ala Ala Glu Val Val Arg Gln Val Arg Arg
    50                  55                  60

Ala Cys Asp Leu His Gly Phe Phe Gln Val Val Gly His Gly Ile Asp
65                  70                  75                  80

Ala Ala Leu Thr Ala Glu Ala His Arg Cys Met Asp Ala Phe Phe Thr
                85                  90                  95

Leu Pro Leu Pro Asp Lys Gln Arg Ala Gln Arg Arg Gln Gly Asp Ser
            100                 105                 110

Cys Gly Tyr Ala Ser Ser Phe Thr Gly Arg Phe Ala Ser Lys Leu Pro
        115                 120                 125

Trp Lys Glu Thr Leu Ser Phe Arg Tyr Thr Asp Asp Asp Asp Gly Asp
    130                 135                 140

Lys Ser Lys Asp Val Val Ala Ser Tyr Phe Val Asp Lys Leu Gly Glu
145                 150                 155                 160

Gly Tyr Arg His His Gly Glu Val Tyr Gly Arg Tyr Cys Ser Glu Met
                165                 170                 175

Ser Arg Leu Ser Leu Glu Leu Met Glu Val Leu Gly Glu Ser Leu Gly
            180                 185                 190

Val Gly Arg Arg His Phe Arg Arg Phe Phe Gln Gly Asn Asp Ser Ile
        195                 200                 205
```

```
Met Arg Leu Asn Tyr Tyr Pro Pro Cys Gln Arg Pro Tyr Asp Thr Leu
    210                 215                 220

Gly Thr Gly Pro His Cys Asp Pro Thr Ser Leu Thr Ile Leu His Gln
225                 230                 235                 240

Asp Asp Val Gly Gly Leu Gln Val Phe Asp Ala Ala Thr Leu Ala Trp
                245                 250                 255

Arg Ser Ile Arg Pro Arg Pro Gly Ala Phe Val Val Asn Ile Gly Asp
            260                 265                 270

Thr Phe Met Ala Leu Ser Asn Gly Arg Tyr Arg Ser Cys Leu His Arg
        275                 280                 285

Ala Val Val Asn Ser Arg Val Ala Arg Arg Ser Leu Ala Phe Phe Leu
    290                 295                 300

Cys Pro Glu Met Asp Lys Val Val Arg Pro Pro Lys Glu Leu Val Asp
305                 310                 315                 320

Asp Ala Asn Pro Arg Ala Tyr Pro Asp Phe Thr Trp Arg Thr Leu Leu
                325                 330                 335

Asp Phe Thr Met Arg His Tyr Arg Ser Asp Met Arg Thr Leu Glu Ala
            340                 345                 350

Phe Ser Asn Trp Leu Ser Thr Ser Ser Asn Gly Gly Gln His Leu Leu
        355                 360                 365

Glu Lys Lys
    370


<210> SEQ ID NO 4
<211> LENGTH: 1517
<212> TYPE: DNA
<213> ORGANISM: Zea mays

<400> SEQUENCE: 4

caggaataaa ataagcctcc gcccggcttc gttgcatcca cgcacgcagc aagcgatcgg      60

atttcgccag catggcggcg gcggccgtgg tgttcgacgc cgaggcgctg agccgggagg     120

agcacatccc ggcgcagttc gtgtggccca ccgaggagcg ggcgccggcg ggcggcgtgg     180

aggaggtcgc catccccgtg gtcgacctcg gcgagttcct ccgccgcggg gtgctcccgc     240

gcggcgtggc ggaggcgtgc gagcgccacg gcgtcttcca ggtggtgaac cacggcgtgg     300

gcgccgcgct gctcgccgag gcctaccgct gttgcgacgc cttttacgcg ctcccgctcg     360

cggacaagca gcgcgcgcag cgccggcacg gggagaacca cggctacgcc agcagcttca     420

cgggccgctt ccactgctgc ctgccgtgga aggagacgct gtccttcaac tgccccgccg     480

gtgccgggac tgcgcgcgcc gtcgtcggct acttcgtcga cgtcctcggc gaggactacc     540

gccacatggg ggaggtgtac caggagtact gcgacgcgat gacgcgtctg gcgctggacg     600

tgacggaggt gctggcggca gcgctggggc tggaccgcgg cgcactgcgc ggcttcttcg     660

agggcggcga ctccgtcatg cggctgaacc actacccggc gtgccggcag ccgcacctga     720

cgctggggac gggcccgcac cgggacccga cgtcgctgac gctgctgcac caggacgacg     780

tgggcgggct gcaggtgcgc gccggcggcg ggccgtggcg cgcggtgcgg ccccgcgcgg     840

acgcgttcgt ggtcaacatt ggcgacacct tcgccgcgct caccgacggg cgtcacacca     900

gctgcctgca ccgcgccgtg gtgaccggcg gcggctcccg ccggtcgctc gccttcttcc     960

tcaacccgcc gctggaccgc gtcgtccgcc cgccgggcgc gctcctccag gagaacaagc    1020

aggcgggccg cccgcgcgcg ttcccggact tcacgtggcg cgagttcctc gagttcacgc    1080

agaagcacta ccggtcggac gcgggcacca tggacgcctt cgtgtcgtgg atcgcgggag    1140
```

-continued gccgccgcca ccatggcgga caggaggagg gcaactgaga tcgatgcatc tctagctgta 1200
ggcagcagcg cagcagctac caagaataat ggccggcgac ggagatgcag ctacgacgca 1260
caaataaatt gagtgtttgt ggtacaataa ggacgaggac gatcaatggc gacctgtaac 1320
cggtgcagtt ttagttaatc tttcatggcg atatggcatt aaccaatcgt tggtgtaaaa 1380
tgcgtgcatg ctttgcatgc caatgttggc catgtgatgg cacagcgtga gtgtagctca 1440
cccaccgtga caacgtgcta atttcgtgtg gtcctagata ccaaggtcgt ctaatgaact 1500
tgatggattg atgattt 1517

<210> SEQ ID NO 5
<211> LENGTH: 1107
<212> TYPE: DNA
<213> ORGANISM: Zea mays

<400> SEQUENCE: 5
atggcggcgg cggccgtggt gttcgacgcc gaggcgctga gccgggagga gcacatcccg 60
gcgcagttcg tgtggcccac cgaggagcgg gcgccggcgg gcggcgtgga ggaggtcgcc 120
atccccgtgg tcgacctcgg cgagttcctc cgccgcgggg tgctcccgcg cggcgtggcg 180
gaggcgtgcg agcgccacgg cgtcttccag gtggtgaacc acggcgtggg cgccgcgctg 240
ctcgccgagg cctaccgctg ttgcgacgcc ttttacgcgc tcccgctcgc ggacaagcag 300
cgcgcgcagc gccggcacgg ggagaaccac ggctacgcca gcagcttcac gggccgcttc 360
cactgctgcc tgccgtggaa ggagacgctg tccttcaact gccccgccgg tgccgggact 420
gcgcgcgccg tcgtcggcta cttcgtcgac gtcctcggcg aggactaccg ccacatgggg 480
gaggtgtacc aggagtactg cgacgcgatg acgcgtctgg cgctggacgt gacggaggtg 540
ctggcggcag cgctggggct ggaccgcggc gcactgcgcg gcttcttcga gggcggcgac 600
tccgtcatgc ggctgaacca ctacccggcg tgccggcagc cgcacctgac gctggggacg 660
ggcccgcacc gggacccgac gtcgctgacg ctgctgcacc aggacgacgt gggcgggctg 720
caggtgcgcg ccggcggcgg gccgtggcgc gcggtgcggc cccgcgcgga cgcgttcgtg 780
gtcaacattg gcgacacctt cgccgcgctc accgacgggc gtcacaccag ctgcctgcac 840
cgcgccgtgg tgaccggcgg cggctcccgc cggtcgctcg ccttcttcct caacccgccg 900
ctggaccgcg tcgtccgccc gccgggcgcg ctcctccagg agaacaagca ggcgggccgc 960
ccgcgcgcgt tcccggactt cacgtggcgc gagttcctcg agttcacgca gaagcactac 1020
cggtcggacg cgggcaccat ggacgccttc gtgtcgtgga tcgcgggagg ccgccgccac 1080
catggcggac aggaggaggg caactga 1107

<210> SEQ ID NO 6
<211> LENGTH: 368
<212> TYPE: PRT
<213> ORGANISM: Zea mays

<400> SEQUENCE: 6

Met Ala Ala Ala Ala Val Val Phe Asp Ala Glu Ala Leu Ser Arg Glu
1 5 10 15

Glu His Ile Pro Ala Gln Phe Val Trp Pro Thr Glu Glu Arg Ala Pro
20 25 30

Ala Gly Gly Val Glu Glu Val Ala Ile Pro Val Val Asp Leu Gly Glu
35 40 45

Phe Leu Arg Arg Gly Val Leu Pro Arg Gly Val Ala Glu Ala Cys Glu
50 55 60

Arg His Gly Val Phe Gln Val Val Asn His Gly Val Gly Ala Ala Leu
65 70 75 80

Leu Ala Glu Ala Tyr Arg Cys Cys Asp Ala Phe Tyr Ala Leu Pro Leu
85 90 95

Ala Asp Lys Gln Arg Ala Gln Arg Arg His Gly Glu Asn His Gly Tyr
100 105 110

Ala Ser Ser Phe Thr Gly Arg Phe His Cys Cys Leu Pro Trp Lys Glu
115 120 125

Thr Leu Ser Phe Asn Cys Pro Ala Gly Ala Gly Thr Ala Arg Ala Val
130 135 140

Val Gly Tyr Phe Val Asp Val Leu Gly Glu Asp Tyr Arg His Met Gly
145 150 155 160

Glu Val Tyr Gln Glu Tyr Cys Asp Ala Met Thr Arg Leu Ala Leu Asp
165 170 175

Val Thr Glu Val Leu Ala Ala Ala Leu Gly Leu Asp Arg Gly Ala Leu
180 185 190

Arg Gly Phe Phe Glu Gly Gly Asp Ser Val Met Arg Leu Asn His Tyr
195 200 205

Pro Ala Cys Arg Gln Pro His Leu Thr Leu Gly Thr Gly Pro His Arg
210 215 220

Asp Pro Thr Ser Leu Thr Leu Leu His Gln Asp Asp Val Gly Gly Leu
225 230 235 240

Gln Val Arg Ala Gly Gly Gly Pro Trp Arg Ala Val Arg Pro Arg Ala
245 250 255

Asp Ala Phe Val Val Asn Ile Gly Asp Thr Phe Ala Ala Leu Thr Asp
260 265 270

Gly Arg His Thr Ser Cys Leu His Arg Ala Val Val Thr Gly Gly Gly
275 280 285

Ser Arg Arg Ser Leu Ala Phe Phe Leu Asn Pro Pro Leu Asp Arg Val
290 295 300

Val Arg Pro Pro Gly Ala Leu Leu Gln Glu Asn Lys Gln Ala Gly Arg
305 310 315 320

Pro Arg Ala Phe Pro Asp Phe Thr Trp Arg Glu Phe Leu Glu Phe Thr
325 330 335

Gln Lys His Tyr Arg Ser Asp Ala Gly Thr Met Asp Ala Phe Val Ser
340 345 350

Trp Ile Ala Gly Gly Arg Arg His His Gly Gly Gln Glu Glu Gly Asn
355 360 365

<210> SEQ ID NO 7
<211> LENGTH: 1522
<212> TYPE: DNA
<213> ORGANISM: Zea mays

<400> SEQUENCE: 7
gcacactcgc agctcgcaca tctcatggtg tcctaagaac ggcaagagcc agctctgcct 60
agcagcagcg cacagccaca tccatggacg ccagcccgac cccaccgctc cccctccgcg 120
ccccaactcc cagcattgac ctcccccgctg gcaaggacag ggccgacgcg gcggctaaca 180
aggccgcggc tgtgttcgac ctgcgccggg agcccaagat cccggagcca ttcctgtggc 240
cgcacgaaga ggcgcggccg acctcggccg cggagctgga ggtgccggtg gtggacgtgg 300
gcgtgctgcg caatggcgac ggcgcggggc tccgccgcgc cgcggcgcaa gtggcggcgg 360
cgtgcgcgac gcacgggttc ttccaggtgt gcgggcacgg cgtggacgcg gcgctggggc 420

```
gcgccgcgct ggacggcgcc agcgacttct tccggctgcc gctggctgag aagcagcggg    480

cccggcgcgt ccccggcacc gtgtccgggt acacgagcgc gcacgccgac cggttcgcgt    540

ccaagctccc ctggaaggag accctgtcct tcggcttcca cgacggcgcc gcggcgcccg    600

tcgtcgtgga ctacttcacc ggcaccctcg gccaagattt cgagccagtg gggcgggtgt    660

accagaggta ctgcgaggag atgaaggagc tgtcgctgac gatcatggag ctgctggagc    720

tgagcctggg cgtggagcgc ggctactacc gggagttctt cgaggacagc cgctccatca    780

tgcggtgcaa ctactacccg ccgtgcccgg tgccggagcg cacgctgggc acgggcccgc    840

actgcgaccc cacggcgctg accatcctcc tgcaggacga cgtcggcggg ctggaggtcc    900

tggtggacgg cgagtggcgc cccgtccggc ccgtcccagg cgccatggtc atcaacatcg    960

gcgacacctt catggcgctg tccaacgggc ggtacaagag ctgcctgcac cgcgcggtgg   1020

tgaaccggcg gcaggagcgg caatcgctgg ccttcttcct gtgcccgcgc gaggaccggg   1080

tggtgcgccc gccggccagc gccgcgccgc ggcagtaccc ggacttcacc tgggccgacc   1140

tcatgcgctt cacgcagcgc cactaccgcg ccgacacccg cacgctggac gccttcaccc   1200

gctggctctc ccacggcccg gcggcggcgg ctccctgcac ctaacgagcc ggccgtctct   1260

ttcgccgggg cccgcgcggg gttcgcccac gtggtgatca ggtggcagac atgtggccca   1320

cgggccccgc gccgccttcc ccatttttgg acgaccctac tgctactact actagtgtac   1380

atatgcaaaa aaatacatat atatataggt actttctcta atatttttat atataagcaa   1440

ggcggcctgg tgttcttttc tttgttttgt cgacaactgt ttgatcccat cctatggacg   1500

atggatagtt caatgtttgt ac                                            1522
```

<210> SEQ ID NO 8
<211> LENGTH: 1161
<212> TYPE: DNA
<213> ORGANISM: Zea mays

<400> SEQUENCE: 8

```
atggacgcca gcccgacccc accgctcccc ctccgcgccc caactcccag cattgacctc     60

cccgctggca aggacagggc cgacgcggcg gctaacaagg ccgcggctgt gttcgacctg    120

cgccgggagc ccaagatccc ggagccattc ctgtggccgc acgaagaggc gcggccgacc    180

tcggccgcgg agctggaggt gccggtggtg gacgtgggcg tgctgcgcaa tggcgacggc    240

gcggggctcc gccgcgccgc ggcgcaagtg gcggcggcgt gcgcgacgca cgggttcttc    300

caggtgtgcg ggcacggcgt ggacgcggcg ctggggcgcg ccgcgctgga cggcgccagc    360

gacttcttcc ggctgccgct ggctgagaag cagcgggccc ggcgcgtccc cggcaccgtg    420

tccgggtaca cgagcgcgca cgccgaccgg ttcgcgtcca agctcccctg gaaggagacc    480

ctgtccttcg gcttccacga cggcgccgcg gcgcccgtcg tcgtggacta cttcaccggc    540

accctcggcc aagatttcga gccagtgggg cgggtgtacc agaggtactg cgaggagatg    600

aaggagctgt cgctgacgat catggagctg ctggagctga gcctgggcgt ggagcgcggc    660

tactaccggg agttcttcga ggacagccgc tccatcatgc ggtgcaacta ctacccgccg    720

tgcccggtgc cggagcgcac gctgggcacg ggcccgcact gcgaccccac ggcgctgacc    780

atcctcctgc aggacgacgt cggcgggctg gaggtcctgg tggacggcga gtggcgcccc    840

gtccggcccg tcccaggcgc catggtcatc aacatcggcg acaccttcat ggcgctgtcc    900

aacgggcggt acaagagctg cctgcaccgc gcggtggtga accggcggca ggagcggcaa    960
```

```
tcgctggcct tcttcctgtg cccgcgcgag gaccgggtgg tgcgcccgcc ggccagcgcc   1020

gcgccgcggc agtacccgga cttcacctgg gccgacctca tgcgcttcac gcagcgccac   1080

taccgcgccg acacccgcac gctggacgcc ttcacccgct ggctctccca cggcccggcg   1140

gcggcggctc cctgcaccta a                                             1161


<210> SEQ ID NO 9
<211> LENGTH: 386
<212> TYPE: PRT
<213> ORGANISM: Zea mays

<400> SEQUENCE: 9

Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
    50                  55                  60

Leu Glu Val Pro Val Val Asp Val Gly Val Leu Arg Asn Gly Asp Gly
65                  70                  75                  80

Ala Gly Leu Arg Arg Ala Ala Ala Gln Val Ala Ala Ala Cys Ala Thr
                85                  90                  95

His Gly Phe Phe Gln Val Cys Gly His Gly Val Asp Ala Ala Leu Gly
            100                 105                 110

Arg Ala Ala Leu Asp Gly Ala Ser Asp Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Gly Ala Ala Ala Pro Val Val Val Asp
                165                 170                 175

Tyr Phe Thr Gly Thr Leu Gly Gln Asp Phe Glu Pro Val Gly Arg Val
            180                 185                 190

Tyr Gln Arg Tyr Cys Glu Glu Met Lys Glu Leu Ser Leu Thr Ile Met
        195                 200                 205

Glu Leu Leu Glu Leu Ser Leu Gly Val Glu Arg Gly Tyr Tyr Arg Glu
    210                 215                 220

Phe Phe Glu Asp Ser Arg Ser Ile Met Arg Cys Asn Tyr Tyr Pro Pro
225                 230                 235                 240

Cys Pro Val Pro Glu Arg Thr Leu Gly Thr Gly Pro His Cys Asp Pro
                245                 250                 255

Thr Ala Leu Thr Ile Leu Leu Gln Asp Asp Val Gly Gly Leu Glu Val
            260                 265                 270

Leu Val Asp Gly Glu Trp Arg Pro Val Arg Pro Val Pro Gly Ala Met
        275                 280                 285

Val Ile Asn Ile Gly Asp Thr Phe Met Ala Leu Ser Asn Gly Arg Tyr
    290                 295                 300

Lys Ser Cys Leu His Arg Ala Val Val Asn Arg Arg Gln Glu Arg Gln
305                 310                 315                 320

Ser Leu Ala Phe Phe Leu Cys Pro Arg Glu Asp Arg Val Val Arg Pro
                325                 330                 335
```

```
Pro Ala Ser Ala Ala Pro Arg Gln Tyr Pro Asp Phe Thr Trp Ala Asp
            340                 345                 350

Leu Met Arg Phe Thr Gln Arg His Tyr Arg Ala Asp Thr Arg Thr Leu
        355                 360                 365

Asp Ala Phe Thr Arg Trp Leu Ser His Gly Pro Ala Ala Ala Ala Pro
    370                 375                 380

Cys Thr
385


<210> SEQ ID NO 10
<211> LENGTH: 1457
<212> TYPE: DNA
<213> ORGANISM: Zea mays

<400> SEQUENCE: 10

taatcacctc atcacaggtc cccccagcct cactctcgcg ccggctcaag gtacattgcg     60

tgtcctagcc aagacacgca gctcatctca gcctcacacg cacagcaaga gcgaggcgtg    120

attcgccatg ggcggcctca ctatggacca ggccttcgtg caggcccccg agcaccgccc    180

caagcccatc gtcaccgagg ccaccggcat ccctctcatc gacctctcgc ctctggccgc    240

cagcggcggc gccgtggacg cgctggccgc cgaggtgggc gcggcgagcc gggactgggg    300

cttcttcgtg gtcgtgggcc acggcgtgcc cgcagagacc gtggcgcgcg cgacggaggc    360

gcagcgagcg ttcttcgcgc tgccggcaga gcggaaggcc gccgtgcgga ggaacgaggc    420

ggagccgctc gggtactacg agtcggagca caccaagaac gtgagggact ggaaggaggt    480

gtacgacctc gtgccgcgcg agccgccgcc gccggcagcc gtggccgacg gcgagcttgt    540

gttcgataac aagtggcccc aggatctacc gggcttcaga gaggcgctgg aggagtacgc    600

gaaagcgatg gaagagctgg cgttcaagct gctggagctg atcgcccgga gcctgaagct    660

gaggcccgac cggctgcacg gcttcttcaa ggaccagacg accttcatcc ggctgaacca    720

ctaccctcct tgcccgagcc ccgacctggc cctcggcgtg gggcggcaca aggacgccgg    780

cgccctgacc atcctgtacc aggacgacgt cggggggctc gacgtccggc ggcgctccga    840

cggcgagtgg gtccgcgtca ggcccgtgcc cgactcgttc atcatcaacg tcggcgacct    900

catccaggta cgagagcgcg gagcaccggg tgtcggtgaa ctcggcgagg gagaggttct    960

ccatgcccta cttcttcaac ccggcgacct acaccatggt ggagccggtg gaggagctgg   1020

tgagcaagga cgatccgccc aggtacgacg cctacaactg ggcgacttc ttcagcacca   1080

ggaagaacag caacttcaag aagctcaacg tggagaacat tcagatcgcg catttcaaga   1140

agagcctcgt cctcgcctaa ctactgctac tgctaggatc catgccattg ccatgtcgtc   1200

ttcagattca gagcacgcca tgtcgtcgct agcttcgtgg tagaacaaat aatgatgtgc   1260

gtgctgtgtg taagcatgga tatggatgtg aatatgtaat atgatgagca ctcctacttt   1320

ggtatgtttg ggaataacag acttgtgttg gtctggttca ttatttgtaa gaaaatcaaa   1380

aagagttagt agggcaggag gctaaccaca gtcatgctgc accacatccc tggtggaaag   1440

ctggccgggt tacgcta                                                  1457


<210> SEQ ID NO 11
<211> LENGTH: 1116
<212> TYPE: DNA
<213> ORGANISM: Zea mays

<400> SEQUENCE: 11

atgggcggcc tcactatgga ccaggccttc gtgcaggccc ccgagcaccg ccccaagccc     60
```

```
atcgtcaccg aggccaccgg catccctctc atcgacctct cgcctctggc cgccagcggc    120

ggcgccgtgg acgcgctggc cgccgaggtg ggcgcggcga gccgggactg ggcttcttc    180

gtggtcgtgg gccacggcgt gcccgcagag accgtggcgc gcgcgacgga ggcgcagcga    240

gcgttcttcg cgctgccggc agagcggaag gccgccgtgc ggaggaacga ggcggagccg    300

ctcgggtact acgagtcgga gcacaccaag aacgtgaggg actggaagga ggtgtacgac    360

ctcgtgccgc gcgagccgcc gccgccggca gccgtggccg acggcgagct tgtgttcgat    420

aacaagtggc cccaggatct accgggcttc agagaggcgc tggaggagta cgcgaaagcg    480

atggaagagc tggcgttcaa gctgctggag ctgatcgccc ggagcctgaa gctgaggccc    540

gaccggctgc acggcttctt caaggaccag acgaccttca tccggctgaa ccactaccct    600

ccttgcccga gccccgacct ggccctcggc gtggggcggc acaaggacgc cggcgccctg    660

accatcctgt accaggacga cgtcgggggg ctcgacgtcc ggcggcgctc cgacggcgag    720

tgggtccgcg tcaggcccgt gcccgactcg ttcatcatca acgtcggcga cctcatccag    780

gtacgagagc gcggagcacc gggtgtcggt gaactcggcg agggagaggt tctccatgcc    840

ctacttcttc aacccggcga cctacaccat ggtggagccg gtggaggagc tggtgagcaa    900

ggacgatccg cccaggtacg acgcctacaa ctggggcgac ttcttcagca ccaggaagaa    960

cagcaacttc aagaagctca acgtggagaa cattcagatc gcgcatttca agaagagcct   1020

cgtcctcgcc taactactgc tactgctagg atccatgcca ttgccatgtc gtcttcagat   1080

tcagagcacg ccatgtcgtc gctagcttcg tggtag                             1116
```

<210> SEQ ID NO 12
<211> LENGTH: 371
<212> TYPE: PRT
<213> ORGANISM: Zea mays

<400> SEQUENCE: 12

```
Met Gly Gly Leu Thr Met Asp Gln Ala Phe Val Gln Ala Pro Glu His
1               5                   10                  15

Arg Pro Lys Pro Ile Val Thr Glu Ala Thr Gly Ile Pro Leu Ile Asp
            20                  25                  30

Leu Ser Pro Leu Ala Ala Ser Gly Gly Ala Val Asp Ala Leu Ala Ala
        35                  40                  45

Glu Val Gly Ala Ala Ser Arg Asp Trp Gly Phe Phe Val Val Val Gly
    50                  55                  60

His Gly Val Pro Ala Glu Thr Val Ala Arg Ala Thr Glu Ala Gln Arg
65                  70                  75                  80

Ala Phe Phe Ala Leu Pro Ala Glu Arg Lys Ala Ala Val Arg Arg Asn
                85                  90                  95

Glu Ala Glu Pro Leu Gly Tyr Tyr Glu Ser Glu His Thr Lys Asn Val
            100                 105                 110

Arg Asp Trp Lys Glu Val Tyr Asp Leu Val Pro Arg Glu Pro Pro Pro
        115                 120                 125

Pro Ala Ala Val Ala Asp Gly Glu Leu Val Phe Asp Asn Lys Trp Pro
    130                 135                 140

Gln Asp Leu Pro Gly Phe Arg Glu Ala Leu Glu Glu Tyr Ala Lys Ala
145                 150                 155                 160

Met Glu Glu Leu Ala Phe Lys Leu Leu Glu Leu Ile Ala Arg Ser Leu
                165                 170                 175

Lys Leu Arg Pro Asp Arg Leu His Gly Phe Phe Lys Asp Gln Thr Thr
```

```
            180                 185                 190

Phe Ile Arg Leu Asn His Tyr Pro Pro Cys Pro Ser Pro Asp Leu Ala
        195                 200                 205

Leu Gly Val Gly Arg His Lys Asp Ala Gly Ala Leu Thr Ile Leu Tyr
    210                 215                 220

Gln Asp Asp Val Gly Gly Leu Asp Val Arg Arg Arg Ser Asp Gly Glu
225                 230                 235                 240

Trp Val Arg Val Arg Pro Val Pro Asp Ser Phe Ile Ile Asn Val Gly
                245                 250                 255

Asp Leu Ile Gln Val Arg Glu Arg Gly Ala Pro Gly Val Gly Glu Leu
            260                 265                 270

Gly Glu Gly Glu Val Leu His Ala Leu Leu Leu Gln Pro Gly Asp Leu
        275                 280                 285

His His Gly Gly Ala Gly Gly Gly Ala Gly Glu Gln Gly Arg Ser Ala
    290                 295                 300

Gln Val Arg Arg Leu Gln Leu Gly Arg Leu Leu Gln His Gln Glu Glu
305                 310                 315                 320

Gln Gln Leu Gln Glu Ala Gln Arg Gly Glu His Ser Asp Arg Ala Phe
                325                 330                 335

Gln Glu Glu Pro Arg Pro Arg Leu Thr Thr Ala Thr Ala Arg Ile His
            340                 345                 350

Ala Ile Ala Met Ser Ser Ser Asp Ser Glu His Ala Met Ser Ser Leu
        355                 360                 365

Ala Ser Trp
    370


<210> SEQ ID NO 13
<211> LENGTH: 1733
<212> TYPE: DNA
<213> ORGANISM: Zea mays

<400> SEQUENCE: 13

atgaggccgc gcctccctcc aaatgttccc tccctgcctt cgtctttgtc gttgctcgca     60

aactccctgt cctcccctgt tacaaatacc cccacccgcc cggacagctt ccctgcatac    120

ttgcagctcg cacatctcat ggtgtcgcag gaacgacaag agccagctgt gcctagcagc    180

agcagcagca gcgccaagcg cgcagccacg tccatggacg ccagcccggc cccgccgctc    240

ctcctccgcg cccccactcc cagccccagc attgacctcc ccgctggcaa ggacaaggcc    300

gacgcggcgg ccagcaaggc cggcgcggcc gtgttcgacc tgcgccggga gcccaagatc    360

cccgcgccat tcctgtggcc gcaggaagag gcgcggccgt cctcggccgc ggagctggag    420

gtgccgatgg tggacgtggg cgtgctgcgc aatggcgacc gcgcggggct gcggcgcgcc    480

gcggcgcagg tggccgcggc gtgcgcgacg cacgggttct tccaggtgtg cgggcacggc    540

gtggacgcgg cgctggggcg cgccgcgctg gacggcgcca gcgacttctt ccggctgccg    600

ctcgccgaga agcagcgcgc ccggcgcgtc cccggcaccg tgtccgggta cacgagcgcg    660

cacgccgacc ggttcgcggc caagctcccc tggaaggaga ccctgtcgtt cggctaccac    720

gacggcgccg cgtcgcctgt cgtcgtggac tacttcgtcg gcaccctcgg ccaggatttc    780

gagccaatgg ggtgggtgta ccagaggtac tgcgaggaga tgaaggagct gtcgctgacg    840

atcatggagc tgctggagct gagcctgggc gtggagctgc gcggctacta ccgggagttc    900

ttcgaggaca gccggtccat catgcggtgc aactactacc cgccgtgccc ggagccggag    960

cgcacgctgg gcacgggccc gcactgcgac cccacggcgc tcaccatcct cctgcaggac   1020
```

gacgtgggcg ggctggaggt gctggtggac ggtgagtggc gccccgtccg gcccgtcccg 1080
ggcgccatgg tcatcaacat cggcgacacc ttcatggcgc tgtcgaacgg gaggtacaag 1140
agctgcctgc accgcgcggt ggtgaaccag cggcgggcgc ggcggtcgct ggccttcttc 1200
ctgtgcccgc gcgaggaccg ggtggtgcgc ccgccggcca gtgctgcgcc gcggcgctac 1260
ccggacttca cctgggccga cctcatgcgc ttcacgcagc gccactaccg cgccgacacc 1320
cgcacgctgg acgccttcac ccgctggctc tcccacggcc cggcccaggc ggcggcgcct 1380
ccctgcacct agcgagccgg gccaaggccg tctctttcgc cccacgtgcg cgcccagctg 1440
ggcaggtggc cagacacgcg gcccgcgggc cccgcgccgc cttgccattt tttgacgctg 1500
gccctactgc tgtgctacta gtgtacatat gcaagagtac atatatatat atatatatac 1560
gtattttcta tatattatat ataaaagcaa ggcggcccgg tgcccttctc ttgttttgtc 1620
cacaactgtt tgatcccatt attctatgga ccatggatac ttcaatgttt gtactaagac 1680
cgtgaacgtg ggattctttt ccttcctctg tgttttttct gagaaaaatt aaa 1733

<210> SEQ ID NO 14
<211> LENGTH: 1392
<212> TYPE: DNA
<213> ORGANISM: Zea mays

<400> SEQUENCE: 14
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc ccgctggcaa ggacaaggcc 300
gacgcggcgg ccagcaaggc cggcgcggcc gtgttcgacc tgcgccggga gcccaagatc 360
cccgcgccat tcctgtggcc gcaggaagag gcgcggccgt cctcggccgc ggagctggag 420
gtgccgatgg tggacgtggg cgtgctgcgc aatggcgacc gcgcggggct gcggcgcgcc 480
gcggcgcagg tggccgcggc gtgcgcgacg cacgggttct tccaggtgtg cgggcacggc 540
gtggacgcgg cgctggggcg cgccgcgctg gacggcgcca gcgacttctt ccggctgccg 600
ctcgccgaga agcagcgcgc ccggcgcgtc cccggcaccg tgtccgggta cacgagcgcg 660
cacgccgacc ggttcgcggc caagctcccc tggaaggaga ccctgtcgtt cggctaccac 720
gacggcgccg cgtcgcctgt cgtcgtggac tacttcgtcg gcaccctcgg ccaggatttc 780
gagccaatgg ggtgggtgta ccagaggtac tgcgaggaga tgaaggagct gtcgctgacg 840
atcatggagc tgctggagct gagcctgggc gtggagctgc gcggctacta ccgggagttc 900
ttcgaggaca gccggtccat catgcggtgc aactactacc cgccgtgccc ggagccggag 960
cgcacgctgg gcacgggccc gcactgcgac ccccacggcgc tcaccatcct cctgcaggac 1020
gacgtgggcg ggctggaggt gctggtggac ggtgagtggc gccccgtccg gcccgtcccg 1080
ggcgccatgg tcatcaacat cggcgacacc ttcatggcgc tgtcgaacgg gaggtacaag 1140
agctgcctgc accgcgcggt ggtgaaccag cggcgggcgc ggcggtcgct ggccttcttc 1200
ctgtgcccgc gcgaggaccg ggtggtgcgc ccgccggcca gtgctgcgcc gcggcgctac 1260
ccggacttca cctgggccga cctcatgcgc ttcacgcagc gccactaccg cgccgacacc 1320
cgcacgctgg acgccttcac ccgctggctc tcccacggcc cggcccaggc ggcggcgcct 1380
ccctgcacct ag 1392

<210> SEQ ID NO 15
<211> LENGTH: 463
<212> TYPE: PRT
<213> ORGANISM: Zea mays

<400> SEQUENCE: 15

```
Met Arg Pro Arg Leu Pro Pro Asn Val Pro Ser Leu Pro Ser Ser Leu
1               5                   10                  15

Ser Leu Leu Ala Asn Ser Leu Ser Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly
                85                  90                  95

Lys Asp Lys Ala Asp Ala Ala Ala Ser Lys Ala Gly Ala Ala Val Phe
            100                 105                 110

Asp Leu Arg Arg Glu Pro Lys Ile Pro Ala Pro Phe Leu Trp Pro Gln
        115                 120                 125

Glu Glu Ala Arg Pro Ser Ser Ala Ala Glu Leu Glu Val Pro Met Val
    130                 135                 140

Asp Val Gly Val Leu Arg Asn Gly Asp Arg Ala Gly Leu Arg Arg Ala
145                 150                 155                 160

Ala Ala Gln Val Ala Ala Ala Cys Ala Thr His Gly Phe Phe Gln Val
                165                 170                 175

Cys Gly His Gly Val Asp Ala Ala Leu Gly Arg Ala Ala Leu Asp Gly
            180                 185                 190

Ala Ser Asp Phe Phe Arg Leu Pro Leu Ala Glu Lys Gln Arg Ala Arg
        195                 200                 205

Arg Val Pro Gly Thr Val Ser Gly Tyr Thr Ser Ala His Ala Asp Arg
    210                 215                 220

Phe Ala Ala Lys Leu Pro Trp Lys Glu Thr Leu Ser Phe Gly Tyr His
225                 230                 235                 240

Asp Gly Ala Ala Ser Pro Val Val Val Asp Tyr Phe Val Gly Thr Leu
                245                 250                 255

Gly Gln Asp Phe Glu Pro Met Gly Trp Val Tyr Gln Arg Tyr Cys Glu
            260                 265                 270

Glu Met Lys Glu Leu Ser Leu Thr Ile Met Glu Leu Leu Glu Leu Ser
        275                 280                 285

Leu Gly Val Glu Leu Arg Gly Tyr Tyr Arg Glu Phe Phe Glu Asp Ser
    290                 295                 300

Arg Ser Ile Met Arg Cys Asn Tyr Tyr Pro Pro Cys Pro Glu Pro Glu
305                 310                 315                 320

Arg Thr Leu Gly Thr Gly Pro His Cys Asp Pro Thr Ala Leu Thr Ile
                325                 330                 335

Leu Leu Gln Asp Asp Val Gly Gly Leu Glu Val Leu Val Asp Gly Glu
            340                 345                 350

Trp Arg Pro Val Arg Pro Val Pro Gly Ala Met Val Ile Asn Ile Gly
        355                 360                 365
```

```
Asp Thr Phe Met Ala Leu Ser Asn Gly Arg Tyr Lys Ser Cys Leu His
    370                 375                 380

Arg Ala Val Val Asn Gln Arg Arg Ala Arg Arg Ser Leu Ala Phe Phe
385                 390                 395                 400

Leu Cys Pro Arg Glu Asp Arg Val Val Arg Pro Pro Ala Ser Ala Ala
                405                 410                 415

Pro Arg Arg Tyr Pro Asp Phe Thr Trp Ala Asp Leu Met Arg Phe Thr
            420                 425                 430

Gln Arg His Tyr Arg Ala Asp Thr Arg Thr Leu Asp Ala Phe Thr Arg
        435                 440                 445

Trp Leu Ser His Gly Pro Ala Gln Ala Ala Ala Pro Pro Cys Thr
    450                 455                 460


<210> SEQ ID NO 16
<211> LENGTH: 1510
<212> TYPE: DNA
<213> ORGANISM: Zea mays

<400> SEQUENCE: 16

aaagagcgcg cgacggcggc ccctgggaga gccatgcgag actggaggcg gaaccgcgca     60

cgacaccaag ctgccgcgcc ggactgctgc acgcaagcgc agcgcaggac cgaccgacct    120

ccgtaggcac gcacggcgcc ggcggcatgg cggagcacct cctgtcgacg gccgtgcacg    180

acacgctgcc ggggagctac gtgcggccgg agccggagcg cccgcgcctc gcggaggtcg    240

tgaccggcgc gcgcatcccc gtcgtggacc tgggcagccc cgaccgcggc gcggtcgtgg    300

ccgccgtcgg cgacgcctgc cgctcgcacg gcttcttcca ggtcgtcaac cacgggatac    360

acgccgccct ggtcgcggcg gtgatggccg cggggcgcgg cttcttccgg ctgccccccg    420

aggagaaggc caagctctac tccgacgacc ccgccaggaa gatccggctg tccaccagct    480

tcaacgtgcg caaggagacg gtgcacaact ggcgcgacta cctccgcctg cactgccatc    540

ccctcgacga gttcctgccc gattggccgt ccaacccgcc cgatttcaag gagaccatgg    600

gcacctactg caaggaggtc cgggagctcg ggttcaggct gtacgccgcg atctcggaga    660

gcctgggcct agaggcgagc tacatgaagg aagcgctggg ggagcaggag cagcacatgg    720

cggtcaactt ctacccgccg tgcccggagc cggagctcac ctacggcctc ccggcgcaca    780

ccgaccccaa cgcgctcacc atcctgctca tggacccgga cgtcgccggc ctgcaggtgc    840

tccacgccgg ccagtgggtc gccgtcaacc cgcagcccgg cgcgctcatc atcaacatcg    900

gcgaccagct gcaggcgctg agcaacgggc agtaccggag cgtgtggcac cgcgcggtgg    960

tgaactcgga ccgggagcgc atgtccgtgg cgtcgttcct gtgcccgtgc aaccacgtcg   1020

tgctcggccc cgcgcggaag ctcgtcaccg aggacacccc ggccgtgtac aggaactaca   1080

cgtacgacaa gtactacgcc aagttctgga gcaggaacct ggaccaggag cactgcctcg   1140

agctcttcag aacctagcga atcggatacg gatggatgga tacattacat acgcgccctc   1200

tgtttttctc catgacgtta gaagaacacg ttctgcaatg tttgtccatt caaggtggta   1260

tcaatcaagg ctgtggtcgt tgcaattctt ccgctccata tacatgatta aatgctttga   1320

aagaaaaaga aaaaaaagaa acacaagtat tatggcacta ctagtgtttt taggaacaag   1380

gaaagagggg ttgcccctgc tggctatata tattaaatat aaataaaggt aaggctgtag   1440

acattggtga ataagagaaa gtatttgagt ttctctattg tcactccaga acagactcct   1500

ttgcctcgat                                                          1510
```

<210> SEQ ID NO 17
<211> LENGTH: 1011
<212> TYPE: DNA
<213> ORGANISM: Zea mays

<400> SEQUENCE: 17

```
atggcggagc acctcctgtc gacggccgtg cacgacacgc tgccggggag ctacgtgcgg      60

ccggagccgg agcgcccgcg cctcgcggag gtcgtgaccg gcgcgcgcat ccccgtcgtg     120

gacctgggca gccccgaccg cggcgcggtc gtggccgccg tcggcgacgc ctgccgctcg     180

cacggcttct tccaggtcgt caaccacggg atacacgccg ccctggtcgc ggcggtgatg     240

gccgcggggc gcggcttctt ccggctgccc cccgaggaga aggccaagct ctactccgac     300

gaccccgcca ggaagatccg gctgtccacc agcttcaacg tgcgcaagga gacggtgcac     360

aactggcgcg actacctccg cctgcactgc catcccctcg acgagttcct gcccgattgg     420

ccgtccaacc cgcccgattt caaggagacc atgggcacct actgcaagga ggtccgggag     480

ctcgggttca ggctgtacgc cgcgatctcg gagagcctgg gcctagaggc gagctacatg     540

aaggaagcgc tgggggagca ggagcagcac atggcggtca acttctaccc gccgtgcccg     600

gagccggagc tcacctacgg cctcccggcg cacaccgacc ccaacgcgct caccatcctg     660

ctcatggacc cggacgtcgc cggcctgcag gtgctccacg ccggccagtg ggtcgccgtc     720

aacccgcagc ccggcgcgct catcatcaac atcggcgacc agctgcaggc gctgagcaac     780

gggcagtacc ggagcgtgtg gcaccgcgcg gtggtgaact cggaccggga gcgcatgtcc     840

gtggcgtcgt tcctgtgccc gtgcaaccac gtcgtgctcg gccccgcgcg gaagctcgtc     900

accgaggaca ccccggccgt gtacaggaac tacacgtacg acaagtacta cgccaagttc     960

tggagcagga acctggacca ggagcactgc ctcgagctct tcagaaccta g             1011
```

<210> SEQ ID NO 18
<211> LENGTH: 336
<212> TYPE: PRT
<213> ORGANISM: Zea mays

<400> SEQUENCE: 18

```
Met Ala Glu His Leu Leu Ser Thr Ala Val His Asp Thr Leu Pro Gly
1               5                   10                  15

Ser Tyr Val Arg Pro Glu Pro Glu Arg Pro Arg Leu Ala Glu Val Val
            20                  25                  30

Thr Gly Ala Arg Ile Pro Val Val Asp Leu Gly Ser Pro Asp Arg Gly
        35                  40                  45

Ala Val Val Ala Ala Val Gly Asp Ala Cys Arg Ser His Gly Phe Phe
    50                  55                  60

Gln Val Val Asn His Gly Ile His Ala Ala Leu Val Ala Ala Val Met
65                  70                  75                  80

Ala Ala Gly Arg Gly Phe Phe Arg Leu Pro Pro Glu Glu Lys Ala Lys
                85                  90                  95

Leu Tyr Ser Asp Asp Pro Ala Arg Lys Ile Arg Leu Ser Thr Ser Phe
            100                 105                 110

Asn Val Arg Lys Glu Thr Val His Asn Trp Arg Asp Tyr Leu Arg Leu
        115                 120                 125

His Cys His Pro Leu Asp Glu Phe Leu Pro Asp Trp Pro Ser Asn Pro
    130                 135                 140

Pro Asp Phe Lys Glu Thr Met Gly Thr Tyr Cys Lys Glu Val Arg Glu
145                 150                 155                 160
```

```
Leu Gly Phe Arg Leu Tyr Ala Ala Ile Ser Glu Ser Leu Gly Leu Glu
                165                 170                 175

Ala Ser Tyr Met Lys Glu Ala Leu Gly Glu Gln Glu Gln His Met Ala
            180                 185                 190

Val Asn Phe Tyr Pro Pro Cys Pro Glu Pro Glu Leu Thr Tyr Gly Leu
        195                 200                 205

Pro Ala His Thr Asp Pro Asn Ala Leu Thr Ile Leu Leu Met Asp Pro
    210                 215                 220

Asp Val Ala Gly Leu Gln Val Leu His Ala Gly Gln Trp Val Ala Val
225                 230                 235                 240

Asn Pro Gln Pro Gly Ala Leu Ile Ile Asn Ile Gly Asp Gln Leu Gln
                245                 250                 255

Ala Leu Ser Asn Gly Gln Tyr Arg Ser Val Trp His Arg Ala Val Val
            260                 265                 270

Asn Ser Asp Arg Glu Arg Met Ser Val Ala Ser Phe Leu Cys Pro Cys
        275                 280                 285

Asn His Val Val Leu Gly Pro Ala Arg Lys Leu Val Thr Glu Asp Thr
    290                 295                 300

Pro Ala Val Tyr Arg Asn Tyr Thr Tyr Asp Lys Tyr Tyr Ala Lys Phe
305                 310                 315                 320

Trp Ser Arg Asn Leu Asp Gln Glu His Cys Leu Glu Leu Phe Arg Thr
                325                 330                 335


<210> SEQ ID NO 19
<211> LENGTH: 1387
<212> TYPE: DNA
<213> ORGANISM: Zea mays

<400> SEQUENCE: 19

gttttctttt tgaacgtaac tgacagaagc tatctgccta gctacggcgt gtcggttgct      60

tgtctcacca aagcagcgac atggaagcct gacagctcgt cgcgtcgcgc catttccacc     120

caacaaagcg gcggcgccag cacgcactgc ttctgcttgt gcgtgctcct ccgttccggg     180

cacgcctcta aagtctatac agcctcgaat ccatcccggc cgccgctcct gggggatact     240

acagcgagcc gaagcgggga tggcggagat ccctgtgatc gacctgcgcg tcgccggctc     300

ggcggccgag gagtccgcgc ggctgcgggc cgcgtgcgag cgcctgggct gcttccgggt     360

gaccggccac ggcgtgccct cggtgctcct ggcagagatg aaggccgccg tgcgcgcgct     420

cttcgacctc cccgacgacg ccaagcgccg caacgccgac gtcatcaccg gcagcggcta     480

cgtcgccccc agcccgacca acccgctcta cgaggccttc gggctcctcg acgccgccgt     540

gcccaccgac gtcgacgcct tttgcgcgct cctcgacgcg ccgcccaaca tcagggagac     600

cgtcaaggcc tacgcggaga agatgcacga tgtgatcgtt ggcgtcgccc gcgagctggc     660

gtctagcctg gggctagtcg aggagcactc gttccaggac tggccgtgcc agttccgcat     720

caacaggtac aactacacgc gggagacggt gggctcctcc ggcgtgcaga cccacacgga     780

ctcgggcttc ctcaccgtgc tccatgagga cgagtgtgtc ggcggcctcg aggtcctgga     840

cccgggcacc ggcgagttcg tgcccgtgga ccccgtcgcg ggctcctttc tcgtaaacat     900

cggcgacgtc ggcacggcgt ggagcaacgg gaggctgcac aacgtgaagc accgggtgcg     960

gtgcgtcgca cccgtgccgc gcatctccat cgccatgttc ctgctcgcac ccaaggacga    1020

cagcgtgagc gcaccggcgg cgttcgtgga cgcggaccac ccgcgcaggt acaaggtgtt    1080

caactacaac gactatcgga ggctcagact gtccaccggc gagcacgcag gcgaggcgct    1140
```

```
cgcacggatg gcggcgtgac gtggctggag ctgcaaattg gattggaagc cgagacaagc   1200

cgttagttat ttaccatgcc cgtgcgttca ccgcacacaa tcatattcaa aagccataaa   1260

ataaaaaata attttaatat cagtcaacat atggtttaaa tatcatatgg agtacaatat   1320

tccgaatttt tttttgtaat ttagtctgtc ttttgaaaaa aatgcacatc tagacctccg   1380

gatgact                                                             1387
```

```
<210> SEQ ID NO 20
<211> LENGTH: 900
<212> TYPE: DNA
<213> ORGANISM: Zea mays

<400> SEQUENCE: 20

atggcggaga tccctgtgat cgacctgcgc gtcgccggct cggcggccga ggagtccgcg     60

cggctgcggg ccgcgtgcga gcgcctgggc tgcttccggg tgaccggcca cggcgtgccc    120

tcggtgctcc tggcagagat gaaggccgcc gtgcgcgcgc tcttcgacct ccccgacgac    180

gccaagcgcc gcaacgccga cgtcatcacc ggcagcggct acgtcgcccc cagcccgacc    240

aacccgctct acgaggcctt cgggctcctc gacgccgccg tgcccaccga cgtcgacgcc    300

ttttgcgcgc tcctcgacgc gccgcccaac atcagggaga ccgtcaaggc ctacgcggag    360

aagatgcacg atgtgatcgt tggcgtcgcc cgcgagctgg cgtctagcct ggggctagtc    420

gaggagcact cgttccagga ctggccgtgc cagttccgca tcaacaggta caactacacg    480

cgggagacgg tgggctcctc cggcgtgcag acccacacgg actcgggctt cctcaccgtg    540

ctccatgagg acgagtgtgt cggcggcctc gaggtcctgg acccgggcac cggcgagttc    600

gtgcccgtgg accccgtcgc gggctccttt ctcgtaaaca tcggcgacgt cggcacggcg    660

tggagcaacg ggaggctgca caacgtgaag caccgggtgc ggtgcgtcgc acccgtgccg    720

cgcatctcca tcgccatgtt cctgctcgca cccaaggacg acagcgtgag cgcaccggcg    780

gcgttcgtgg acgcggacca cccgcgcagg tacaaggtgt tcaactacaa cgactatcgg    840

aggctcagac tgtccaccgg cgagcacgca ggcgaggcgc tcgcacggat ggcggcgtga    900
```

```
<210> SEQ ID NO 21
<211> LENGTH: 299
<212> TYPE: PRT
<213> ORGANISM: Zea mays

<400> SEQUENCE: 21

Met Ala Glu Ile Pro Val Ile Asp Leu Arg Val Ala Gly Ser Ala Ala
1               5                   10                  15

Glu Glu Ser Ala Arg Leu Arg Ala Ala Cys Glu Arg Leu Gly Cys Phe
            20                  25                  30

Arg Val Thr Gly His Gly Val Pro Ser Val Leu Leu Ala Glu Met Lys
        35                  40                  45

Ala Ala Val Arg Ala Leu Phe Asp Leu Pro Asp Asp Ala Lys Arg Arg
    50                  55                  60

Asn Ala Asp Val Ile Thr Gly Ser Gly Tyr Val Ala Pro Ser Pro Thr
65                  70                  75                  80

Asn Pro Leu Tyr Glu Ala Phe Gly Leu Leu Asp Ala Ala Val Pro Thr
                85                  90                  95

Asp Val Asp Ala Phe Cys Ala Leu Leu Asp Ala Pro Pro Asn Ile Arg
            100                 105                 110

Glu Thr Val Lys Ala Tyr Ala Glu Lys Met His Asp Val Ile Val Gly
        115                 120                 125
```

```
Val Ala Arg Glu Leu Ala Ser Ser Leu Gly Leu Val Glu Glu His Ser
    130                 135                 140

Phe Gln Asp Trp Pro Cys Gln Phe Arg Ile Asn Arg Tyr Asn Tyr Thr
145                 150                 155                 160

Arg Glu Thr Val Gly Ser Ser Gly Val Gln Thr His Thr Asp Ser Gly
                165                 170                 175

Phe Leu Thr Val Leu His Glu Asp Glu Cys Val Gly Gly Leu Glu Val
            180                 185                 190

Leu Asp Pro Gly Thr Gly Glu Phe Val Pro Val Asp Pro Val Ala Gly
        195                 200                 205

Ser Phe Leu Val Asn Ile Gly Asp Val Gly Thr Ala Trp Ser Asn Gly
    210                 215                 220

Arg Leu His Asn Val Lys His Arg Val Arg Cys Val Ala Pro Val Pro
225                 230                 235                 240

Arg Ile Ser Ile Ala Met Phe Leu Leu Ala Pro Lys Asp Asp Ser Val
                245                 250                 255

Ser Ala Pro Ala Ala Phe Val Asp Ala Asp His Pro Arg Arg Tyr Lys
            260                 265                 270

Val Phe Asn Tyr Asn Asp Tyr Arg Arg Leu Arg Leu Ser Thr Gly Glu
        275                 280                 285

His Ala Gly Glu Ala Leu Ala Arg Met Ala Ala
    290                 295


<210> SEQ ID NO 22
<211> LENGTH: 1496
<212> TYPE: DNA
<213> ORGANISM: Zea mays

<400> SEQUENCE: 22

gtcggtctct tgtctcacca aaccggcgac atggtacatg gaggccagcc cgtcgcttgg     60

cgccacaagt ctcggtgccg tccgtccgac aagcggcgcc agcgcacgct ggctgctcgt    120

gcacgcctct aaatacggcc ccggacccgc caccaagcga aggccaatcc cgtccgccgc    180

cccccaccaa ccacgaacca cgcaagcgaa cccggccggc gcggggcagc ggcgatggcg    240

gagatcccgg tgatcgacct gcgcctcgcc ggctcgtcgc ccgacgagtc ggcgcggctg    300

cgcgacgcgt gcgagcgcct gggctgcttt cgggtgaccg gccacggcgc gcccgcgggg    360

ctcctggccg acatgaaggc cgccgtgcgc gcgctcttcg acctccccga cgacgccaag    420

cgccgcaacg ccgacgtcat ccccggcagc ggctacgtcg cgccctgccc cgccaacccg    480

ctctacgagg ccttcgggct cctcgacgcc gccgcgcccg ccgacgtcga cgccttctgc    540

gcgcgcctcg acgcgccgcc caaagtcagg gagaccgtca agacctacgc ggagaagatg    600

cacgacgtga tcgtcggcgt cgccggcgag ctggccacca gcctggggct gggcctggag    660

gagcactcgt tccaggactg gccgtgccag ttccgcatca acaggtacaa ctacacgcag    720

gagacggtgg gctcctccgg cgtgcagacc cacacggact cgggcttcct caccgtgctc    780

caggaggacg agtgcgtcgg cggcctcgag gtgctggacc ccgccgccgg tgagttcgtg    840

cccgtggacc ccgtcgccgg ctccttcctc gtcaacatcg gcgacgtcgg cacggcgtgg    900

agcaacggga ggctccacaa cgtgaagcac cgggtgcggt gcgtcgcgcc cgtgccgcgc    960

atctccatcg ccatgttcct gctggcgccc aaggacgacc gcgtgagcgc cccggaggcg   1020

ttggtcgacg cgggccaccc gcgtcggtac aagccgttca actacgacga ctaccggagg   1080

ctccggctgt ccaccggcga gcgcgcaggc gaggcgctcg cgcggatggc ggcgtgatgt   1140
```

cgtcacgcac gtgcaagccg ttaattatag gctcgcgcat gcatacgcct acacgagagg 1200
ttgtctcgtt aagccgttct attaaaatgt gtgggggaga aagatgacta ccgtggtgcc 1260
atgtggattg ctatcgggtc tgatcaataa aatcttgcaa cacttgcacg tgcgattcca 1320
tatcctagca cgggtgggcg ccacgctagt aggtagagac cggagcggcc aaaaaatggc 1380
tacagcacca gtaggtgaac tctcaagcaa cactggctat cccacttctg acgttgtctc 1440
tctcatcact atgtatgacc agcgaatgaa gtgtttaaaa atctgacgcc gtgaaa 1496

<210> SEQ ID NO 23
<211> LENGTH: 903
<212> TYPE: DNA
<213> ORGANISM: Zea mays

<400> SEQUENCE: 23
atggcggaga tcccggtgat cgacctgcgc ctcgccggct cgtcgcccga cgagtcggcg 60
cggctgcgcg acgcgtgcga gcgcctgggc tgctttcggg tgaccggcca cggcgcgccc 120
gcggggctcc tggccgacat gaaggccgcc gtgcgcgcgc tcttcgacct ccccgacgac 180
gccaagcgcc gcaacgccga cgtcatcccc ggcagcggct acgtcgcgcc ctgccccgcc 240
aacccgctct acgaggcctt cggctcctc gacgccgccg cgcccgccga cgtcgacgcc 300
ttctgcgcgc gcctcgacgc gccgcccaaa gtcagggaga ccgtcaagac ctacgcggag 360
aagatgcacg acgtgatcgt cggcgtcgcc ggcgagctgg ccaccagcct ggggctgggc 420
ctggaggagc actcgttcca ggactggccg tgccagttcc gcatcaacag gtacaactac 480
acgcaggaga cggtgggctc ctccggcgtg cagacccaca cggactcggg cttcctcacc 540
gtgctccagg aggacgagtg cgtcggcggc ctcgaggtgc tggaccccgc cgccggtgag 600
ttcgtgcccg tggaccccgt cgccggctcc ttcctcgtca acatcggcga cgtcggcacg 660
gcgtggagca acgggaggct ccacaacgtg aagcaccggg tgcggtgcgt cgcgcccgtg 720
ccgcgcatct ccatcgccat gttcctgctg gcgcccaagg acgaccgcgt gagcgccccg 780
gaggcgttgg tcgacgcggg ccacccgcgt cggtacaagc cgttcaacta cgacgactac 840
cggaggctcc ggctgtccac cggcgagcgc gcaggcgagg cgctcgcgcg gatggcggcg 900
tga 903

<210> SEQ ID NO 24
<211> LENGTH: 300
<212> TYPE: PRT
<213> ORGANISM: Zea mays

<400> SEQUENCE: 24

Met Ala Glu Ile Pro Val Ile Asp Leu Arg Leu Ala Gly Ser Ser Pro
1 5 10 15

Asp Glu Ser Ala Arg Leu Arg Asp Ala Cys Glu Arg Leu Gly Cys Phe
20 25 30

Arg Val Thr Gly His Gly Ala Pro Ala Gly Leu Leu Ala Asp Met Lys
35 40 45

Ala Ala Val Arg Ala Leu Phe Asp Leu Pro Asp Asp Ala Lys Arg Arg
50 55 60

Asn Ala Asp Val Ile Pro Gly Ser Gly Tyr Val Ala Pro Cys Pro Ala
65 70 75 80

Asn Pro Leu Tyr Glu Ala Phe Gly Leu Leu Asp Ala Ala Ala Pro Ala
85 90 95

```
Asp Val Asp Ala Phe Cys Ala Arg Leu Asp Ala Pro Pro Lys Val Arg
            100                 105                 110

Glu Thr Val Lys Thr Tyr Ala Glu Lys Met His Asp Val Ile Val Gly
        115                 120                 125

Val Ala Gly Glu Leu Ala Thr Ser Leu Gly Leu Gly Leu Glu Glu His
    130                 135                 140

Ser Phe Gln Asp Trp Pro Cys Gln Phe Arg Ile Asn Arg Tyr Asn Tyr
145                 150                 155                 160

Thr Gln Glu Thr Val Gly Ser Ser Gly Val Gln Thr His Thr Asp Ser
                165                 170                 175

Gly Phe Leu Thr Val Leu Gln Glu Asp Glu Cys Val Gly Gly Leu Glu
            180                 185                 190

Val Leu Asp Pro Ala Ala Gly Glu Phe Val Pro Val Asp Pro Val Ala
        195                 200                 205

Gly Ser Phe Leu Val Asn Ile Gly Asp Val Gly Thr Ala Trp Ser Asn
    210                 215                 220

Gly Arg Leu His Asn Val Lys His Arg Val Arg Cys Val Ala Pro Val
225                 230                 235                 240

Pro Arg Ile Ser Ile Ala Met Phe Leu Leu Ala Pro Lys Asp Asp Arg
                245                 250                 255

Val Ser Ala Pro Glu Ala Leu Val Asp Ala Gly His Pro Arg Arg Tyr
            260                 265                 270

Lys Pro Phe Asn Tyr Asp Asp Tyr Arg Arg Leu Arg Leu Ser Thr Gly
        275                 280                 285

Glu Arg Ala Gly Glu Ala Leu Ala Arg Met Ala Ala
    290                 295                 300


<210> SEQ ID NO 25
<211> LENGTH: 1614
<212> TYPE: DNA
<213> ORGANISM: Zea mays

<400> SEQUENCE: 25

accacacgaa ttgcacatct ccacagctca cgattccaac actagctaca tatatatgta      60

gctttctagg ctactatata cactcaccac caagtgtgaa gtgtgtatat atagtgacag     120

ctactgcaat atatacatac gcgtcaccta tatattagcc aagctagcta tatgagcttg     180

gttgcggcgc caatggcgat cgtcgacgtg gccaacgccc agctgcagca agcagcagca     240

gcagctgcca agaaagacga ggacggccat gagcagcagg agtcgtccta cgactacggc     300

gcgctgatga aaggcgtgag gcacctgtcg gacagcggca ttaccaggct gcccgacagg     360

tacgtcctgc ccgcgtccga ccgccccggc gtccttgccg tctcgtcgtc cgtggcgggc     420

agcggcaggg tcaagctccc tgtcgtcaac ctcgccggcc tccgcgaccc ctgccagcgc     480

gccgccgtgc tggccacgct cgacgccgcg tgccgggagt acggcttctt tcaggtggta     540

aaccacgggt tcgggagcga cgtgagcggc gggatgctgg acgtggcgca gcgcttcttc     600

gagctgccgc tggccgagcg agcgcggcac atgtcggcgg acgtgcgggc gccggtgcgc     660

tacggcacca gcttcaacca ggccaaggac gacgtgctct gctggcgcga cttcctcaag     720

ctcgtctgcc agccgctgca ggcggtgctc ccgtactggc cccagcagcc ggcggacctc     780

agggacgtgg ccaccaggta cgccacggcg agccaccggc tgttcatgga ggtcatggag     840

gcggcgctgg aggccctggg catccccacg gccggcggcg tgctcgggga gctggcagcg     900

tcgtcgtcgc acatgatgac ggtgaactgc tacccggcgt gcccgcagcc tgagctcacg     960
```

```
ctggggatgc cctcgcactc ggactacggc ctcttcacgt tcgtcctgca ggaccacgtc   1020

gagggcctcc aggtcatgca cgacggccgc tggctcacca tcgaccccat cccgggatcg   1080

ttcgtcgtca acgtcggcga ccacctagag atctacagca acgggcggta caagagcgcg   1140

ctgcaccggg tgcacgtgaa ctccacgcgg ccgcgcatct cggtggcgtc gttccacagc   1200

ctgccggcgg agcgagtgat cgggccggcg ccggagctgg tggacgacga ggccggcaac   1260

ccgcggcggt acatggacac cgacttcgct accttcctcg cctacctcgc atccgcggac   1320

ggcaagaaca agaccttcct ccagtcaagg aagctgcctg ctgctgctcc tccatgcctc   1380

tagctaacta gatagctgct tattaatctg acagaataaa attaatcagt tcagcgcaca   1440

attccacaag cgaaaacaaa cctggatttg ttttaattag ctctgccctt cattattaca   1500

ttcaagctag ctcttggtca acgcatgcac acaagcttga gcattgactg gtccctttc   1560

aatcggttgc attgtactcc ctccgtacca aaattggttg tcgctatagt attt         1614
```

```
<210> SEQ ID NO 26
<211> LENGTH: 1212
<212> TYPE: DNA
<213> ORGANISM: Zea mays

<400> SEQUENCE: 26

atgagcttgg ttgcggcgcc aatggcgatc gtcgacgtgg ccaacgccca gctgcagcaa     60

gcagcagcag cagctgccaa gaaagacgag gacggccatg agcagcagga gtcgtcctac    120

gactacggcg cgctgatgaa aggcgtgagg cacctgtcgg acagcggcat taccaggctg    180

cccgacaggt acgtcctgcc cgcgtccgac cgccccggcg tccttgccgt ctcgtcgtcc    240

gtggcgggca gcggcagggt caagctccct gtcgtcaacc tcgccggcct ccgcgacccc    300

tgccagcgcg ccgccgtgct ggccacgctc gacgccgcgt gccgggagta cggcttcttt    360

caggtggtaa accacgggtt cgggagcgac gtgagcggcg ggatgctgga cgtggcgcag    420

cgcttcttcg agctgccgct ggccgagcga gcgcggcaca tgtcggcgga cgtgcgggcg    480

ccggtgcgct acggcaccag cttcaaccag gccaaggacg acgtgctctg ctggcgcgac    540

ttcctcaagc tcgtctgcca gccgctgcag gcggtgctcc cgtactggcc ccagcagccg    600

gcggacctca gggacgtggc caccaggtac gccacggcga gccaccggct gttcatggag    660

gtcatggagg cggcgctgga ggccctgggc atccccacgg ccggcggcgt gctcggggag    720

ctggcagcgt cgtcgtcgca catgatgacg gtgaactgct acccggcgtg cccgcagcct    780

gagctcacgc tggggatgcc ctcgcactcg gactacggcc tcttcacgtt cgtcctgcag    840

gaccacgtcg agggcctcca ggtcatgcac gacggccgct ggctcaccat cgaccccatc    900

ccgggatcgt tcgtcgtcaa cgtcggcgac cacctagaga tctacagcaa cgggcggtac    960

aagagcgcgc tgcaccgggt gcacgtgaac tccacgcggc cgcgcatctc ggtggcgtcg   1020

ttccacagcc tgccggcgga gcgagtgatc gggccggcgc cggagctggt ggacgacgag   1080

gccggcaacc cgcggcggta catggacacc gacttcgcta ccttcctcgc ctacctcgca   1140

tccgcggacg gcaagaacaa gaccttcctc cagtcaagga agctgcctgc tgctgctcct   1200

ccatgcctct ag                                                       1212
```

```
<210> SEQ ID NO 27
<211> LENGTH: 403
<212> TYPE: PRT
<213> ORGANISM: Zea mays

<400> SEQUENCE: 27
```

-continued

```
Met Ser Leu Val Ala Ala Pro Met Ala Ile Val Asp Val Ala Asn Ala
1               5                   10                  15

Gln Leu Gln Gln Ala Ala Ala Ala Ala Ala Lys Lys Asp Glu Asp Gly
            20                  25                  30

His Glu Gln Gln Glu Ser Ser Tyr Asp Tyr Gly Ala Leu Met Lys Gly
        35                  40                  45

Val Arg His Leu Ser Asp Ser Gly Ile Thr Arg Leu Pro Asp Arg Tyr
    50                  55                  60

Val Leu Pro Ala Ser Asp Arg Pro Gly Val Leu Ala Val Ser Ser Ser
65                  70                  75                  80

Val Ala Gly Ser Gly Arg Val Lys Leu Pro Val Val Asn Leu Ala Gly
                85                  90                  95

Leu Arg Asp Pro Cys Gln Arg Ala Ala Val Leu Ala Thr Leu Asp Ala
            100                 105                 110

Ala Cys Arg Glu Tyr Gly Phe Phe Gln Val Val Asn His Gly Phe Gly
        115                 120                 125

Ser Asp Val Ser Gly Gly Met Leu Asp Val Ala Gln Arg Phe Phe Glu
    130                 135                 140

Leu Pro Leu Ala Glu Arg Ala Arg His Met Ser Ala Asp Val Arg Ala
145                 150                 155                 160

Pro Val Arg Tyr Gly Thr Ser Phe Asn Gln Ala Lys Asp Asp Val Leu
                165                 170                 175

Cys Trp Arg Asp Phe Leu Lys Leu Val Cys Gln Pro Leu Gln Ala Val
            180                 185                 190

Leu Pro Tyr Trp Pro Gln Gln Pro Ala Asp Leu Arg Asp Val Ala Thr
        195                 200                 205

Arg Tyr Ala Thr Ala Ser His Arg Leu Phe Met Glu Val Met Glu Ala
    210                 215                 220

Ala Leu Glu Ala Leu Gly Ile Pro Thr Ala Gly Gly Val Leu Gly Glu
225                 230                 235                 240

Leu Ala Ala Ser Ser Ser His Met Met Thr Val Asn Cys Tyr Pro Ala
                245                 250                 255

Cys Pro Gln Pro Glu Leu Thr Leu Gly Met Pro Ser His Ser Asp Tyr
            260                 265                 270

Gly Leu Phe Thr Phe Val Leu Gln Asp His Val Glu Gly Leu Gln Val
        275                 280                 285

Met His Asp Gly Arg Trp Leu Thr Ile Asp Pro Ile Pro Gly Ser Phe
    290                 295                 300

Val Val Asn Val Gly Asp His Leu Glu Ile Tyr Ser Asn Gly Arg Tyr
305                 310                 315                 320

Lys Ser Ala Leu His Arg Val His Val Asn Ser Thr Arg Pro Arg Ile
                325                 330                 335

Ser Val Ala Ser Phe His Ser Leu Pro Ala Glu Arg Val Ile Gly Pro
            340                 345                 350

Ala Pro Glu Leu Val Asp Asp Glu Ala Gly Asn Pro Arg Arg Tyr Met
        355                 360                 365

Asp Thr Asp Phe Ala Thr Phe Leu Ala Tyr Leu Ala Ser Ala Asp Gly
    370                 375                 380

Lys Asn Lys Thr Phe Leu Gln Ser Arg Lys Leu Pro Ala Ala Ala Pro
385                 390                 395                 400

Pro Cys Leu
```

<210> SEQ ID NO 28
<211> LENGTH: 1863
<212> TYPE: DNA
<213> ORGANISM: Zea mays

<400> SEQUENCE: 28
tgccaccata ccactagtgc aaggtcctag atttacactt ggtgctacac cttgcttcgc 60
ccccttcctt ccttccttcc ttccttccct ccttccttgg tctctaggca gctagcagtg 120
tggtgctgct gccggccgcc tattggccgc ctgggactgg gatccattaa ttactgcgcg 180
cgcgcggcta accaaccaat cccagcgtgc gtaatctatt gcccacatgc cgacgccgtc 240
gcacctcaac aagaacccgc gctacctgga cttccgggcg gcgcggcggg tgccggagtc 300
gcacgcctgg ccgggcctgc acgaccaccc cgtcgtggac ggcggcgcgc cgggccccga 360
cgccgtgccg gtggtggacc tgggcgccgc ggacccggcg ccggcgccgg cggcggcggt 420
ggcccgcgcc gccgagcaat ggggcgcgtt cctgctcacg ggccacggcg tccccgcgga 480
cctgctggcg cgcgtggagg accggatcgc caccatgttc gcgctgccgg ccgacgacaa 540
gatgcgcgcc gtgcgcgggc ccggcgacgc ctgcggctac ggctccccgc ccatctcctc 600
cttcttctcc aagtgcatgt ggtccgaggg ctacaccttc tcgccggcct ccctccgcgc 660
cgacctccgc aagctctggc ccaaggccgg cgacgactac accagcttct gtgatgtgat 720
ggaggagttc cacaagcaca tgcgcgccct cgcggacaag ctgctggagc tgttcctcat 780
ggcgctgggg ctcaccgacg agcaggccag cgccgtcgag gccgagcgga ggatcgccga 840
gacgatgacc gccaccatgc atctcaactg gtacccgagg tgcccggacc cgcggcgcgc 900
gctggggctg atcgcgcaca ccgactcggg cttcttcacc ttcgtgatgc agagcctcgt 960
gcccgggctg cagctcttcc gccacgcccc ggaccggtgg gtggcggtgc cggccgtgcc 1020
gggcgccttc gtcgtcaacg tgggcgacct cttccacatc ctcaccaacg gccggttcca 1080
cagcgtgtac caccgcgccg tcgtgaaccg ggacctcgac aggatctcgc tcggctactt 1140
cctcggcccg ccgccgcacg ccaaggtggc gccgctgcgc gaggccgtgc cgcccggccg 1200
ggcccccgcg taccgcgccg tcacgtggcc cgagtacatg ggcgtccgca agaaggcctt 1260
caccaccggc gcctccgcgc tcaagatggt cgccctcgcc gccgccgccg acctcgacga 1320
cgacggcgac gccgccgtcg tccatcagca gcagcagcta gtcgtctcgt cgtagccgag 1380
accgatcgcc ggagactgat gctgatgatg atgcatatat acatgagaga aatcgtcgag 1440
tagactagcc gattgcaaaa gcaaccccag ctgccgaaac ctggcatatc gatcccattc 1500
tctgctgcgc acatgtatgc atgcatgcgc ttcgtccgtt cgactcgtgt gtgcttgctt 1560
gcttgcgcgt gcagcagaac taattccgtt ccgcagctag ctgctctgct ctgctctgct 1620
ggaatgtaat taagtagtag tatatggtag tagagaaaag attagctagg cgatcgatat 1680
agatgacggg ccggggaaga agacgaatta attaagatcg atcgacgacg acgagctgtg 1740
cgtggctggc tgtgttcttc tctagcctag ttacagaggc cggctgctgc tgcttccaat 1800
cgggctgctt gtcgctactg acgatcgtta gtggatccat taactaatct ggaattctgg 1860
att 1863

<210> SEQ ID NO 29
<211> LENGTH: 1149
<212> TYPE: DNA
<213> ORGANISM: Zea mays

<400> SEQUENCE: 29

```
atgccgacgc cgtcgcacct caacaagaac ccgcgctacc tggacttccg ggcggcgcgg     60

cgggtgccgg agtcgcacgc ctggccgggc ctgcacgacc accccgtcgt ggacggcggc    120

gcgccgggcc ccgacgccgt gccggtggtg gacctgggcg ccgcggaccc ggcgccggcg    180

ccggcggcgg cggtggcccg cgccgccgag caatggggcg cgttcctgct cacgggccac    240

ggcgtccccg cggacctgct ggcgcgcgtg gaggaccgga tcgccaccat gttcgcgctg    300

ccggccgacg acaagatgcg cgccgtgcgc gggcccggcg acgcctgcgg ctacggctcc    360

ccgcccatct cctccttctt ctccaagtgc atgtggtccg agggctacac cttctcgccg    420

gcctccctcc gcgccgacct ccgcaagctc tggcccaagg ccggcgacga ctacaccagc    480

ttctgtgatg tgatggagga gttccacaag cacatgcgcg ccctcgcgga caagctgctg    540

gagctgttcc tcatggcgct ggggctcacc gacgagcagg ccagcgccgt cgaggccgag    600

cggaggatcg ccgagacgat gaccgccacc atgcatctca actggtaccc gaggtgcccg    660

gacccgcggc gcgcgctggg gctgatcgcg cacaccgact cgggcttctt caccttcgtg    720

atgcagagcc tcgtgcccgg gctgcagctc ttccgccacg ccccggaccg gtgggtggcg    780

gtgccggccg tgccgggcgc cttcgtcgtc aacgtgggcg acctcttcca catcctcacc    840

aacggccggt tccacagcgt gtaccaccgc gccgtcgtga accgggacct cgacaggatc    900

tcgctcggct acttcctcgg cccgccgccg cacgccaagg tggcgccgct gcgcgaggcc    960

gtgccgcccg gccgggcccc cgcgtaccgc gccgtcacgt ggcccgagta catgggcgtc   1020

cgcaagaagg ccttcaccac cggcgcctcc gcgctcaaga tggtcgccct cgccgccgcc   1080

gccgacctcg acgacgacgg cgacgccgcc gtcgtccatc agcagcagca gctagtcgtc   1140

tcgtcgtag                                                           1149
```

<210> SEQ ID NO 30
<211> LENGTH: 382
<212> TYPE: PRT
<213> ORGANISM: Zea mays

<400> SEQUENCE: 30

```
Met Pro Thr Pro Ser His Leu Asn Lys Asn Pro Arg Tyr Leu Asp Phe
1               5                   10                  15

Arg Ala Ala Arg Arg Val Pro Glu Ser His Ala Trp Pro Gly Leu His
            20                  25                  30

Asp His Pro Val Val Asp Gly Gly Ala Pro Gly Pro Asp Ala Val Pro
        35                  40                  45

Val Val Asp Leu Gly Ala Ala Asp Pro Ala Pro Ala Pro Ala Ala Ala
    50                  55                  60

Val Ala Arg Ala Ala Glu Gln Trp Gly Ala Phe Leu Leu Thr Gly His
65                  70                  75                  80

Gly Val Pro Ala Asp Leu Leu Ala Arg Val Glu Asp Arg Ile Ala Thr
                85                  90                  95

Met Phe Ala Leu Pro Ala Asp Asp Lys Met Arg Ala Val Arg Gly Pro
            100                 105                 110

Gly Asp Ala Cys Gly Tyr Gly Ser Pro Pro Ile Ser Ser Phe Phe Ser
        115                 120                 125

Lys Cys Met Trp Ser Glu Gly Tyr Thr Phe Ser Pro Ala Ser Leu Arg
    130                 135                 140

Ala Asp Leu Arg Lys Leu Trp Pro Lys Ala Gly Asp Asp Tyr Thr Ser
145                 150                 155                 160

Phe Cys Asp Val Met Glu Glu Phe His Lys His Met Arg Ala Leu Ala
```

```
                165                 170                 175

Asp Lys Leu Leu Glu Leu Phe Leu Met Ala Leu Gly Leu Thr Asp Glu
            180                 185                 190

Gln Ala Ser Ala Val Glu Ala Glu Arg Arg Ile Ala Glu Thr Met Thr
        195                 200                 205

Ala Thr Met His Leu Asn Trp Tyr Pro Arg Cys Pro Asp Pro Arg Arg
    210                 215                 220

Ala Leu Gly Leu Ile Ala His Thr Asp Ser Gly Phe Phe Thr Phe Val
225                 230                 235                 240

Met Gln Ser Leu Val Pro Gly Leu Gln Leu Phe Arg His Ala Pro Asp
                245                 250                 255

Arg Trp Val Ala Val Pro Ala Val Pro Gly Ala Phe Val Val Asn Val
            260                 265                 270

Gly Asp Leu Phe His Ile Leu Thr Asn Gly Arg Phe His Ser Val Tyr
        275                 280                 285

His Arg Ala Val Val Asn Arg Asp Leu Asp Arg Ile Ser Leu Gly Tyr
    290                 295                 300

Phe Leu Gly Pro Pro Pro His Ala Lys Val Ala Pro Leu Arg Glu Ala
305                 310                 315                 320

Val Pro Pro Gly Arg Ala Pro Ala Tyr Arg Ala Val Thr Trp Pro Glu
                325                 330                 335

Tyr Met Gly Val Arg Lys Lys Ala Phe Thr Thr Gly Ala Ser Ala Leu
            340                 345                 350

Lys Met Val Ala Leu Ala Ala Ala Ala Asp Leu Asp Asp Asp Gly Asp
        355                 360                 365

Ala Ala Val Val His Gln Gln Gln Gln Leu Val Val Ser Ser
    370                 375                 380
```

<210> SEQ ID NO 31
<211> LENGTH: 1439
<212> TYPE: DNA
<213> ORGANISM: Zea mays

<400> SEQUENCE: 31

```
gacctccatt ttgattatct ctatcctgta cgtgccgaga gtccttcaaa gccgacgacg     60

agacgacgat gcagtcgtcg tcgtcatcag cctcgacgcc ggctgccgct tccggcctcg    120

tcttcgatct cgggtctgcg gcgggcgtgc cggagacaca cgcgtggccg gggtgaacg     180

agtacccgtc ggtggagtcc gctggccgcg acgtggtccc ggtggtggac atgggggtgg    240

cctgcccgga cgcgacgcgg gcgttggcgc gcgccgcaga cgagtggggc gtgtttctgc    300

tcgtcggcca cggcgtgccc cgggaagtgg cggcgcgtgc cgaggagcag gtcgcgcgcc    360

tgttcgtgct cccggctcct gacaaggccc gcgcggggcg ccgcccgggg gagcccacgg    420

ccaccggcta cggcaggccg cccctggcac tccgcttctc caagctcatg tggtccgagg    480

ggtacacgtt ccgcgccgcc accgtccgcg aagagttccg ccgcgtctgg cccgacggcg    540

gcgacgacta cctccgcttc tgcgacgtga tggaggagta cgacagagag atgagggctc    600

tcggtggcag gctgctcgac ctcttcttca tggcgctcgg cctcaccgac gtccagttcg    660

ccaccggcga gacggagcgg aggatccgcg agacctggac ggcgacgatg cacccaatcc    720

tgtgtccgga accggagcgc gccatcgggc tgacggcgca cacggactcg ggcttcatca    780

cgctcatcat gcagagcccc gtgcccgggc tgcagctgct ccgccgcggg ccggaccggt    840

gggtgacggt gccggcgccg ccgggcgcgc tcatcgtcat gctcggcgac ctgttccagg    900
```

```
tgctcacgaa cggccgcttc cggagcccta tccaccgcgc cgtcgtaagc cgagagcgcg    960

agcggatctc cgtgccctac ttcctctgcc cgccggagga catgacggtg gcgccgctcg   1020

cgtccgctct gctgccgggg aggaaggccg tgttccgggc cgtgacgtgg ccagagtaca   1080

tggaggtcaa gcacaaggtg ttcggcacgg atgcgccggc cctggagatg ctgcagctgc   1140

aggtggatga ggaagaacaa ggtgaaaggg ccgccaccac ctaagcccta aggaactact   1200

agctgaatcc ataaactaat aaagaattcg tgaataaggg cgttggaaga ctggacacaa   1260

cacaagagag ttgctatata tcgtatttct gaaatttaag gcaaatatct tagttaaaaa   1320

actggtatat ttaaatagac aatatatatc taaaataaag atagttcacc atttttacgg   1380

tcgaacaatg ataaagttat atattgtctg aatagtaaca aattaaagat ttccaggag    1439
```

<210> SEQ ID NO 32
<211> LENGTH: 1116
<212> TYPE: DNA
<213> ORGANISM: Zea mays

<400> SEQUENCE: 32

```
atgcagtcgt cgtcgtcatc agcctcgacg ccggctgccg cttccggcct cgtcttcgat     60

ctcgggtctg cggcgggcgt gccggagaca cacgcgtggc cgggggtgaa cgagtacccg    120

tcggtggagt ccgctggccg cgacgtggtc ccggtggtgg acatgggggt ggcctgcccg    180

gacgcgacgc gggcgttggc gcgcgccgca gacgagtggg gcgtgtttct gctcgtcggc    240

cacggcgtgc cccgggaagt ggcggcgcgt gccgaggagc aggtcgcgcg cctgttcgtg    300

ctcccggctc ctgacaaggc ccgcgcgggg cgccgccccg gggagcccac ggccaccggc    360

tacggcaggc cgcccctggc actccgcttc tccaagctca tgtggtccga ggggtacacg    420

ttccgcgccg ccaccgtccg cgaagagttc cgccgcgtct ggcccgacgg cggcgacgac    480

tacctccgct tctgcgacgt gatggaggag tacgacagag agatgagggc tctcggtggc    540

aggctgctcg acctcttctt catggcgctc ggcctcaccg acgtccagtt cgccaccggc    600

gagacggagc ggaggatccg cgagacctgg acggcgacga tgcacccaat cctgtgtccg    660

gaaccggagc gcgccatcgg gctgacggcg cacacggact cgggcttcat cacgctcatc    720

atgcagagcc ccgtgcccgg gctgcagctg ctccgccgcg ggccggaccg gtgggtgacg    780

gtgccggcgc cgccgggcgc gctcatcgtc atgctcggcg acctgttcca ggtgctcacg    840

aacggccgct tccggagccc tatccaccgc gccgtcgtaa gccgagagcg cgagcggatc    900

tccgtgccct acttcctctg cccgccggag gacatgacgg tggcgccgct cgcgtccgct    960

ctgctgccgg ggaggaaggc cgtgttccgg gccgtgacgt ggccagagta catggaggtc   1020

aagcacaagg tgttcggcac ggatgcgccg gccctggaga tgctgcagct gcaggtggat   1080

gaggaagaac aaggtgaaag ggccgccacc acctaa                             1116
```

<210> SEQ ID NO 33
<211> LENGTH: 371
<212> TYPE: PRT
<213> ORGANISM: Zea mays

<400> SEQUENCE: 33

```
Met Gln Ser Ser Ser Ser Ser Ala Ser Thr Pro Ala Ala Ala Ser Gly
1               5                   10                  15

Leu Val Phe Asp Leu Gly Ser Ala Ala Gly Val Pro Glu Thr His Ala
            20                  25                  30

Trp Pro Gly Val Asn Glu Tyr Pro Ser Val Glu Ser Ala Gly Arg Asp
```

```
        35                  40                  45

Val Val Pro Val Val Asp Met Gly Val Ala Cys Pro Asp Ala Thr Arg
    50                  55                  60

Ala Leu Ala Arg Ala Ala Asp Glu Trp Gly Val Phe Leu Leu Val Gly
65                  70                  75                  80

His Gly Val Pro Arg Glu Val Ala Ala Arg Ala Glu Glu Gln Val Ala
                85                  90                  95

Arg Leu Phe Val Leu Pro Ala Pro Asp Lys Ala Arg Ala Gly Arg Arg
            100                 105                 110

Pro Gly Glu Pro Thr Ala Thr Gly Tyr Gly Arg Pro Pro Leu Ala Leu
        115                 120                 125

Arg Phe Ser Lys Leu Met Trp Ser Glu Gly Tyr Thr Phe Arg Ala Ala
    130                 135                 140

Thr Val Arg Glu Glu Phe Arg Arg Val Trp Pro Asp Gly Gly Asp Asp
145                 150                 155                 160

Tyr Leu Arg Phe Cys Asp Val Met Glu Glu Tyr Asp Arg Glu Met Arg
                165                 170                 175

Ala Leu Gly Gly Arg Leu Leu Asp Leu Phe Phe Met Ala Leu Gly Leu
            180                 185                 190

Thr Asp Val Gln Phe Ala Thr Gly Glu Thr Glu Arg Arg Ile Arg Glu
        195                 200                 205

Thr Trp Thr Ala Thr Met His Pro Ile Leu Cys Pro Glu Pro Glu Arg
    210                 215                 220

Ala Ile Gly Leu Thr Ala His Thr Asp Ser Gly Phe Ile Thr Leu Ile
225                 230                 235                 240

Met Gln Ser Pro Val Pro Gly Leu Gln Leu Leu Arg Arg Gly Pro Asp
                245                 250                 255

Arg Trp Val Thr Val Pro Ala Pro Pro Gly Ala Leu Ile Val Met Leu
            260                 265                 270

Gly Asp Leu Phe Gln Val Leu Thr Asn Gly Arg Phe Arg Ser Pro Ile
        275                 280                 285

His Arg Ala Val Val Ser Arg Glu Arg Glu Arg Ile Ser Val Pro Tyr
    290                 295                 300

Phe Leu Cys Pro Pro Glu Asp Met Thr Val Ala Pro Leu Ala Ser Ala
305                 310                 315                 320

Leu Leu Pro Gly Arg Lys Ala Val Phe Arg Ala Val Thr Trp Pro Glu
                325                 330                 335

Tyr Met Glu Val Lys His Lys Val Phe Gly Thr Asp Ala Pro Ala Leu
            340                 345                 350

Glu Met Leu Gln Leu Gln Val Asp Glu Glu Glu Gln Gly Glu Arg Ala
        355                 360                 365

Ala Thr Thr
    370


<210> SEQ ID NO 34
<211> LENGTH: 8800
<212> TYPE: DNA
<213> ORGANISM: Zea mays

<400> SEQUENCE: 34

taaatttgtg atccttgtga agttgttata tcatgaattg tgaacttgtt gcatttgtga      60

tcttttgtca actttgttgt attgtgaagt ttgatatgtt taccgatcgt attttagatt     120

tcgatcgtta ccggtgtatt ttccgcacca aacttttgtt tccgatgttt tcgaaatacc     180
```

-continued

```
gatatcgttt ccgtttctat agttaccctt ttcaatttta tttccgatta aaaatatgaa    240
aacggtaatg gttttagtgt ttatcgaccg ttttcatctc taatcatccc tgccggtgaa    300
gtttaatttt tcccttggct aaagagatgc aagctgctgt aaaatacgtt aaaacaggca    360
aggcagcccc agcagccagc atcgcgtgcc cgtctatgta catcagtgga tacgtagcat    420
ctctagtgag taatataacg attgcatttg gctggaggac gtatgttata taagtatgtc    480
atttaccagt tgcattagta tcttccctaa ctcctataat aactctcttc gtggaatgga    540
cgtagacgta tgctatataa gtattaaaaa atagtttttt aagctggtgt cctcaatttt    600
gctattgttc tcgtttttat ctttagttgt gtcacaaatt taatccgtac aacaaatcaa    660
aaataccata cccttcttat attaattttc taacataaca tttgtttaga tattttcagt    720
cgtgaaaata caattctaat tctaacgtcg tagtatcaaa tcaaaccatc cagaatttga    780
ccaagcttaa ttataaaaaa tataaaattt atgatactga atagatagca ttagatttgt    840
tatataatat atttttataa aataccattt ttatggtata aatattggta ctcctttact    900
ttaaactata gatagttttg actaaggatg caactagaat tgcatcctct tttcactgca    960
ccttcattag ttttaatatt tatttagatg ggcccttgca aactgtagat atcatctctt   1020
gcaacattct ttctatagca ccacgaaaat gtattgcggc tttgaaatta taattgaatt   1080
agttgtatca tttctttcac cgatgcgtta aattcaaaat taagtgttat atttcttcat   1140
aatttgttaa atatatagac cctataatcc accattattt actataatag catacattaa   1200
cattggtttt agcctacact acgacactcg aggcattgaa ttttcctcta tcaaagaatt   1260
atatgtgtag tagtattgtt cttgacaaaa agggggatta aaattaaact accaatattg   1320
atacttatct tatcacatcc atgaatacaa tcaacactct tacaaaagat aagatacaag   1380
attaaaaagt accatgataa tacattaaga ttattagcaa tgcattaaat taaataaatg   1440
tgcaagtgaa tcatgatttt agttttatct attttacttt taaaatatga tattctctga   1500
ctacttctaa gcataaatgt gattctaagt catgaccgat cgtgcttatt cagaaaaatg   1560
aaggagacac agatttctat aaaaaaaggt tgtcatggga ctattgggtc aaccatctta   1620
ttcatttggg aaaataagtt tagaacacat caacccattt tagatgttga gtttggccct   1680
aatggtccat tgaccttact tttgtgggtt gacatagacc atctatccca agttattgtt   1740
gtgtcacatt ccctgatatc atgaatctat attttagctt tccgttttca tatttttagt   1800
cgttacatat tttttatccg cgtactagat taaaactcta gttgttgcaa tacattttgt   1860
tcattttttt ctatttcttc tttactaaca acatattcta gttcctagct acattcttaa   1920
gtaccatagt gctataaaca ttttttatcc tacattattc cacttaagaa attgaatttt   1980
ctgcataaaa aaattatatg tccagtagtg ttgtcttata aaagcataaa gtgattaaaa   2040
ttaaaaccat tattgatatc ttatttttca aaaaaaaata taagcttata gaaagtgaat   2100
taatttcatg gtaaattaat atagtttaaa ttgaattatt agtgttatta ctatgtttat   2160
tatcaatgaa acatttttca tggttgatat aacttagtgt tacttatttt agtatttttt   2220
atataattct agttaacttt tagtttttga tttaaaaaaa cgagaattgt gtccttttgt   2280
ggagtgagta taaagaaagt aatatctgtt catcataatt tggtttttta aggtacgtga   2340
aacttgcttt atatttggac tcaagctatg tctaaataca tagtaaaaaa gcaatatttc   2400
tagaaaagac aaaacatctt ataatttaga atcaaggaaa tatatagatt ttatgtgcag   2460
tgagaagcca tttacaatgg aacgttcaac gttgggccaa tagatatttt gcgatatgat   2520
gatgggcata tttttgcatg gttgtccctc cactagctat agtttgatga tacgatacgc   2580
```

```
tgcacacacc attgggttgt accatgttag tgtagcaaca gtagaaaccc aattgtggcc   2640
gtgaaccatg ataatactag gtagagtgct agctagaggt ttcaggctat tgatgcgtga   2700
attaaacttt ctgttgtgtt gcgaggaaac gagtattgtg aaatatttga aacggttttt   2760
tttgtgaaag atttgaaacg gtatttttgt tgtgaaataa agatcaaggc taaataaatt   2820
caaactaata aaacatatta attgacggcc tgaagccccc gcccccatgg ccccatgcca   2880
tagcatcagg tcccacatga catgaggccg cgcctccctc tatgttggct ccctgccttc   2940
gccgttgtcg tcgctcccga actccctctc ctcccctgtt acaaataccc ccacccgccc   3000
ggacagcttc cctgcacact cgcagctcgc acatctcatg gtgtcctaag aacggcaaga   3060
gccagctctg cctagcagca gcgcacagcc acatccatgg acgccagccc gaccccaccg   3120
ctccccctcc gcgccccaac tcccagcatt gacctccccg ctggcaagga cagggccgac   3180
gcggcggcta acaaggccgc ggctgtgttc gacctgcgcc gggagcccaa gatcccggag   3240
ccattcctgt ggccgcacga agaggcgcgg ccgacctcgg ccgcggagct ggaggtgccg   3300
gtggtggacg tgggcgtgct gcgcaatggc gacggcgcgg ggctccgccg cgccgcggcg   3360
caagtggcgg cggcgtgcgc gacgcacggg ttcttccagg tgtgcgggca cggcgtggac   3420
gcggcgctgg ggcgcgccgc gctggacggc gccagcgact tcttccggct gccgctggct   3480
gagaagcagc gggcccggcg cgtccccggc accgtgtccg ggtacacgag cgcgcacgcc   3540
gaccggttcg cgtccaagct cccctggaag gagaccctgt ccttcggctt ccacgacggc   3600
gccgcggcgc ccgtcgtcgt ggactacttc accggcaccc tcggccaaga tttcgagcca   3660
gtggggtgag taaagaagaa gatggcgccg aatttacatt tataagtagg accagcagaa   3720
gcccctgccc ctgggggcct tagcattgca ttcgactgat gaatacgcat ggcaggcggg   3780
tgtaccagag gtactgcgag gagatgaagg agctgtcgct gacgatcatg gagctgctgg   3840
agctgagcct gggcgtggag cgcggctact accgggagtt cttcgaggac agccgctcca   3900
tcatgcggtg caactactac ccgccgtgcc cggtgccgga gcgcacgctg ggcacgggcc   3960
cgcactgcga ccccacggcg ctgaccatcc tcctgcagga cgacgtcggc gggctggagg   4020
tcctggtgga cggcgagtgg cgccccgtcc ggcccgtccc aggcgccatg gtcatcaaca   4080
tcggcgacac cttcatggta acgaacgaaa gcgccggctc ctctgctttt cttggcctct   4140
ttgtccctgc cctgtgctgc tgtgcatatt cattcattca gttctctgtg gggttttttt   4200
tttgtttaat tttttttgg gatcgtatcc agtgcacaag ggccacgccg tgcacaaatg   4260
cacaaaacga aatctggccg tccattttcc atccaacgac atgacggcgc ggggggtttt   4320
tcacaaaaca gactcggcaa gctacggagg ttgcgggagg gttcatctgc atatttacga   4380
cggccgttgg atggaaaatg gacggccaga tttcgttttg tgtatttgtg cacggcgtgg   4440
cccttgtgca ctggatacga tcccattttt ttttttgccc cgaatcctag tggacctaac   4500
tggacagatt acagcacgca cacgtaggca tgtcatgtag cagcactgca gtcgggtgca   4560
gtccagtcca gtcctgtcca gccgcgacac tgtagtacat agcgatgcaa cggagacacg   4620
cgttggagtt ggttccatct cttctcggcg gccgtgccga ggcttccgcg gggaagctgc   4680
gacaacagaa cggaccgccg ggggtgggca ggcagcaagc tccctgttgg cttgtgccgt   4740
tgcgcagcgg cgggtaccgg acaacgcttt cggcggcgcg cggcctcgtc ggcttcccct   4800
gtttttgatg ccgcctctcg gtgtccgggg accgggagga tcgatggggc ccgtgccgtc   4860
tgatccgcca cgcgagcggt cctatgcgat gcgccgcacg agcgcggggg ggccgtggaa   4920
```

cagtacacag ctgggtcact cactcactca tcccgctggt tgtggctgct tggttgcaac 4980
ttggctcggc tgtctgtctg ttgccccgc cgcgttttct agccgtttcc gctttgctcg 5040
cggtttcgct ggcgatccgg cacgcggcgc ccacacccgg ggctggcccc ttggccgagt 5100
gggtggcagg cacttgcatg catccggccg gtttcccgcg accaagctgg cccgccgcaa 5160
caatgagagt gagacgagac tttgtgtcag tgtgtgtatg tacatgtatg tctgcgcgac 5220
agccctaccg tccgacacga tgattcttgt gcactgtact gtactgtact aactcccccc 5280
accccctccg gtatgtaacg catgccatat gcaggcgctg tccaacgggc ggtacaagag 5340
ctgcctgcac cgcgcggtgg tgaaccggcg gcaggagcgg caatcgctgg ccttcttcct 5400
gtgcccgcgc gaggaccggg tggtgcgccc gccggccagc gccgcgccgc ggcagtaccc 5460
ggacttcacc tgggccgacc tcatgcgctt cacgcagcgc cactaccgcg ccgacacccg 5520
cacgctggac gccttcaccc gctggctctc ccacggcccg gcggcggcgg ctccctgcac 5580
ctaacgagcc ggccgtctct ttcgccgggg cccgcgcggg gttcgcccac gtggtgatca 5640
ggtggcagac atgtggccca cgggccccgc gccgccttcc ccatttttgg acgaccctac 5700
tgctactact actagtgtac atatgcaaaa aaatacatat atatataggt actttctcta 5760
atatttttat atataagcaa ggcggcctgg tgttcttttc tttgttttgt cgacaactgt 5820
ttgatcccat cctatggacg atggatagtt caatgtttgt acgtacgtaa ctactctcta 5880
tagactagaa tgggctcatg aaactggacc gatcgacacg gacgtcacgt gcgtctggta 5940
ccggtagtgc aacgggtgcc gaatgtttgc tgggcccgga cgagaatcgc ttctcctcgt 6000
cctcggtcct caccctgaac gaacgaataa ggaaaatgct gcaccgaaag ctccagacgt 6060
ttccgaattc caaattccaa aaccccaaat cttcttgctt cacatcagtc ttacccggtt 6120
catctgtgac aaaaaaaaaa tagtgctagt ttaggaactc aggtcgagat tgaaggcaat 6180
tgtggaggaa tttaccctat aatccttatg agaatttgag ttcccaaact aactgagttg 6240
gagcattcaa catttcccta aattttgtgc acatgtttct ttgctattta tctttggaca 6300
tgggacgatg ggagacgcag atttagggga cccttcaatt cagaacttca ggtgcacaaa 6360
ccgaggttgg cttgcctgca ttcttgtttc ggacatgccc aactaggcca ctactcacta 6420
ccttcatctg agataccaat tgctgaccta aatgacaagt atacacttac atttcagtga 6480
tagctgcaac aaaaaaaaaa atcttaccgc attttatctc tgcattctgc atgccgcatc 6540
ctgaacatta cgtatctttc ccggtgctct gttgcgttct cacgcagttg atggcatgca 6600
gtcttgcgcc accgaatcca gtgtactggt cgtggtgact tgtcgcacag acagcagccc 6660
ggcagcacca agcgtgtcac tgtaaactgt tgggcgttaa acaacaactt gcacaacagc 6720
tcaaatatgg catatgctat ccgacaaact gaacaaggtg cccaattgat ctgaatgtac 6780
ctgtgatttc cagcactatc gtacagcaac gttgtcaaaa caagtggggt ggggttgggg 6840
acagattttt tcgataaaga agcttttata aaaaataaca atgatacaaa tcctgggtta 6900
tagatgtaca gaaagcacga agcacgaaag tccagtccaa agcacgtttt tttgcctggt 6960
actagcccga tccggccggc acgaataagc gggtcgagct cggacgggaa gctaagcacg 7020
acggactagc ccgacacgac ccgtttacct ctaatcccgt taaacccgct tttttgcact 7080
aaaccgtgct taccgaaccg tttagcccgt tttttggcct gatttttcgt gcttaacggg 7140
ccaggctcgg acaaggaaac aagcccgcgg gcttagacga tccggcctgg ttttttaacc 7200
gtgcctagcg ggtcgagccc aaaataggtc gggcttcact gggcccgagc cgggcgaccc 7260
gtttggccat ctctaacctg agtacaactt ccgacttctg caaaatacat acagccaaat 7320
aaaagaaaag taaaaagatc taaaaaatct cagctagaaa caatcaatcc gaagactaga 7380
tcgcctccca taagtctgga aaaaagagac catggccact tgcaccaaga tgtgtgcatt 7440
attctacggt tacaccaaag atttttgttc tttaagggct agtttgggaa ccataatttt 7500
caaagggatt tctattttcc taaggaaaat tagttcattt ttccataaga aattagaaat 7560
ccattggaaa attgtggttc tcaaactagc cctaagcgtc gaaaagaacc atatgcatat 7620
ctagagacaa aattcctcta atttctattc aggcttcagc acatatactt cacgtgcttg 7680
cgtcaagttc cttgggccgc cacatggact tatggacttc tcgacgcagc gaaagccgtc 7740
gttgcccttg gtgtagctag gtcatccgca cctcccactg gccagtggcc actgcaggga 7800
cttggccatg ggcttgtttg gttcagcttt tttctgacca gcttttctga aaatctggct 7860
gtgtgaagaa tctggctgtg agagaatctg agtatcatta cgattacgtg tggatgaaga 7920
taaagttgtt catagggctc aggatctaga aagtgacgga ttcctactat tacaatgact 7980
caaccgatta tgtgtttatg ttgattttgg atgatttttg ccccaacaaa ttttatagaa 8040
gctggctgaa aagctgagcg tttggcagtc cacaacagtt tttggtggcc agaagctgcc 8100
agaagccgat acaaacaggg tccatgcttt ccatttcgtt taccgtgtac gcggtgtccc 8160
tcacaatcaa tcagtttacc ttgtggctcc aacacacatc aacctcggca caacaacact 8220
gtgaatcatt ttcggcggtc catattattt tcgacggttc atccctggcc gccgaaaatt 8280
gtctgttatt ttcggcggct tgacctagcc gtcgaaaata ggctgctatt ttcggcggcc 8340
aaatccgagc cgccgaaaat aaggctttta aaaaccgtcg gctccttctt cttctctgtt 8400
ctttctctcc tctcccaaag cccgccgccg ctcacccgcc gctcgctcgc cgggctgccc 8460
gccactccgc cgtcgtcgtc gagccaccgc atcgagaggt aaattttttt tgcgtgtttt 8520
attccttatt ttcggcggtt gatatttagg cgccgccaaa attagtgtat atttgtaatt 8580
gtgtttgttt aattactatt tgtaattagt attattgttt aattcgattt cattaatgta 8640
ttagtggtat atgtgattta gggattaggg gcatattgta tttaggcatt aatttcatat 8700
taatatgtgg tattattata ttattggttt taatagtaca ttatattggt acgtagaata 8760
gttgcattat tagtgtttgt ggtacttagt ttgacttgat 8800

<210> SEQ ID NO 35
<211> LENGTH: 8859
<212> TYPE: DNA
<213> ORGANISM: Zea mays

<400> SEQUENCE: 35
cctattttgt gtctaatact cttcttatat taattgtttg gtcaaacttt agataaattt 60
gactaatgat gcaattaaaa ctgcatcacc tttactaagg tactgcttta tatgtttcga 120
caaaattttc aattattctc tatgtgtttt aatctttgcg ctacacctcc attgatttaa 180
atactcattt attttaaacc ataacttaaa ttatatcgga tctttgcatc ctttctatgg 240
caccatacat gaatcgatat tttggctgca aatttttaat catgttagtt ttagcatttt 300
ttcatatcca tgtgttaagt ttgaatcatg tgttgttttt atataattta ttgaaaatat 360
agatcctaaa cttcactaat acttacaaca atagcatcat catgtgtttt aatccacgcc 420
acaacactca aggcattgaa ttttcttcta ccaaagagtt gtatgtgtgt attgttcttt 480
aaaaaataga gtgattataa ttaaactacc agtattcata tgtaaaatgt atagacatct 540
aaaataaaat ttgcaaaaaa cattgttgca gactttcaat ataattaaga atgggtttta 600

```
gggtcatgat atatggtttg ttaaagaaac ttgttttttt ttgcaattga taaactataa    660
aatacatttt cactattgtg tgcatatgta cttggtatac atagtggcat atatcatttt    720
tgtttacttt gaggtttgaa ttatctatgt taaaattgga taacatagat acattggtgt    780
gcgtcctttg gcccatttac ttgactgagg agcaatacta taaagtaaaa catatttgga    840
tattttatct taaactccta gcataatatt gatttaatta tgaacaaata tatgtttagg    900
tgatagtttc atgggtggta aactatataa gaaggcttac catgatcttt gcaaactcta    960
ggctatgaaa gagttccatg atttgtctta gaagcataga caaaacagtg ataatgatct   1020
aaatcacact tatggcactg atgaccatat atgcaaagct aaatgcatgt taagttgtat   1080
tatatcatat gtttacaatg actatcgcat ataacgagga atacattgtc tatatagata   1140
gctattactg tagtagtgcc aaatgttgga caacatgaat cataatcttc aaacctagag   1200
aaattgtagt cagtcgtaca catatcgtct agtaagttgt ctatactttt tatttattgt   1260
atcaaatttt attgttatct tgcttgcttg tttgtttgta ccatagacac aatatggtca   1320
aaaagtggtc aatcgattcg aagaagattg caattgacga gtgctaacag ttgatccttt   1380
tgttgtgcac gctagcggag tagcatgaaa agagtaaaat atgaaattag cgttctaaac   1440
tgtttgtgct ataggtactt cgtatttaat ggagtgacta actataggaa ggtgagagct   1500
cagaagtcag caccctcaca cagagttcta gagttagtgg tcatcgaacc acgacaaact   1560
acatgatgag cagaagaggc aacatcaaga ctatgatcaa tagtttcggg tcaatgaatg   1620
acatcgtgat gagtatttat ctaactatat agaacaacaa cacatgatgt tttaagtaag   1680
ttcaactgat cttctattgc tatctttaag tatttaacgt agcgaataat gttttatcta   1740
tttcattcat aaataatgtt gtgacaaaag gggataacca tcacttttac catgttctag   1800
ataccacaac catctccacc atcataatgg gttcttcatt ggtgcttgga cctcaaataa   1860
tcatatctat agccaactta gctcaattct aataaaatta ggcaacttgg cttcattgta   1920
gcaaaaatag ccaacttagc tcaattttat ctaaacttag ctaatctagc acaacttaga   1980
tcaatattag gaaaaactaa tcaatctaat ctagctcaac tatagcgaaa gatagatatt   2040
gtagcataac ttagtagatc tatctcaaat tttagcaaaa actaatcaat ttagataaac   2100
tctataaaat tttaatcatt atgacttatt tccaactaat tgtaacttgc atgattttta   2160
tgttccttct ttataattag caacacctaa agacacgaat gatgaggggt ctaacgcatt   2220
cattaaccag ttgttaaata atactctagg tagatgataa gaactctaat tattctatga   2280
atctaagcta aaagatgttt aatatttaag tattggtgtt tattatgtta tttagaacga   2340
ttcatgttac ttaaagattt gttatgattt ttaaatatga ttatgataat ttatgtggtg   2400
tggattaact tgtgaacata tgtgatgtag atgaatatgt atgttgtgga tggaaccata   2460
tgaatatata tacacactca tatactattc gttggtgtag gtaaagcttc atccatcggt   2520
aattactaaa tggtcttcag tcattaccac taggtgaagc ttcacacgac cgataattat   2580
tgaagaacgc tcattaattt ccggtaatgg cttattggcc ttcactagtc ggtgaaaatt   2640
agctattttt ataccaataa aaattagcta atatatgtaa accaggtcta atttttatgg   2700
gcctcttacc gaccaaaatt gattagatta ttgttacaat agttttagtc aaaagctagc   2760
tatgctataa aaattttgaa ttaaagtgag tttcgtaata aaaattgcat acttttaaaa   2820
taaaataatt aaaaaacagt ttttagaaat acaatcaaac accttatgct ataaaaaaat   2880
tgtaatgtac ctacaaatat ataatacttt actttaaaat aggcctgtgc cttctcggct   2940
ctatatgggc tgcctccaac gaagcgccat ggccatgggc tccactgtgt cgggtcccac   3000
```

```
atgaggccgc gcctccctcc aaatgttccc tccctgcctt cgtctttgtc gttgctcgca   3060
aactccctgt cctcccctgt tacaaatacc cccacccgcc cggacagctt ccctgcatac   3120
ttgcagctcg cacatctcat ggtgtcgcag gaacgacaag agccagctgt gcctagcagc   3180
agcagcagca gcgccaagcg cgcagccacg tccatggacg ccagcccggc cccgccgctc   3240
ctcctccgcg cccccactcc cagccccagc attgacctcc ccgctggcaa ggacaaggcc   3300
gacgcggcgg ccagcaaggc cggcgcggcc gtgttcgacc tgcgccggga gcccaagatc   3360
cccgcgccat tcctgtggcc gcaggaagag gcgcggccgt cctcggccgc ggagctggag   3420
gtgccgatgg tggacgtggg cgtgctgcgc aatggcgacc gcgcggggct gcggcgcgcc   3480
gcggcgcagg tggccgcggc gtgcgcgacg cacgggttct tccaggtgtg cgggcacggc   3540
gtggacgcgg cgctggggcg cgccgcgctg gacggcgcca gcgacttctt ccggctgccg   3600
ctcgccgaga agcagcgcgc ccggcgcgtc cccggcaccg tgtccgggta cacgagcgcg   3660
cacgccgacc ggttcgcggc caagctcccc tggaaggaga ccctgtcgtt cggctaccac   3720
gacggcgccg cgtcgcctgt cgtcgtggac tacttcgtcg gcaccctcgg ccaggatttc   3780
gagccaatgg ggtaagtaag gtagtaagaa ggagcgccgg tttacattta ccgcacgtcg   3840
gcgtgcggtc gagtcgggac tcgggagacg tatgaacccc cgtcccgtcc catgcatgtg   3900
tggcaggtgg gtgtaccaga ggtactgcga ggagatgaag gagctgtcgc tgacgatcat   3960
ggagctgctg gagctgagcc tgggcgtgga gctgcgcggc tactaccggg agttcttcga   4020
ggacagccgg tccatcatgc ggtgcaacta ctacccgccg tgcccggagc cggagcgcac   4080
gctgggcacg ggcccgcact gcgaccccac ggcgctcacc atcctcctgc aggacgacgt   4140
gggcgggctg gaggtgctgg tggacggtga gtggcgcccc gtccggcccg tcccgggcgc   4200
catggtcatc aacatcggcg acaccttcat ggtaacgaaa cgaaagcgct cgctcctctg   4260
ttttccttgg ccgctcttgt cctgtgtgta tattcagttg agctctctct gtgctgttat   4320
ttcccgaatc ctagtggacc taaacgggca ggttattaca gcacgcacac gtaggcatgt   4380
catgtagcta gtacatacat agcgatgccg atgcaaatgc aatagagaca tgcgttcgag   4440
ttggttccta tctcggcggg ctacggcagg tacacgcggc cgcggcgcgc tctctctagt   4500
ctatccgcgg ccgcgcccag gccgatcgag gcttccgggg gagagttgcg acaagagaac   4560
ggaccgaggg ggtcggctag cggtagcaag ttccctgttg gtttgtggcg ttggagcgtt   4620
gcggagaggc ttgcgcggcg gcggggacgt cgacggggac gtggcgggga gacgatacga   4680
tgggtgccgg gcagggcaac gctttcggcg ggtggccgtg tccaggtgcg cgcggccttg   4740
tcggtttccc cctctcggtg tccatggccg agaaatgggt cgacgaccga gaccgacgct   4800
cggtgcggcg cccatcccgt ctgatccgcc gcgccacgcg agcggcccta tgcgatgccg   4860
cacgggcgcg gagggccgtc gcgcggagta taatgtatag tatatagtac aaggttggtt   4920
ggagtcgggt tgggttggat cgggtcaccg gtacgtggtg gctgctgttg cccccgccgt   4980
ttccgcttgc acttttgtcg cggtttcgct ggcgatccgg cacgcggcgc ccacaccacg   5040
ccggggctcc aaacagctcg ggcccttggc cgtgtgggtg gcaggcactt gcacgcgtcc   5100
ggttgtcgcg gcctggcccg ccgccgggcg caccgcaaca atgagacagc ccgacacgat   5160
gattcttgtg cactgtgcta acccgcatgc catgcaggcg ctgtcgaacg ggaggtacaa   5220
gagctgcctg caccgcgcgg tggtgaacca gcggcgggcg cggcggtcgc tggccttctt   5280
cctgtgcccg cgcgaggacc gggtggtgcg cccgccggcc agtgctgcgc cgcggcgcta   5340
```

```
cccggacttc acctgggccg acctcatgcg cttcacgcag cgccactacc gcgccgacac   5400
ccgcacgctg gacgccttca cccgctggct ctcccacggc ccggcccagg cggcggcgcc   5460
tccctgcacc tagcgagccg ggccaaggcc gtctctttcg ccccacgtgc gcgcccagct   5520
gggcaggtgg ccagacacgc ggcccgcggg ccccgcgccg ccttgccatt ttttgacgct   5580
ggccctactg ctgtgctact agtgtacata tgcaagagta catatatata tatatatata   5640
cgtattttct atatattata tataaaagca aggcggcccg gtgcccttct cttgttttgt   5700
ccacaactgt ttgatcccat tattctatgg accatggata cttcaatgtt tgtactaaga   5760
ccgtgaacgt gggattcttt tccttcctct gtgtttttc tgagaaaaat taaactgatt    5820
tctgtgaaat ttctttgttt taacaagaaa acagaaaaat tacatgagga aaacgctcca   5880
tttatttcaa caagaaaaaa atacatgaaa cagaaggaga aaaaacgtgt tcgttctatc   5940
attttcacac gagaaaaaaa aacatagaaa acagaaaaac tccccgcgtt cagatgagct   6000
caagaaaatg gaacgacacg gacgtcaccc gcgtcttgta gcagtgggcg cacgggtgcc   6060
gaatgtttgc tgggccccca agagaatcgc ttctcctcac gctgaatgaa tgaatcaacg   6120
agggaaacgc tgcaccctga gttccagacg tttccgaatt ccaaacgttt ttgtggcgtg   6180
cgtccatggg gcgcccccaa acttcggacg tttccggcgc tccaacaaat cttctcgctt   6240
cacacgtcac cgtcgtcccg gattcatttg cctcgtcgct ccaccattcg ctgctctcct   6300
ctccacgtac tcttaccctg acctttggga aagaactgaa cattcgagat gcacaacagt   6360
tcaaatataa catatgcagc acaagatcgt tcgactgcta tccgacaagc caacaacgtg   6420
cccagtagaa ctgaatgtac ctgtgatttc cagcactaac ttacagcaac gttgtgaaaa   6480
aacaaaaacg aaaacaaacg gcagaaaaaa cagatgtatt gttctacagt tacaccaaat   6540
attttctggt cctttcagca ccaacaagag ccatacgcat atctagaaga caaaattcct   6600
ctaatttcac ccctacgtgg tagcagttcc tcctcaacac agttcacgtg ctagcgtcga   6660
gttctttggg ccgccacatc gacttctcga cgcagagcag gccctcgctg cccttggtgt   6720
aggtcatccg cacctcccac tgcacggact tggccatgct ctccagctca tttatcgtgt   6780
ccgcggtgtc cctcacgatc agcttgccct gtggcctcag tacacggtcg acctcggcga   6840
aaactgcagc cagtttgcat ctgtaaacag gcaacacaga tttttagtat ctaaaacact   6900
gcaggcaaac gccacaggtt ttagtcgcaa gaagcaataa aagcatgcaa acaatgctac   6960
gtgtacgtat caaaggaaca tgtcaaaact cgttgcatga acgatcattg atgtttcctt   7020
gctgaactag tcacatcagt ctgcttcaac ttctgggttt cactagtaga tataccagaa   7080
gggtagaata atgtgaagag caagaaatac agacctcttt ctgagctttg agaacagatg   7140
gtccgcgtgc agaaggtcat acgttcttgg gtaagtgctg aaagactcgc accagtcatg   7200
gtacatgcca aacaaaccgc gctcgtagat gatgggcagc gtgtctggtg aatcgatcgg   7260
cacgatattc atgacccaga ccttttggtc cctcagagct gcagcaaaac tgccatgcaa   7320
caatgtaaag cattagtcaa gaagaaggtg tacagtgcat ttctccttgt caacagtctt   7380
cagtaacaaa aaaaaagtgt tatgcttgac tgaatctttc aaagaaatat gcttgatgac   7440
ttatggtgga caagttgcct gttatagtgt tatgttttaa ttaactatgt gccagcttgg   7500
gtaactagta gttatgtagt gtgatctgaa ttaccaaaat ataaataaat aaataaacat   7560
gcccaagaaa ctacgaaaac catttactta ccctccatag acagctctca tgtccatgac   7620
atttctcact ttggaccagt caattcccat gccattcaca tacgatttac ttacaacccg   7680
tttccagtgg gcattatctg cctcaaaatc ttcatttgca ggctttccat agacaccaac   7740
```

```
cttggaacca tcaatccaga aaggggtctt ctcaagcctt tgcggccata actctggcca   7800

ttttgatcct cggacttttg agccaccagg cagtttgtgc atgcatgctt ccaacggtac   7860

attcctgcaa atcaaaaggc tgtgtaagca aagcagagaa gcacttttct ccattgaaaa   7920

tatactcttc tcaaagaacc gaaaccatac caagcagcat ctgcatcatc agattccttg   7980

cacaatggcg ggctgttttc agatcttttc tcatagcaaa tattgtccat tggtttctga   8040

tatatgacca taccaacttg gtttaactta tccttagtct tgttgaccat cttccagcac   8100

atggactttg tcaaagtaga catggctgaa aagggtatgt ggccacatgt tatgttagaa   8160

ataaaattca attttgaaca gttggtccat agcatgtatt ttgaacaaat gcaatccttc   8220

tccatccatg aaagaagttg acccttcata cttaggatta ttcagtactt tcactcatgt   8280

ctgctgaatt tgttctcttg gtagttgcta tacaagaaag ggggaagtac agagtagcta   8340

aacttataca agctatagtc tgatatttgt atgaaacata aattttggta tggatgtctt   8400

attaaaatgg gaggttgtat aatatttttc tagcctacct caacttgctt gagactaaaa   8460

ggctttgttg ttgttgttga ggctgtatgg tgctttgact ttacaaatca agttatcagc   8520

taccctactt atggatatac acctctcata aaatgatggt aagaagtttc gatatgtcac   8580

attaacataa gaacttcatt cagttagggt acaacgaagt taagtagtta cggaaatacc   8640

attccaaatc tcaacatcct ctgggagctt ttggtaaaca ggagtggcag accagacaaa   8700

gtaaccacca gggcgtaaca agcggttcaa ttccagcaaa agcatgccac ctaaaagtag   8760

cgagccagca ataagattca gttctatagc aaatcaataa atgaaaggag gacatgtcaa   8820

tatgtaacca gcaggacaaa ccttcgatgt gccaaggga                          8859
```

<210> SEQ ID NO 36
<211> LENGTH: 1788
<212> TYPE: DNA
<213> ORGANISM: Zea mays

<400> SEQUENCE: 36

```
aatcccagcg tgcgtaatct attgcccaca tgccgacgcc gtcgcacctc aacaagaacc     60

cgcgctacct ggacttccgg gcggcgcggc gggtgccgga gtcgcacgcc tggccgggcc    120

tgcacgacca ccccgtcgtg gacggcggcg cgccgggccc cgacgccgtg ccggtggtgg    180

acctgggcgc cgcggacccg gcgccggcgc cggcggcggc ggtggcccgc gccgccgagc    240

aatggggcgc gttcctgctc acgggccacg gcgtccccgc ggacctgctg gcgcgcgtgg    300

aggaccggat cgccaccatg ttcgcgctgc cggccgacga caagatgcgc gccgtgcgcg    360

ggcccggcga cgcctgcggc tacggctccc cgcccatctc ctccttcttc tccaagtgca    420

tgtggtccga gggctacacc ttctcgccgg cctccctccg cgccgacctc cgcaagctct    480

ggcccaaggc cggcgacgac tacaccagct tctggtacgt tgcgttgcgt gcttgtgtgc    540

gcgcacacct gccgaccgcg gccacaccgt acgcaaccca cgcgtacgta cgtgcgctag    600

ctacctgctt cgctcgcttc gctcctctcg cctcgccatg catatgcacg tacggccgta    660

caggtacagc agcaggtcac acgcacgaac gcacgcacgc accagcaccg atatgataca    720

tcatcgacgt gtcgtccccc cgtctaaggc catgcatgca tgcaagcacg cctagctagc    780

ccttttggct tgctagctga cgaggggagc taggacgagc atacttactg tgcgcgtcat    840

gctcaattgc tcacactata ctactacttg ttactacagt gatgtgatgg aggagttcca    900

caagcacatg cgcgccctcg cggacaagct gctggagctg ttcctcatgg cgctggggct    960
```

```
caccgacgag caggccagcg ccgtcgaggc cgagcggagg atcgccgaga cgatgaccgc   1020
caccatgcat ctcaactggt gggtatatat tattgtctgt catgttgtcg tcgtcgtacg   1080
cgttgcggtt gggtgtacat gtatataaca caaacaacaa aaaactaacg ccgtgccgac   1140
gacgacgacg atcatcaggt acccgaggtg cccggacccg cggcgcgcgc tggggctgat   1200
cgcgcacacc gactcgggct tcttcacctt cgtgatgcag agcctcgtgc ccgggctgca   1260
gctcttccgc cacgccccgg accggtgggt ggcggtgccg gccgtgccgg gcgccttcgt   1320
cgtcaacgtg ggcgacctct tccacatcct caccaacggc cggttccaca gcgtgtacca   1380
ccgcgccgtc gtgaaccggg acctcgacag gatctcgctc ggctacttcc tcggcccgcc   1440
gccgcacgcc aaggtggcgc cgctgcgcga ggccgtgccg cccggccggg cccccgcgta   1500
ccgcgccgtc acgtggcccg agtacatggg cgtccgcaag aaggccttca ccaccggcgc   1560
ctccgcgctc aagatggtcg ccctcgccgc cgccgccgac ctcgacgacg acggcgacgc   1620
cgccgtcgtc catcagcagc agcagctagt cgtctcgtcg tagccgagac cgatcgccgg   1680
agactgatgc tgatgatgat gcatatatac atgagagaaa tcgtcgagta gactagccga   1740
ttgcaaaagc aaccccagct gccgaaacct ggcatatcga tcccattc                1788
```

<210> SEQ ID NO 37
<211> LENGTH: 1698
<212> TYPE: DNA
<213> ORGANISM: Zea mays

<400> SEQUENCE: 37

```
cgtgccgaga gtccttcaaa gccgacgacg agacgacgat gcagtcgtcg tcgtcatcag     60
cctcgacgcc ggctgccgct tccggcctcg tcttcgatct cggtctgcg gcgggcgtgc    120
cggagacaca cgcgtggccg gggtgaacg agtacccgtc ggtggagtcc gctggccgcg    180
acgtggtccc ggtggtggac atgggggtgg cctgcccgga cgcgacgcgg gcgttggcgc    240
gcgccgcaga cgagtggggc gtgtttctgc tcgtcggcca cggcgtgccc cgggaagtgg    300
cggcgcgtgc cgaggagcag gtcgcgcgcc tgttcgtgct cccggctcct gacaaggccc    360
gcgcggggcg ccgccccggg gagcccacgg ccaccggcta cggcaggccg cccctggcac    420
tccgcttctc caagctcatg tggtccgagg ggtacacgtt ccgcgccgcc accgtccgcg    480
aagagttccg ccgcgtctgg cccgacggcg gcgacgacta cctccgcttc tggtacgtac    540
gagcgccatg tcacgtgctt gtgctttcat gcctcgtacc gtcgtcgtgc tgtacgtgtt    600
atgtttatcg gccggtacgt cacgcgtgct acactggtta acgacgtgag cgtgcccacg    660
ttgactgcat gcatgtgcat gcgcgcgccc agcgacgtga tggaggagta cgacagagag    720
atgagggctc tcggtggcag gctgctcgac ctcttcttca tggcgctcgg cctcaccgac    780
gtccagttcg ccaccggcga gacggagcgg aggatccgcg agacctggac ggcgacgatg    840
cacccaatcc tgtacgtacg tcaaaaacga atatctgacc aatgcaaacg tttttctgca    900
atgccagtca tccactcatc ctgtacgtac ctctggactc tgcttgtcca tctactgatg    960
acacgtatgg taggtacccc aggtgtccgg aaccggagcg cgccatcggg ctgacggcgc   1020
acacggactc gggcttcatc acgctcatca tgcagagccc cgtgcccggg ctgcagctgc   1080
tccgccgcgg gccggaccgg tgggtgacgg tgccggcgcc gccgggcgcg ctcatcgtca   1140
tgctcggcga cctgttccag gtgctcacga acggccgctt ccggagccct atccaccgcg   1200
ccgtcgtaag ccgagagcgc gagcggatct ccgtgcccta cttcctctgc ccgccggagg   1260
acatgacggt ggcgccgctc gcgtccgctc tgctgccggg gaggaaggcc gtgttccggg   1320
```

ccgtgacgtg gccagagtac atggaggtca agcacaaggt gttcggcacg gatgcgccgg 1380
ccctggagat gctgcagctg caggtggatg aggaagaaca aggtgaaagg gccgccacca 1440
cctaagccct aaggaactac tagctgaatc cataaactaa taaagaattc gtgaataagg 1500
gcgttggaag actggacaca acacaagaga gttgctatat atcgtatttc tgaaatttaa 1560
ggcaaatatc ttagttaaaa aactggtata tttaaataga caatatatat ctaaaataaa 1620
gatagttcac catttttacg gtcgaacaat gataaagtta tatattgtct gaatagtaac 1680
aaattaaaga tttccagg 1698

<210> SEQ ID NO 38
<211> LENGTH: 4095
<212> TYPE: DNA
<213> ORGANISM: Zea mays

<400> SEQUENCE: 38
cggtctaagt gaccgtttga gagaggaaaa gggttgaaag agacccggtc tttgtgacca 60
cctcaacggg gagtaggttt ataagaaccg aacctcggta aaacgaatca ccgtgtcatc 120
cgccttattt gcttgtgatt tgttttcgcc ctctctttcg gactcgttta tatttctaac 180
gctaaccccg acttgtagtt gtgcttaaag tttgtaaatt tcagattcgc cctattcacc 240
ccctctaggc gactttcata taaatattgg gagaaatatg aaaaacaaat gaaggtcgaa 300
cgagtcagag acaccataaa aaagaggtcg tcttaactag ggtgctaaac ctcaacattg 360
tagtagatct tagtactgag tttgacatct ttgacaccaa caagatggtg atacgttact 420
ttctacgtta acttgggtag gtatatcgac tatagtggcc tataacacta ggctatgtaa 480
tatgatattg tgttgagtct ttataaacat gatttttttt aaaaaaaaga gctaaaataa 540
aaaatagaaa tcgacggtac gatgcaagtt cttctcaaga caaccaaacg cacccttgcc 600
cctttattga aattgaagta tgtgctttat caaatgttta aatactaatt ataagtatta 660
aatataattt aattataata ctaattatat agataaagac taaataacaa gacaaattta 720
ttaaatataa ttaattcatt attaacaaat acttaatgta gcacgatcga atcatggact 780
aattagtctt gatagactcg tcttaccatt taatcataat tagttttgta tactgtttat 840
aatatttcta actagctagt attaaacttt tgatgtaacc taactaaagt ttagtcacgc 900
caatacataa ggactcggat cgttcgatca cccatgacat cacgtatact aagagcatct 960
ccaaaagctc tccagaagtc tcccctaaat ctattttttt gggaaaaaca caaaaacatg 1020
tctccaacag ttcccttaaa gcgcccccaa ctttttcata gcccttaaaa ctccctcatt 1080
tgtagctaca aatgaggggt tttttgggct ccccagaaac aaactgttga tttaagggat 1140
ctgttggaga aaggattaaa atttaccctc acttattatt tagatgtccc ttaaaactga 1200
ttttgaggag tcgttttatg tagagctctt ggagatgctc taacacaccg agcacaaccg 1260
catcatcaat caaaacaacc caaagtttgt tcggtacaag tcatcagcct gtgtacacac 1320
atcagcctcg gccccgggag aagcgctagc aaacaaggtt cacctaaaaa tccatccaga 1380
ttcattgaat ccaaccagca caaacgtccc atttattaat cacctcatca caggtccccc 1440
cagcctcact ctcgcgccgg ctcaaggtac attgcgtgtc ctagccaaga cacgcagctc 1500
atctcagcct cacacgcaca gcaagagcga ggcgtgattc gccatgggcg gcctcactat 1560
ggaccaggcc ttcgtgcagg cccccgagca ccgccccaag cccatcgtca ccgaggccac 1620
cggcatccct ctcatcgacc tctcgcctct ggccgccagc ggcggcgccg tggacgcgct 1680

```
ggccgccgag gtgggcgcgg cgagccggga ctggggcttc ttcgtggtcg tgggccacgg   1740
cgtgcccgca gagaccgtgg cgcgcgcgac ggaggcgcag cgagcgttct tcgcgctgcc   1800
ggcagagcgg aaggccgccg tgcggaggaa cgaggcggag ccgctcgggt actacgagtc   1860
ggagcacacc aagaacgtga gggactggaa ggaggtgtac gacctcgtgc cgcgcgagcc   1920
gccgccgccg gcagccgtgg ccgacggcga gcttgtgttc gataacaagt ggccccagga   1980
tctaccgggc ttcaggtgac gaaattaact atatatccct ttcgatcata gttgcgttaa   2040
taaattaagg gaatcgtgag cgtacgtacg taagtttccg cagagaggcg ctggaggagt   2100
acgcgaaagc gatggaagag ctggcgttca agctgctgga gctgatcgcc cggagcctga   2160
agctgaggcc cgaccggctg cacggcttct tcaaggacca gacgaccttc atccggctga   2220
accactaccc tccttgcccg agccccgacc tggccctcgg cgtggggcgg cacaaggacg   2280
ccggcgccct gaccatcctg taccaggacg acgtcggggg gctcgacgtc cggcggcgct   2340
ccgacggcga gtgggtccgc gtcaggcccg tgcccgactc gttcatcatc aacgtcggcg   2400
acctcatcca ggtacgtgcc cacctgatga actgagctga acgtaggttg catgcactgc   2460
atgtgtatag gcttctcaga tcgcttcgtg tggcgtaagg tgtggagcaa cgacaggtac   2520
gagagcgcgg agcaccgggt gtcggtgaac tcggcgaggg agaggttctc catgccctac   2580
ttcttcaacc cggcgaccta caccatggtg gagccggtgg aggagctggt gagcaaggac   2640
gatccgccca ggtacgacgc ctacaactgg ggcgacttct tcagcaccag gaagaacagc   2700
aacttcaaga agctcaacgt ggagaacatt cagatcgcgc atttcaagaa gagcctcgtc   2760
ctcgcctaac tactgctact gctaggatcc atgccattgc catgtcgtct tcagattcag   2820
agcacgccat gtcgtcgcta gcttcgtggt agaacaaata atgatgtgcg tgctgtgtgt   2880
aagcatggat atggatgtga atatgtaata tgatgagcac tcctactttg gtatgtttgg   2940
gaataacaga cttgtgttgg tctggttcat tatttgtaag aaaatcaaaa agagttagta   3000
gggcaggagg ctaaccacag tcatgctgca ccacatccct ggtggaaagc tggccgggtt   3060
acgctacgct cgtgcagcca gattactgca gggccgggat atgcttccgg tggaaggaag   3120
gggacggtgg ctgaggacca tggggctgga gcctgggaga gaggtcgagc tagaagaaag   3180
ggggagagag aagacgcaca acgaagatgg gtcagccagg gatttcgacc caagggggag   3240
ctagtggatt ttgggagaaa acagaaaaga gaaaagagaa aagaagaaaa atttgttggt   3300
gtgaacacaa ggttgatttg tcttttctta tttggattga tgatgagtcg tggactaacc   3360
gacccgtgag ctattgtgtc gtataatcat gtctctcggt ttctggtgtg caggtttgaa   3420
gcacagagac ggtggtcgac gcaaaggtga acgtcatgca ggttcgtgcc gatggaccgg   3480
gagcagtgaa agacgagcgt tggacttga acaagggacc agagtcgccg gatgactagc   3540
cgcagtggct gacgcctgga acacgcatag acgtgaggac gtggtagagc aggtgaaaat   3600
cgcctagagg gggggggggt gaatagacaa aacctaaaaa ttataaactt tgaacacaaa   3660
ctttacctga ggttaccgtt agaacgagta ttaatgaaat cggagtgcgg aaggcaagtt   3720
cttcttgcta cgagttgctt aatcaatatt gataactttg ggagtcaact caaaatgatc   3780
acaagcaaaa gaactagaga gagaggagag gaagaatcaa ctcgcaaagt aatgatcaac   3840
acaaatgaac acaatgattt atttctcgag gtttggttcc gaagaaccta ctccccgttc   3900
aggagtccac ataggacatg tctctttcaa ccctttctct ctctcaaatg gtcacataga   3960
ctggttcagt tgagagcacc tagagggggg tgaataggtg atcttgtaaa atcaaacact   4020
aatagccaca aaacttagtt taaagtgtta gtacggctaa gtagctttga agcgagttat   4080
```

tgtgaacaca acaat 4095

<210> SEQ ID NO 39
<211> LENGTH: 21
<212> TYPE: DNA
<213> ORGANISM: Artificial Sequence
<220> FEATURE:
<223> OTHER INFORMATION: suppression oligo

<400> SEQUENCE: 39
ctccatcatg cggtgcaact a 21

<210> SEQ ID NO 40
<211> LENGTH: 21
<212> TYPE: RNA
<213> ORGANISM: Artificial Sequence
<220> FEATURE:
<223> OTHER INFORMATION: suppression oligo

<400> SEQUENCE: 40
uaguugcacc gcaugaugga g 21

<210> SEQ ID NO 41
<211> LENGTH: 19
<212> TYPE: DNA
<213> ORGANISM: Artificial Sequence
<220> FEATURE:
<223> OTHER INFORMATION: suppression oligo

<400> SEQUENCE: 41
ggtactgcga ggagatgaa 19

<210> SEQ ID NO 42
<211> LENGTH: 21
<212> TYPE: RNA
<213> ORGANISM: Artificial Sequence
<220> FEATURE:
<223> OTHER INFORMATION: suppression oligo

<400> SEQUENCE: 42
uucaucuccu cgcaguaccu a 21

<210> SEQ ID NO 43
<211> LENGTH: 19
<212> TYPE: DNA
<213> ORGANISM: Artificial Sequence
<220> FEATURE:
<223> OTHER INFORMATION: suppression oligo

<400> SEQUENCE: 43
caggcgccat ggtcatcaa 19

<210> SEQ ID NO 44
<211> LENGTH: 21
<212> TYPE: RNA
<213> ORGANISM: Artificial Sequence
<220> FEATURE:
<223> OTHER INFORMATION: suppression oligo

<400> SEQUENCE: 44
uugaugacca uggcgccugg a 21

<210> SEQ ID NO 45
<211> LENGTH: 19
<212> TYPE: DNA

<213> ORGANISM: Artificial Sequence
<220> FEATURE:
<223> OTHER INFORMATION: suppression oligo

<400> SEQUENCE: 45
tcatgcggtg caactacta 19

<210> SEQ ID NO 46
<211> LENGTH: 21
<212> TYPE: RNA
<213> ORGANISM: Artificial Sequence
<220> FEATURE:
<223> OTHER INFORMATION: suppression oligo

<400> SEQUENCE: 46
uaguaguugc accgcaugau a 21

<210> SEQ ID NO 47
<211> LENGTH: 19
<212> TYPE: DNA
<213> ORGANISM: Artificial Sequence
<220> FEATURE:
<223> OTHER INFORMATION: suppression oligo

<400> SEQUENCE: 47
tcgctcgcct tcttcctca 19

<210> SEQ ID NO 48
<211> LENGTH: 21
<212> TYPE: RNA
<213> ORGANISM: Artificial Sequence
<220> FEATURE:
<223> OTHER INFORMATION: suppression oligo

<400> SEQUENCE: 48
ugaggaagaa ggcgagcgac a 21

<210> SEQ ID NO 49
<211> LENGTH: 19
<212> TYPE: DNA
<213> ORGANISM: Artificial Sequence
<220> FEATURE:
<223> OTHER INFORMATION: suppression oligo

<400> SEQUENCE: 49
tccaacgggc ggtacaaga 19

<210> SEQ ID NO 50
<211> LENGTH: 21
<212> TYPE: RNA
<213> ORGANISM: Artificial Sequence
<220> FEATURE:
<223> OTHER INFORMATION: suppression oligo

<400> SEQUENCE: 50
ucuuguaccg cccguuggac c 21

<210> SEQ ID NO 51
<211> LENGTH: 19
<212> TYPE: DNA
<213> ORGANISM: Artificial Sequence
<220> FEATURE:
<223> OTHER INFORMATION: suppression oligo

<400> SEQUENCE: 51
gcatcaacag gtacaacta 19

<210> SEQ ID NO 52
<211> LENGTH: 21
<212> TYPE: RNA
<213> ORGANISM: Artificial Sequence
<220> FEATURE:
<223> OTHER INFORMATION: suppression oligo

<400> SEQUENCE: 52
uaguuguacc uguugaugcg a 21

<210> SEQ ID NO 53
<211> LENGTH: 19
<212> TYPE: DNA
<213> ORGANISM: Artificial Sequence
<220> FEATURE:
<223> OTHER INFORMATION: suppression oligo

<400> SEQUENCE: 53
tggacgatgg atagttcaa 19

<210> SEQ ID NO 54
<211> LENGTH: 21
<212> TYPE: RNA
<213> ORGANISM: Artificial Sequence
<220> FEATURE:
<223> OTHER INFORMATION: suppression oligo

<400> SEQUENCE: 54
uugaacuauc caucguccau c 21

<210> SEQ ID NO 55
<211> LENGTH: 19
<212> TYPE: DNA
<213> ORGANISM: Artificial Sequence
<220> FEATURE:
<223> OTHER INFORMATION: suppression oligo

<400> SEQUENCE: 55
tggaccatgg atacttcaa 19

<210> SEQ ID NO 56
<211> LENGTH: 21
<212> TYPE: RNA
<213> ORGANISM: Artificial Sequence
<220> FEATURE:
<223> OTHER INFORMATION: suppression oligo

<400> SEQUENCE: 56
uugaaguauc cauggyccau c 21

<210> SEQ ID NO 57
<211> LENGTH: 19
<212> TYPE: DNA
<213> ORGANISM: Artificial Sequence
<220> FEATURE:
<223> OTHER INFORMATION: suppression oligo

<400> SEQUENCE: 57
gcaaggtcct agatttaca 19

<210> SEQ ID NO 58
<211> LENGTH: 21
<212> TYPE: RNA
<213> ORGANISM: Artificial Sequence
<220> FEATURE:

<223> OTHER INFORMATION: suppression oligo

<400> SEQUENCE: 58
uguaaaucua ggaccuugca a 21

<210> SEQ ID NO 59
<211> LENGTH: 19
<212> TYPE: DNA
<213> ORGANISM: Artificial Sequence
<220> FEATURE:
<223> OTHER INFORMATION: suppression oligo

<400> SEQUENCE: 59
cagagtacat ggaggtcaa 19

<210> SEQ ID NO 60
<211> LENGTH: 21
<212> TYPE: RNA
<213> ORGANISM: Artificial Sequence
<220> FEATURE:
<223> OTHER INFORMATION: suppression oligo

<400> SEQUENCE: 60
uugaccucca uguacucugg a 21

<210> SEQ ID NO 61
<211> LENGTH: 19
<212> TYPE: DNA
<213> ORGANISM: Artificial Sequence
<220> FEATURE:
<223> OTHER INFORMATION: suppression oligo

<400> SEQUENCE: 61
ccatgcccta cttcttcaa 19

<210> SEQ ID NO 62
<211> LENGTH: 21
<212> TYPE: RNA
<213> ORGANISM: Artificial Sequence
<220> FEATURE:
<223> OTHER INFORMATION: suppression oligo

<400> SEQUENCE: 62
uugaagaagu agggcaugga a 21

<210> SEQ ID NO 63
<211> LENGTH: 19
<212> TYPE: DNA
<213> ORGANISM: Artificial Sequence
<220> FEATURE:
<223> OTHER INFORMATION: suppression oligo

<400> SEQUENCE: 63
acatggcggt caacttcta 19

<210> SEQ ID NO 64
<211> LENGTH: 21
<212> TYPE: RNA
<213> ORGANISM: Artificial Sequence
<220> FEATURE:
<223> OTHER INFORMATION: suppression oligo

<400> SEQUENCE: 64
uagaaguuga ccgccaugug a 21

<210> SEQ ID NO 65
<211> LENGTH: 726
<212> TYPE: DNA
<213> ORGANISM: Rice tungro bacilliform virus

<400> SEQUENCE: 65
tcctacaaaa gggagtagta atatttaatg agcttgaagg aggatatcaa ctctctccaa 60
ggtttattgg agacctttat gctcatggtt ttattaaaca aataaacttc acaaccaagg 120
ttcctgaagg gctaccgcca atcatagcgg aaaaacttca agactataag ttccctggat 180
caaataccgt cttaatagaa cgagagattc ctcgctggaa cttcaatgaa atgaaaagag 240
aaacacagat gaggaccaac ttatatatct tcaagaatta tcgctgtttc tatggctatt 300
caccattaag gccatacgaa cctataactc ctgaagaatt tgggtttgat tactacagtt 360
gggaaaatat ggttgatgaa gacgaaggag aagttgtata catctccaag tatactaaga 420
ttatcaaagt cactaaagag catgcatggg cttggccaga acatgatgga gacacaatgt 480
cctgcaccac atcaatagaa gatgaatgga tccatcgtat ggacaatgct taaagaagct 540
ttatcaaaag caactttaag tacgaatcaa taaagaagga ccagaagata taaagcggga 600
acatcttcac atgctaccac atggctagca tctttacttt agcatctcta ttattgtaag 660
agtgtataat gaccagtgtg cccctggact ccagtatata aggagcacca gagtagtgta 720
atagat 726

<210> SEQ ID NO 66
<211> LENGTH: 165
<212> TYPE: DNA
<213> ORGANISM: Rice tungro bacilliform virus

<400> SEQUENCE: 66
acgaatcaat aaagaaggac cagaagatat aaagctggaa catcttcaca tgctaccaca 60
tggctagcat ctttacttta gcatctctat tattgtaaga gtgtataatg accagtgtgc 120
ccctggactc cagtatataa ggagcaccag agtagtgtaa tagat 165

<210> SEQ ID NO 67
<211> LENGTH: 2000
<212> TYPE: DNA
<213> ORGANISM: Zea mays

<400> SEQUENCE: 67
ctgcaatata tacaccaaaa gtattataaa ctgtcatata tatgaccaaa accttttat 60 tttagaaaag tatattaatc atggtatatt aatcaaagtt gttgttgggg ctgcaaaaat 120
catacccttc ttccacaagc tgttccttga actgcaggta ctcaggaact ctcagctcct 180
caacagcgag ctcactgacg ttgaccctca catactccca gacaccaggc ctagggcgga 240
tggcaagtgc aacccatggg gggatgacaa tcgcctcctg taagataata gagctagaat 300
gattaaagaa ggtgcacact acaaaaggaa cagtgctgtc cagcgagatc tgaatctgat 360
gcaaacctga gctgccctca ggacatcctc aaaagcacca tccttgagct tctcgcgctc 420
agcctcaggg atcgcattgt tgtactcggc aatgatctgg tggggctgca gcataccctt 480
tccaaggttt ttcagcctgc gcaaaacgat gtgccaaata acatcagact atgccagatc 540
tataaactca tcaaacatat acaatttcaa gaaatagttt agacgtatga tcagcagtca 600
gtagcgtggg aacatatgca acatagcgaa gaggcacaac agcaaattca ttcgaaaaaa 660
tgaaaacaaa gattcctctc ttttaactga acttctcgaa accccttttca tgcctacaca 720

```
tccgatctag tcagatgcct atgcgttcat gctgaacaga acgtgtcaga actaagcata    780
aactggttag caagcattat cgtattcgat agacccttta gtaacaagct atacattggg    840
taagttcaga ctccaatcat tctgttcaga aacatcgtat tgaatataaa actaaagaac    900
acacatgcag gtgcagccag atctaacagc agtttacagt cggtactaaa aaaagcatgg    960
tgtatgtatg tatcatcagt atccagtact aggtttcgac aaaatcctgg atgctaatta   1020
aatactcatc ttattaggga acacaggaac attatgtcta cagcattgaa tgatggccac   1080
atcatgctag atctaacaat acataatatg atggaactgg tcttaaaaag tcgcattcgc   1140
tcaaataata cccgtagcaa aataaatgta aacttgcaga cgaagcgggg gaaatgaggg   1200
cagacctggt gaagacggcg acaagctcat tggggtgggc agagagtgag tcgccaatgc   1260
gctccctgac gctgtggagg cggctcagga cacggtcacc tgcaccttcc cccattgctg   1320
tcctcttcct ggatcctcag gcctgcacag cgaaaccgaa acggaagcgg aagcttcagt   1380
cagcagagaa aactgaaacc gaaaaacggt tcagatccgt tgacataaaa gctgcgatga   1440
catcctaaaa ctaaaacccc tccagcaaga cataaaccca actgccaaca accagtcttt   1500
taagtctcga cacacccttg acgctgcgcc acgaaactat attgcaggca agaaaccaac   1560
agaacctaac tctggaaggg gggaaagaaa cggcagacag gagcaagacc caaaaaaaaa   1620
cgactcagat cctggtacta tagtcctagt acctagacca gaaagaagaa acaaccaata   1680
caacaagagg catacaagaa ctgaatcgat gaactgaaac gcttcagagg accgaggaat   1740
ggcggagaag ggaggcgcct atttatacag atctgacgag agaaccgaac aaaaacacat   1800
cgatgggaac catggagaag aaaagggctg gccgcatggc accaatggcc tcggcctcca   1860
aaaagccgtt gaatccaaag caggcgagga cgaagcgtga cgcggcaggg tacttctcta   1920
gaaaagcacg gcatcagcaa ggtggggggg ctggggttcc ttattgcagg caatcacgag   1980
gtgattagca caaacggaag                                               2000
```

```
<210> SEQ ID NO 68
<211> LENGTH: 2000
<212> TYPE: DNA
<213> ORGANISM: Oryza sativa

<400> SEQUENCE: 68
```

```
ctgaaatata catcagagat attacaatga catatatatc gataaaagaa aaataataaa     60
attaagtttt aaattttaag aatatatgtt tttagtatcc caattatgca gatttcatac    120
ccttcttcca caagctgttc cttgaactgc aagtactcgg ggactgtcag caactcaaca    180
gcgagctcgc tcacattgac cctcacatac tcccagacac cgggcctcgg gcggatggca    240
agggcaaccc atggggagat aacaatcccc tcctgcatga taaaaaaacaa ttacaagtta   300
agttagagca agcggtagag taaagatgga tctctgtgat gcaatgaaat ctgaatctga    360
ttcaaacctg tgcactcctc aggacatcct caaaagcacc gtccttcagc ttctcacgat    420
cagcctcaga gattgcgttg ttgtactcag caatgatctg gtgggcctga agcattccct    480
ttccgaggtt aaccagcctg cgcaaataac agtgtcaaca aaaatatcag gccagatcta    540
tcaactcagc ctataaatat ctcaataaga taattttagc acttgagcat ttgcgcataa    600
taagaaaatt tgctattagc cacttaaaaa gaccatatat gatctgtttg cattgagatg    660
aattaaaaat ttcattgtag atatgaaatg attagttttg accatttaat tggacttaat    720
gaaatatgcg cgataatcag atctacgcgc tcgcgccaat agatctagta agatgtaggt    780
tttttatttt ttttgtgaaa ctttgctacc acaacaagca tctgtaccag tgcagaattc    840
```

```
attacttgta ttcagtttgt aaaccgtata tataatataa ataacatgca catgcagtca    900

gatctagcac taccagtcca cagtaatcca aaactacatt tgtatatttc atcattattc    960

agtagtacta ggtttgtaca aaatcttggc tgcagaaggc cgcacttaaa tattcattct   1020

aatcagaaac ttaaaaaaaa agtgactaca aaatgattgc atccaattca gtaaatatga   1080

gccattcctg gccagatcta acaatctcaa caacaaagat cctatatgaa catctccttc   1140

taaaagaaaa tacagtaaca tctgaaggca gtagactaga aaccaacaaa atctaatgct   1200

gggaaatcac taaatcagca cgaacctggt gaagacggcg acgagctcat tggggtgggc   1260

ggagagggag tcgccgatgc gctccctgac gctgtggagg cggctcagga cgcggtcgcc   1320

ggcagcttcc cccattgctc tcctcttcct cttggctcct caagcctgcg tgcacaacca   1380

accaccatca tcagatacat ccagacccag tcaacacaat cactccagga aaaaaaaaag   1440

tcaagccata aaccccaacc aaaaaccacg cctttgacaa acactggaag aaaaagaaaa   1500

tcgcagcttt ttcacaagca atctagaaga aaagaaaaag aaaagactac atagcagcta   1560

taattgactg agaagcatac aggaatcaaa caatggagaa ggggagggag gaagaacaat   1620

gatgctccag gctgaggacc gaggaactgg gtgaagcggg gtaggcgcgt atttatgcag   1680

atctgaggag agaaaccacc aaaacaatcc gatggtttca acgaaaaaga tcgtcgcttc   1740

ttgctgcacc agctcaccca tagccgttga gatcgaagct aagctagcag cagcaaagct   1800

ggaacgaaga gtgacgcatt caagctcctc tcctctcctc tcctctcctc cggagcacga   1860

ggccagcatg ggatggattg gggtttcttg ttggccatgg caaaggagga ggtcattaac   1920

gttgacacgg cgtaatttaa ttaaatctta tcttaaaata tgatttaagt ggtagtaaca   1980

aggaagatta atactatgaa                                               2000


<210> SEQ ID NO 69
<211> LENGTH: 2000
<212> TYPE: DNA
<213> ORGANISM: Oryza sativa

<400> SEQUENCE: 69

gctgtttaag aaaaacagaa gtaaaattca gtcactgtta ttttgcttca gttataatct     60

gcaaatcgtc gttctggtac ttactgtcca tcaacaagct gttccttgaa tgccaagtac    120

tcagaaacac tcagctcttc cactgccaac tcacttacat tcacccgaat gtagtcccag    180

acaccaggcc ttggcctgat ggccagtgca acccagggcg gcagcacaat ggcttcctac    240

atacagtcaa ggaagtaagt tagaaagact ggtatttgac tttgagttga ctatcataac    300

catcctggct cattgccaaa tttacctgag cagcccggag aatgtcttca aagggagcat    360

atttctcttt gtcagcttcg atcaaggcat cgaactccgc aagcagctgg tgacgctgga    420

gcattccctt tccctggtta acatacctgc atagagtgat atttaagaaa tagaaccaat    480

gcttagatct cacatccttt ctgcggctga actatgttaa tggcactacc acataaacct    540

gatttttact tcttattttt aagaccacat gatctgtact taatctagct atgaacaaac    600

aatatttcaa catcatctaa gattcatgac tcaagacaaa aatgttagag ctcatcacag    660

attattatag ataccatcat taaaactaaa gagatgcata accttgtcag ctaagaattt    720

gtaacatact aacatgttat cgtttcacat ctgggttgac taagaactaa ccaactgtat    780

ggataaaatc attgaaaact caaaacaatt agtagcaggt tccaagaaga cacaagatat    840

tatattgaga tcttcaccta gagaagagtg caatcaactc attgggatga gacgagaagg    900
```

```
tggcaccgag gcgttcgcgg agactgtgga ggcgagctag cttggcagcc atgactcaat    960
ttcaggaact gcaaagaaag gttacactta gcaacacgta ccaaaaccac tcacttgcac   1020
aagaataatt agtcaacagc catcactaag cattgcaaga ctatctctga acaggaaagc   1080
catgctaaat caacactaat aacatcacac aaaagcattg gaagatcaaa acataactaa   1140
aaacagctgt ttcatctaca caactgaaag catctatggt ttacgaagca gagtgcgagt   1200
actgattcaa aataaatcaa cctgaaccaa tatactctga caatgttttc aaagggataa   1260
aagaaccagc tttatcaaat ggatttgttg ggttttagta agtatcattg agataccgat   1320
ggcatatctc aaactttgca aaattataat ggcatggttc caaattaccc tttagtatta   1380
gcaccagtta gatcctaatt cctaaatccg ataggacaga gcgaaagatc cctggagata   1440
tgaagatttg gctacagatt aagcagagcc aacatgaagt tccgaatatt atgaatccgc   1500
aagcggggag atcaaagaga agaatacgga aggtcgcgac tccatgaaag aatccaacca   1560
aaaacccaaa gatttttctc agttcaaaaa aaaaaaaccc ttcatttttg gttcgccatc   1620
caccgacagg caccaagaca ttcctcagga agcaaaaaag attaagcaga acaagtgata   1680
agcaagacac agtatcaacg gactacgagt cgagaaaatc actgaggcgc gattcttact   1740
gcaccaagta aaaaaaaatt tgggggcaaa aagaactctg caatggggcg gagcaacgtg   1800
gcagcaaaac taaaggtcga ggatttgagg tttttgccg gttttcctcg aaaccccgaa   1860
tccgctcata gtaaacccac taaactgcag cagaaacccc cctcttggtt cagatttacc   1920
gaaagcagta aacccaagaa catgtcagca aaaactcctg caagattcag ctgacgaccc   1980
accaaagaat cgcaagaaat                                               2000

<210> SEQ ID NO 70
<211> LENGTH: 2000
<212> TYPE: DNA
<213> ORGANISM: Oryza sativa

<400> SEQUENCE: 70

tggcggacgc gccacgcaca aacacaaacc tgcacacccc tgtgtcagag gaggagaggc     60
caagaaagga aatcgagtgg aggaagtgag gagcggcgga gacgtaggag gaggaggggg    120
agatggaaat ggaaagccgc gcgagagagg aggcgcgtgc tggatgggag gaggaggagg    180
aggtggtggg tttgtgtttg gagagacgag cgagagaggc gaagcattta aagggaggaa    240
gagggggaga gagagagaga gagagagaga gagagagaga gagagagaaa ggaggaatat    300
aataaagggt ggtgcacctg ccaactgcta tgctcaccaa cactttgtac acacccagtt    360
acaccccccct gcctttatta tttccagtgc agtaataact tcaacaatta ttgaaatgaa    420
aatggaatta atggagttag tatcggatta gcgacacgct tgccgagctt ctagacggtg    480
cgattatttc agcgggaacg actttctgta ggtgaattta atagaggagt gttttaaatc    540
cactcgacgt tgtaatagct ggtttaattc gtttgtactg tcgagtagtt atccaaaatc    600
aattttggat atttaaaaga aaaaaaaaca gatccgaagt attggaccta ctggcaaata    660
ggaattttgc tatatatagg tgtgcgttca tttataatgg agtagcatgg agttttatta    720
atccagtaaa tgttttcatt gatttaatta atataacgaa tttcgcttga ggccatattt    780
gttaaacgct tttatctcta tcatcattca tcctaccagt aaagagcacc ggagatcgca    840
cttcatttaa atatatgtcc atgttggata aaccatagtt tattatagtg ttcttttata    900
tgttttgtgg ggaatttaga ttgtttaata tggcatacat atccatccat cattattata    960
ttctaacaca actggataag tgttctaaac tattgtagaa taactttgta gtatgatcga   1020
```

```
tcttgtggaa taaaaaaagt ctgacaataa cctttcataa aggaatatga atacccgtaa   1080
tcaacgcatc aaatcattca cggtgtacgc ctagcgaatt cgttggcgag tgctcgtgcg   1140
gccgtgggct cgctgtgatg catgcatggc tctctggcta cgtcgagata gcgattagta   1200
gcaaaattaa gcaagccact tattaattaa tctttggaga tatcatatga ttaaggcatt   1260
aattcgtacg tactcgtcgt cagcgttttc tgcaaagtcc actacagttt tttctttctt   1320
tgctgaaaat gctgatgtgt tggagatgga gtgacgtgca caacctgccg ccacgtggat   1380
ggttgctgga gcctacgtgt catcttaatt tgaacaaaaa aaaaagagga ataatacatc   1440
aatacatttt cgaatttcag ttctgccatt gaccagtaat acacatgtcg gcctcacatt   1500
ttaccctgat cttagtaacg ggtggtcgcc tggtcggtca ctgaaaaaag ttcaggaaat   1560
tatagtcaaa ctgaaacgaa catattcact ccttaaaaaa actaaatctt tttatatatt   1620
tgtgatattg taaaatagct acgggataat gatatagata tatatagtga taagggatag   1680
atggatcgag atatggagtt gtgctttctt taatttccac tacttgggct accatattat   1740
ggtagttggt atgaaaagat acacagcagt atagtgatgt gatcaatgac atgtatatct   1800
cacatgctcc catgttggag tcaaattttg ctagactaaa atccaattcc aagcagtccc   1860
tagccaagaa caaacaaaat tcagtgaggt cactgctgca ccaaggactg catgcatgca   1920
ggagaagggc attttctctt ttttcttttg gagactcgat tcaattcggt cggtcggtcg   1980
caatggtcag cttaattaaa                                               2000
```

```
<210> SEQ ID NO 71
<211> LENGTH: 2000
<212> TYPE: DNA
<213> ORGANISM: Oryza sativa

<400> SEQUENCE: 71
```

```
tgtgaaaggt ggcggcacca gcttagccgc agcttctctc gtcgtctccc tgaaacgaga     60
gggaggaagt tggtagcgtg atatatttag gcatgtcatc tcttgtataa gaagtcttat    120
ctgtgctaat tcacacggtt ctctaatctc tctccattct gtttttgtaa attggttcag    180
tagatagcgt agggttatgc ttatatatac tccgtgaagt atatatttaa aaattagtca    240
cacgtaaagt actatacatg ttttatcgtc taataacaat aaaaacacta atcataaaat    300
ttttttaaat aatacgaatg gttaaacgtt gaatatgaac cgtgcaaaac tatatttatt    360
ttgtaacaga gaaaatattt cacattaatt agattgttgt tttatggaag gttggagagc    420
tgcgccgccg ttgcgcagac ctaggaggct gcttataagt tataatcaat caattcacgg    480
atgccggctg ggacgcggcc catcgtccgg gaagacgaca actcaacgca aaaagccgat    540
atgcctccaa attgccattg ccacctctac ggctgtttat actgctccaa atcaaaagcg    600
tccatggaag aatctagtat ttcccgcaaa gacgatgatg atatgcagga ttggatatat    660
agggggttgt tgcatgattg ctagaactcc cgtttccgaa gttgttcgtc catttttaaa    720
gctgccaaat aggaatttat tttgttttca agtgtaatag agttctgtcc agatgagtga    780
attataattt ggttcacatt ttatttgcta agtttcagtt tgaacattct caaataactt    840
ttttcttcac tttttaaccg agtaacttag ttattttttc cgtttggacc acccaacaat    900
ttgttgctaa gtgcatctca cccgtcaaat aattcctttg aatccaaatt caattatatc    960
ccaaaaataa aaaacttctg aattccacat caattcaaac cccaaccatt ttaatttctc   1020
tccatatttt ccatttctct atttttacct ttctcttttt tccatctatt tattttttc   1080
```

```
cttttctatt tctttctttc tccttccttt ctctgtttcc ttcttcttct cctcggctag   1140

gcccgagcca gcccgtgccg cctcgcgcca accctgtgcc gccttacgcc gcgcttgcgt   1200

gcgctcgcgc ccacctcgtg cccaacccgc gcacgccaca cgcacacacg aggacgatcg   1260

acggacgaat gcaatcatat ccccttcctt actcagctag aaggctcaag aaccgcaact   1320

ttgatctctt ccaccctctc aaatccgccc caacccctgc tgactcaatc gccattaccg   1380

gaggaaaaat ccccgaaacc ctattaccgg cgccactaac agagctccaa aattcgtcgc   1440

ataattcgaa aatattctga aattgaaggt aaaaatggaa tctacatgcg aagtactccc   1500

tttcccctcc aatccgtcac tggaacgccg ccggcgccgc ctcccgctgc cactgccctg   1560

tttggccgcc gacagccgca cggcgcgccg ctgctccagg ccgccctagc ttcaaccacc   1620

gccacctttg gctccgcctc cctcctctta tgctcaccaa gcccgcctcc ctcgccggag   1680

atcgccggaa ccaccgccgc catggccgcc accgcctcct gcttctggcc gccgccgcca   1740

gcctcgccac cggcgcctat gccaccgccg accacggaaa cggagtccct acaccttggg   1800

gaccacaaaa ccggcggcat ccctcccaaa accggcctcc tccaccgccg gcgttcgtgg   1860

gattccggcc agttctgtgc agagcgagag aagaagagga aaaatagatt ttcctattga   1920

aagataaatc agaaaattcc tttttctttt cctatcaagt tgaccatccg tttgacctca   1980

aaatcaaaat ctgagaccta                                               2000
```

<210> SEQ ID NO 72
<211> LENGTH: 786
<212> TYPE: DNA
<213> ORGANISM: Zea mays

<400> SEQUENCE: 72

```
gacatggagg tggaaggcct gacgtagata gagaagatgc tcttagcttt cattgtcttt     60

cttttgtagt catctgattt acctctctcg tttatacaac tggtttttta aacactcctt    120

aacttttcaa attgtctctt tctttaccct agactagata attttaatgg tgattttgct    180

aatgtggcgc catgttagat agaggtaaaa tgaactagtt aaaagctcag agtgataaat    240

caggctctca aaaattcata aactgttttt taaatatcca aatattttta catggaaaat    300

aataaaattt agtttagtat taaaaaattc agttgaatat agttttgtct tcaaaaatta    360

tgaaactgat cttaattatt tttccttaaa accgtgctct atctttgatg tctagtttga    420

gacgattata taattttttt tgtgcttaac tacgacgagc tgaagtacgt agaaatacta    480

gtggagtcgt gccgcgtgtg cctgtagcca ctcgtacgct acagcccaag cgctagagcc    540

caagaggccg gaggtggaag gcgtcgcggc actatagcca ctcgccgcaa gagcccaaga    600

gaccggagct ggaaggatga gggtctgggt gttcacgaat tgcctggagg caggaggctc    660

gtcgtccgga gccacaggcg tggagacgtc cgggataagg tgagcagccg ctgcgatagg    720

ggcgcgtgtg aaccccgtcg cgccccacgg atggtataag aataaaggca ttccgcgtgc    780

aggatt                                                               786
```

<210> SEQ ID NO 73
<211> LENGTH: 1160
<212> TYPE: DNA
<213> ORGANISM: Zea mays

<400> SEQUENCE: 73

```
atgtgctggt gccccataag gtaggcacct aggtctgtgt ttgaagcatc gacagatttg     60

taaacatgtt cctatgaacc tatttctgat tgataatttg tcaaaactca tcatttgtct    120
```

tcatccttgc ctgcttgcgt tcacgtgaca aagtacgtgt atgtcttcgg cctttgctgt 180
gtatgtttcg cattgcttag atgtggtgaa agaacatcag aagatgcatt gatggcgtgc 240
ttaaaccagt gatgtgctcc aggtgttcct gcagtctgca gagatattta ctcttgtagt 300
cttgttgaca gcacagttgt atgtgatttc ttggatgtaa tgtaaaccaa atgaaagata 360
ggaacagttc gtcctcttcc gtatacgaag gtcactgtat catttgtcgt ggcacaagat 420
gatctgcagg caggactgca acatggtttc ttggactgtc ctgaatgccc gttcttgttc 480
tttagttgag ccagagcagc agcctggtgt cggtgcctga gacctgacga agcacacggc 540
aaacaaacaa gtcgcagcag ctagcagggg cgttgccatc gccacaagcc cccaagagac 600
ccgccgagga aaagaaaaaa aaactacggc cgccgttgcc aagccgagcg tgcgaaccga 660
tccacggatg ggagatcaga gatcacccac cgcaggcggg cggcagtggc tggcgaggtg 720
cgtccacaga acctgctgca ggtccctgtc cgtcccggcg accccttttc taggcgagca 780
actccccatg gcagagctgc acgcagcagg gcccgtcgtt ggttgcagct ttaacccttt 840
ttgttttaac catacaatgc agagtcgcag aggtgaaaca ggacggaaat tacagaaaag 900
atggtggtgt gccagcagcc ccagcatgaa gaagatcagg acaaaagaaa agcttgtgat 960
tggtgacagc aacaggattg gattggagcc aagctaggca gtgagaggca ggcagcaaga 1020
cgcgtcagcc actgaaatcc agagggcaac ctcggcctca caactcatat ccccttgtgc 1080
tgttgcgcgc cgtggttagc caggtgtgct gcaggcctcc tccttgttta tatatgggag 1140
atgctctcac cctctaaggt 1160

<210> SEQ ID NO 74
<211> LENGTH: 1532
<212> TYPE: DNA
<213> ORGANISM: Oryza sativa

<400> SEQUENCE: 74
tagtcctcta atatatgaaa ttttgatata ggtaaagaag ggtattgcaa ggataagaat 60
gtaaaaagaa ataagagtaa tccttaccga taatagtatt ccttctctac cgttaaaagt 120
taaacctgtg cgtgtagcat tttaatccag gatctatcga atccgtccct cgttggcgtg 180
ggcgacgaac acgtgcagaa gaagctttcc ccagaaagca cctcaccgcc tcgccgtctg 240
gcagactggc acgcggggcc ctaccctcgc tgcgcctggg cccgtccgcc ttctgcacac 300
tgtcacgccc ccacccgctc gccgcctcgc gcctctctct ccgcctccgc cgcggccgcc 360
cgacgtgata gcgacacgta ggactcgcca aacacaaaaa atccatcgcg atttttggaa 420
ttttgttaca aaccaaatcc cgcattagag atttaatttg atttaattta attacgtagg 480
agtaccagat aaggagatcg agttaaaaaa gctaacggcg cggcgtggtt atctccgaat 540
cggctgtggc tccccgcgtc ggcgtcggcg cggcggcggc gcgccggccg aaccctggcc 600
gtcggatcgg gcgtcgtcct gggccccacg cgccacgggc ggctgtcgtt tgctcctcgg 660
agcggggtgg gcccaccatg gccaccacca caggtcgcgg tcgcggctga cctggcggtg 720
gtcccgtgct cgcggtgttt tttttttttc actctctttc tctcggtgga cagtagcggg 780
ggccgcggcc cgcgggggca gagattgcaa aaacagcgga aacggaagat tgcaaaattg 840
caactgcttt cctgttttta attcgggatc aaaaagattc tttcgtcggg gtccccgtgc 900
cattgttgta ttgcgcgtag gtccttgctt gtaaaagata atctccttaa ttttttcttt 960
gtactactag tgtatatgca gtaagaatat accatgagta aaatgaacca caaaactaat 1020
tacgatatac cattctcatg tagacgttct cttttctttt gctagtcata cgtgcatata 1080
taaccaaaca aaaaaatgtt tgaagtactc ctatccaatt tattactcca gtagacaaca 1140
aaagaaaatg tttgaagtaa taactgatcc atggtacagt agggttgtcg tcaatcttgt 1200
gtttctttca ttccattgta cttacaatcg tactccagct agcacagcac aatgggctta 1260
agctttggac cccaaattct gatcttgtcg gggacccgta cgaaaatact cccgtagaga 1320
tgcagatacc gtcacaacct acaaccaacg aatgttaaga aaacaaaggg aaaaaaaaag 1380
aggcgaattc ggaggagaaa aaacggtggc taaaatatag tgcgggtgtg gggacgcgac 1440
gcgagcgacg aaagaggaga gaggatgggt tggcctgccc ccccctcccc tgtctataaa 1500
tgcagaggcg ccgagtgccc tagtcgccgc tc 1532

<210> SEQ ID NO 75
<211> LENGTH: 841
<212> TYPE: DNA
<213> ORGANISM: Oryza sativa

<400> SEQUENCE: 75
tcgaggtcat tcatatgctt gagaagagag tcgggatagt ccaaaataaa acaaaggtaa 60
gattacctgg tcaaaagtga aaacatcagt taaaaggtgg tataaagtaa aatatcggta 120
ataaaaggtg gcccaaagtg aaatttactc ttttctacta ttataaaaat tgaggatgtt 180
tttgtcggta ctttgatacg tcatttttgt atgaattggt ttttaagttt attcgctttt 240
ggaaatgcat atctgtattt gagtcgggtt ttaagttcgt ttgcttttgt aaatacagag 300
ggatttgtat aagaaatatc tttagaaaaa cccatatgct aatttgacat aatttttgag 360
aaaaatatat attcaggcga attctcacaa tgaacaataa taagattaaa atagctttcc 420
cccgttgcag cgcatgggta tttttctag taaaaataaa agataaactt agactcaaaa 480
catttacaaa aacaacccct aaagttccta aagcccaaag tgctatccac gatccatagc 540
aagcccagcc caacccaacc caacccaacc caccccagtc cagccaactg gacaatagtc 600
tccacacccc cccactatca ccgtgagttg tccgcacgca ccgcacgtct cgcagccaaa 660
aaaaaaaaga aagaaaaaaa agaaaaagaa aaaacagcag gtgggtccgg gtcgtggggg 720
ccggaaacgc gaggaggatc gcgagccagc gacgaggccg gccctccctc cgcttccaaa 780
gaaacgcccc ccatcgccac tatatacata cccccccctc tcctcccatc cccccaaccc 840
t 841

<210> SEQ ID NO 76
<211> LENGTH: 1392
<212> TYPE: DNA
<213> ORGANISM: Oryza sativa

<400> SEQUENCE: 76
ctcgaggtca ttcatatgct tgagaagaga gtcgggatag tccaaaataa aacaaaggta 60
agattacctg gtcaaaagtg aaaacatcag ttaaaaggtg gtataagtaa aatatcggta 120
ataaaaggtg gcccaaagtg aaatttactc ttttctacta ttataaaaat tgaggatgtt 180
ttgtcggtac tttgatacgt catttttgta tgaattggtt tttaagttta ttcgcgattt 240
tggaaatgca tatctgtatt tgagtcgggt tttaagttcg tttgcttttg taaatacaga 300
gggatttgta taagaaatat ctttaaaaaa acccatatgc taatttgaca taatttttga 360
gaaaaatata tattcaggcg aattctcaca atgaacaata ataagattaa aatagcttgc 420
ccccgttgca gcgatgggta tttttctag taaaataaaa gataaactta gactcaaaac 480
atttacaaaa acaaccccta aagtcctaaa gcccaaagtg ctatgcacga tccatagcaa 540
gcccagccca acccaaccca acccaaccca ccccagtgca gccaactggc aaatagtctc 600
cacaccccgg cactatcacc gtgagttgtc cgcaccaccg cacgtctcgc agccaaaaaa 660
aaaaaaagaa agaaaaaaaa gaaaaagaaa aaacagcagg tgggtccggg tcgtgggggc 720
cggaaaagcg aggaggatcg cgagcagcga cgaggccggc cctccctccg cttccaaaga 780
aacgcccccc atcgccacta tatacatacc ccccctctc ctcccatccc cccaacccta 840
ccaccaccac caccaccacc tcctccccc tcgctgccgg acgacgagct cctcccccct 900 cccctccgc cgccgccggt aaccaccccg cgtccctctc ctctttcttt ctccgttttt 960
tttttccgtc tcgtctcgat ctttggcctt ggtagtttgg gggcgagagg cggcttcgtc 1020
gcccagatcg gtgcgcggga ggggcgggat ctcgcggctg ggtctcggcg tgcggccgga 1080
tcctcgcggg gaatggggct ctcggatgta gatctgatcc gccgttgttg ggggagatga 1140
tggggcgttt aaaatttcgc catgctaaac aagatcagga agaggggaaa agggcactat 1200
ggtttatatt tttatatatt tctgctgctg ctcgtcaggc ttagatgtgc tagatctttc 1260
tttcttcttt ttgtgggtag aatttgaatc cctcagcatt gttcatcggt agtttttctt 1320
ttcatgattt gtgacaaatg cagcctcgtg cggagctttt ttgtaggtag aagatggctg 1380
acgccgagga ta 1392

<210> SEQ ID NO 77
<211> LENGTH: 743
<212> TYPE: DNA
<213> ORGANISM: Oryza sativa

<400> SEQUENCE: 77
gaattcccgg acctccatgc ctacatcaac taatttgatt ccttgagttt acgtttagtg 60
atatgtctat ttttagagct tgttggggct tcggcctcag ctctagccag ccaaacatgt 120
tctaccaagt accctatgtt ggcatgatat agtgatgcat tataacaata aatgagcgag 180
ggattgctgg ctgaaaaagc tatactagct gcatttggtt atagttaacc gaactattaa 240
ttgcgtgtac aacaaaataa aaaaaatgca tgttgcacat tctttcatta acattatgtt 300
ttggtagtgt gaattagaaa tttgattgac agtagatcga caaacatagt ttcaatatgc 360
ttaagttagt tatgacttta acatatcagt ctccttgata ttttcgtttt agattcgtct 420
ctctactagt gtgtatgtcc accttccata gcagtgaagg gttccattcc atccctggta 480
aaaaaaaatc aaccactact atttatttcc taaaaagcaa aatgataaaa tatcattttt 540
ttaataaaaa taaaaaaatt ttggggtaca taattgatgt tgccccttgg gattaacctt 600
aaaaaagggc gaattttcta gggtttggcc aagttttgca atgcaccaaa ttattcccct 660
tgggccggcc gccaccccaa aaaaaacccc aacccccaac tttccattga aggccgggcc 720
cccttaaatc ctcatccccc caa 743

<210> SEQ ID NO 78
<211> LENGTH: 144
<212> TYPE: DNA
<213> ORGANISM: Oryza sativa

<400> SEQUENCE: 78
taaaaaaggg cgaattttct agggtttggc caagttttgc aatgcaccaa attattcccc 60
ttgggccggc cgccacccca aaaaaaaccc caacccccaa ctttccattg aaggccgggc 120

```
ccccttaaat cctcatcccc ccaa                                          144


<210> SEQ ID NO 79
<211> LENGTH: 612
<212> TYPE: DNA
<213> ORGANISM: Cauliflower mosaic virus

<400> SEQUENCE: 79

ggtccgattg agacttttca acaaagggta atatccggaa acctcctcgg attccattgc     60

ccagctatct gtcactttat tgtgaagata gtggaaaagg aaggtggctc ctacaaatgc    120

catcattgcg ataaaggaaa ggccatcgtt gaagatgcct ctgccgacag tggtcccaaa    180

gatggacccc cacccacgag gagcatcgtg gaaaaagaag acgttccaac cacgtcttca    240

aagcaagtgg attgatgtga tggtccgatt gagacttttc aacaaagggt aatatccgga    300

aacctcctcg gattccattg cccagctatc tgtcacttta ttgtgaagat agtggaaaag    360

gaaggtggct cctacaaatg ccatcattgc gataaaggaa aggccatcgt tgaagatgcc    420

tctgccgaca gtggtcccaa agatggaccc ccacccacga ggagcatcgt ggaaaaagaa    480

gacgttccaa ccacgtcttc aaagcaagtg gattgatgtg atatctccac tgacgtaagg    540

gatgacgcac aatcccacta tccttcgcaa gacccttcct ctatataagg aagttcattt    600

catttggaga gg                                                        612


<210> SEQ ID NO 80
<211> LENGTH: 837
<212> TYPE: DNA
<213> ORGANISM: Coix lacryma-jobi

<400> SEQUENCE: 80

agcagactcg cattatcgat ggagctctac caaactggcc ctaggcatta acctaccatg     60

gatcacatcg taaaaaaaaa accctaccat ggatcctatc tgttttcttt ttgccctgaa    120

agagtgaagt catcatcata tttaccatgg cgcgcgtagg agcgcttcgt cgaagaccca    180

tagggggggcg gtactcgcac cgtggttgtt tcctgttatg taatatcgga tgggggagca    240

gtcggctagg ttggtcccat cggtactggt cgtcccctag tgcgctagat gcgcgatgtt    300

tgtcctcaaa aactcttttc ttcttaataa caatcatacg caaatttttt gcgtattcga    360

gaaaaaaaga agattctatc tgtttttttt ttgaaatggc tccaatttat aggaggagcc    420

cgtttaacgg cgtcgacaaa tctaacggac accaaccagc gaatgagcga acccaccagc    480

gccaagctag ccaagcgaag cagacggccg agacgctgac acccttgcct tggcgcggca    540

tctccgtcgc tggctcgctg gctctggccc cttcgcgaga gttccggtcc acctccacct    600

gtgtcggttt ccaactccgt tccgccttcg cgtgggactt gttccgttca tccgttggcg    660

gcatccggaa attgcgtggc gtagagcacg gggccctcct ctcacacggc acggaaccgt    720

cacgagctca cggcaccggc agcacggcgg ggattccttc cccaccaccg ctccttccct    780

ttcccttcct cgcccgccat cataaatagc cacccctccc agcttccttc gccacat       837


<210> SEQ ID NO 81
<211> LENGTH: 947
<212> TYPE: DNA
<213> ORGANISM: Oryza sativa

<400> SEQUENCE: 81

aatccgaaaa gtttctgcac cgttttcacg tcctaactaa caatataggg aacgtgtgct     60

aaatataaaa tgagacctta tatatgtagc gctgataact agaactatgt aagaaaaact    120
```

```
catccaccta ctttagtggc aatcgggcta aataaaaaag agtcgctaca ctagtttcgt    180

tttccttagt aattaagtgg gaaaatgaaa tcattattgc ttagaatata cgttcacatc    240

tctgtcatga agttaaatta ttcgaggtag ccataattgt catcaaactc ttcttgaata    300

aaaaaatctt tctagctgaa ctcaatgggt aaagagagat attttttttt aaaaaaaaat    360

agaatgaaga tattctgaac gtatcggcaa agatttaaac atataattat ataattttat    420

agtttgtgca ttcgttatat cgcacgtcat taaggacatg tcttactcca tctcaatttt    480

tatttagtaa ttaaagacaa ttgacttatt tttattattt atcttttttc gattagatgc    540

aaggtactta cgcacacact ttgtgctcat gtgcatgtgt gagtgcacct cctcaataca    600

cgttcaacta gcgacacatc tccaatatca ctcgcctatt taatacattt aggtagcaat    660

atctgaattc aagcactcca ccatcaccag accactttta ataatatcta aaatacaaaa    720

aataatttta cagaatagca tgaaaagtat gaaacgaact atttaggttt ttcacataca    780

aaaaaaaaaa gaattttgct cgtgcgcgag cgccaatctc ccatattggg cacacaggca    840

acaacagagt ggctgcccac agaacaaccc acaaaaaacg atgatctaac ggaggacagc    900

aagtccgcaa caacctttta acagcaggct ttgcggccag gagagag                  947
```

```
<210> SEQ ID NO 82
<211> LENGTH: 721
<212> TYPE: DNA
<213> ORGANISM: Mirabilis mosaic caulimovirus

<400> SEQUENCE: 82

tggagattca gaaaaatctc catcaacaaa taatccaagt aaggattaat ggattgatca     60

acatccttac cgctatgggt aagattgatg aaaagtcaaa aacaaaaatc aattatgcac    120

accagcatgt gttgatcacc agctattgtg ggacaccaat ttcgtccaca gacatcaaca    180

tcttatcgtc ctttgaagat aagataataa tgttgaagat aagagtggga gccaccacta    240

aaacattgct ttgtcaaaag ctaaaaaaga tgatgcccga cagccacttg tgtgaagcat    300

gtgaagccgg tccctccact aagaaaatta gtgaagcatc ttccagtggt ccctccactc    360

acagctcaat cagtgagcaa caggacgaag gaaatgacgt aagccatgac gtctaatccc    420

acaagaattt ccttatataa ggaacacaaa tcagaaggaa gagatcaatc gaaatcaaaa    480

tcggaatcga aatcaaaatc ggaatcgaaa tctctcatct ctctctacct tctctctaaa    540

aaacacttag atgtgtgagt aatcacccac ttggggttgt aatatgtagt agtaaataag    600

ggaaccttag ggtataccat tgttgtaata ttattttcag tatcaataaa ataatctttc    660

agtttatctt atattcattt gtgtgacacc gtattcccat aaaaccgatc ctaatctctc    720

c                                                                    721
```

```
<210> SEQ ID NO 83
<211> LENGTH: 352
<212> TYPE: DNA
<213> ORGANISM: Peanut chlorotic streak caulimovirus

<400> SEQUENCE: 83

acagagggat ttctctgaag atcatgtttg ccagctatgc gaacaatcat cgggagatct     60

tgagccaatc aaagaggagt gatgtagacc taaagcaata atggagccat gacgtaaggg    120

cttacgccat tacgaaataa ttaaaggctg atgtgacctg tcggtctctc agaaccttta    180

ctttttatat ttggcgtgta tttttaaatt tccacggcaa tgacgatgtg acctgtgcat    240
```

ccgctttgcc tataaataag ttttagtttg tattgatcga cacgatcgag aagacacggc 300
catttggacg atcatttgag agtctaaaag aacgagtctt gtaatatgtt tt 352

<210> SEQ ID NO 84
<211> LENGTH: 1648
<212> TYPE: DNA
<213> ORGANISM: Sorghum bicolor

<400> SEQUENCE: 84
cactcgcaca tctcatggtg tcccaagaac ggcaagagcc agcactgcct ctgcctagca 60
acagcagcag cgccaagcga gcagccgcgt ccatggacgc cagcagcccg gccccgccgc 120
tcctcctccg cgcccccact cccagtccca gcattgacct ccccgctgcc gctggcaagg 180
ccgcggccgt gttcgacctg cggcgggagc ccaagatccc ggcgccattc ctgtggccgc 240
acgaggaggc gcgcccgacc tcggccgcgg agctggaggt tccggtggtg gacgtgggcg 300
tgctgcgcaa tggcgaccgc gcggggctgc ggcgcgccgc ggcgcaggtg gcctcggcgt 360
gcgcgacgca cgggttcttc caggtgtgcg ggcacggcgt ggacgcggcc ctggggcgcg 420
ccgcgctgga cggcgccagc gacttcttcc ggctgccgct ggccgacaag cagcgcgccc 480
ggcgcgtccc cggcaccgtg tccgggtaca cgagcgcgca cgccgaccgg ttcgcgtcca 540
agctcccctg gaaggagacc ctgtccttcg gcttccacga cggcgccgcg tcgcccgtcg 600
tcgtggacta cttcaccggc accctcggcc aagatttcga gccaatgggg cgggtgtacc 660
agaggtactg cgagaagatg aaggagctgt cgctgacgat catggagctg ctggagctga 720
gcctgggcgt ggagcgcggc tactaccggg agttcttcga ggacagccgc tccatcatgc 780
ggtgcaacta ctacccgccg tgcccggagc cggagcgcac gctgggcacg ggcccgcact 840
gcgaccctac ggcgctgacc atcctcctgc aggacgacgt cggcgggctg gaggtgctgg 900
tggacggcga gtggcgcccc gtccggcccg tcccaggcgc catggtcatc aacatcggcg 960
acaccttcat ggcgctgtcg aacgggcggt acaagagctg cctgcaccgc gcggtggtga 1020
accagcggca ggagcggcgg tcgctggcct tcttcctgtg cccgcgcgag gaccgggtgg 1080
tgcggccgcc ggccagcagc gccacgccgc ggcagtaccc ggacttcacc tgggccgacc 1140
tcatgcgctt cacgcagcgc cactaccgcg ccgacacccg cacgctggac gccttcaccc 1200
gctggctctc ccacggccca gtcccagccc aggaggcggc ggctccctgc acctagcgag 1260
cgagcgagcc gggccaaaca aacaaggggc aaaggccatc tctttcgccg gggcccgcgc 1320
gcggggttcg cccacgtgcg cgcccaggtg ggcgctggcc gcgggcaggt ggcggacatg 1380
tggcctgcgg gccccgcgcc gccttcccat ttttggacgc tgccgcgcat gccgcatgcg 1440
tgcgtcgacg gccctactac ttctactact gctactgcga ctactagtgt acatacgcaa 1500
aaatacatat atacgtattt tctatatata tatatataag caaggcggcc ccccggtgac 1560
cttttctttg tttttgtcga caactgtgtt ttgatcccat tctagctgtt ctatggacca 1620
tggatggttc gttcaatgtt tgtacgta 1648

<210> SEQ ID NO 85
<211> LENGTH: 1242
<212> TYPE: DNA
<213> ORGANISM: Sorghum bicolor

<400> SEQUENCE: 85
atggtgtccc aagaacggca agagccagca ctgcctctgc ctagcaacag cagcagcgcc 60
aagcgagcag ccgcgtccat ggacgccagc agcccggccc cgccgctcct cctccgcgcc 120

```
cccactccca gtcccagcat tgacctcccc gctgccgctg gcaaggccgc ggccgtgttc    180

gacctgcggc gggagcccaa gatcccggcg ccattcctgt ggccgcacga ggaggcgcgc    240

ccgacctcgg ccgcggagct ggaggttccg gtggtggacg tgggcgtgct gcgcaatggc    300

gaccgcgcgg ggctgcggcg cgccgcggcg caggtggcct cggcgtgcgc gacgcacggg    360

ttcttccagg tgtgcgggca cggcgtggac gcggccctgg ggcgcgccgc gctggacggc    420

gccagcgact tcttccggct gccgctggcc gacaagcagc gcgcccggcg cgtccccggc    480

accgtgtccg ggtacacgag cgcgcacgcc gaccggttcg cgtccaagct cccctggaag    540

gagaccctgt ccttcggctt ccacgacggc gccgcgtcgc ccgtcgtcgt ggactacttc    600

accggcaccc tcggccaaga tttcgagcca atggggcggg tgtaccagag gtactgcgag    660

aagatgaagg agctgtcgct gacgatcatg gagctgctgg agctgagcct gggcgtggag    720

cgcggctact accgggagtt cttcgaggac agccgctcca tcatgcggtg caactactac    780

ccgccgtgcc cggagccgga gcgcacgctg ggcacgggcc cgcactgcga ccctacggcg    840

ctgaccatcc tcctgcagga cgacgtcggc gggctggagg tgctggtgga cggcgagtgg    900

cgccccgtcc ggcccgtccc aggcgccatg gtcatcaaca tcggcgacac cttcatggcg    960

ctgtcgaacg ggcggtacaa gagctgcctg caccgcgcgg tggtgaacca gcggcaggag   1020

cggcggtcgc tggccttctt cctgtgcccg cgcgaggacc gggtggtgcg gccgccggcc   1080

agcagcgcca cgccgcggca gtacccggac ttcacctggg ccgacctcat gcgcttcacg   1140

cagcgccact accgcgccga cacccgcacg ctggacgcct tcacccgctg gctctcccac   1200

ggcccagtcc cagcccagga ggcggcggct ccctgcacct ag                      1242
```

<210> SEQ ID NO 86
<211> LENGTH: 413
<212> TYPE: PRT
<213> ORGANISM: Sorghum bicolor

<400> SEQUENCE: 86

```
Met Val Ser Gln Glu Arg Gln Glu Pro Ala Leu Pro Leu Pro Ser Asn
1               5                   10                  15

Ser Ser Ser Ala Lys Arg Ala Ala Ala Ser Met Asp Ala Ser Ser Pro
            20                  25                  30

Ala Pro Pro Leu Leu Leu Arg Ala Pro Thr Pro Ser Pro Ser Ile Asp
        35                  40                  45

Leu Pro Ala Ala Ala Gly Lys Ala Ala Ala Val Phe Asp Leu Arg Arg
    50                  55                  60

Glu Pro Lys Ile Pro Ala Pro Phe Leu Trp Pro His Glu Glu Ala Arg
65                  70                  75                  80

Pro Thr Ser Ala Ala Glu Leu Glu Val Pro Val Val Asp Val Gly Val
                85                  90                  95

Leu Arg Asn Gly Asp Arg Ala Gly Leu Arg Arg Ala Ala Ala Gln Val
            100                 105                 110

Ala Ser Ala Cys Ala Thr His Gly Phe Phe Gln Val Cys Gly His Gly
        115                 120                 125

Val Asp Ala Ala Leu Gly Arg Ala Ala Leu Asp Gly Ala Ser Asp Phe
    130                 135                 140

Phe Arg Leu Pro Leu Ala Asp Lys Gln Arg Ala Arg Arg Val Pro Gly
145                 150                 155                 160

Thr Val Ser Gly Tyr Thr Ser Ala His Ala Asp Arg Phe Ala Ser Lys
                165                 170                 175
```

```
Leu Pro Trp Lys Glu Thr Leu Ser Phe Gly Phe His Asp Gly Ala Ala
            180                 185                 190

Ser Pro Val Val Val Asp Tyr Phe Thr Gly Thr Leu Gly Gln Asp Phe
        195                 200                 205

Glu Pro Met Gly Arg Val Tyr Gln Arg Tyr Cys Glu Lys Met Lys Glu
    210                 215                 220

Leu Ser Leu Thr Ile Met Glu Leu Leu Glu Leu Ser Leu Gly Val Glu
225                 230                 235                 240

Arg Gly Tyr Tyr Arg Glu Phe Phe Glu Asp Ser Arg Ser Ile Met Arg
                245                 250                 255

Cys Asn Tyr Tyr Pro Pro Cys Pro Glu Pro Glu Arg Thr Leu Gly Thr
            260                 265                 270

Gly Pro His Cys Asp Pro Thr Ala Leu Thr Ile Leu Leu Gln Asp Asp
        275                 280                 285

Val Gly Gly Leu Glu Val Leu Val Asp Gly Glu Trp Arg Pro Val Arg
    290                 295                 300

Pro Val Pro Gly Ala Met Val Ile Asn Ile Gly Asp Thr Phe Met Ala
305                 310                 315                 320

Leu Ser Asn Gly Arg Tyr Lys Ser Cys Leu His Arg Ala Val Val Asn
                325                 330                 335

Gln Arg Gln Glu Arg Arg Ser Leu Ala Phe Phe Leu Cys Pro Arg Glu
            340                 345                 350

Asp Arg Val Val Arg Pro Pro Ala Ser Ser Ala Thr Pro Arg Gln Tyr
        355                 360                 365

Pro Asp Phe Thr Trp Ala Asp Leu Met Arg Phe Thr Gln Arg His Tyr
    370                 375                 380

Arg Ala Asp Thr Arg Thr Leu Asp Ala Phe Thr Arg Trp Leu Ser His
385                 390                 395                 400

Gly Pro Val Pro Ala Gln Glu Ala Ala Ala Pro Cys Thr
                405                 410


<210> SEQ ID NO 87
<211> LENGTH: 12906
<212> TYPE: DNA
<213> ORGANISM: Sorghum bicolor

<400> SEQUENCE: 87

cactcgcaca tctcatggtg tcccaagaac ggcaagagcc agcactgcct ctgcctagca      60

acagcagcag cgccaagcga gcagccgcgt ccatggacgc cagcagcccg gccccgccgc     120

tcctcctccg cgcccccact cccagtccca gcattgacct ccccgctgcc gctggcaagg     180

ccgcggccgt gttcgacctg cggcgggagc ccaagatccc ggcgccattc ctgtggccgc     240

acgaggaggc gcgcccgacc tcggccgcgg agctggaggt tccggtggtg gacgtgggcg     300

tgctgcgcaa tggcgaccgc gcggggctgc ggcgcgccgc ggcgcaggtg gcctcggcgt     360

gcgcgacgca cgggttcttc caggtgtgcg ggcacggcgt ggacgcggcc ctggggcgcg     420

ccgcgctgga cggcgccagc gacttcttcc ggctgccgct ggccgacaag cagcgcgccc     480

ggcgcgtccc cggcaccgtg tccgggtaca cgagcgcgca cgccgaccgg ttcgcgtcca     540

agctcccctg gaaggagacc ctgtccttcg gcttccacga cggcgccgcg tcgcccgtcg     600

tcgtggacta cttcaccggc accctcggcc aagatttcga gccaatgggg taagcgaagc     660

accgatttac atttaccgcg cgtcggcccc tgaggcctgg gtcttagtct tagcactgca     720

tatacggtcg gtagctctgg atatgatacg tatatatgaa accccgttcc aatcccatgc     780
```

```
acggtgtaca caggcgggtg taccagaggt actgcgagaa gatgaaggag ctgtcgctga    840
cgatcatgga gctgctggag ctgagcctgg gcgtggagcg cggctactac cgggagttct    900
tcgaggacag ccgctccatc atgcggtgca actactaccc gccgtgcccg gagccggagc    960
gcacgctggg cacgggcccg cactgcgacc ctacggcgct gaccatcctc ctgcaggacg   1020
acgtcggcgg gctggaggtg ctggtggacg gcgagtggcg ccccgtccgg cccgtcccag   1080
gcgccatggt catcaacatc ggcgacacct tcatggtaac ccctgctctg tttttcttg   1140
tcctcctctt gtcctgtgtg tgtgtatatt cacttctctc tgttttttg ccccgaatcc   1200
tagtggacct aactggacgg attacagcac gcacacgtag gcatgtcatg tagcagcagt   1260
ctgcagcact gtagtactta gcgatgcaat agagacatgc gttccagtcg gttccatctc   1320
ggtgggctac agctacagtc ctacacggac gcggctcgta gtcgtaggga cgggcgcgtt   1380
ctctgtatcc acacacggct gcgcccaggc cgaggcttcc gccgcgggaa agttgcgaca   1440
acagaacggg gtttgtgccg ttggagcgtt gcggagaggc agaggcttgg ggggacgggg   1500
gcgcgatacg ctgcgatggg tgggtgaccg aggcgacgct ttcggcgggg gcccgggcct   1560
gcccaggtgc gcgcggcctc gtcgccttcc cctgtttttt tgatgccgcc gctcggtcct   1620
cggtgttctg gctccgcccg cccgctcgct gggtgcccat cccatctgat ccgatccgct   1680
ccgctccgcg gtggcggtcc tatgcgatgc cgccgcacga gcgcgggggg ccgcccgtgg   1740
aggagtagaa agtggtacaa ggttggttgg aacttggaat tgtgggggt tactgctgct   1800
ggtggctgct gctttgcaac ttgccaggct gctgcctgtt gcccccccgcg ttttctagcc   1860
gtttccgctc gcgatccggc acgcggcgcc cacaccgggg ctccagctcg gccccttggc   1920
cgtgtaggta gcaggcactt gcatctgtcc gttcgacacg atgattcttg tgcactgtgt   1980
acgtatgtac taacccttc tggtatgatg tacgcatggc atgcaggcgc tgtcgaacgg   2040
gcggtacaag agctgcctgc accgcgcggt ggtgaaccag cggcaggagc ggcggtcgct   2100
ggccttcttc ctgtgcccgc gcgaggaccg ggtggtgcgg ccgccggcca gcagcgccac   2160
gccgcggcag tacccggact tcacctgggc cgacctcatg cgcttcacgc agcgccacta   2220
ccgcgccgac acccgcacgc tggacgcctt cacccgctgg ctctcccacg gcccagtccc   2280
agcccaggag gcggcggctc cctgcaccta gcgagcgagc gagccgggcc aaacaaacaa   2340
ggggcaaagg ccatctcttt cgccggggcc cgcgcgcggg gttcgcccac gtgcgcgccc   2400
aggtgggcgc tggccgcggg caggtggcgg acatgtggcc tgcgggcccc gcgccgcctt   2460
cccatttttg gacgctgccg cgcatgccgc atgcgtgcgt cgacggccct actacttcta   2520
ctactgctac tgcgactact agtgtacata cgcaaaaata catatatacg tattttctat   2580
atatatatat ataagcaagg cggccccccg gtgacctttt ctttgttttt gtcgacaact   2640
gtgttttgat cccattctag ctgttctatg gaccatggat ggttcgttca atgtttgtac   2700
gtactccacg taaccaaact actctagtgg actagtagat cgggctcatg tgatgaaact   2760
ggaccgacgc ggacgtcacg tgcgtcaccc gcgtctggta gcggtagcgc acgagcgccg   2820
aatgtttcct gggcccgcaa gagaatcgct tctcatctcc tctcaccatg aatggggaaa   2880
aatgctgcgt cgaaagttcc agacgtttcc aaattccaaa cggttttgtg gcgtccgatc   2940
catggggcgc cccaaacttc caagacgttt tcaggttcca aatcttcgtg ctccacatca   3000
ccttcttccc agattcattt gcctcgtcgc ttgctctcct gtgttattca cgggtcccac   3060
tgttgccccg tctgcgagaa agaaatttat tagagttgaa gcattcgaca tttcgactga   3120
```

-continued

```
ctgattgtta gtatcactaa attttgtgca catgtttctt tggtcattca tctctggata   3180
ttttttttag ataatggata taaatatcgg gcctctacat ctgaggaagt acacagccaa   3240
ttattttcat ctctggacat gggacgatgg aagaggcaga tagatttagg agacccttca   3300
attcagaatt tcaggtgcac aaggcctgcc tggcttgccc ggattcttgt ttcggacatg   3360
accaactagg ccgcactact tgcactgata gctggagaaa aaacaaaact ttgcaaacag   3420
caggattatc tacaagggaa actccatcca cgtgaaccag catttcaggg agagatgcga   3480
caaaaaaaaa gaggcggcaa caaaaaaatc ttactgcaat tttatctctg cattgaacct   3540
cttccaacca tgccgcatcc tgtactgttt tgtatctttc ccggtggtcc gttgcgttct   3600
cacgcagttg ataacatgca gtcacgcacc accgaatcca gtgtactagg ggtagtgact   3660
tgtcacgcgg aacaacaggt cggtagcacc aagcaagtcg ctgtagactt gggcgtttaa   3720
caacgacttg cacaacagtt caaatatagc atatgcaatt atgcacaaga ttgttcgact   3780
gctatccgac aaactgaaga agctgcccaa ttgaacagaa tgtaccagtg atttccagca   3840
cactatctta cagcagcgtt gagaatgaaa caacaaatgg gggaaaacag atgtgtatta   3900
ttctacagtt acaccaaaga gtttgtcctt tcagcatcaa caagaatcat atgcatatct   3960
agtgacaaaa attcctctaa ttttacccta cttggtaaca gttctcttca acacatatat   4020
ttcacgtgct tgcatcgagt tccttgggcc gccacatcga cttctcgacg caaagcaagc   4080
cctcgttgcc cttggtgtag gtcattcgca cctcccactg cagggacttg gccatgcttt   4140
ccagttcgtt tattgtgtcc gcagtgtccc tcacaatcag tttgccttgg ggcctcagta   4200
cacgatcaac ctcggcaaaa actgccatca atttgcatct gtaaacaagc aacacagatt   4260
tagcatctgt aaacaccaca ggtttcattg caagaagcat aaagcatgca aacatgctac   4320
ttgtacatgt caaagaaaca tgtcaaactc aaacacatga aaatcattat tattgttttc   4380
ttgctgaact gatcacatta gttggtttca atttctgagt tccactagta atctatacca   4440
gaaggataga ataatgtcaa gaacaagaga tacaaacctc tttgtgagct ttgagaatag   4500
atggtccgcg tgcagaaggt cataagttct tgggtaagtg ctcaaagact cgcaccagtc   4560
atggtacata ccaaacaaac cacgctcgta aatgatgggc agtgtgtctg gtgaatcaat   4620
cggcacaata ttcatgaccc agaccttttg gtccctcaga gctgcagcaa aactgccatg   4680
caacgatgta aagcattagt aaaaatattg ggttttttaa accaaaacca agaaagataa   4740
ttcctccagc ttaactgaaa gaaagaaaga aaaaaactgc ttaatgactt atggtggaca   4800
agttgcctgt tatgttttat gatagctatg tgccagcttg gctaactggt agttatgtag   4860
tgtgatctga attaccaaaa aagagaagaa aaaaaaatca tgcccaagaa actgagaaag   4920
acacccattt acttaccctc catacacagc tctcatgtcc attacatttc tcactttgga   4980
ccagtcaatt cccatgccat tcacatacga tttacttaca accctttttcc agtgagcatt   5040
atctgcctcg aaatcttcat ttgcaggctt tccatagacc ccaaccttgg aaccatcaat   5100
ccagaaagga gtcttctcaa gcctttgtgg ccaaaactct ggccattttg accctcgaac   5160
tttcgagcca acaggcagtt tgtgcatgca tgcttccaaa ggtacattcc tgcaaatcaa   5220
aagattgtgt aagcaaagca gaggaagcac ttcgccgcat tgaaaatacg ttcttctcaa   5280
agaaacaaaa ccataccaag ctgcatctgc atcatcagat tccttgcaca atggtgggtt   5340
gttttcggat cttttctcat agcaaatgtt gtccattggt ttctgaaata tgaccatacc   5400
aacttgattt aacttatcct tagtcttgtt gaccatcttc cagcacatgg actttgtcaa   5460
agtggacatc gctgaaaaga ttaaggggtc atatgttatg atagaaataa aattcaattt   5520
```

```
tgcactgttg gtacatagca tctgttttga acaaatgcaa tccttcctta tccatgaaag   5580
aagttaaccc ctgatactta ggattattca gtactttcac tcatgaactg ctgaatttgt   5640
tctgccagta gttgctatac tagaaatgtt cagtgtacca aacataaatt tggtacgggt   5700
tccttattaa agatgggagg ctgtatggta tttcgacgta acaaatcaag ttagcagcta   5760
ccctacttat ggatatacac ttctcaaaat gaatatacat agttttgata ggtgacatta   5820
attaatataa gaacttcatg cagttagggt gaaactaaac taagcagtta cggaaatacc   5880
attccaaatc tcaacatcct ctgggagctt ttggtaaaca ggagtggcag accagacaaa   5940
gtaaccacca gggcgtaaca agcggttcaa ttccagcaaa agcatgccac ctaaaaggag   6000
tcagtaataa gattcagttc tatagcaaat caataaatga aaggaagaca tgtcaccaac   6060
aagacaaacc ttcaatgtgc caagggaccc tgcagcgagc gcaatgaatg acatcaaaga   6120
ctctgctggg gtatggaagt ctcttggtgc ccatcacagc tgatattgct ggaattcccc   6180
tttctaatgc aaattgtact tgagcttcat gctcatcttt cggagcaaaa gacatggtaa   6240
gcacatctct atcaaacatg tagcctccaa agctggcaac tccacaaccg acatctagaa   6300
tgacgcggct tcgtttgccc catgcaatat caggcagtgc ctgtgaatga cagtttaatc   6360
agcatatgat gaaagcaagt gtgataatat caagttcaaa gatgcaacat gaaactttca   6420
taatcatgga cagtactaag cttgcttgat agattaatgt atggatgaga ctaaaaaaaa   6480
ggaaagttgt atccatcaga acgagaggct gaaaacacat ggctggctgt gaaagcctga   6540
tgtcgtttag tctagcataa acaaactgtc ctcagcatgt agatttccat agggtggcat   6600
ttgacaaatt atgattgtgg actagcgaat caatcactga ttctcaaaag tgtgagacag   6660
atgagttcaa gtctaagggg tgactaatat gggatgctgg gatgatgatg atgatatata   6720
cctgctgaat agtatcaata tagtggaggg caccattctt gaactgagtc ccaccccag    6780
ggaacaggag gtagtcacct gatactttaa cccaattttg atgtcccttg tactctgcga   6840
gcctagtgtg aggaacattg ctgtaccata cctgcaaaaa gcagcacaag atggtaataa   6900
gtaaacagag atcttggtca gctaaagatg attcagtgtc gtacaattta gaatagacag   6960
aatcaccttg tccctgctcc ttggccactc aattgggcgt ttatatcctt ctgggagtgg   7020
aacaaggcag gtaggaggct cctcagggca atgcctctca cgatgttcat aatgtttagt   7080
agttcgaagc ttcttgatag ccttctcgtt gtcaaggcaa ggtatgtaat ctgtcgaggc   7140
actgctatta catagtttcc aggaatagct agtcgcatca cctgaagact ttgatgacgc   7200
ttggacttcc ttttcattct tggactctgc agcctgtgtg gggaatgaac cattctgggt   7260
atttgactcc ttcagaagct ctgattgggc cccatcagga aatacctcgt tggagtttga   7320
gctctgatcc ttctctccat tttcttccac cttctcttct atctgaggtt gctcctcctg   7380
agtggcatca ccttcaggct tctcttcttg atcatccttg ctctctccat caggtttttc   7440
atcaccactc tcatttgtga tttcatcatc tttcttctcc ccactcttct ccccgtcacc   7500
atcgttcttc atgtcatctg accgcccttc tgattttcca tttgcatcat caaacatatc   7560
cttggtctca gctttctctg tcggcacttc cggctccttc tcttcaggct tctcctctgg   7620
cttctcagtg aacttctctt ccatcgtggc atccttgtta ttcggctcct ccggcatcgt   7680
ggcatcattg ttgtcggtgt cctcaaattt ctcagaacct tcaccagcat tgtcctgtga   7740
ggccccaaaa ttgacaggcg caggctgctg cttcaccacc ggcttcttat tcgaggagat   7800
ctccagcggg aagacagtgg acgaggtcat catccacgcg ccgaccaggc agagcgccac   7860
```

aaagacgacg accgtggtgg tcgtgcagaa cgacgacgac gtcgaggacg gccggcggcc 7920
gtccatcttc ccacctcggc caaatgccat tagtgcctgg cgaacatgta ccagagcacc 7980
gaccttcacg cgatttatct ccaccaacta ctgctggacc aagaacccccc aaaaaaatcg 8040
cacctttgtc tgctttgtgc tgctacagcc gcgcggcacc tgaagcaaac cacaaaaaaa 8100
acttaaatcg ccgcggacat aaatcaaggt gctggatcta aagaacaaac gctggatcta 8160
ctcaagcaac aacggaagga agatccgcta ttggtgctag tattagcttc ttgtttccta 8220
gtactacagc ggctctttcc cagtataaga acacgggaaa acgcggagaa atccccccttc 8280
gtggccaaac atggaaagaa aattagtaaa gcgtgtgctt taaaaccccc tcgttctgtt 8340
ccttccgcgg agagctaccg catcttccaa ttgagctggt tctcagctgg gcgcaaaacg 8400
cgcactaatc aatgtccgat tccatccaca aagaaaaaaa agacgggaac agctaatcca 8460
gcagctcgct cgctagctag ctagctcatc ggcggaagga cggaaccagc tttgctggat 8520
ccaggacagc aagagtgtgc aaggagaaag aacggagcag caatgcggat tgcggaggcg 8580
gtggattggt acctcgccgg aaccgaccgg agtggtcgcg gtggccctcc gcgcggatct 8640
cgaagaggag cgaggaaggg gaaggcggat gcgcgtcctt gggttctctg ccaccgcact 8700
gggcctcgcc gcgttataaa ggcgggcggg cgggcgggca gcgcagtgtg agtggagtgc 8760
aatctgttgt gtagtgtgtg aagaggcgga agcggaagcg gaggagatgg gttcgcatta 8820
gacgaccgta cgtaattata cgctatacta gtacttgggt tagattactc gggagatctt 8880
ggccaaaatg tccggtctga gtgtttggta gttttatgga tttgcccttt taagatgttg 8940
gtatttctcc gggagcttag aaagaagaaa tggcgatgct ttaggccttg tttagatgcg 9000
aaaaaaattt ggatttcgct actgtggcat ttttatttgt ttgtagcaaa tattgtccaa 9060
acacggacta actaagattc atctcgcgat ttacagttaa actgtacaat tagtttttat 9120
tttcatttat atttaatgtt tcatggatgt gtcgaaagat acgatatgat agaaaatttt 9180
gaaaactttt tagttattga ggttaactaa acaatgcctt aattgagaat ttactcgagc 9240
aaaaagagtt aggtcagtct cagtggagag tttcatggtg ttgtttccaa gactgccata 9300
tcatgtgaaa tgaaatgaaa cttggttgaa acactcactc tcaatggaga gtttcatttt 9360
atagtttcat gggcatttaa tttcaatact catagagagt tgatatcgtg ccaactcatt 9420
tcttctctct cttcttaaat acacagtcat atcatcaaaa aaaatcctat gtagcaacat 9480
atttaatgca aataaaactc atatggtgga ctgtaggagt agcattaggc caagggcaca 9540
cacacggtca cggtgtgagt gcgacggtgc gagtgggccc gcggcggtag taagtgcgtg 9600
cgcgcccggc gcccccctcc gcggcgacga cgcagcggca gcgcgtcgtc cagtgcaccg 9660
tctgctgttc ggcgctgcgg gtcctccgcg ccacggcgca gtgaaccggg cgcgtgcatc 9720
ccgggagcgg cggcttggca ctcccctgct tgtcggtggc ggccgtcggc atcgctcggc 9780
cccggagcgt cacgaggctg ctgattggga gcgagagcga gtagtggggc tggttgggga 9840
caatcccatt cccacccggc ccaccaggct gggactggcc cactagtcac tagtgggtgg 9900
ctcatgggtg tgggtgggct ggctaatgcc gcctgcccaa caaccaaccc aacccctgtg 9960
gacgctggta ccggtagttg ccgcgccatg gtggactgct gccgcctgat gcctttgcct 10020
gccacgctcc acgagttgag gcgcaccaaa ctgtgctgtg ctcctgattt gtgctaatcg 10080
gccgacgcgt accattcttt ctttctttcg tctacgcgca gagaggccgg ttgactgttt 10140
cttcgttgga gggccatgtt gactcgtact aataataaaa ataataatac taggttgact 10200
ttttcaattc caacgcagca gtgcaaagct gcccacctat gagcacaggt cctttttttaa 10260

```
ctccgttttt gtacgtacac acgtactgtc cagcctgtgt ctaataatct taccaaaaac  10320
ctgtcatctc actatcaacc aatcaggctc tccgcctgtt cgtcgaggaa cagcagttgt  10380
tttccctact ccaacataga gtacactatg gacgcacatt accatgccag cttgagctta  10440
gcattgccca ccgttggata actgccatgc cattctcagg ccctgtttag ttcccatcta  10500
aaaattttc atccattcca tcgaatcttt ggacacatgc atggaacatt aaatgtagat  10560
aaaaaaataa actaattaca cagtttagtt gagaatcgcg agacgaatct tttaagtcta  10620
gttactccat aattagcctt aagtgctaca gtaatccaca tatactaatg acagattaat  10680
tatgcttaat aaatttgtct tacagtttcc tgacgagcta tgtaatttgt tttttatta  10740
gtttctaaaa acccctcccg acatccttcc gacatatccg atgtgacaac caaaaaattt  10800
tcatcttcaa tctaaacagg ccctcactct catcatctca tgccggggca gcaggtccgt  10860
cgtcaggtct gtcgtcccgt cccgtgccgt ctgaagcaac aggcgagaga aacgccgttc  10920
catcggtttg ccgagcgtgc agaggataga gctatactcg atccggagag gattgtgaaa  10980
cgaagcacgg ttaagcagtg ccgcgcacgt gctgctctgc tcctggatcc gatccagatc  11040
gactcggggc gtctcggcct cagcggcgat ggcaatcatc gcgcgcgctg ctggagctgg  11100
acgttttcgt cttgcattgc aggaggcgga acagaacgga gaaagccacg gcgcgctttg  11160
ccgacgccac gcgctgacac gagggacccg ttcagcggcc agcacgcagc ctaatcatgc  11220
ctgtcggggg gagctcatcc gttcctgaat ttgggtcatg ctccagtatc aggtattcag  11280
gtactagtac tcctgagcca tgtgctgcga caaaaaagcg aggctcctgt agtagagcct  11340
tgtttactta caaaattttt tacattctca gttatattaa atcttgtgac acatgcataa  11400
agcattaaat atacataaaa gaaataatta tttacacagt tacttataat ttgcgaaacg  11460
aatcttttaa gactggttag tttatgatta gataatattt attaaataca aatgaaagta  11520
atattattta tattttgcaa aaagtaaata agacctaggt agctaggcca acgtgagcat  11580
gtcggacccg gaccggttcg ttctacggcg cgtcccgcaa acctgcagcc aggtagtagt  11640
agtacaccgt gcacgggaga ggtgcgccat gcatgctcgg gcaaaagatc atagagaaag  11700
gtgcagcgtt tcagttgcac acctgaccga gtgacgcctc gccttgtttg gctttgttcc  11760
caaaattttt taaaattcct catcacatta aatctttgaa cgaatatatg gagcattaaa  11820
tataaataaa agaaataatt aatcatacaa tttgtctgta atttgcgaga cgaatctttt  11880
gagcctagtt agtttataat taaataatat ttgttaaata caaacgaaaa tgctacgtta  11940
gccaaaacta aaatttttct ccaaacgtga cccagcacct tccgatcaat catcactcag  12000
cgggtcacgt cagaagatca gatggacctt gccgtccggg cctgtctctc ggcctcctcc  12060
ccatctggaa cgaacagagg tccagtcctg tttcgagtcg agctgagtcg atcagatggg  12120
cctaaatagg ccgaagacgt aggcaaaggg cccgctgatt tatctgattc ttctaggacc  12180
gtgcatgcgc ggatgggcct aggtggaaac ccaacagatg tgaggcttca aagaggaaga  12240
agtccgttac acatggagag ttagtctata atgggataat atttaccaca aacaaataaa  12300
aatactacag tagcgaaatc caaaattttt cacatctaaa caaggcccta gatgttttgt  12360
cagtgccaga ccagagaaaa tctcgtcttc tgctgtcaat agctttgatg attcctggcg  12420
gcagaggtaa agcttgcctg ggccttgttt agttccgaaa agtgaaaagt tttcggtact  12480
gtagcacttt tgtttgttcg tgacaaatat catccaatta tggactaact agaattaaaa  12540
gattcgtctc gtgatctaca gctaaactgt gtaattagtt tttgttttcg tctatattta  12600
```

```
atgtttcatg catgtgccac aagattcgat gtgacggaga attttgaaaa tttttttggtt  12660

ttcagagtga actaaacaag gcccagatgt aattgaccat gccatcgagc gcgagttgac  12720

tagagtgagt cggccctgat ggttaagtag tgcagactgc caagtggaca accgtctatc  12780

aactttgcag agtggggcga atgcactgag gatgttggag aggggcaagc caaggtaaac  12840

ttgaggaaag atgcttgttg acactgtagt atgtgaacaa tcctgtttaa ttttgtgtcc  12900

tcgacg                                                              12906
```

<210> SEQ ID NO 88
<211> LENGTH: 1790
<212> TYPE: DNA
<213> ORGANISM: Setaria italica

<400> SEQUENCE: 88

```
tctcatggtg tcccaagcac agcaagagcc agctctgcct cacagcagca gcaccgccaa     60

gcgcgcagcc gcgtcactca tggacgcccg cccggcccag cctctcctcc tccgcgcccc    120

gactcccagc attgacctcc ccgcgtccaa gccggacagg gccgccgcgg cggccggcaa    180

ggccgccgcc gcctccgtgt tcgacctgcg gcgggagccc aagatcccgg cgccattcgt    240

gtggccgcac gacgacgcgc ggccggcgtc ggcggcggag ctggacgtgc cgttggtgga    300

cgtgggcgtg ctgcgcaatg gcgaccgcgc ggggctgcgg cgcgctgcgg cgcaggtggc    360

cgcggcgtgc gcgacgcacg ggttcttcca ggtgtgcggg cacggcgtgg gcgcggacct    420

ggcgcgcgcg gcgctggacg gcgccagtga cttcttccgg ctgccgctgg cggagaagca    480

gcgcgcccgg cgcgtcccgg ggaccgtgtc cgggtacacg agcgcgcacg ccgaccggtt    540

cgcgtccaag ctcccctgga aggagaccct ctccttcggg ttccacgacg gcgccgcgtc    600

gcccgtcgtc gtcgactact tcgccggcac cctcgggcag gacttcgagg cagtggggcg    660

ggtgtaccag aggtactgcg aggagatgaa ggctctgtcg ctgacgatca tggagctcct    720

ggagctgagc ctgggcgtgg agcgcggcta ctaccgcgac ttcttcgagg acagccgctc    780

catcatgcgg tgcaactact acccgccgtg cccggagccg gagcgcacgc tgggcacggg    840

cccgcactgc gaccccaccg cgctgaccat cctcctccag gacgacgtcg gcgggctcga    900

ggtcctcgtc gacggcgact ggcgccccgt ccgccccgtc cccggcgcca tggtcatcaa    960

catcggcgac accttcatgg ctctgtccaa cgggcggtac aagagctgcc tgcaccgggc   1020

ggtggtgaac cagcggcagg agcggcggtc gctggccttc ttcctgtgcc cgcgcgagga   1080

ccgggtggtg cgcccgccgg ccagcggcgc cgtcggcgag gcgccccgcc gctacccgga   1140

cttcacctgg gccgacctca tgcgcttcac gcagcgccac taccgcgccg acacccgcac   1200

gctggacgcc ttcacacgct ggctctccca cggcccggcc caggacgcgc cagtggcggc   1260

ggcggcttcc acctagctag cggcgcggat ccgaccgagc ccattgacga cgccgtccct   1320

ttccgccgcc gccggggccc gcgcgggggt tcaccccacg tgcgcgccca ggtgggcgag   1380

gtggcggcct cgtggcccgc gggccccgcg ccgccttccc atttttgggc gctgccgccc   1440

cgcgcgcatg ccggatgcgt gcgtccacgg cctactgctg ctactagtgt acatatacaa   1500

acatacatat atacgtagta taaatatata agcaagcggc ccggtgcccc ttttcgtttt   1560

cttgttttgt cgatcacaat ctctggattc gatggatgga taaatgtttg tacgcatgca   1620

tgtagatggg ctcatgaaat ttcagaatct ggaacggacg aggagctcac gtgcctcttc   1680

cgtgtctggt agcggtagct gcgtgccaaa tgtctggtgg gcccaaagaa attctagtgc   1740

cacccgtccg gatccggcat ccgaaagttc ccgacggttc gacacccgaa               1790
```

<210> SEQ ID NO 89
<211> LENGTH: 1272
<212> TYPE: DNA
<213> ORGANISM: Setaria italica

<400> SEQUENCE: 89
atggtgtccc aagcacagca agagccagct ctgcctcaca gcagcagcac cgccaagcgc 60
gcagccgcgt cactcatgga cgcccgcccg gcccagcctc tcctcctccg cgccccgact 120
cccagcattg acctccccgc gtccaagccg gacagggccg ccgcggcggc cggcaaggcc 180
gccgccgcct ccgtgttcga cctgcggcgg gagcccaaga tcccggcgcc attcgtgtgg 240
ccgcacgacg acgcgcggcc ggcgtcggcg gcggagctgg acgtgccgtt ggtggacgtg 300
ggcgtgctgc gcaatggcga ccgcgcgggg ctgcggcgcg ctgcggcgca ggtggccgcg 360
gcgtgcgcga cgcacgggtt cttccaggtg tgcgggcacg gcgtgggcgc ggacctggcg 420
cgcgcggcgc tggacggcgc cagtgacttc ttccggctgc cgctggcgga gaagcagcgc 480
gcccggcgcg tcccggggac cgtgtccggg tacacgagcg cgcacgccga ccggttcgcg 540
tccaagctcc cctggaagga gaccctctcc ttcgggttcc acgacggcgc cgcgtcgccc 600
gtcgtcgtcg actacttcgc cggcaccctc gggcaggact tcgaggcagt ggggcgggtg 660
taccagaggt actgcgagga gatgaaggct ctgtcgctga cgatcatgga gctcctggag 720
ctgagcctgg gcgtggagcg cggctactac cgcgacttct tcgaggacag ccgctccatc 780
atgcggtgca actactaccc gccgtgcccg gagccggagc gcacgctggg cacgggcccg 840
cactgcgacc ccaccgcgct gaccatcctc ctccaggacg acgtcggcgg gctcgaggtc 900
ctcgtcgacg gcgactggcg ccccgtccgc cccgtccccg gcgccatggt catcaacatc 960
ggcgacacct tcatggctct gtccaacggg cggtacaaga gctgcctgca ccgggcggtg 1020
gtgaaccagc ggcaggagcg gcggtcgctg gccttcttcc tgtgcccgcg cgaggaccgg 1080
gtggtgcgcc cgccggccag cggcgccgtc ggcgaggcgc cccgccgcta cccggacttc 1140
acctgggccg acctcatgcg cttcacgcag cgccactacc gcgccgacac ccgcacgctg 1200
gacgccttca cacgctggct ctcccacggc ccggcccagg acgcgccagt ggcggcggcg 1260
gcttccacct ag 1272

<210> SEQ ID NO 90
<211> LENGTH: 423
<212> TYPE: PRT
<213> ORGANISM: Setaria italica

<400> SEQUENCE: 90

Met Val Ser Gln Ala Gln Gln Glu Pro Ala Leu Pro His Ser Ser Ser
1 5 10 15

Thr Ala Lys Arg Ala Ala Ala Ser Leu Met Asp Ala Arg Pro Ala Gln
20 25 30

Pro Leu Leu Leu Arg Ala Pro Thr Pro Ser Ile Asp Leu Pro Ala Ser
35 40 45

Lys Pro Asp Arg Ala Ala Ala Ala Ala Gly Lys Ala Ala Ala Ala Ser
50 55 60

Val Phe Asp Leu Arg Arg Glu Pro Lys Ile Pro Ala Pro Phe Val Trp
65 70 75 80

Pro His Asp Asp Ala Arg Pro Ala Ser Ala Ala Glu Leu Asp Val Pro
85 90 95

```
Leu Val Asp Val Gly Val Leu Arg Asn Gly Asp Arg Ala Gly Leu Arg
            100                 105                 110

Arg Ala Ala Ala Gln Val Ala Ala Ala Cys Ala Thr His Gly Phe Phe
        115                 120                 125

Gln Val Cys Gly His Gly Val Gly Ala Asp Leu Ala Arg Ala Ala Leu
    130                 135                 140

Asp Gly Ala Ser Asp Phe Phe Arg Leu Pro Leu Ala Glu Lys Gln Arg
145                 150                 155                 160

Ala Arg Arg Val Pro Gly Thr Val Ser Gly Tyr Thr Ser Ala His Ala
                165                 170                 175

Asp Arg Phe Ala Ser Lys Leu Pro Trp Lys Glu Thr Leu Ser Phe Gly
            180                 185                 190

Phe His Asp Gly Ala Ala Ser Pro Val Val Val Asp Tyr Phe Ala Gly
        195                 200                 205

Thr Leu Gly Gln Asp Phe Glu Ala Val Gly Arg Val Tyr Gln Arg Tyr
    210                 215                 220

Cys Glu Glu Met Lys Ala Leu Ser Leu Thr Ile Met Glu Leu Leu Glu
225                 230                 235                 240

Leu Ser Leu Gly Val Glu Arg Gly Tyr Tyr Arg Asp Phe Phe Glu Asp
                245                 250                 255

Ser Arg Ser Ile Met Arg Cys Asn Tyr Tyr Pro Pro Cys Pro Glu Pro
            260                 265                 270

Glu Arg Thr Leu Gly Thr Gly Pro His Cys Asp Pro Thr Ala Leu Thr
        275                 280                 285

Ile Leu Leu Gln Asp Asp Val Gly Gly Leu Glu Val Leu Val Asp Gly
    290                 295                 300

Asp Trp Arg Pro Val Arg Pro Val Pro Gly Ala Met Val Ile Asn Ile
305                 310                 315                 320

Gly Asp Thr Phe Met Ala Leu Ser Asn Gly Arg Tyr Lys Ser Cys Leu
                325                 330                 335

His Arg Ala Val Val Asn Gln Arg Gln Glu Arg Arg Ser Leu Ala Phe
            340                 345                 350

Phe Leu Cys Pro Arg Glu Asp Arg Val Val Arg Pro Pro Ala Ser Gly
        355                 360                 365

Ala Val Gly Glu Ala Pro Arg Arg Tyr Pro Asp Phe Thr Trp Ala Asp
    370                 375                 380

Leu Met Arg Phe Thr Gln Arg His Tyr Arg Ala Asp Thr Arg Thr Leu
385                 390                 395                 400

Asp Ala Phe Thr Arg Trp Leu Ser His Gly Pro Ala Gln Asp Ala Pro
                405                 410                 415

Val Ala Ala Ala Ala Ser Thr
            420
```

<210> SEQ ID NO 91
<211> LENGTH: 2888
<212> TYPE: DNA
<213> ORGANISM: Setaria italica

<400> SEQUENCE: 91

```
tctcatggtg tcccaagcac agcaagagcc agctctgcct cacagcagca gcaccgccaa      60

gcgcgcagcc gcgtcactca tggacgcccg cccggcccag cctctcctcc tccgcgcccc     120

gactcccagc attgacctcc ccgcgtccaa gccggacagg gccgccgcgg cggccggcaa     180

ggccgccgcc gcctccgtgt tcgacctgcg gcgggagccc aagatcccgg cgccattcgt     240
```

-continued

```
gtggccgcac gacgacgcgc ggccggcgtc ggcggcggag ctggacgtgc cgttggtgga    300
cgtgggcgtg ctgcgcaatg gcgaccgcgc ggggctgcgg cgcgctgcgg cgcaggtggc    360
cgcggcgtgc gcgacgcacg ggttcttcca ggtgtgcggg cacggcgtgg gcgcggacct    420
ggcgcgcgcg gcgctggacg gcgccagtga cttcttccgg ctgccgctgg cggagaagca    480
gcgcgcccgg cgcgtcccgg ggaccgtgtc cgggtacacg agcgcgcacg ccgaccggtt    540
cgcgtccaag ctcccctgga aggagaccct ctccttcggg ttccacgacg gcgccgcgtc    600
gcccgtcgtc gtcgactact tcgccggcac cctcgggcag gacttcgagg cagtggggta    660
agtatgtagg aatgaacttg gcacgcattg catccacatg gcgtgctgat cgaacgagct    720
gagccaaccg gcatgcacac atggcgtggc aggcgggtgt accagaggta ctgcgaggag    780
atgaaggctc tgtcgctgac gatcatggag ctcctggagc tgagcctggg cgtggagcgc    840
ggctactacc gcgacttctt cgaggacagc cgctccatca tgcggtgcaa ctactacccg    900
ccgtgcccgg agccggagcg cacgctgggc acgggcccgc actgcgaccc caccgcgctg    960
accatcctcc tccaggacga cgtcggcggg ctcgaggtcc tcgtcgacgg cgactggcgc   1020
cccgtccgcc ccgtccccgg cgccatggtc atcaacatcg gcgacacctt catggtacgg   1080
ccgccgctaa tccatccttt tgttgctctt atctcctctg gcgagtgcga gtaacgaaag   1140
cgctagctcc cctgctcctt gtcctgctct gtttcccaag tcctaatgga gctaaccggg   1200
cagactgcaa cacgcacgcg taggcatgtc acgtagccac cacttgcact gtgctgcgca   1260
gcgacgacgc aacgcggacg tgcgttcgag tcggttccat ctcggcgccg ctacacgcgg   1320
ccgcggctcc tagcctccta gggctccctg atccctatcc ccgagccctt ccgcgggaaa   1380
agttcgttgg cgacggcaga ggagagccga cgggtccgtg ccgttggagc gtggcggcag   1440
gagaggccgg gagggtgttt tgttgcgttg cgcggcggcg cggaggatgc gatggcgcgg   1500
gcgggcggcg ctttcggcgg tggcccccgc gacccacgtg cgcgcgcggt ctcgtcgcct   1560
tccctgtttt ggtgccacct ctctgtgtcc gggaatgggt tggcttagcg gcgaccgaga   1620
ccgggcggtg gtctggcctg ctcccggcgc ccatcccgcc tggtctctca tcctgctcct   1680
cctatgcgcg agggggcctg tagcggctgg agtacaagca gattggttgg gttgggttgc   1740
tgctgcttgg ctgttgcccg cccgctttct agccgtttcc gctcgccatc cggcacgcgg   1800
cgcccacgcc ggggctccag ctcggcccct ttggccgtgt gggtggcagg caccccctgca   1860
tcgtctcgtg cgtccggttt ccgcgcctgg ccccccgcct tgaggtttcc ctgtgctttt   1920
gacaagactt tcgtagatat atgtgtgtgt atgtgtgtgt gtgcgtgcgc gcgtgtgtgt   1980
atatatatat ataaataaat aacatctgtg aatgatggat tacacgtgta gctgaccggc   2040
tgattgtgtt cgcgtgtgtg tcttcgatgc attgcaggct ctgtccaacg ggcggtacaa   2100
gagctgcctg caccgggcgg tggtgaacca gcggcaggag cggcggtcgc tggccttctt   2160
cctgtgcccg cgcgaggacc gggtggtgcg cccgccggcc agcggcgccg tcggcgaggc   2220
gccccgccgc tacccggact tcacctgggc cgacctcatg cgcttcacgc agcgccacta   2280
ccgcgccgac acccgcacgc tggacgcctt cacacgctgg ctctcccacg gcccggccca   2340
ggacgcgcca gtggcggcgg cggcttccac ctagctagcg gcgcggatcc gaccgagccc   2400
attgacgacg ccgtcccttt ccgccgccgc cggggcccgc gcgggggttc accccacgtg   2460
cgcgcccagg tgggcgaggt ggcggcctcg tggcccgcgg gccccgcgcc gccttcccat   2520
ttttgggcgc tgccgccccg cgcgcatgcc ggatgcgtgc gtccacggcc tactgctgct   2580
actagtgtac atatacaaac atacatatat acgtagtata aatatataag caagcggccc   2640
```

```
ggtgcccctt ttcgttttct tgttttgtcg atcacaatct ctggattcga tggatggata   2700
aatgtttgta cgcatgcatg tagatgggct catgaaattt cagaatctgg aacggacgag   2760
gagctcacgt gcctcttccg tgtctggtag cggtagctgc gtgccaaatg tctggtgggc   2820
ccaaagaaat tctagtgcca cccgtccgga tccggcatcc gaaagttccc gacggttcga   2880
cacccgaa                                                            2888
```

<210> SEQ ID NO 92
<211> LENGTH: 1567
<212> TYPE: DNA
<213> ORGANISM: Oryza sativa

<400> SEQUENCE: 92

```
tgcccagaca gctcgccctg cacacacaca cacactcaca ctcacacacg ctctcaactc     60
actcccgctc aacacagcgc tcacttctca tctccaatct catggtggcc gagcacccca    120
cgccaccaca gccgcaccaa ccaccgccca tggactccac cgccggctct ggcattgccg    180
ccccggcggc ggcggcggtg tgcgacctga ggatggagcc caagatcccg gagccattcg    240
tgtggccgaa cggcgacgcg aggccggcgt cggcggcgga gctggacatg cccgtggtcg    300
acgtgggcgt gctccgcgac ggcgacgccg aggggctgcg ccgcgccgcg gcgcaggtgg    360
ccgccgcgtg cgccacgcac gggttcttcc aggtgtccga gcacggcgtc gacgccgctc    420
tggcgcgcgc cgcgctcgac ggcgccagcg acttcttccg cctcccgctc gccgagaagc    480
gccgcgcgcg ccgcgtcccg ggcaccgtgt ccggctacac cagcgcccac gccgaccgct    540
tcgcctccaa gctcccatgg aaggagaccc tctccttcgg cttccacgac cgcgccgccg    600
cccccgtcgt cgccgactac ttctccagca ccctcggccc cgacttcgcg ccaatgggga    660
gggtgtacca gaagtactgc gaggagatga aggagctgtc gctgacgatc atggaactcc    720
tggagctgag cctgggcgtg gagcgaggct actacaggga gttcttcgcg gacagcagct    780
caatcatgcg gtgcaactac tacccgccat gcccggagcc ggagcggacg ctcggcacgg    840
gcccgcactg cgaccccacc gccctcacca tcctcctcca ggacgacgtc ggcggcctcg    900
aggtcctcgt cgacggcgaa tggcgccccg tcagccccgt ccccggcgcc atggtcatca    960
acatcggcga caccttcatg gcgctgtcga acgggaggta taagagctgc ctgcacaggg   1020
cggtggtgaa ccagcggcgg gagcggcggt cgctggcgtt cttcctgtgc ccgcgggagg   1080
acagggtggt gcggccgccg ccgagcgccg ccacgccgca gcactacccg gacttcacct   1140
gggccgacct catgcgcttc acgcagcgcc actaccgcgc cgacacccgc acgctcgacg   1200
ccttcacgcg ctggctcgcg ccgccggccg ccgacgccgc cgcgacggcg caggtcgagg   1260
cggccagctg atcgccgaac ggaacgaaac ggaacgaaca gaagccgatt tttggcgggg   1320
cccacgccca cgtgaggccc cacgtggaca gtgggcccgg gcggaggtgg cacccacgtg   1380
gaccgcgggc cccgcgccgc cttccaattt tggaccctac cgctgtacat attcatatat   1440
tgcaagaaga agcaaaacgt acgtgtgggt tgggttgggc ttctctctat tactaaaaaa   1500
aatataatgg aacgacggat gaatggatgc ttatttattt atctaaattg aattcgaatt   1560
cggctca                                                             1567
```

<210> SEQ ID NO 93
<211> LENGTH: 1170
<212> TYPE: DNA
<213> ORGANISM: Oryza sativa

<400> SEQUENCE: 93

```
atggtggccg agcaccccac gccaccacag ccgcaccaac caccgcccat ggactccacc     60
gccggctctg gcattgccgc cccggcggcg gcggcggtgt gcgacctgag gatggagccc    120
aagatcccgg agccattcgt gtggccgaac ggcgacgcga ggccggcgtc ggcggcggag    180
ctggacatgc ccgtggtcga cgtgggcgtg ctccgcgacg gcgacgccga ggggctgcgc    240
cgcgccgcgg cgcaggtggc cgccgcgtgc gccacgcacg ggttcttcca ggtgtccgag    300
cacggcgtcg acgccgctct ggcgcgcgcc gcgctcgacg gcgccagcga cttcttccgc    360
ctcccgctcg ccgagaagcg ccgcgcgcgc cgcgtcccgg gcaccgtgtc cggctacacc    420
agcgcccacg ccgaccgctt cgcctccaag ctcccatgga aggagaccct ctccttcggc    480
ttccacgacc gcgccgccgc ccccgtcgtc gccgactact tctccagcac cctcggcccc    540
gacttcgcgc caatggggag ggtgtaccag aagtactgcg aggagatgaa ggagctgtcg    600
ctgacgatca tggaactcct ggagctgagc ctgggcgtgg agcgaggcta ctacagggag    660
ttcttcgcgg acagcagctc aatcatgcgg tgcaactact acccgccatg cccggagccg    720
gagcggacgc tcggcacggg cccgcactgc gaccccaccg ccctcaccat cctcctccag    780
gacgacgtcg gcggcctcga ggtcctcgtc gacggcgaat ggcgccccgt cagccccgtc    840
cccggcgcca tggtcatcaa catcggcgac accttcatgg cgctgtcgaa cgggaggtat    900
aagagctgcc tgcacagggc ggtggtgaac cagcggcggg agcggcggtc gctggcgttc    960
ttcctgtgcc cgcgggagga cagggtggtg cggccgccgc cgagcgccgc cacgccgcag   1020
cactacccgg acttcacctg ggccgacctc atgcgcttca cgcagcgcca ctaccgcgcc   1080
gacacccgca cgctcgacgc cttcacgcgc tggctcgcgc cgccggccgc cgacgccgcc   1140
gcgacggcgc aggtcgaggc ggccagctga                                    1170
```

<210> SEQ ID NO 94
<211> LENGTH: 389
<212> TYPE: PRT
<213> ORGANISM: Oryza sativa

<400> SEQUENCE: 94

```
Met Val Ala Glu His Pro Thr Pro Pro Gln Pro His Gln Pro Pro Pro
1               5                   10                  15

Met Asp Ser Thr Ala Gly Ser Gly Ile Ala Ala Pro Ala Ala Ala Ala
            20                  25                  30

Val Cys Asp Leu Arg Met Glu Pro Lys Ile Pro Glu Pro Phe Val Trp
        35                  40                  45

Pro Asn Gly Asp Ala Arg Pro Ala Ser Ala Ala Glu Leu Asp Met Pro
    50                  55                  60

Val Val Asp Val Gly Val Leu Arg Asp Gly Asp Ala Glu Gly Leu Arg
65                  70                  75                  80

Arg Ala Ala Ala Gln Val Ala Ala Ala Cys Ala Thr His Gly Phe Phe
                85                  90                  95

Gln Val Ser Glu His Gly Val Asp Ala Ala Leu Ala Arg Ala Ala Leu
            100                 105                 110

Asp Gly Ala Ser Asp Phe Phe Arg Leu Pro Leu Ala Glu Lys Arg Arg
        115                 120                 125

Ala Arg Arg Val Pro Gly Thr Val Ser Gly Tyr Thr Ser Ala His Ala
    130                 135                 140

Asp Arg Phe Ala Ser Lys Leu Pro Trp Lys Glu Thr Leu Ser Phe Gly
145                 150                 155                 160
```

```
Phe His Asp Arg Ala Ala Ala Pro Val Val Ala Asp Tyr Phe Ser Ser
                165                 170                 175

Thr Leu Gly Pro Asp Phe Ala Pro Met Gly Arg Val Tyr Gln Lys Tyr
            180                 185                 190

Cys Glu Glu Met Lys Glu Leu Ser Leu Thr Ile Met Glu Leu Leu Glu
        195                 200                 205

Leu Ser Leu Gly Val Glu Arg Gly Tyr Tyr Arg Glu Phe Phe Ala Asp
    210                 215                 220

Ser Ser Ser Ile Met Arg Cys Asn Tyr Tyr Pro Pro Cys Pro Glu Pro
225                 230                 235                 240

Glu Arg Thr Leu Gly Thr Gly Pro His Cys Asp Pro Thr Ala Leu Thr
                245                 250                 255

Ile Leu Leu Gln Asp Asp Val Gly Gly Leu Glu Val Leu Val Asp Gly
            260                 265                 270

Glu Trp Arg Pro Val Ser Pro Val Pro Gly Ala Met Val Ile Asn Ile
        275                 280                 285

Gly Asp Thr Phe Met Ala Leu Ser Asn Gly Arg Tyr Lys Ser Cys Leu
    290                 295                 300

His Arg Ala Val Val Asn Gln Arg Arg Glu Arg Arg Ser Leu Ala Phe
305                 310                 315                 320

Phe Leu Cys Pro Arg Glu Asp Arg Val Val Arg Pro Pro Pro Ser Ala
                325                 330                 335

Ala Thr Pro Gln His Tyr Pro Asp Phe Thr Trp Ala Asp Leu Met Arg
            340                 345                 350

Phe Thr Gln Arg His Tyr Arg Ala Asp Thr Arg Thr Leu Asp Ala Phe
        355                 360                 365

Thr Arg Trp Leu Ala Pro Pro Ala Ala Asp Ala Ala Ala Thr Ala Gln
    370                 375                 380

Val Glu Ala Ala Ser
385
```

<210> SEQ ID NO 95
<211> LENGTH: 3140
<212> TYPE: DNA
<213> ORGANISM: Oryza sativa

<400> SEQUENCE: 95

```
tgcccagaca gctcgccctg cacacacaca cacactcaca ctcacacacg ctctcaactc      60

actcccgctc aacacagcgc tcacttctca tctccaatct catggtggcc gagcacccca     120

cgccaccaca gccgcaccaa ccaccgccca tggactccac cgccggctct ggcattgccg     180

ccccggcggc ggcggcggtg tgcgacctga ggatggagcc caagatcccg gagccattcg     240

tgtggccgaa cggcgacgcg aggccggcgt cggcggcgga gctggacatg cccgtggtcg     300

acgtgggcgt gctccgcgac ggcgacgccg aggggctgcg ccgcgccgcg gcgcaggtgg     360

ccgccgcgtg cgccacgcac gggttcttcc aggtgtccga gcacggcgtc gacgccgctc     420

tggcgcgcgc cgcgctcgac ggcgccagcg acttcttccg cctcccgctc gccgagaagc     480

gccgcgcgcg ccgcgtcccg ggcaccgtgt ccggctacac cagcgcccac gccgaccgct     540

tcgcctccaa gctcccatgg aaggagaccc tctccttcgg cttccacgac cgcgccgccg     600

cccccgtcgt cgccgactac ttctccagca ccctcggccc cgacttcgcg ccaatggggt     660

aattaaaacg atggtggacg acattgcatt tcaaattcaa aacaaattca aaacacaccg     720

accgagatta tgctgaattc aaacgcgttt gtgcgcgcag gagggtgtac cagaagtact     780
```

```
gcgaggagat gaaggagctg tcgctgacga tcatggaact cctggagctg agcctgggcg    840
tggagcgagg ctactacagg gagttcttcg cggacagcag ctcaatcatg cggtgcaact    900
actacccgcc atgcccggag ccggagcgga cgctcggcac gggcccgcac tgcgacccca    960
ccgccctcac catcctcctc caggacgacg tcggcggcct cgaggtcctc gtcgacggcg   1020
aatggcgccc cgtcagcccc gtccccggcg ccatggtcat caacatcggc gacaccttca   1080
tggtaaacca tctcctattc tcctctcctc tgttctcctc tgcttcgaag caacagaaca   1140
agtaattcaa gctttttttt ctctctcgcg cgaaattgac gagaaaaata agatcgtggt   1200
aggggcgggg ctttcagctg aaagcgggaa gaaaccgacc tgacgtgatt tctctgttcc   1260
aatcacaaac aatggaatgc cccactcctc catgtgttat gatttatctc acatcttata   1320
gttaatagga gtaagtaaca agctactttt ttcatattat agttcgtttg attttttttt   1380
tttaaagttt ttttagtttt atccaaattt attgaaaaac ttagcaacgt ttataatacc   1440
aaattagtct catttagttt aatattgtat atattttgat aatatattta tgttatatta   1500
aaaatattac tatattttc tataaacatt attaaaagcc atttataata taaaatggaa   1560
ggagtaatta atatggatct cccccgacat gagaatattt tccgatggtg tgacgacgcc   1620
atgtaagctt cggtgggcct ggacggccag aggtgccaac agccacgtcc aacaacccct   1680
gggtcccccc ctaacactcc aaacagtagt gagtagtgtc tcgtcgcgtt ttagtatttg   1740
atgacaaaca aagtgtgagt tgagttagcc accaccaact tgcacacgag cacatacatt   1800
tgtgtccatt ctcgccagtc acttccatct ctagtcctaa ctcctatcta gcgatgtaag   1860
cggataattt catcatccgt atataaacct gtttgttata gttaatttcc tatataatac   1920
tataacagta tacattttaa aagaaaacaa aattaggata aacaggccct gctcctatcc   1980
atccatggca cttggaagga ccagactcgg tcatgccatg ccaagccaag atatgggtta   2040
tggaagagta gagaagagga gagatgagag ataagcatgc gttctcctcc tcgttggatg   2100
tgtattttgg agggatttgt gtagtagtag cagcggcgcc gcggggacgg atgcggatgg   2160
tggcgctttc ggtggcgttt tcccgggggg gttttggttt ggcgcttggg ggggatggca   2220
tggcgcggcg tgcggctgca cgccacacac acgcgcgcgc acgcacgtac gtcgtcgtcg   2280
ccgcgggcgg acggtagctt agggtggtgt gttccgcgcg cgggcgcgga ttgttccatg   2340
ccgatcgatt tggcgccacc ctcgccgcgg ctcttgtcgc gtcgtgcgcc tctctcgcgc   2400
ggtttgtcct tgtcgcgttg ctcagccggc gacgggggca cggacattgg cgatgtagcc   2460
ctgcacgtgt cggcctctcc gttgatgaat gatgatgtat gtatgtattt ttttttgtct   2520
gaaggaattt gtggggaatt gttgtgtgtg caggcgctgt cgaacgggag gtataagagc   2580
tgcctgcaca gggcggtggt gaaccagcgg cgggagcggc ggtcgctggc gttcttcctg   2640
tgcccgcggg aggacagggt ggtgcggccg ccgccgagcg ccgccacgcc gcagcactac   2700
ccggacttca cctgggccga cctcatgcgc ttcacgcagc gccactaccg cgccgacacc   2760
cgcacgctcg acgccttcac gcgctggctc gcgccgccgg ccgccgacgc cgccgcgacg   2820
gcgcaggtcg aggcggccag ctgatcgccg aacggaacga aacggaacga acagaagccg   2880
atttttggcg gggcccacgc ccacgtgagg ccccacgtgg acagtgggcc cgggcggagg   2940
tggcacccac gtggaccgcg ggccccgcgc cgccttccaa ttttggaccc taccgctgta   3000
catattcata tattgcaaga agaagcaaaa cgtacgtgtg ggttgggttg ggcttctctc   3060
tattactaaa aaaaatataa tggaacgacg gatgaatgga tgcttattta tttatctaaa   3120
```

ttgaattcga attcggctca 3140

<210> SEQ ID NO 96
<211> LENGTH: 1170
<212> TYPE: DNA
<213> ORGANISM: Triticum aestivum

<400> SEQUENCE: 96
atggacacca gccctgcaac tcccctgctc ctccagcctc ctgctcccag cattgacccg 60
ttcgccgcca aggcggccgt caacaagggc ggcggcgcgg caaccgcggt gtacgacctc 120
cggagggagc cgaagatccc cgccccgttc gtgtggccgc acgccgaggt gcgccccacc 180
acggcccagg agctggccgt gccggtggtg gacgtgggcg tgctgcgcaa tggcgacgcc 240
gcggggctcc gccgcgccgt ggcgcaggtg gccgcggcgt gcgccacgca cgggttcttc 300
caggtgtccg ggcacggcgt ggacgaggcc ctggcgcgcg cggcgctgga cggcgcgagc 360
ggcttcttcc ggctgccgct ggccgagaag cagcgcgcgc ggcgcgtccc ggggaccgtg 420
tccgggtaca cgagcgcgca cgccgaccgg ttcgcctcca agctcccctg gaaggagacc 480
ctctccttcg gcttccacga ccgcgccggc gccgcgcccg tcgtggtgga ctacttcacc 540
agcaccctcg ggccggacta cgagccaatg ggagggtgt accaggagta ctgcgggaag 600
atgaaggagc tgtcgctgag gatcatggag ctgctggagc tgagccaggg cgtggagaag 660
cgcgggtact accgggagtt cttcgcggac agcagctcca tcatgcggtg caactactac 720
ccgccgtgcc cggagccgga gcgcacgctg ggcacgggcc cgcactgcga ccccacggcg 780
ctcaccatcc tactgcagga cgacgtgggc gggctggagg tcctcgtcga cggcgactgg 840
cgccccgtcc gccccgtccc cggcgccatg gtcatcaaca tcggcgacac cttcatggcg 900
ctgtcgaacg ggcggtacaa gagctgcctg caccgcgcgg tggtgaaccg gcggcaggag 960
cggcggtcgc tggccttctt cctgtgcccg cgcgaggacc gcgtggtgcg gccgccgccg 1020
ggcctgagga gcccgcggcg gtacccggac ttcacctggg ctgacctcat gcgcttcacg 1080
cagcgccact accgcgccga cacgcgcacc ctcgacgcct tcacccagtg gttctcctcc 1140
tcctcctcct cggcccagga ggcggcctga 1170

<210> SEQ ID NO 97
<211> LENGTH: 389
<212> TYPE: PRT
<213> ORGANISM: Triticum aestivum

<400> SEQUENCE: 97

Met Asp Thr Ser Pro Ala Thr Pro Leu Leu Leu Gln Pro Pro Ala Pro
1 5 10 15

Ser Ile Asp Pro Phe Ala Ala Lys Ala Ala Val Asn Lys Gly Gly Gly
20 25 30

Ala Ala Thr Ala Val Tyr Asp Leu Arg Arg Glu Pro Lys Ile Pro Ala
35 40 45

Pro Phe Val Trp Pro His Ala Glu Val Arg Pro Thr Thr Ala Gln Glu
50 55 60

Leu Ala Val Pro Val Val Asp Val Gly Val Leu Arg Asn Gly Asp Ala
65 70 75 80

Ala Gly Leu Arg Arg Ala Val Ala Gln Val Ala Ala Ala Cys Ala Thr
85 90 95

His Gly Phe Phe Gln Val Ser Gly His Gly Val Asp Glu Ala Leu Ala
100 105 110

```
Arg Ala Ala Leu Asp Gly Ala Ser Gly Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Arg Ala Gly Ala Ala Pro Val Val Val
                165                 170                 175

Asp Tyr Phe Thr Ser Thr Leu Gly Pro Asp Tyr Glu Pro Met Gly Arg
            180                 185                 190

Val Tyr Gln Glu Tyr Cys Gly Lys Met Lys Glu Leu Ser Leu Arg Ile
        195                 200                 205

Met Glu Leu Leu Glu Leu Ser Gln Gly Val Glu Lys Arg Gly Tyr Tyr
    210                 215                 220

Arg Glu Phe Phe Ala Asp Ser Ser Ser Ile Met Arg Cys Asn Tyr Tyr
225                 230                 235                 240

Pro Pro Cys Pro Glu Pro Glu Arg Thr Leu Gly Thr Gly Pro His Cys
                245                 250                 255

Asp Pro Thr Ala Leu Thr Ile Leu Leu Gln Asp Asp Val Gly Gly Leu
            260                 265                 270

Glu Val Leu Val Asp Gly Asp Trp Arg Pro Val Arg Pro Val Pro Gly
        275                 280                 285

Ala Met Val Ile Asn Ile Gly Asp Thr Phe Met Ala Leu Ser Asn Gly
    290                 295                 300

Arg Tyr Lys Ser Cys Leu His Arg Ala Val Val Asn Arg Arg Gln Glu
305                 310                 315                 320

Arg Arg Ser Leu Ala Phe Phe Leu Cys Pro Arg Glu Asp Arg Val Val
                325                 330                 335

Arg Pro Pro Pro Gly Leu Arg Ser Pro Arg Arg Tyr Pro Asp Phe Thr
            340                 345                 350

Trp Ala Asp Leu Met Arg Phe Thr Gln Arg His Tyr Arg Ala Asp Thr
        355                 360                 365

Arg Thr Leu Asp Ala Phe Thr Gln Trp Phe Ser Ser Ser Ser Ser Ser
    370                 375                 380

Ala Gln Glu Ala Ala
385
```

<210> SEQ ID NO 98
<211> LENGTH: 3050
<212> TYPE: DNA
<213> ORGANISM: Triticum aestivum

<400> SEQUENCE: 98

```
ctcatggtgc tccagaccgc tcagcaagaa ccatccctga cgcgtccgcc tcactgcagc      60

gtcgccagcg cgcgctcgcc ggcggccatg gacaccagcc ctgcaactcc cctgctcctc     120

cagcctcctg ctcccagcat tgacccgttc gccgccaagg cggccgtcaa caagggcggc     180

ggcgcggcaa ccgcggtgta cgacctccgg agggagccga agatccccgc cccgttcgtg     240

tggccgcacg ccgaggtgcg ccccaccacg gcccaggagc tggccgtgcc ggtggtggac     300

gtgggcgtgc tgcgcaatgg cgacgccgcg gggctccgcc gcgccgtggc gcaggtggcc     360

gcggcgtgcg ccacgcacgg gttcttccag gtgtccgggc acggcgtgga cgaggccctg     420

gcgcgcgcgg cgctggacgg cgcgagcggc ttcttccggc tgccgctggc cgagaagcag     480

cgcgcgcggc gcgtcccggg gaccgtgtcc gggtacacga gcgcgcacgc cgaccggttc     540
```

```
gcctccaagc tcccctggaa ggagaccctc tccttcggct tccacgaccg cgccggcgcc    600
gcgcccgtcg tggtggacta cttcaccagc accctcgggc cggactacga gccaatgggg    660
taatatatcc acccgcccac acccctatcc ggccagcacg aatccatccc cgccactgca    720
tttttttcct tttgtttccg cgcgaccgta cgttcgatcg gcgcccacgt acgtacgtgc    780
gtacgcagta gcagtacttg aagccgccgt actacgtgct gagtagtgac aactgaacac    840
gtgcaggagg gtgtaccagg agtactgcgg gaagatgaag gagctgtcgc tgaggatcat    900
ggagctgctg gagctgagcc agggcgtgga gaagcgcggg tactaccggg agttcttcgc    960
ggacagcagc tccatcatgc ggtgcaacta ctacccgccg tgcccggagc cggagcgcac   1020
gctgggcacg ggcccgcact gcgaccccac ggcgctcacc atcctactgc aggacgacgt   1080
gggcgggctg gaggtcctcg tcgacggcga ctggcgcccc gtccgccccg tccccggcgc   1140
catggtcatc aacatcggcg acaccttcat ggtaattact cctctctcag cgttgctttc   1200
gctgattaat tgcagaaaca gtagtcaact acccatgctc tgttccgctg tgctctgctt   1260
cccaacgagc gaaccggccc ataaaaactg ccttgctgtc ttggaaccaa gaggaaaggg   1320
accgtgggag cctaccgaca cgacgtgatt gcactctgct tcctaacaag cgagccgccg   1380
gtagggctat caccgtaagg gctcctttga ttcaaaggaa tttcttagga tttctgaagg   1440
attgaaatcc ttaggatttt ttcctatgtt ggtacttcga ttcataggat tgaatcccat   1500
aggatttttt tcctatgaaa tcttctgtac tacatttcat aggaaatcta acatccactc   1560
caaccttttt ttatatttcc tttgtttttc atgtgccatc aaacactcct tgttaatcct   1620
ataggattca agtgggcatg ccactccaat cctatacttt tcccattcct acgttttcaa   1680
aatcctacga atcaaagagg ccctaaagct gctgacatga cgtgattttt tttttctttt   1740
ctttctttct ttctcagctc caatcaacgc tggttattag atcattagag tggacaggtt   1800
gaattaacat gcagtagtta gtagttagca gccacaaacg ggtcccgttc tctgaagtct   1860
gaactgacat aagtcctgat catcgaccat tctttgcttc ctaggacgat gcctgttgga   1920
acttgcgtcc aatgcccgtt agggagtggt aattgtcatc acttttagac tcgtcgattc   1980
cactgatgaa gacgtagcac atggatgagc caacgtatcc gtttctagtg gtctcgaaaa   2040
gtagggtttc attcattcta tctatctatc cgtccgtcca aaagggctgc gatgcgagca   2100
cttgagtcgg agccaatcag agcgcgagaa aagatagggg gggtagcaag ccatgtcgga   2160
ggggcgtttg cttccggcag gtttggattc ttgtggtagg cgggcggctc tgtacagtag   2220
cggcggtgac ggtgaggtgg cggcgctttc ggtggcgggc caacccaggt gcatgcacgc   2280
gcgctcgtcg ttttcccgcc tgaatctgcc gctgcgccca tggcaagggg gtgggtgctg   2340
ccgccgggcg atggagtaga tcacggtcgc cgtcgggctc ggccagttga tcacggttcg   2400
ttcgtgcggt actaggttcc cccacggcac tgtgactgca tcgttccggc cctcgccatt   2460
ggcgatcggg caatctcctg ttcatccgtc gctgttgatt cctcggccac gatagaccat   2520
gcgcgtgccg gtcgtcgccc cgtcgcgctc gcttcacgtg ctcgtcgcgt ggctcccgtc   2580
ccacacgagg ccgccgcttt ctgacccagt ggagcgcgtg atttacagtt tatatatgtc   2640
gctgcatttt tctttttgtg tgctgctcat tttgcttgga cggagaccgg gaacgattag   2700
ccacggatct aacgcgttgt tgcttgtttt caatgcatgc atgcaggcgc tgtcgaacgg   2760
gcggtacaag agctgcctgc accgcgcggt ggtgaaccgg cggcaggagc ggcggtcgct   2820
ggccttcttc ctgtgcccgc gcgaggaccg cgtggtgcgg ccgccgccgg gcctgaggag   2880
```

cccgcggcgg tacccggact tcacctgggc tgacctcatg cgcttcacgc agcgccacta 2940
ccgcgccgac acgcgcaccc tcgacgcctt cacccagtgg ttctcctcct cctcctcctc 3000
ggcccaggag gcggcctgat tctgctctgc cacgaaacga tcggtccaca 3050

<210> SEQ ID NO 99
<211> LENGTH: 1486
<212> TYPE: DNA
<213> ORGANISM: Hordeum vulgare

<400> SEQUENCE: 99
gaccagtagc atatagtttt tcttgtgttt gccatggtgg acgtgtcgaa ctttgtagaa 60
gccaatggca atgcagcagt atcgattcct gccatggaag ttgctgggag tcctcacgtc 120
ccgttcgttc ctcgggacgc gaacgcgaca gacagcaaga atgccaagga cgtcctcgac 180
ctctggcggc agcagaaaca aatcccggct cccttcatct ggccccacgc cgacgcgcgg 240
ccgtcgtcga tcttggagct ggacgtgccc gtggtcgaca tcggcgcggc cctgcacagc 300
gccgccggga tggcccgcgc cgcggcgcag gtggccgagg catgcgcgag ccacggcttc 360
ttccaggtga ccgggcacgg cgtcgacccc gcgctggccc aagcagcgct cgacggcgca 420
gcggacttct tccgcctgcc gctcgccacc aagcagcgcg cccgccgatc cccggggacc 480
gtcaaagggt acgcctccgc ccacgccgac cgcttcgccg ccaagcttcc ctggaaggag 540
actctctcct tcatccacaa ccacgtccac gaggacgtcg gcgcccgcgc aagcagtcac 600
gtcgtcgact acttcacctc cgcccttggc gacgacttca tgcacctagg ggaggtgtac 660
caggagtact gtgaggcgat ggaggacgcg tcgctggcga taatggaggt gctgggggtg 720
agcctggggc tggggagagg gtactacagg gacttcttcg ccgacggcag ctccatcatg 780
aggtgcaact actacccgcg gtgcccggag ccggaccgga cgctggggac ggggccgcac 840
tgcgacccgt cggcgctgac catcctgctg caggacggcg aggtggacgg gctccaggtg 900
ctcgtcgacg gcgcatggcg ctccgtgcgg cccaagcccg gcgagctcgt cgtaaacatc 960
ggcgacacct tcatggcgct gtcgaacggc cggtacaaga gctgcctcca ccgcgcggtg 1020
gtgcaccggg agaaggagcg ccggtcgctg gcctacttcc tcgccccgcg ggaggaccgg 1080
gtggttcgcc cgccgccttc gccggcgccg gcgccgcggc tctacccgga cttcacctgg 1140
gcggagctca tgcgattcac gcagcgccac taccgcgccg acgcccgcac gctcgacgcc 1200
ttcgcgtgct ggctcgacct gcccagctgc cccaccacgc cccaggccca agggactgtc 1260
tagtgtctgt gatgtatcat ctgtctcagc tgttgtatac gaccacttgt gtctgctagc 1320
tctgcgcttg tgtttcttat gtgagctaac taactaaata gtgtgtatat ttcttgccgc 1380
gccttatgca agccctagtc tagaacatgt aataattaac ttaagcatat acgttgatct 1440
ttggtgtatt tttcatattt ccttcataat gaataatcta ttatgc 1486

<210> SEQ ID NO 100
<211> LENGTH: 1230
<212> TYPE: DNA
<213> ORGANISM: Hordeum vulgare

<400> SEQUENCE: 100
atggtggacg tgtcgaactt tgtagaagcc aatggcaatg cagcagtatc gattcctgcc 60
atggaagttg ctgggagtcc tcacgtcccg ttcgttcctc gggacgcgaa cgcgacagac 120
agcaagaatg ccaaggacgt cctcgacctc tggcggcagc agaaacaaat cccggctccc 180
ttcatctggc cccacgccga cgcgcggccg tcgtcgatct tggagctgga cgtgcccgtg 240

```
gtcgacatcg gcgcggccct gcacagcgcc gccgggatgg cccgcgccgc ggcgcaggtg    300

gccgaggcat gcgcgagcca cggcttcttc caggtgaccg ggcacggcgt cgaccccgcg    360

ctggcccaag cagcgctcga cggcgcagcg gacttcttcc gcctgccgct cgccaccaag    420

cagcgcgccc gccgatcccc ggggaccgtc aaagggtacg cctccgccca cgccgaccgc    480

ttcgccgcca agcttccctg gaaggagact ctctccttca tccacaacca cgtccacgag    540

gacgtcggcg cccgcgcaag cagtcacgtc gtcgactact tcacctccgc ccttggcgac    600

gacttcatgc acctagggga ggtgtaccag gagtactgtg aggcgatgga ggacgcgtcg    660

ctggcgataa tggaggtgct gggggtgagc ctggggctgg ggagagggta ctacagggac    720

ttcttcgccg acggcagctc catcatgagg tgcaactact acccgcggtg cccggagccg    780

gaccggacgc tggggacggg gccgcactgc gacccgtcgg cgctgaccat cctgctgcag    840

gacggcgagg tggacgggct ccaggtgctc gtcgacggcg catggcgctc cgtgcggccc    900

aagcccggcg agctcgtcgt aaacatcggc gacaccttca tggcgctgtc gaacggccgg    960

tacaagagct gcctccaccg cgcggtggtg caccgggaga aggagcgccg gtcgctggcc   1020

tacttcctcg ccccgcggga ggaccgggtg gttcgcccgc cgccttcgcc ggcgccggcg   1080

ccgcggctct acccggactt cacctgggcg gagctcatgc gattcacgca gcgccactac   1140

cgcgccgacg cccgcacgct cgacgccttc gcgtgctggc tcgacctgcc cagctgcccc   1200

accacgcccc aggcccaagg gactgtctag                                     1230
```

```
<210> SEQ ID NO 101
<211> LENGTH: 409
<212> TYPE: PRT
<213> ORGANISM: Hordeum vulgare

<400> SEQUENCE: 101

Met Val Asp Val Ser Asn Phe Val Glu Ala Asn Gly Asn Ala Ala Val
1               5                   10                  15

Ser Ile Pro Ala Met Glu Val Ala Gly Ser Pro His Val Pro Phe Val
            20                  25                  30

Pro Arg Asp Ala Asn Ala Thr Asp Ser Lys Asn Ala Lys Asp Val Leu
        35                  40                  45

Asp Leu Trp Arg Gln Gln Lys Gln Ile Pro Ala Pro Phe Ile Trp Pro
    50                  55                  60

His Ala Asp Ala Arg Pro Ser Ser Ile Leu Glu Leu Asp Val Pro Val
65                  70                  75                  80

Val Asp Ile Gly Ala Ala Leu His Ser Ala Ala Gly Met Ala Arg Ala
                85                  90                  95

Ala Ala Gln Val Ala Glu Ala Cys Ala Ser His Gly Phe Phe Gln Val
            100                 105                 110

Thr Gly His Gly Val Asp Pro Ala Leu Ala Gln Ala Ala Leu Asp Gly
        115                 120                 125

Ala Ala Asp Phe Phe Arg Leu Pro Leu Ala Thr Lys Gln Arg Ala Arg
    130                 135                 140

Arg Ser Pro Gly Thr Val Lys Gly Tyr Ala Ser Ala His Ala Asp Arg
145                 150                 155                 160

Phe Ala Ala Lys Leu Pro Trp Lys Glu Thr Leu Ser Phe Ile His Asn
                165                 170                 175

His Val His Glu Asp Val Gly Ala Arg Ala Ser Ser His Val Val Asp
            180                 185                 190
```

```
Tyr Phe Thr Ser Ala Leu Gly Asp Asp Phe Met His Leu Gly Glu Val
        195                 200                 205

Tyr Gln Glu Tyr Cys Glu Ala Met Glu Asp Ala Ser Leu Ala Ile Met
    210                 215                 220

Glu Val Leu Gly Val Ser Leu Gly Leu Gly Arg Gly Tyr Tyr Arg Asp
225                 230                 235                 240

Phe Phe Ala Asp Gly Ser Ser Ile Met Arg Cys Asn Tyr Tyr Pro Arg
                245                 250                 255

Cys Pro Glu Pro Asp Arg Thr Leu Gly Thr Gly Pro His Cys Asp Pro
            260                 265                 270

Ser Ala Leu Thr Ile Leu Leu Gln Asp Gly Glu Val Asp Gly Leu Gln
        275                 280                 285

Val Leu Val Asp Gly Ala Trp Arg Ser Val Arg Pro Lys Pro Gly Glu
    290                 295                 300

Leu Val Val Asn Ile Gly Asp Thr Phe Met Ala Leu Ser Asn Gly Arg
305                 310                 315                 320

Tyr Lys Ser Cys Leu His Arg Ala Val Val His Arg Glu Lys Glu Arg
                325                 330                 335

Arg Ser Leu Ala Tyr Phe Leu Ala Pro Arg Glu Asp Arg Val Val Arg
            340                 345                 350

Pro Pro Pro Ser Pro Ala Pro Ala Pro Arg Leu Tyr Pro Asp Phe Thr
        355                 360                 365

Trp Ala Glu Leu Met Arg Phe Thr Gln Arg His Tyr Arg Ala Asp Ala
    370                 375                 380

Arg Thr Leu Asp Ala Phe Ala Cys Trp Leu Asp Leu Pro Ser Cys Pro
385                 390                 395                 400

Thr Thr Pro Gln Ala Gln Gly Thr Val
                405
```

<210> SEQ ID NO 102
<211> LENGTH: 1423
<212> TYPE: DNA
<213> ORGANISM: Sorghum bicolor

<400> SEQUENCE: 102

```
cctctcatca caggccccag cctcactctt ctcacagcaa gacatcgcag cctcacaacc      60

acacagcaac gtgatcgcca tgggcgggct caccatggag caggccttcg tgcaggcccc     120

cgagcaccgc cccaagccca ccgtcaccga ggccaccggc atcctggtca tcgacctctc     180

gcctctcacc gccagcgaca ccgacgcggc cgcggtggac gcgctggccg ccgaggtggg     240

cgcggcgagc cgggactggg gcttcttcgt ggtggttggc cacggcgtgc ccgcggagac     300

cgtggcgcgc gcgacggcgg cgcagcgcgc gttcttcgcg ctgccggcgg agcggaaggc     360

cgccgtgcgg aggagcgagg cggagccgct cgggtactac gagtcggagc acaccaagaa     420

cgtcagggac tggaaggagg tgttcgacct cgtcccgcgc gatccgccgc cgccagcagc     480

cgtggccgac ggcgagctcg tcttcaagaa caagtggccc caggatctgc cgggcttcag     540

agaggcgctg gaggagtacg cggcagcgat ggaggagctg tcgttcaagc tgctggagct     600

gatcgcccgg agcttgaagc tgaggcccga ccggctgcac ggcttcttca aggaccagac     660

gacgttcatc cggctgaacc actaccctcc atgcccgagc ccggacctgg cgctgggagt     720

ggggcggcac aaggacgcgg gggcgctgac catcctgtac caggacgaag tgggcgggct     780

ggacgtccgg cggcgctcct ccgacggcgg cggcggcgag tgggtgcggg tgaggcccgt     840

gccggagtcg ttcgtcatca acgtcggcga cctcgtccag gtgtggagca acgacaggta     900
```

```
cgagagcgcg gagcaccggg tgtcggtgaa ctcggcgagg gagaggttct ccatgcccta    960

cttcttcaac ccggcgagct acaccatggt ggagccggtg gaggagctgg tgagcgacga   1020

cgacccgccc aggtacgacg cctacagctg gggcgagttc ttcagcacca ggaagaacag   1080

caacttcaag aagctcagcg tggagaacat tcagatcgcg catttcaaga agaccctcgt   1140

cctcgcctag ataagcagca ggatactaca ggtctacagg actaggacaa gccgatcgag   1200

gtgaccggcc gtcgtcttca gattcagtat atgcgtgtcg ccgttcgtgt tagaacaaat   1260

taataatgtg cgcgctgtgt gctgtgtgtg tggagtaaaa aaaaactaaa catggatgtg   1320

catgttcaaa aaaaaaaaca tggatgcgag tatgtttggg aataataaca ggcttgtgac   1380

ggtctggttt atttgcaaat tcaaaccgaa ttggttgatc ttc                     1423
```

```
<210> SEQ ID NO 103
<211> LENGTH: 1071
<212> TYPE: DNA
<213> ORGANISM: Sorghum bicolor

<400> SEQUENCE: 103

atgggcgggc tcaccatgga gcaggccttc gtgcaggccc ccgagcaccg ccccaagccc     60

accgtcaccg aggccaccgg catcctggtc atcgacctct cgcctctcac cgccagcgac    120

accgacgcgg ccgcggtgga cgcgctggcc gccgaggtgg gcgcggcgag ccgggactgg    180

ggcttcttcg tggtggttgg ccacggcgtg cccgcggaga ccgtggcgcg cgcgacggcg    240

gcgcagcgcg cgttcttcgc gctgccggcg gagcggaagg ccgccgtgcg gaggagcgag    300

gcggagccgc tcgggtacta cgagtcggag cacaccaaga acgtcaggga ctggaaggag    360

gtgttcgacc tcgtcccgcg cgatccgccg ccgccagcag ccgtggccga cggcgagctc    420

gtcttcaaga acaagtggcc ccaggatctg ccgggcttca gagaggcgct ggaggagtac    480

gcggcagcga tggaggagct gtcgttcaag ctgctggagc tgatcgcccg gagcttgaag    540

ctgaggcccg accggctgca cggcttcttc aaggaccaga cgacgttcat ccggctgaac    600

cactaccctc catgcccgag cccggacctg gcgctgggag tggggcggca caaggacgcg    660

ggggcgctga ccatcctgta ccaggacgaa gtgggcgggc tggacgtccg gcggcgctcc    720

tccgacggcg gcggcggcga gtgggtgcgg gtgaggcccg tgccggagtc gttcgtcatc    780

aacgtcggcg acctcgtcca ggtgtggagc aacgacaggt acgagagcgc ggagcaccgg    840

gtgtcggtga actcggcgag ggagaggttc tccatgccct acttcttcaa cccggcgagc    900

tacaccatgg tggagccggt ggaggagctg gtgagcgacg acgacccgcc caggtacgac    960

gcctacagct ggggcgagtt cttcagcacc aggaagaaca gcaacttcaa gaagctcagc   1020

gtggagaaca ttcagatcgc gcatttcaag aagaccctcg tcctcgccta g            1071
```

```
<210> SEQ ID NO 104
<211> LENGTH: 356
<212> TYPE: PRT
<213> ORGANISM: Sorghum bicolor

<400> SEQUENCE: 104

Met Gly Gly Leu Thr Met Glu Gln Ala Phe Val Gln Ala Pro Glu His
1               5                   10                  15

Arg Pro Lys Pro Thr Val Thr Glu Ala Thr Gly Ile Leu Val Ile Asp
            20                  25                  30

Leu Ser Pro Leu Thr Ala Ser Asp Thr Asp Ala Ala Ala Val Asp Ala
        35                  40                  45
```

```
Leu Ala Ala Glu Val Gly Ala Ala Ser Arg Asp Trp Gly Phe Phe Val
    50                  55                  60

Val Val Gly His Gly Val Pro Ala Glu Thr Val Ala Arg Ala Thr Ala
65                  70                  75                  80

Ala Gln Arg Ala Phe Phe Ala Leu Pro Ala Glu Arg Lys Ala Ala Val
                85                  90                  95

Arg Arg Ser Glu Ala Glu Pro Leu Gly Tyr Tyr Glu Ser Glu His Thr
            100                 105                 110

Lys Asn Val Arg Asp Trp Lys Glu Val Phe Asp Leu Val Pro Arg Asp
        115                 120                 125

Pro Pro Pro Pro Ala Ala Val Ala Asp Gly Glu Leu Val Phe Lys Asn
    130                 135                 140

Lys Trp Pro Gln Asp Leu Pro Gly Phe Arg Glu Ala Leu Glu Glu Tyr
145                 150                 155                 160

Ala Ala Ala Met Glu Glu Leu Ser Phe Lys Leu Leu Glu Leu Ile Ala
                165                 170                 175

Arg Ser Leu Lys Leu Arg Pro Asp Arg Leu His Gly Phe Phe Lys Asp
            180                 185                 190

Gln Thr Thr Phe Ile Arg Leu Asn His Tyr Pro Pro Cys Pro Ser Pro
        195                 200                 205

Asp Leu Ala Leu Gly Val Gly Arg His Lys Asp Ala Gly Ala Leu Thr
    210                 215                 220

Ile Leu Tyr Gln Asp Glu Val Gly Gly Leu Asp Val Arg Arg Arg Ser
225                 230                 235                 240

Ser Asp Gly Gly Gly Gly Glu Trp Val Arg Val Arg Pro Val Pro Glu
                245                 250                 255

Ser Phe Val Ile Asn Val Gly Asp Leu Val Gln Val Trp Ser Asn Asp
            260                 265                 270

Arg Tyr Glu Ser Ala Glu His Arg Val Ser Val Asn Ser Ala Arg Glu
        275                 280                 285

Arg Phe Ser Met Pro Tyr Phe Phe Asn Pro Ala Ser Tyr Thr Met Val
    290                 295                 300

Glu Pro Val Glu Glu Leu Val Ser Asp Asp Asp Pro Pro Arg Tyr Asp
305                 310                 315                 320

Ala Tyr Ser Trp Gly Glu Phe Phe Ser Thr Arg Lys Asn Ser Asn Phe
                325                 330                 335

Lys Lys Leu Ser Val Glu Asn Ile Gln Ile Ala His Phe Lys Lys Thr
            340                 345                 350

Leu Val Leu Ala
        355
```

<210> SEQ ID NO 105
<211> LENGTH: 1499
<212> TYPE: DNA
<213> ORGANISM: Sorghum bicolor

<400> SEQUENCE: 105

```
cctctcatca caggccccag cctcactctt ctcacagcaa gacatcgcag cctcacaacc      60

acacagcaac gtgatcgcca tgggcgggct caccatggag caggccttcg tgcaggcccc     120

cgagcaccgc cccaagccca ccgtcaccga ggccaccggc atcctggtca tcgacctctc     180

gcctctcacc gccagcgaca ccgacgcggc cgcggtggac gcgctggccg ccgaggtggg     240

cgcggcgagc cgggactggg gcttcttcgt ggtggttggc cacggcgtgc ccgcggagac     300
```

cgtggcgcgc gcgacggcgg cgcagcgcgc gttcttcgcg ctgccggcgg agcggaaggc 360
cgccgtgcgg aggagcgagg cggagccgct cgggtactac gagtcggagc acaccaagaa 420
cgtcagggac tggaaggagg tgttcgacct cgtcccgcgc gatccgccgc cgccagcagc 480
cgtggccgac ggcgagctcg tcttcaagaa caagtggccc caggatctgc cgggcttcag 540
gtgacgaaat caacttatct tttcgatcat attttaccat ttaatagttt aacaataatt 600
gaactttttt ttgcagagag gcgctggagg agtacgcggc agcgatggag gagctgtcgt 660
tcaagctgct ggagctgatc gcccggagct tgaagctgag gcccgaccgg ctgcacggct 720
tcttcaagga ccagacgacg ttcatccggc tgaaccacta ccctccatgc ccgagcccgg 780
acctggcgct gggagtgggg cggcacaagg acgcgggggc gctgaccatc ctgtaccagg 840
acgaagtggg cgggctggac gtccggcggc gctcctccga cggcggcggc ggcgagtggg 900
tgcgggtgag gcccgtgccg gagtcgttcg tcatcaacgt cggcgacctc gtccaggtgt 960
ggagcaacga caggtacgag agcgcggagc accgggtgtc ggtgaactcg gcgagggaga 1020
ggttctccat gccctacttc ttcaacccgg cgagctacac catggtggag ccggtggagg 1080
agctggtgag cgacgacgac ccgcccaggt acgacgccta cagctggggc gagttcttca 1140
gcaccaggaa gaacagcaac ttcaagaagc tcagcgtgga gaacattcag atcgcgcatt 1200
tcaagaagac cctcgtcctc gcctagataa gcagcaggat actacaggtc tacaggacta 1260
ggacaagccg atcgaggtga ccggccgtcg tcttcagatt cagtatatgc gtgtcgccgt 1320
tcgtgttaga acaaattaat aatgtgcgcg ctgtgtgctg tgtgtgtgga gtaaaaaaaa 1380
actaaacatg gatgtgcatg ttcaaaaaaa aaaacatgga tgcgagtatg tttgggaata 1440
ataacaggct tgtgacggtc tggtttattt gcaaattcaa accgaattgg ttgatcttc 1499

<210> SEQ ID NO 106
<211> LENGTH: 1490
<212> TYPE: DNA
<213> ORGANISM: Setaria italica

<400> SEQUENCE: 106
accccacaca cacacccgca ctgcatgcgg cgtcctagct aatcagtcgc tgctggcagc 60
ctcacaagtc acacaactcc gacgcaggaa agctcgatcc atcgccatgg gcggcttctc 120
catggatcag tccttcgtgc aggcccccga gcaccgcccc aagcccaccg tcaccgaggc 180
cacgggcatc ccgctcatcg acctctcgcc actcaccggc ggtggcggcg gcgacgcggc 240
cgccgtggac gcgctggccg ccgaggtggg cgcggcgagc cgggactggg gcttcttcgt 300
ggtggtgggg cacggtgtgc cggcggagac cgtggcgcgc gccacggagg cgcagcgcgc 360
gttcttcgcc ctgccggcgg agcggaaagc cgccgtgcgg aggagcgagg cggagccgct 420
cgggtactac gagtcggagc acaccaagaa cgtcagggac tggaaggagg tgtacgacct 480
cgtcccgggc gggcttcagc cgccgatagc cgtggccgac ggcgaggtcg tgttcgaaaa 540
caagtggccc gaagacctgc cgggattcag agaggcgttg gaggagtaca tgcaagcgat 600
ggaagagctg gcattcaaga tactggagct gatcgcccgg agcctgaacc tgaggcctga 660
cagactgcac ggcttcttca aggaccagac caccttcatc cggctcaacc actaccctcc 720
ctgcccgagc cccgacctcg ccctcggcgt cggccggcac aaggacgccg gagcactgac 780
catcctctac caggacgacg tcggcgggct cgacgtccgg cgccgttccg acggcgattg 840
ggtccgcgtc aagcctgtcc ccgactcctt catcatcaac gtcggcgacc tcatccaggt 900
ttggagcaac gacaggtacg agagcgcgga gcaccgggtt acggtgaact cggccaagga 960
gaggttctcc aggccctact tcttcaaccc ggcgggctac accatggtgg agccggtgga 1020
ggagctggtg agcgaggagg acccgccccg gtacgacgcc tacaactggg gcaacttctt 1080
cagcaccagg aagaacagca acttcaagaa gctgagcgtg gagaacatcc agatcgcgca 1140
tttcaagagg agcgtcgccg cctaggatac gcacagaaag atcccatatg ctgacttgct 1200
gatgaggcga caggcggccg tgtcgtcttc agattcagag actgggagta aacatttgtg 1260
cggtgttctg taatcgtgat gtgacgagaa ctttagatat atgtttggaa ataacagcct 1320
tgtgttggtc tggcttatcc gcaaagtcaa gattttcttc tacattttgg gattattgtt 1380
ggtaagcatt aagcaacgtc cagttcttac ttcttagctc gatcagtgga cgtaggaccg 1440
gcctctgatg acaagggtga tttatgagaa atgtcatgta tatatgttcc 1490

<210> SEQ ID NO 107
<211> LENGTH: 1059
<212> TYPE: DNA
<213> ORGANISM: Setaria italica

<400> SEQUENCE: 107
atgggcggct tctccatgga tcagtccttc gtgcaggccc ccgagcaccg ccccaagccc 60
accgtcaccg aggccacggg catcccgctc atcgacctct cgccactcac cggcggtggc 120
ggcggcgacg cggccgccgt ggacgcgctg gccgccgagg tgggcgcggc gagccgggac 180
tggggcttct tcgtggtggt ggggcacggt gtgccggcgg agaccgtggc gcgcgccacg 240
gaggcgcagc gcgcgttctt cgccctgccg gcggagcgga aagccgccgt gcggaggagc 300
gaggcggagc cgctcgggta ctacgagtcg gagcacacca agaacgtcag ggactggaag 360
gaggtgtacg acctcgtccc gggcgggctt cagccgccga tagccgtggc cgacggcgag 420
gtcgtgttcg aaaacaagtg gcccgaagac ctgccgggat tcagagaggc gttggaggag 480
tacatgcaag cgatggaaga gctggcattc aagatactgg agctgatcgc ccggagcctg 540
aacctgaggc ctgacagact gcacggcttc ttcaaggacc agaccacctt catccggctc 600
aaccactacc ctccctgccc gagccccgac ctcgccctcg gcgtcggccg gcacaaggac 660
gccggagcac tgaccatcct ctaccaggac gacgtcggcg ggctcgacgt ccggcgccgt 720
tccgacggcg attgggtccg cgtcaagcct gtccccgact ccttcatcat caacgtcggc 780
gacctcatcc aggtttggag caacgacagg tacgagagcg cggagcaccg ggttacggtg 840
aactcggcca aggagaggtt ctccaggccc tacttcttca acccggcggg ctacaccatg 900
gtggagccgg tggaggagct ggtgagcgag gaggacccgc cccggtacga cgcctacaac 960
tggggcaact tcttcagcac caggaagaac agcaacttca agaagctgag cgtggagaac 1020
atccagatcg cgcatttcaa gaggagcgtc gccgcctag 1059

<210> SEQ ID NO 108
<211> LENGTH: 352
<212> TYPE: PRT
<213> ORGANISM: Setaria italica

<400> SEQUENCE: 108

Met Gly Gly Phe Ser Met Asp Gln Ser Phe Val Gln Ala Pro Glu His
1 5 10 15

Arg Pro Lys Pro Thr Val Thr Glu Ala Thr Gly Ile Pro Leu Ile Asp
20 25 30

Leu Ser Pro Leu Thr Gly Gly Gly Gly Gly Asp Ala Ala Ala Val Asp
35 40 45

```
Ala Leu Ala Ala Glu Val Gly Ala Ala Ser Arg Asp Trp Gly Phe Phe
    50                  55                  60

Val Val Val Gly His Gly Val Pro Ala Glu Thr Val Ala Arg Ala Thr
65                  70                  75                  80

Glu Ala Gln Arg Ala Phe Phe Ala Leu Pro Ala Glu Arg Lys Ala Ala
                85                  90                  95

Val Arg Arg Ser Glu Ala Glu Pro Leu Gly Tyr Tyr Glu Ser Glu His
            100                 105                 110

Thr Lys Asn Val Arg Asp Trp Lys Glu Val Tyr Asp Leu Val Pro Gly
        115                 120                 125

Gly Leu Gln Pro Pro Ile Ala Val Ala Asp Gly Glu Val Val Phe Glu
    130                 135                 140

Asn Lys Trp Pro Glu Asp Leu Pro Gly Phe Arg Glu Ala Leu Glu Glu
145                 150                 155                 160

Tyr Met Gln Ala Met Glu Glu Leu Ala Phe Lys Ile Leu Glu Leu Ile
                165                 170                 175

Ala Arg Ser Leu Asn Leu Arg Pro Asp Arg Leu His Gly Phe Phe Lys
            180                 185                 190

Asp Gln Thr Thr Phe Ile Arg Leu Asn His Tyr Pro Pro Cys Pro Ser
        195                 200                 205

Pro Asp Leu Ala Leu Gly Val Gly Arg His Lys Asp Ala Gly Ala Leu
    210                 215                 220

Thr Ile Leu Tyr Gln Asp Asp Val Gly Gly Leu Asp Val Arg Arg Arg
225                 230                 235                 240

Ser Asp Gly Asp Trp Val Arg Val Lys Pro Val Pro Asp Ser Phe Ile
                245                 250                 255

Ile Asn Val Gly Asp Leu Ile Gln Val Trp Ser Asn Asp Arg Tyr Glu
            260                 265                 270

Ser Ala Glu His Arg Val Thr Val Asn Ser Ala Lys Glu Arg Phe Ser
        275                 280                 285

Arg Pro Tyr Phe Phe Asn Pro Ala Gly Tyr Thr Met Val Glu Pro Val
    290                 295                 300

Glu Glu Leu Val Ser Glu Glu Asp Pro Pro Arg Tyr Asp Ala Tyr Asn
305                 310                 315                 320

Trp Gly Asn Phe Phe Ser Thr Arg Lys Asn Ser Asn Phe Lys Lys Leu
                325                 330                 335

Ser Val Glu Asn Ile Gln Ile Ala His Phe Lys Arg Ser Val Ala Ala
            340                 345                 350
```

<210> SEQ ID NO 109
<211> LENGTH: 1886
<212> TYPE: DNA
<213> ORGANISM: Setaria italica

<400> SEQUENCE: 109

```
accccacaca cacacccgca ctgcatgcgg cgtcctagct aatcagtcgc tgctggcagc      60

ctcacaagtc acacaactcc gacgcaggaa agctcgatcc atcgccatgg gcggcttctc     120

catggatcag tccttcgtgc aggcccccga gcaccgcccc aagcccaccg tcaccgaggc     180

cacgggcatc ccgctcatcg acctctcgcc actcaccggc ggtggcggcg gcgacgcggc     240

cgccgtggac gcgctggccg ccgaggtggg cgcggcgagc cgggactggg gcttcttcgt     300

ggtggtgggg cacggtgtgc cggcggagac cgtggcgcgc gccacggagg cgcagcgcgc     360

gttcttcgcc ctgccggcgg agcggaaagc cgccgtgcgg aggagcgagg cggagccgct     420
```

cgggtactac gagtcggagc acaccaagaa cgtcagggac tggaaggagg tgtacgacct 480
cgtcccgggc gggcttcagc cgccgatagc cgtggccgac ggcgaggtcg tgttcgaaaa 540
caagtggccc gaagacctgc cgggattcag gtgaatcaac ttgcgcatat tgttgtttct 600
ggcattgcat atgatcgtcg tgccagtatg ttttgacaat atttttgttt tcatattttt 660
ggtgaagatg ggaaaatctt tgttgaaata atcagggaat tttcacatct ttttttaatc 720
aaagatagaa taggttcggt tactgaattt tgatgatgga cagaaaaagc tgtgttttca 780
ctttccatct cagcgatgtt tttttgtgga tgaattctcc taaatttttg tcttttcatg 840
ttaaaacttg aacgggaatt ctcgcagaga ggcgttggag gagtacatgc aagcgatgga 900
agagctggca ttcaagatac tggagctgat cgcccggagc ctgaacctga ggcctgacag 960
actgcacggc ttcttcaagg accagaccac cttcatccgg ctcaaccact accctccctg 1020
cccgagcccc gacctcgccc tcggcgtcgg ccggcacaag gacgccggag cactgaccat 1080
cctctaccag gacgacgtcg gcgggctcga cgtccggcgc cgttccgacg gcgattgggt 1140
ccgcgtcaag cctgtccccg actccttcat catcaacgtc ggcgacctca tccaggtaca 1200
acaaacaaaa acacacgtca ttctcaaatc ttttcgtgct gttaatgctc attcacgaat 1260
tgatatctta catgaacgac tgagactttt tcaggtttgg agcaacgaca ggtacgagag 1320
cgcggagcac cgggttacgg tgaactcggc caaggagagg ttctccaggc cctacttctt 1380
caacccggcg ggctacacca tggtggagcc ggtggaggag ctggtgagcg aggaggaccc 1440
gccccggtac gacgcctaca actggggcaa cttcttcagc accaggaaga acagcaactt 1500
caagaagctg agcgtggaga acatccagat cgcgcatttc aagaggagcg tcgccgccta 1560
ggatacgcac agaaagatcc catatgctga cttgctgatg aggcgacagg cggccgtgtc 1620
gtcttcagat tcagagactg ggagtaaaca tttgtgcggt gttctgtaat cgtgatgtga 1680
cgagaacttt agatatatgt ttggaaataa cagccttgtg ttggtctggc ttatccgcaa 1740
agtcaagatt ttcttctaca ttttgggatt attgttggta agcattaagc aacgtccagt 1800
tcttacttct tagctcgatc agtggacgta ggaccggcct ctgatgacaa gggtgattta 1860
tgagaaatgt catgtatata tgttcc 1886

<210> SEQ ID NO 110
<211> LENGTH: 1379
<212> TYPE: DNA
<213> ORGANISM: Oryza sativa

<400> SEQUENCE: 110
aagccacacg cacacacaca cacacgctga cacacgagac gaacacttgt gctacagctt 60
ctcgccacca gctactgatc gaccatgggc ggcctctcca tggaccaggc gttcgtgcag 120
gcccccgagc accgccccaa ggcgtccgtc gccgaggccg acggcatccc ggtcatcgac 180
ctctcccctc tcctcgccgc cggcgatggc gacgccgacg gggtggacgc gctcgcggcg 240
gaggtcggga gggcgagccg ggactggggc ttcttcgtgg tggtgcgcca cggtgtgccc 300
gcggaggcgg tggcgcgcgc ggcggaggcg cagaggacgt tcttcgcgct gccgccggag 360
cggagggcgg ccgtggcgcg gagcgaggcg gcgccgatgg ggtactacgc gtccgagcac 420
accaagaacg tcagggactg gaaggaggtg ttcgacctcg tcccgcgcca gacgccgccg 480
ccgccgacga ccgccgtggc cgacggcgac ctggtgttcg acaacaagtg gcccgacgac 540
ctgccgggat tcagggaggc aatggaggag tacggcgaag cggtggagga gctggcgttc 600

```
aagctgctgg agctgatcgc caggagcctc ggcctgagac ccgaccgcct ccatggcttc    660

ttcaaggacg accagaccac cttcatccgg ctcaaccact accctccctg cccgagcccc    720

gacctcgccc tcggcgtcgg ccgccacaag gacgccggcg cgctcaccgt gctctaccag    780

gacgatgtcg gcggcctcga cgtccgccgc cgatccgacg gcgagtgggt gcgcgtcagg    840

cccgtccctc actccttcat catcaacgtc ggcgacatca tccaggtgtg gagcaatgac    900

aggtacgaga gcgcggagca ccgggtggcg gtgaacgtgg agaaggagag gttctccatc    960

cctttcttct tcaacccggc gggccacacc atggtggagc cactggagga ggtcgtgagc   1020

gacgagagcc cggccaggta caacccctac aactggggcg aattcttcag caccaggaag   1080

aacagcaact tcaagaagct ggacgtggag aacgtccaga tcacgcattt caggaagaat   1140

taacgcgccg gctagatcat gttcagtaaa ttttcagatg atgatgcgtg gacaaccata   1200

tagcctttgc gtcataagtt aataatgtct gtgacagtat atcatgtaaa caatcgtatg   1260

atgtggcttc tctatctgcc ggtgatggta atgtgacatt gtagaagagg gtttgtgaga   1320

tacttccttc acttaacttt tacgaatgaa tatagacaac cacaacatcc ttgtcgtga    1379
```

<210> SEQ ID NO 111
<211> LENGTH: 1059
<212> TYPE: DNA
<213> ORGANISM: Oryza sativa

<400> SEQUENCE: 111

```
atgggcggcc tctccatgga ccaggcgttc gtgcaggccc ccgagcaccg ccccaaggcg     60

tccgtcgccg aggccgacgg catcccggtc atcgacctct cccctctcct cgccgccggc    120

gatggcgacg ccgacggggt ggacgcgctc gcggcggagg tcgggagggc gagccgggac    180

tggggcttct tcgtggtggt gcgccacggt gtgcccgcgg aggcggtggc gcgcgcggcg    240

gaggcgcaga ggacgttctt cgcgctgccg ccggagcgga gggcggccgt ggcgcggagc    300

gaggcggcgc cgatggggta ctacgcgtcc gagcacacca agaacgtcag ggactggaag    360

gaggtgttcg acctcgtccc gcgccagacg ccgccgccgc cgacgaccgc cgtggccgac    420

ggcgacctgg tgttcgacaa caagtggccc gacgacctgc cgggattcag ggaggcaatg    480

gaggagtacg gcgaagcggt ggaggagctg gcgttcaagc tgctggagct gatcgccagg    540

agcctcggcc tgagacccga ccgcctccat ggcttcttca aggacgacca gaccaccttc    600

atccggctca accactaccc tccctgcccg agccccgacc tcgccctcgg cgtcggccgc    660

cacaaggacg ccggcgcgct caccgtgctc taccaggacg atgtcggcgg cctcgacgtc    720

cgccgccgat ccgacggcga gtgggtgcgc gtcaggcccg tccctcactc cttcatcatc    780

aacgtcggcg acatcatcca ggtgtggagc aatgacaggt acgagagcgc ggagcaccgg    840

gtggcggtga acgtggagaa ggagaggttc tccatccctt tcttcttcaa cccggcgggc    900

cacaccatgg tggagccact ggaggaggtc gtgagcgacg agagcccggc caggtacaac    960

ccctacaact ggggcgaatt cttcagcacc aggaagaaca gcaacttcaa gaagctggac   1020

gtggagaacg tccagatcac gcatttcagg aagaattaa                          1059
```

<210> SEQ ID NO 112
<211> LENGTH: 352
<212> TYPE: PRT
<213> ORGANISM: Oryza sativa

<400> SEQUENCE: 112

Met Gly Gly Leu Ser Met Asp Gln Ala Phe Val Gln Ala Pro Glu His

-continued

```
1               5                   10                  15

Arg Pro Lys Ala Ser Val Ala Glu Ala Asp Gly Ile Pro Val Ile Asp
            20                  25                  30

Leu Ser Pro Leu Leu Ala Ala Gly Asp Gly Asp Ala Asp Gly Val Asp
        35                  40                  45

Ala Leu Ala Ala Glu Val Gly Arg Ala Ser Arg Asp Trp Gly Phe Phe
    50                  55                  60

Val Val Val Arg His Gly Val Pro Ala Glu Ala Val Ala Arg Ala Ala
65                  70                  75                  80

Glu Ala Gln Arg Thr Phe Phe Ala Leu Pro Pro Glu Arg Arg Ala Ala
                85                  90                  95

Val Ala Arg Ser Glu Ala Ala Pro Met Gly Tyr Tyr Ala Ser Glu His
            100                 105                 110

Thr Lys Asn Val Arg Asp Trp Lys Glu Val Phe Asp Leu Val Pro Arg
        115                 120                 125

Gln Thr Pro Pro Pro Pro Thr Thr Ala Val Ala Asp Gly Asp Leu Val
    130                 135                 140

Phe Asp Asn Lys Trp Pro Asp Asp Leu Pro Gly Phe Arg Glu Ala Met
145                 150                 155                 160

Glu Glu Tyr Gly Glu Ala Val Glu Glu Leu Ala Phe Lys Leu Leu Glu
                165                 170                 175

Leu Ile Ala Arg Ser Leu Gly Leu Arg Pro Asp Arg Leu His Gly Phe
            180                 185                 190

Phe Lys Asp Asp Gln Thr Thr Phe Ile Arg Leu Asn His Tyr Pro Pro
        195                 200                 205

Cys Pro Ser Pro Asp Leu Ala Leu Gly Val Gly Arg His Lys Asp Ala
    210                 215                 220

Gly Ala Leu Thr Val Leu Tyr Gln Asp Asp Val Gly Gly Leu Asp Val
225                 230                 235                 240

Arg Arg Arg Ser Asp Gly Glu Trp Val Arg Val Arg Pro Val Pro His
                245                 250                 255

Ser Phe Ile Ile Asn Val Gly Asp Ile Ile Gln Val Trp Ser Asn Asp
            260                 265                 270

Arg Tyr Glu Ser Ala Glu His Arg Val Ala Val Asn Val Glu Lys Glu
        275                 280                 285

Arg Phe Ser Ile Pro Phe Phe Phe Asn Pro Ala Gly His Thr Met Val
    290                 295                 300

Glu Pro Leu Glu Glu Val Val Ser Asp Glu Ser Pro Ala Arg Tyr Asn
305                 310                 315                 320

Pro Tyr Asn Trp Gly Glu Phe Phe Ser Thr Arg Lys Asn Ser Asn Phe
                325                 330                 335

Lys Lys Leu Asp Val Glu Asn Val Gln Ile Thr His Phe Arg Lys Asn
            340                 345                 350


<210> SEQ ID NO 113
<211> LENGTH: 2027
<212> TYPE: DNA
<213> ORGANISM: Oryza sativa

<400> SEQUENCE: 113

aagccacacg cacacacaca cacacgctga cacacgagac gaacacttgt gctacagctt      60

ctcgccacca gctactgatc gaccatgggc ggcctctcca tggaccaggc gttcgtgcag     120

gcccccgagc accgccccaa ggcgtccgtc gccgaggccg acggcatccc ggtcatcgac     180
```

ctctcccctc tcctcgccgc cggcgatggc gacgccgacg gggtggacgc gctcgcggcg 240
gaggtcggga gggcgagccg ggactggggc ttcttcgtgg tggtgcgcca cggtgtgccc 300
gcggaggcgg tggcgcgcgc ggcggaggcg cagaggacgt tcttcgcgct gccgccggag 360
cggagggcgg ccgtggcgcg gagcgaggcg gcgccgatgg ggtactacgc gtccgagcac 420
accaagaacg tcagggactg gaaggaggtg ttcgacctcg tcccgcgcca gacgccgccg 480
ccgccgacga ccgccgtggc cgacggcgac ctggtgttcg acaacaagtg gcccgacgac 540
ctgccgggat tcaggtcagg tcaccacatc gatcgatcgt cttcttcatc ctcgcatcaa 600
ttcagttcaa cctcatcgaa ttcttgagca gggaggcaat ggaggagtac ggcgaagcgg 660
tggaggagct ggcgttcaag ctgctggagc tgatcgccag gagcctcggc ctgagacccg 720
accgcctcca tggcttcttc aaggacgacc agaccacctt catccggctc aaccactacc 780
ctccctgccc gagccccgac ctcgccctcg gcgtcggccg ccacaaggac gccggcgcgc 840
tcaccgtgct ctaccaggac gatgtcggcg gcctcgacgt ccgccgccga tccgacggcg 900
agtgggtgcg cgtcaggccc gtccctcact ccttcatcat caacgtcggc gacatcatcc 960
aggtactttt ttttttgagc agctacatat ttatcaacaa attttcttct aacaatttat 1020
cggacataaa tatattacaa tgaaagaata attgtatcat aacttgtgtg tccttatatg 1080
taagttttag aaatcctata gtaacatggt attttcgcga aagcggagat tgtgagaccg 1140
tatcttttca cccatgcgcg tcatatgatt tttttttctt gccaacttaa ataaatttca 1200
aagtaaatct aatagattaa aattatgtga aacttacata taagttttct acggtaacac 1260
gctattttca cgaaacggag gtcgttccaa gttgaatgaa tcttgaagta aatctaacga 1320
tttaaaatta tgtgcataca cgttatatta cagttatata caagttataa tataattaca 1380
ctacaattat aacggtattc atagttgaca aacttttaaa agagaattag ttaataaata 1440
tataacaaca ttgtagttta attgttacta tttgacatca tttttatttg cattttgaat 1500
ttgactgaaa aaattgagag tgcgcttgtc caggtgtgga gcaatgacag gtacgagagc 1560
gcggagcacc gggtggcggt gaacgtggag aaggagaggt tctccatccc tttcttcttc 1620
aacccggcgg gccacaccat ggtggagcca ctggaggagg tcgtgagcga cgagagcccg 1680
gccaggtaca acccctacaa ctggggcgaa ttcttcagca ccaggaagaa cagcaacttc 1740
aagaagctgg acgtggagaa cgtccagatc acgcatttca ggaagaatta acgcgccggc 1800
tagatcatgt tcagtaaatt ttcagatgat gatgcgtgga caaccatata gcctttgcgt 1860
cataagttaa taatgtctgt gacagtatat catgtaaaca atcgtatgat gtggcttctc 1920
tatctgccgg tgatggtaat gtgacattgt agaagagggt ttgtgagata cttccttcac 1980
ttaactttta cgaatgaata tagacaacca caacatcctt gtcgtga 2027

<210> SEQ ID NO 114
<211> LENGTH: 1747
<212> TYPE: DNA
<213> ORGANISM: Triticum aestivum

<400> SEQUENCE: 114
tcactcaagg ccacaacaca ctcgccagtc catcgccacc atacgtgaca acttgagtta 60
cttgatctgt tgctcatcga tctcgacatc gccatgggcg gcctctccat ggaccaggcc 120
ttcgtgcagg cccccgagca tcgcaccaag gcgaacctcg ccgacgcggc cggcatcccg 180
gtcatcgacc tctcccctct cgccgccggc gacaaggccg gcctggacgc cctcgcggcc 240
gaggtgggca gggcgagccg tgactggggg ttcttcgtgg tggtgcgcca cggcgtgccg 300
gcggagacgg tggcgcgggc gctggaggcg cagagggcct tcttcgcgct gcccgcggac 360
cggaaggcgg ccgtgcggag ggacgaggcg gcgccgctgg ggtactacga gtcggagcac 420
accaagaacg tcagggactg gaaggaggtg ttcgacctcg tcccccgcga gccgccgccg 480
cctgccgcgg ttgccgacgg cgagctcatg ttcgagaaca agtggcccga ggacctgccg 540
gggttcagag aggctctcga agagtacgag aaagcgatgg aggagctggc gttcaagctg 600
ctggagctga tcgcccggag cctgggactg agaccggacc ggctgcacgg cttcttcaag 660
gaccagacca ccttcatccg gctgaaccac tacccgccct gccccagccc cgacctcgcc 720
ctcggcgtcg gtcgccacaa ggacgccggc gcgctcacca tcctctacca ggacgacgtc 780
ggcgggctcg acgtccggcg ccgctccgac ggcgagtggg tgcgcgtcag gcctgtcccg 840
gactcctacg tcatcaacgt cggcgacatc atccaggtgt ggagcaacga caggtacgag 900
agcgcggagc acagggtgtc ggtgaactcg cacaaggaga ggttctccat gccctacttc 960
ttcgaccccg ggagcgacgc catgatcgag ccgttggagg agatggtgag cgacgaaagg 1020
ccggccaggt acgacgccta caactggggc aacttcttca gcaccaggaa gaacagcaac 1080
ttcaggaagc tcgccgtcga aaacgtccag atcgcacact tcagaaagga ccgaccttaa 1140
atgaaggatc cctcatgaat tcatgatcct tccgctctcc tcagtgatcc tagtgctaca 1200
actacaagca tctccccgtt tgtagtaatc atatataaat aagtattccc tccgtaaact 1260
aatataagag catttaaaac actactctag tgatctaaat gctcttatat tagtttacag 1320
agagagtatt gtgtattaat aatgactttc tctgtttcaa aataagtgat gacgtggttt 1380
tagttcaatt ttttttagag aggaggcatc tgacgggcct taaactgagg accttagagt 1440
acaaacaagg ttcgacgaaa gtaagtttaa gggatacaag gccgtagcca acaaaacgcg 1500
acgcagcgcg caatctaaaa tcagcgtgct gtcaaggtag ctggagacgt ccatgccgtt 1560
aatctctctc aagaagctcg ccgaagctca gtgcaccttg cgtgcactct tgtgaagagc 1620
accttcacgt gtcctttgtc ctgagatttt gtcaacagtt tccatgactg caagaaaaac 1680
actagtttgt ataatagctc agcgggatgt cgaatgaatt gcccctcaat caaagcttta 1740
tttctag 1747

<210> SEQ ID NO 115
<211> LENGTH: 1047
<212> TYPE: DNA
<213> ORGANISM: Triticum aestivum

<400> SEQUENCE: 115
atgggcggcc tctccatgga ccaggccttc gtgcaggccc ccgagcatcg caccaaggcg 60
aacctcgccg acgcggccgg catcccggtc atcgacctct cccctctcgc cgccggcgac 120
aaggccggcc tggacgccct cgcggccgag gtgggcaggg cgagccgtga ctgggggttc 180
ttcgtggtgg tgcgccacgg cgtgccggcg gagacggtgg cgcgggcgct ggaggcgcag 240
agggccttct tcgcgctgcc cgcggaccgg aaggcggccg tgcggaggga cgaggcggcg 300
ccgctggggt actacgagtc ggagcacacc aagaacgtca gggactggaa ggaggtgttc 360
gacctcgtcc cccgcgagcc gccgccgcct gccgcggttg ccgacggcga gctcatgttc 420
gagaacaagt ggcccgagga cctgccgggg ttcagagagg ctctcgaaga gtacgagaaa 480
gcgatggagg agctggcgtt caagctgctg gagctgatcg cccggagcct gggactgaga 540
ccggaccggc tgcacggctt cttcaaggac cagaccacct tcatccggct gaaccactac 600

```
ccgccctgcc ccagccccga cctcgccctc ggcgtcggtc gccacaagga cgccggcgcg    660

ctcaccatcc tctaccagga cgacgtcggc gggctcgacg tccggcgccg ctccgacggc    720

gagtgggtgc gcgtcaggcc tgtcccggac tcctacgtca tcaacgtcgg cgacatcatc    780

caggtgtgga gcaacgacag gtacgagagc gcggagcaca gggtgtcggt gaactcgcac    840

aaggagaggt tctccatgcc ctacttcttc gaccccggga gcgacgccat gatcgagccg    900

ttggaggaga tggtgagcga cgaaaggccg gccaggtacg acgcctacaa ctggggcaac    960

ttcttcagca ccaggaagaa cagcaacttc aggaagctcg ccgtcgaaaa cgtccagatc   1020

gcacacttca gaaaggaccg accttaa                                       1047


<210> SEQ ID NO 116
<211> LENGTH: 348
<212> TYPE: PRT
<213> ORGANISM: Triticum aestivum

<400> SEQUENCE: 116

Met Gly Gly Leu Ser Met Asp Gln Ala Phe Val Gln Ala Pro Glu His
1               5                   10                  15

Arg Thr Lys Ala Asn Leu Ala Asp Ala Ala Gly Ile Pro Val Ile Asp
            20                  25                  30

Leu Ser Pro Leu Ala Ala Gly Asp Lys Ala Gly Leu Asp Ala Leu Ala
        35                  40                  45

Ala Glu Val Gly Arg Ala Ser Arg Asp Trp Gly Phe Phe Val Val Val
    50                  55                  60

Arg His Gly Val Pro Ala Glu Thr Val Ala Arg Ala Leu Glu Ala Gln
65                  70                  75                  80

Arg Ala Phe Phe Ala Leu Pro Ala Asp Arg Lys Ala Ala Val Arg Arg
                85                  90                  95

Asp Glu Ala Ala Pro Leu Gly Tyr Tyr Glu Ser Glu His Thr Lys Asn
            100                 105                 110

Val Arg Asp Trp Lys Glu Val Phe Asp Leu Val Pro Arg Glu Pro Pro
        115                 120                 125

Pro Pro Ala Ala Val Ala Asp Gly Glu Leu Met Phe Glu Asn Lys Trp
    130                 135                 140

Pro Glu Asp Leu Pro Gly Phe Arg Glu Ala Leu Glu Glu Tyr Glu Lys
145                 150                 155                 160

Ala Met Glu Glu Leu Ala Phe Lys Leu Leu Glu Leu Ile Ala Arg Ser
                165                 170                 175

Leu Gly Leu Arg Pro Asp Arg Leu His Gly Phe Phe Lys Asp Gln Thr
            180                 185                 190

Thr Phe Ile Arg Leu Asn His Tyr Pro Pro Cys Pro Ser Pro Asp Leu
        195                 200                 205

Ala Leu Gly Val Gly Arg His Lys Asp Ala Gly Ala Leu Thr Ile Leu
    210                 215                 220

Tyr Gln Asp Asp Val Gly Gly Leu Asp Val Arg Arg Arg Ser Asp Gly
225                 230                 235                 240

Glu Trp Val Arg Val Arg Pro Val Pro Asp Ser Tyr Val Ile Asn Val
                245                 250                 255

Gly Asp Ile Ile Gln Val Trp Ser Asn Asp Arg Tyr Glu Ser Ala Glu
            260                 265                 270

His Arg Val Ser Val Asn Ser His Lys Glu Arg Phe Ser Met Pro Tyr
        275                 280                 285

Phe Phe Asp Pro Gly Ser Asp Ala Met Ile Glu Pro Leu Glu Glu Met
```

```
    290                 295                 300

Val Ser Asp Glu Arg Pro Ala Arg Tyr Asp Ala Tyr Asn Trp Gly Asn
305                 310                 315                 320

Phe Phe Ser Thr Arg Lys Asn Ser Asn Phe Arg Lys Leu Ala Val Glu
                325                 330                 335

Asn Val Gln Ile Ala His Phe Arg Lys Asp Arg Pro
            340                 345


<210> SEQ ID NO 117
<211> LENGTH: 1863
<212> TYPE: DNA
<213> ORGANISM: Triticum aestivum

<400> SEQUENCE: 117

tcactcaagg ccacaacaca ctcgccagtc catcgccacc atacgtgaca acttgagtta     60

cttgatctgt tgctcatcga tctcgacatc gccatgggcg gcctctccat ggaccaggcc    120

ttcgtgcagg cccccgagca tcgcaccaag gcgaacctcg ccgacgcggc cggcatcccg    180

gtcatcgacc tctcccctct cgccgccggc gacaaggccg gcctggacgc cctcgcggcc    240

gaggtgggca gggcgagccg tgactggggg ttcttcgtgg tggtgcgcca cggcgtgccg    300

gcggagacgg tggcgcgggc gctggaggcg cagagggcct tcttcgcgct gcccgcggac    360

cggaaggcgg ccgtgcggag ggacgaggcg gcgccgctgg ggtactacga gtcggagcac    420

accaagaacg tcagggactg gaaggaggtg ttcgacctcg tcccccgcga gccgccgccg    480

cctgccgcgg ttgccgacgg cgagctcatg ttcgagaaca agtggcccga ggacctgccg    540

gggttcaggt acggtcatca actcaatcaa ttctgcgacc ccgagagaaa tggttcacta    600

ttattcgtgg ttcatacgta tgattcagac gttaatctcg atgcaaattg atttgtgcat    660

gcagagaggc tctcgaagag tacgagaaag cgatggagga gctggcgttc aagctgctgg    720

agctgatcgc ccggagcctg ggactgagac cggaccggct gcacggcttc ttcaaggacc    780

agaccacctt catccggctg aaccactacc cgccctgccc cagccccgac ctcgccctcg    840

gcgtcggtcg ccacaaggac gccggcgcgc tcaccatcct ctaccaggac gacgtcggcg    900

ggctcgacgt ccggcgccgc tccgacggcg agtgggtgcg cgtcaggcct gtcccggact    960

cctacgtcat caacgtcggc gacatcatcc aggtgtggag caacgacagg tacgagagcg   1020

cggagcacag ggtgtcggtg aactcgcaca aggagaggtt ctccatgccc tacttcttcg   1080

accccgggag cgacgccatg atcgagccgt tggaggagat ggtgagcgac gaaaggccgg   1140

ccaggtacga cgcctacaac tggggcaact tcttcagcac caggaagaac agcaacttca   1200

ggaagctcgc cgtcgaaaac gtccagatcg cacacttcag aaaggaccga ccttaaatga   1260

aggatccctc atgaattcat gatccttccg ctctcctcag tgatcctagt gctacaacta   1320

caagcatctc cccgtttgta gtaatcatat ataaataagt attccctccg taaactaata   1380

taagagcatt taaaacacta ctctagtgat ctaaatgctc ttatattagt ttacagagag   1440

agtattgtgt attaataatg actttctctg tttcaaaata agtgatgacg tggttttagt   1500

tcaatttttt ttagagagga ggcatctgac gggccttaaa ctgaggacct tagagtacaa   1560

acaaggttcg acgaaagtaa gtttaaggga tacaaggccg tagccaacaa aacgcgacgc   1620

agcgcgcaat ctaaaatcag cgtgctgtca aggtagctgg agacgtccat gccgttaatc   1680

tctctcaaga agctcgccga agctcagtgc accttgcgtg cactcttgtg aagagcacct   1740

tcacgtgtcc tttgtcctga gattttgtca acagtttcca tgactgcaag aaaaacacta   1800
```

gtttgtataa tagctcagcg ggatgtcgaa tgaattgccc ctcaatcaaa gctttatttc 1860
tag 1863

<210> SEQ ID NO 118
<211> LENGTH: 349
<212> TYPE: PRT
<213> ORGANISM: Hordeum vulgare

<400> SEQUENCE: 118

```
Met Gly Gly Leu Ser Met Gly Gln Ala Phe Val Gln Ala Pro Glu His
1               5                   10                  15

Arg Thr Lys Pro Thr Leu Ala Asp Ala Asp Gly Ile Pro Val Ile Asp
            20                  25                  30

Leu Ser Pro Leu Ala Ala Gly Asp Glu Ala Gly Val Asp Ala Leu Ala
        35                  40                  45

Ala Glu Val Gly Arg Ala Ser Arg Asp Trp Gly Phe Phe Val Val Val
    50                  55                  60

Arg His Gly Val Pro Ala Glu Thr Val Ala Arg Ala Leu Glu Ala Gln
65                  70                  75                  80

Arg Ala Phe Phe Ala Leu Pro Ala Glu Arg Lys Ala Ala Val Arg Arg
                85                  90                  95

Asp Glu Ala Ala Pro Leu Gly Tyr Tyr Glu Ser Glu His Thr Lys Asn
            100                 105                 110

Val Arg Asp Trp Lys Glu Val Phe Asp Phe Val Pro Arg Glu Pro Pro
        115                 120                 125

Pro Pro Ala Ala Val Ala Asp Gly Glu Leu Val Phe Glu Asn Lys Trp
    130                 135                 140

Pro Glu Asp Leu Pro Gly Phe Arg Val Ala Phe Glu Glu Tyr Ala Lys
145                 150                 155                 160

Ala Met Glu Glu Leu Ala Phe Lys Leu Leu Glu Leu Ile Ala Arg Ser
                165                 170                 175

Leu Gly Leu Thr Pro Asp Arg Leu Asn Gly Phe Phe Lys Asp His Gln
            180                 185                 190

Thr Thr Phe Ile Arg Leu Asn His Tyr Pro Pro Cys Pro Ser Pro Asp
        195                 200                 205

Leu Ala Leu Gly Val Gly Arg His Lys Asp Ala Gly Ala Leu Thr Val
    210                 215                 220

Leu Tyr Gln Asp Asp Val Gly Gly Leu Asp Val Arg His Arg Ser Asp
225                 230                 235                 240

Gly Glu Trp Val Arg Val Arg Pro Val Pro Asp Ser Tyr Val Ile Asn
                245                 250                 255

Val Gly Asp Ile Ile Gln Val Trp Ser Asn Asp Arg Tyr Glu Ser Ala
            260                 265                 270

Glu His Arg Val Ser Val Asn Ser Asp Lys Glu Arg Phe Ser Met Pro
        275                 280                 285

Tyr Phe Phe Asn Pro Gly Ser Asp Ala Met Val Glu Pro Leu Glu Glu
    290                 295                 300

Met Val Ser Asp Glu Arg Pro Ala Arg Tyr Asp Ala Tyr Asn Trp Gly
305                 310                 315                 320

His Phe Phe Ser Thr Arg Lys Asn Ser Asn Phe Lys Lys Leu Asp Val
                325                 330                 335

Glu Asn Val Gln Ile Ala His Phe Arg Lys Leu His Leu
            340                 345
```

<210> SEQ ID NO 119
<211> LENGTH: 1963
<212> TYPE: DNA
<213> ORGANISM: Sorghum bicolor

<400> SEQUENCE: 119

```
tataaatacc acgccatgta cttctctgct tctacacttc tccagcttct ctcatgccat      60

accactagtg caaggtccta gatttacact tggtgctaca gcttcttcct ccctccctcc     120

cctctctagg cagctagcac gcagcgcagc acacgaaaca tctattgacc ggccgcctcc     180

gccggggatc cataattact atactaccaa tcggccagcg tcatgccgac gccgtcgcac     240

ctcgcgaacc cgcgctactt cgacttccgt gcggcgcggc gggtgccgga gacgcacgcc     300

tggccggggc tgcacgacca ccccgtcgtg gacggcggcg cgccggggcc agacgccgtc     360

cccgtggtgg acctcgcggg ggcggcggac gagccgagag ccgcggtggt ggcccaagtg     420

gcgcgcgccg ccgagcaatg gggcgcgttc ctgctcacgg ggcacggcgt ccccgcggag     480

ctgctggcgc gcgtcgagga ccggatcgcc accatgttcg cgctgccagc ggacgacaag     540

atgcgcgccg tgcgcgggcc tggcgacgcc tgcggctacg gctccccgcc catctcctcc     600

ttcttctcca agtgcatgtg gtcggaggga tacaccttct cgccggccaa cctccgcgcc     660

gacctccgca agctctggcc taaggccggc gacgactaca ccagcttctg tgatgtgatg     720

gaggagttcc acaagcacat gcgtgccctc gcggacaagc tgctggagct gttcctcatg     780

gcgctggggc tcaccgacga gcaggtcggc ggcgtggagg cggagcggag gatcgccgag     840

acgatgaccg ccaccatgca cctcaactgg taccctcggt gcccggaccc gcgccgcgcg     900

ctggggctga tcgcgcacac cgactcgggc ttcttcacct tcgtgctgca gagcctcgtc     960

ccggggctgc agctcttccg ccacgccccg gaccggtggg tggcggtgcc ggcggtaccg    1020

ggcgccttcg tcgtcaacgt gggcgacctc ttccacatcc tcaccaacgg ccggttccac    1080

agcgtgtacc accgcgccgt cgtgaaccgg gacctcgaca ggatatctct cggctacttc    1140

ctcggcccgc cgccgcacgc caaggtggcg ccgctaaggg aggccgtgcc gcccggccgc    1200

acccccgcgt accgcgccgt cacgtggccc gagtacatgg gcgtccgcaa gaaggccttc    1260

accaccggcg catccgcgct caagatggtc gccctcgccg ccgccgccgc cgccgccgac    1320

ctcgacgatg acgccggtgc tggcgccgcc gccgaacctg tcgtccatca gcagctactc    1380

gtctcgtcgt agccgatcga tcgccggatc ggtcgagact gatgatgatg atgcatatat    1440

actcgtcgat ggagtagaca gactaatcaa gcaaccctga aactatgaat gcatgcgtgc    1500

gcttcgtgct tgcttgcgca tgcagctagc aggcttcatt ccgttccgca gctgctctgc    1560

tccaacctgc tctgctggat tgatgtatat ggtagaagaa ttaagagatc gatggatgac    1620

ggaggaagaa gaagacgaag acgacgatga ggaaaaggac acgctgtacg tagctggttc    1680

ttctagtcta gtttacagca ggccgggcgg ccggctgctg cttccaatcg agtttgtcgt    1740

tactgacgat tgttagtgga tcgattaact aatctggaat tctggattat taatataatg    1800

catgtggttt ggcatctggc gtaaagcagg taatggtacc tagccagtag ccagtagcca    1860

ggctggtcaa tgataggtct ataccctgat cctgtactgt tgtttctttc ggtctttctg    1920

agagagaaaa aaaacgaata tatggcgtac tcaattcatc aaa                     1963
```

<210> SEQ ID NO 120
<211> LENGTH: 1170
<212> TYPE: DNA
<213> ORGANISM: Sorghum bicolor

<400> SEQUENCE: 120
atgccgacgc cgtcgcacct cgcgaacccg cgctacttcg acttccgtgc ggcgcggcgg 60
gtgccggaga cgcacgcctg gccggggctg cacgaccacc ccgtcgtgga cggcggcgcg 120
ccggggccag acgccgtccc cgtggtggac ctcgcggggg cggcggacga gccgagagcc 180
gcggtggtgg cccaagtggc gcgcgccgcc gagcaatggg gcgcgttcct gctcacgggg 240
cacggcgtcc ccgcggagct gctggcgcgc gtcgaggacc ggatcgccac catgttcgcg 300
ctgccagcgg acgacaagat gcgcgccgtg cgcgggcctg gcgacgcctg cggctacggc 360
tccccgccca tctcctcctt cttctccaag tgcatgtggt cggagggata caccttctcg 420
ccggccaacc tccgcgccga cctccgcaag ctctggccta aggccggcga cgactacacc 480
agcttctgtg atgtgatgga ggagttccac aagcacatgc gtgccctcgc ggacaagctg 540
ctggagctgt tcctcatggc gctggggctc accgacgagc aggtcggcgg cgtggaggcg 600
gagcggagga tcgccgagac gatgaccgcc accatgcacc tcaactggta ccctcggtgc 660
ccggacccgc gccgcgcgct ggggctgatc gcgcacaccg actcgggctt cttcaccttc 720
gtgctgcaga gcctcgtccc ggggctgcag ctcttccgcc acgccccgga ccggtgggtg 780
gcggtgccgg cggtaccggg cgccttcgtc gtcaacgtgg gcgacctctt ccacatcctc 840
accaacggcc ggttccacag cgtgtaccac cgcgccgtcg tgaaccggga cctcgacagg 900
atatctctcg gctacttcct cggcccgccg ccgcacgcca aggtggcgcc gctaagggag 960
gccgtgccgc ccggccgcac ccccgcgtac cgcgccgtca cgtggcccga gtacatgggc 1020
gtccgcaaga aggccttcac caccggcgca tccgcgctca agatggtcgc cctcgccgcc 1080
gccgccgccg ccgccgacct cgacgatgac gccggtgctg gcgccgccgc cgaacctgtc 1140
gtccatcagc agctactcgt ctcgtcgtag 1170

<210> SEQ ID NO 121
<211> LENGTH: 389
<212> TYPE: PRT
<213> ORGANISM: Sorghum bicolor

<400> SEQUENCE: 121

```
Met Pro Thr Pro Ser His Leu Ala Asn Pro Arg Tyr Phe Asp Phe Arg
1               5                   10                  15

Ala Ala Arg Arg Val Pro Glu Thr His Ala Trp Pro Gly Leu His Asp
            20                  25                  30

His Pro Val Val Asp Gly Gly Ala Pro Gly Pro Asp Ala Val Pro Val
        35                  40                  45

Val Asp Leu Ala Gly Ala Ala Asp Glu Pro Arg Ala Ala Val Val Ala
    50                  55                  60

Gln Val Ala Arg Ala Ala Glu Gln Trp Gly Ala Phe Leu Leu Thr Gly
65                  70                  75                  80

His Gly Val Pro Ala Glu Leu Leu Ala Arg Val Glu Asp Arg Ile Ala
                85                  90                  95

Thr Met Phe Ala Leu Pro Ala Asp Asp Lys Met Arg Ala Val Arg Gly
            100                 105                 110

Pro Gly Asp Ala Cys Gly Tyr Gly Ser Pro Pro Ile Ser Ser Phe Phe
        115                 120                 125

Ser Lys Cys Met Trp Ser Glu Gly Tyr Thr Phe Ser Pro Ala Asn Leu
    130                 135                 140

Arg Ala Asp Leu Arg Lys Leu Trp Pro Lys Ala Gly Asp Asp Tyr Thr
145                 150                 155                 160
```

Ser Phe Cys Asp Val Met Glu Glu Phe His Lys His Met Arg Ala Leu
165 170 175

Ala Asp Lys Leu Leu Glu Leu Phe Leu Met Ala Leu Gly Leu Thr Asp
180 185 190

Glu Gln Val Gly Gly Val Glu Ala Glu Arg Arg Ile Ala Glu Thr Met
195 200 205

Thr Ala Thr Met His Leu Asn Trp Tyr Pro Arg Cys Pro Asp Pro Arg
210 215 220

Arg Ala Leu Gly Leu Ile Ala His Thr Asp Ser Gly Phe Phe Thr Phe
225 230 235 240

Val Leu Gln Ser Leu Val Pro Gly Leu Gln Leu Phe Arg His Ala Pro
245 250 255

Asp Arg Trp Val Ala Val Pro Ala Val Pro Gly Ala Phe Val Val Asn
260 265 270

Val Gly Asp Leu Phe His Ile Leu Thr Asn Gly Arg Phe His Ser Val
275 280 285

Tyr His Arg Ala Val Val Asn Arg Asp Leu Asp Arg Ile Ser Leu Gly
290 295 300

Tyr Phe Leu Gly Pro Pro Pro His Ala Lys Val Ala Pro Leu Arg Glu
305 310 315 320

Ala Val Pro Pro Gly Arg Thr Pro Ala Tyr Arg Ala Val Thr Trp Pro
325 330 335

Glu Tyr Met Gly Val Arg Lys Lys Ala Phe Thr Thr Gly Ala Ser Ala
340 345 350

Leu Lys Met Val Ala Leu Ala Ala Ala Ala Ala Ala Ala Asp Leu Asp
355 360 365

Asp Asp Ala Gly Ala Gly Ala Ala Ala Glu Pro Val Val His Gln Gln
370 375 380

Leu Leu Val Ser Ser
385

<210> SEQ ID NO 122
<211> LENGTH: 2321
<212> TYPE: DNA
<213> ORGANISM: Sorghum bicolor

<400> SEQUENCE: 122
tataaatacc acgccatgta cttctctgct tctacacttc tccagcttct ctcatgccat 60
accactagtg caaggtccta gatttacact tggtgctaca gcttcttcct ccctccctcc 120
cctctctagg cagctagcac gcagcgcagc acacgaaaca tctattgacc ggccgcctcc 180
gccggggatc cataattact atactaccaa tcggccagcg tcatgccgac gccgtcgcac 240
ctcgcgaacc cgcgctactt cgacttccgt gcggcgcggc gggtgccgga gacgcacgcc 300
tggccggggc tgcacgacca ccccgtcgtg gacggcggcg cgccggggcc agacgccgtc 360
cccgtggtgg acctcgcggg ggcggcggac gagccgagag ccgcggtggt ggcccaagtg 420
gcgcgcgccg ccgagcaatg gggcgcgttc ctgctcacgg ggcacggcgt ccccgcggag 480
ctgctggcgc gcgtcgagga ccggatcgcc accatgttcg cgctgccagc ggacgacaag 540
atgcgcgccg tgcgcgggcc tggcgacgcc tgcggctacg gctccccgcc catctcctcc 600
ttcttctcca agtgcatgtg gtcggaggga tacaccttct cgccggccaa cctccgcgcc 660
gacctccgca agctctggcc taaggccggc gacgactaca ccagcttctg gtacgtgcac 720
ccgccggccg cgcgccgcca cacaccgtac ccacacacgt gcgcgctcgc gcctagctac 780
tagtagctgc tttgctttgc ttacctttga ttctcgcctt tgccatgcat atgcatgatg 840
cacgtacagg tactgcaggt acaacatgtc acacgcacgc acgcacgcac aacccatagt 900
ccgatacgat acatcatcga tcgacgtgtc gtcaccgtct aaggccatgc atgcatgcaa 960
gcacacgcct agaccttttt agcatgctgg ctgacgagga gtatactagc taataagcta 1020
cttgtcactg cgcgtcttgc ttaattacac tagtgcatat ttctacagtg atgtgatgga 1080
ggagttccac aagcacatgc gtgccctcgc ggacaagctg ctggagctgt tcctcatggc 1140
gctggggctc accgacgagc aggtcggcgg cgtggaggcg gagcggagga tcgccgagac 1200
gatgaccgcc accatgcacc tcaactggta ccctcggtgc ccggacccgc gccgcgcgct 1260
ggggctgatc gcgcacaccg actcgggctt cttcaccttc gtgctgcaga gcctcgtccc 1320
ggggctgcag ctcttccgcc acgccccgga ccggtgggtg gcggtgccgg cggtaccggg 1380
cgccttcgtc gtcaacgtgg gcgacctctt ccacatcctc accaacggcc ggttccacag 1440
cgtgtaccac cgcgccgtcg tgaaccggga cctcgacagg atatctctcg gctacttcct 1500
cggcccgccg ccgcacgcca aggtggcgcc gctaagggag gccgtgccgc ccggccgcac 1560
ccccgcgtac cgcgccgtca cgtggcccga gtacatgggc gtccgcaaga aggccttcac 1620
caccggcgca tccgcgctca agatggtcgc cctcgccgcc gccgccgccg ccgccgacct 1680
cgacgatgac gccggtgctg gcgccgccgc cgaacctgtc gtccatcagc agctactcgt 1740
ctcgtcgtag ccgatcgatc gccggatcgg tcgagactga tgatgatgat gcatatatac 1800
tcgtcgatgg agtagacaga ctaatcaagc aaccctgaaa ctatgaatgc atgcgtgcgc 1860
ttcgtgcttg cttgcgcatg cagctagcag gcttcattcc gttccgcagc tgctctgctc 1920
caacctgctc tgctggattg atgtatatgg tagaagaatt aagagatcga tggatgacgg 1980
aggaagaaga agacgaagac gacgatgagg aaaaggacac gctgtacgta gctggttctt 2040
ctagtctagt ttacagcagg ccgggcggcc ggctgctgct tccaatcgag tttgtcgtta 2100
ctgacgattg ttagtggatc gattaactaa tctggaattc tggattatta atataatgca 2160
tgtggtttgg catctggcgt aaagcaggta atggtaccta gccagtagcc agtagccagg 2220
ctggtcaatg ataggtctat accctgatcc tgtactgttg tttctttcgg tctttctgag 2280
agagaaaaaa aacgaatata tggcgtactc aattcatcaa a 2321

<210> SEQ ID NO 123
<211> LENGTH: 1796
<212> TYPE: DNA
<213> ORGANISM: Setaria italica

<400> SEQUENCE: 123
actagtgcaa ggtcctagat ttacacttgg tgcttgcttg tttcttccta gttgctactg 60
gtagcacgca gtggctggct ggccgtaatc tattgtctgg gctcgatcgg tgattaggaa 120
gtagccaaag caagctaagg ccgccgccgc cgccgccatg ccgacgccgt cgcacctcaa 180
gaacccgctc tacttcgact tccgcgccgc gcggcgggtg ccggagtccc acgcctggcc 240
ggggctcgac gaccaccccg tggtggacgg cggcggcgcg ccggggtccc cggacgccgt 300
gccggtggtg gacctgcgcg agccgggcgc cgcggcggtg gcccgcgtgg cgcgcgccgc 360
cgagcagtgg ggcgcgttcc tgctcaccgg ccacggcgtc cccgcggagc tcctggcgcg 420
cgtcgaggac cgcgtcgcgt gcatgttcgc gctgccggcc gccgacaaga tgcgcgccgt 480
gcgcgggccg ggggacgcct gcggctacgg ctcgccgccc atctcctcct tcttctccaa 540

```
gtgcatgtgg tccgagggct acaccttctc gccggcctcc ctccgccgcg acctccgcaa    600

gctctggccc aaggccggcg acgactacga cagcttctgt gacgtgatgg aggagttcca    660

caaggagatg cgcgccctcg ccgacaggct cctggagctg ttcctcaggg cgctcgggct    720

caccggcgag caggtcggcg ccgtcgaggc ggagcggagg atcggcgaga cgatgaccgc    780

caccatgcac ctcaactggt atccgaggtg cccggacccg cggcgcgcgc tggggctgat    840

cgcgcacacg gactcgggct tcttcacctt cgtgctgcag agcctcgtgc cggggctgca    900

gctgttccgg cacggcccca accggtgggt ggcggtgccg gccgtgccgg gcgccttcgt    960

cgtcaacgtc ggcgacctct tccacatcct cacgaacggc cgcttccaca gcgtgtacca   1020

ccgcgccgtc gtcaaccggg acctcgaccg gatatcgctc ggctacttcc tcggcccgcc   1080

gccccacgcc aaggtggcgc cgctccggga ggtcgtgccg ccgggccggg cccccgccta   1140

ccgcgccgtc acgtggcccg agtacatggg cgtccgcaag aaggccttca ccaccggcgc   1200

ctccgcgctc aagatggtcg ccgccgccgc cgccgccacc gaatccgacg acaccgacgc   1260

agccgccgcc gccgttcacc agccgccggt cgtcgtctca tcgtagccga tcgatcgccg   1320

gaaacacaga cgatgcatac cgtaccccga gcaatctaat caaaacaagg catccattct   1380

cgcgcgcatg cagcggccag ccgggcttcc gcagctgctc ggcctcctct gctggctgtg   1440

gaaatggaaa attttaatct gagatgaaga cgaagacgaa gacgaaacgg agaggaaaag   1500

gacatgctgt agctgtttct tctagttgcg caggccgctc ccagtcgagt ttgtcgttac   1560

tgacgattat tactctgatg aaaactaatc tgaattaatg catgtagttt ggcaatttgg   1620

tactaaaggt aggcacctag ccaggctggt caatgatagg tctataacct gatcctgttc   1680

tctgttgttt tcctttgtct gagaaaaaat ggaaataatt gatccggccg gacgggtgta   1740

ctgataggtg atgctgaatt gctgatgcaa gaggttgcga gctgcagtga gcagca       1796
```

<210> SEQ ID NO 124
<211> LENGTH: 1149
<212> TYPE: DNA
<213> ORGANISM: Setaria italica

<400> SEQUENCE: 124

```
atgccgacgc cgtcgcacct caagaacccg ctctacttcg acttccgcgc cgcgcggcgg     60

gtgccggagt cccacgcctg gccggggctc gacgaccacc ccgtggtgga cggcggcggc    120

gcgccggggt ccccggacgc cgtgccggtg gtggacctgc gcgagccggg cgccgcggcg    180

gtggcccgcg tggcgcgcgc cgccgagcag tggggcgcgt tcctgctcac cggccacggc    240

gtccccgcgg agctcctggc gcgcgtcgag gaccgcgtcg cgtgcatgtt cgcgctgccg    300

gccgccgaca agatgcgcgc cgtgcgcggg ccgggggacg cctgcggcta cggctcgccg    360

cccatctcct ccttcttctc caagtgcatg tggtccgagg gctacacctt ctcgccggcc    420

tccctccgcc gcgacctccg caagctctgg cccaaggccg gcgacgacta cgacagcttc    480

tgtgacgtga tggaggagtt ccacaaggag atgcgcgccc tcgccgacag gctcctggag    540

ctgttcctca gggcgctcgg gctcaccggc gagcaggtcg gcgccgtcga ggcggagcgg    600

aggatcggcg agacgatgac cgccaccatg cacctcaact ggtatccgag gtgcccggac    660

ccgcggcgcg cgctggggct gatcgcgcac acggactcgg gcttcttcac cttcgtgctg    720

cagagcctcg tgccggggct gcagctgttc cggcacggcc ccaaccggtg ggtggcggtg    780

ccggccgtgc cgggcgcctt cgtcgtcaac gtcggcgacc tcttccacat cctcacgaac    840

ggccgcttcc acagcgtgta ccaccgcgcc gtcgtcaacc gggacctcga ccggatatcg    900
```

ctcggctact tcctcggccc gccgccccac gccaaggtgg cgccgctccg ggaggtcgtg 960
ccgccgggcc gggcccccgc ctaccgcgcc gtcacgtggc ccgagtacat gggcgtccgc 1020
aagaaggcct tcaccaccgg cgcctccgcg ctcaagatgg tcgccgccgc cgccgccgcc 1080
accgaatccg acgacaccga cgcagccgcc gccgccgttc accagccgcc ggtcgtcgtc 1140
tcatcgtag 1149

<210> SEQ ID NO 125
<211> LENGTH: 382
<212> TYPE: PRT
<213> ORGANISM: Setaria italica

<400> SEQUENCE: 125

Met Pro Thr Pro Ser His Leu Lys Asn Pro Leu Tyr Phe Asp Phe Arg
1 5 10 15

Ala Ala Arg Arg Val Pro Glu Ser His Ala Trp Pro Gly Leu Asp Asp
20 25 30

His Pro Val Val Asp Gly Gly Gly Ala Pro Gly Ser Pro Asp Ala Val
35 40 45

Pro Val Val Asp Leu Arg Glu Pro Gly Ala Ala Ala Val Ala Arg Val
50 55 60

Ala Arg Ala Ala Glu Gln Trp Gly Ala Phe Leu Leu Thr Gly His Gly
65 70 75 80

Val Pro Ala Glu Leu Leu Ala Arg Val Glu Asp Arg Val Ala Cys Met
85 90 95

Phe Ala Leu Pro Ala Ala Asp Lys Met Arg Ala Val Arg Gly Pro Gly
100 105 110

Asp Ala Cys Gly Tyr Gly Ser Pro Pro Ile Ser Ser Phe Phe Ser Lys
115 120 125

Cys Met Trp Ser Glu Gly Tyr Thr Phe Ser Pro Ala Ser Leu Arg Arg
130 135 140

Asp Leu Arg Lys Leu Trp Pro Lys Ala Gly Asp Asp Tyr Asp Ser Phe
145 150 155 160

Cys Asp Val Met Glu Glu Phe His Lys Glu Met Arg Ala Leu Ala Asp
165 170 175

Arg Leu Leu Glu Leu Phe Leu Arg Ala Leu Gly Leu Thr Gly Glu Gln
180 185 190

Val Gly Ala Val Glu Ala Glu Arg Arg Ile Gly Glu Thr Met Thr Ala
195 200 205

Thr Met His Leu Asn Trp Tyr Pro Arg Cys Pro Asp Pro Arg Arg Ala
210 215 220

Leu Gly Leu Ile Ala His Thr Asp Ser Gly Phe Phe Thr Phe Val Leu
225 230 235 240

Gln Ser Leu Val Pro Gly Leu Gln Leu Phe Arg His Gly Pro Asn Arg
245 250 255

Trp Val Ala Val Pro Ala Val Pro Gly Ala Phe Val Val Asn Val Gly
260 265 270

Asp Leu Phe His Ile Leu Thr Asn Gly Arg Phe His Ser Val Tyr His
275 280 285

Arg Ala Val Val Asn Arg Asp Leu Asp Arg Ile Ser Leu Gly Tyr Phe
290 295 300

Leu Gly Pro Pro Pro His Ala Lys Val Ala Pro Leu Arg Glu Val Val
305 310 315 320

-continued

Pro Pro Gly Arg Ala Pro Ala Tyr Arg Ala Val Thr Trp Pro Glu Tyr
325 330 335

Met Gly Val Arg Lys Lys Ala Phe Thr Thr Gly Ala Ser Ala Leu Lys
340 345 350

Met Val Ala Ala Ala Ala Ala Ala Thr Glu Ser Asp Asp Thr Asp Ala
355 360 365

Ala Ala Ala Ala Val His Gln Pro Pro Val Val Val Ser Ser
370 375 380

<210> SEQ ID NO 126
<211> LENGTH: 2146
<212> TYPE: DNA
<213> ORGANISM: Setaria italica

<400> SEQUENCE: 126
actagtgcaa ggtcctagat ttacacttgg tgcttgcttg tttcttccta gttgctactg 60
gtagcacgca gtggctggct ggccgtaatc tattgtctgg gctcgatcgg tgattaggaa 120
gtagccaaag caagctaagg ccgccgccgc cgccgccatg ccgacgccgt cgcacctcaa 180
gaacccgctc tacttcgact tccgcgccgc gcggcgggtg ccggagtccc acgcctggcc 240
ggggctcgac gaccaccccg tggtggacgg cggcggcgcg ccggggtccc cggacgccgt 300
gccggtggtg gacctgcgcg agccgggcgc cgcggcggtg gcccgcgtgg cgcgcgccgc 360
cgagcagtgg ggcgcgttcc tgctcaccgg ccacggcgtc cccgcggagc tcctggcgcg 420
cgtcgaggac cgcgtcgcgt gcatgttcgc gctgccggcc gccgacaaga tgcgcgccgt 480
gcgcgggccg gggacgcct gcggctacgg ctcgccgccc atctcctcct tcttctccaa 540
gtgcatgtgg tccgagggct acaccttctc gccggcctcc ctccgccgcg acctccgcaa 600
gctctggccc aaggccggcg acgactacga cagcttctgg tacgtcgtcg tctatagcta 660
gtagctagcc gccggcacac gtgcgcctga cctgctccgc catgcatggt gcacgtatgc 720
agatcgatca cacgcaccga tcgatcgacg tgtcccggtc aaggccatgc atgcatgcaa 780
gcaaccaaca gcacgcctcc tgatactgct tgttgcttac accgttggta tgtgcctgtt 840
gcctacagtg acgtgatgga ggagttccac aaggagatgc gcgccctcgc cgacaggctc 900
ctggagctgt tcctcagggc gctcgggctc accggcgagc aggtcggcgc cgtcgaggcg 960
gagcggagga tcggcgagac gatgaccgcc accatgcacc tcaactggta tgtgccatgc 1020
catgaccacc tgcgtctatg aactaacgga agcttccatc gcgtgtccat gacgatttag 1080
aagctgtagt ccagagcttg agacaaacga aacgaagctt acatggtggc gtgacgtgtc 1140
gcgtgcaggt atccgaggtg cccggacccg cggcgcgcgc tggggctgat cgcgcacacg 1200
gactcgggct tcttcacctt cgtgctgcag agcctcgtgc cggggctgca gctgttccgg 1260
cacggcccca accggtgggt ggcggtgccg gccgtgccgg gcgccttcgt cgtcaacgtc 1320
ggcgacctct tccacatcct cacgaacggc cgcttccaca gcgtgtacca ccgcgccgtc 1380
gtcaaccggg acctcgaccg gatatcgctc ggctacttcc tcggcccgcc gccccacgcc 1440
aaggtggcgc cgctccggga ggtcgtgccg ccgggccggg cccccgccta ccgcgccgtc 1500
acgtggcccg agtacatggg cgtccgcaag aaggccttca ccaccggcgc ctccgcgctc 1560
aagatggtcg ccgccgccgc cgccgccacc gaatccgacg acaccgacgc agccgccgcc 1620
gccgttcacc agccgccggt cgtcgtctca tcgtagccga tcgatcgccg gaaacacaga 1680
cgatgcatac cgtaccccga gcaatctaat caaaacaagg catccattct cgcgcgcatg 1740
cagcggccag ccgggcttcc gcagctgctc ggcctcctct gctggctgtg gaaatggaaa 1800

```
attttaatct gagatgaaga cgaagacgaa gacgaaacgg agaggaaaag gacatgctgt   1860

agctgtttct tctagttgcg caggccgctc ccagtcgagt ttgtcgttac tgacgattat   1920

tactctgatg aaaactaatc tgaattaatg catgtagttt ggcaatttgg tactaaaggt   1980

aggcacctag ccaggctggt caatgatagg tctataacct gatcctgttc tctgttgttt   2040

tcctttgtct gagaaaaaat ggaaataatt gatccggccg gacgggtgta ctgataggtg   2100

atgctgaatt gctgatgcaa gaggttgcga gctgcagtga gcagca                  2146
```

<210> SEQ ID NO 127
<211> LENGTH: 1933
<212> TYPE: DNA
<213> ORGANISM: Oryza sativa

<400> SEQUENCE: 127

```
actactcatt ccactattgt aaagtcatag aaaaaattta tatagagaga aaaaattagt     60

gttgttattg ttactggctt tctgccagac gagacgagcg agcgcgcgag tgtgttgctc    120

tctggtcatc gtcgtcgtcg tcgcgatgcc gacgccgtcg cacttgaaga acccgctctg    180

cttcgacttc cgggcggcga ggcgggtgcc ggagacgcac gcgtggccgg ggctggacga    240

ccacccggtg gtggacggcg gcggcggcgg cggcgaggac gcggtgccgg tggtggacgt    300

cggggcgggc gacgcggcgg cgcgggtggc gcgggcggcg gagcagtggg gcgcgttcct    360

tctggtcggg cacggcgtgc cggcggcgct gctgtcgcgc gtcgaggagc gcgtcgcccg    420

cgtgttctcc ctgccggcgt cggagaagat gcgcgccgtc cgcggccccg gcgagccctg    480

cggctacggc tcgccgccca tctcctcctt cttctccaag ctcatgtggt ccgagggcta    540

caccttctcc ccttcctccc tccgctccga gctccgccgc ctctggccca agtccggcga    600

cgactacctc ctcttctgtg acgtgatgga ggagtttcac aaggagatgc ggcggctagc    660

cgacgagttg ctgaggttgt tcttgagggc gctggggctc accggcgagg aggtcgccgg    720

agtcgaggcg gagaggagga tcggcgagag gatgacggcg acggtgcacc tcaactggta    780

cccgaggtgc ccggagccgc ggcgagcgct ggggctcatc gcgcacacgg actcgggctt    840

cttcaccttc gtgctccaga gcctcgtccc ggggctgcag ctgttccgtc gagggcccga    900

ccggtgggtg gcggtgccgg cggtggcggg ggccttcgtc gtcaacgtcg gcgacctctt    960

ccacatcctc accaacggcc gcttccacag cgtctaccac cgcgccgtcg tgaaccgcga   1020

ccgcgaccgg gtctcgctcg gctacttcct cggcccgccg ccggacgccg aggtggcgcc   1080

gctgccggag gccgtgccgg ccggccggag ccccgcctac cgcgctgtca cgtggccgga   1140

gtacatggcc gtccgcaaga aggccttcgc caccggcggc tccgccctca agatggtctc   1200

caccgacgcc gccgccgccg ccgacgaaca cgacgacgtc gccgccgccg ccgacgtcca   1260

cgcataagct atagctacta gctacctcga tctcacgcaa aaaaaaaaag aaacaattaa   1320

tagagcaaaa aaaaaaagaa gagaaaatgg tggtacttgt gtttaaggtt tcctccatgc   1380

aaaatggttt gcatgcatgc atgcaaagct agcatctgca gctgcaagaa ttacaagagc   1440

agagaagcag acagctagat ggagataatt aattaattaa ttaatctaat taagcatgca   1500

ataattaaga ttattattct gatttcagaa ctgaaaaaaa aagtgtggtt aattaattat   1560

tggttaggct taattttatc tagatgtaga aaaagaatca agatcttcaa gcaagagaga   1620

agaggatcga agaagaagga aaagaaaacg aaaaggacat gctgtgttgt ctcttctagt   1680

tgtaccctgg ctgctgatta agtgctttgt tttgttgctg caagcttgtc gttactgatt   1740
```

attagttagt tatgcatcta attgattaaa ctaatctgtt tggcattttg gctcgagcta 1800
agctatagcc aggctggtca atgataggaa cttgtacaat ttaagcaatt gaacctgatc 1860
ctgtactggc atgtatgtat atatgcaagt gatgagaacc actagctagt atagctagac 1920
atgtatttgt ata 1933

<210> SEQ ID NO 128
<211> LENGTH: 1122
<212> TYPE: DNA
<213> ORGANISM: Oryza sativa

<400> SEQUENCE: 128
atgccgacgc cgtcgcactt gaagaacccg ctctgcttcg acttccgggc ggcgaggcgg 60
gtgccggaga cgcacgcgtg gccggggctg gacgaccacc cggtggtgga cggcggcggc 120
ggcggcggcg aggacgcggt gccggtggtg gacgtcgggg cgggcgacgc ggcggcgcgg 180
gtggcgcggg cggcggagca gtggggcgcg ttccttctgg tcgggcacgg cgtgccggcg 240
gcgctgctgt cgcgcgtcga ggagcgcgtc gcccgcgtgt tctccctgcc ggcgtcggag 300
aagatgcgcg ccgtccgcgg ccccggcgag ccctgcggct acggctcgcc gcccatctcc 360
tccttcttct ccaagctcat gtggtccgag ggctacacct tctccccttc ctccctccgc 420
tccgagctcc gccgcctctg gcccaagtcc ggcgacgact acctcctctt ctgtgacgtg 480
atggaggagt ttcacaagga gatgcggcgg ctagccgacg agttgctgag gttgttcttg 540
agggcgctgg ggctcaccgg cgaggaggtc gccggagtcg aggcggagag gaggatcggc 600
gagaggatga cggcgacggt gcacctcaac tggtacccga ggtgcccgga gccgcggcga 660
gcgctggggc tcatcgcgca cacggactcg ggcttcttca ccttcgtgct ccagagcctc 720
gtcccggggc tgcagctgtt ccgtcgaggg cccgaccggt gggtggcggt gccggcggtg 780
gcgggggcct tcgtcgtcaa cgtcggcgac ctcttccaca tcctcaccaa cggccgcttc 840
cacagcgtct accaccgcgc cgtcgtgaac cgcgaccgcg accgggtctc gctcggctac 900
ttcctcggcc cgccgccgga cgccgaggtg gcgccgctgc cggaggccgt gccggccggc 960
cggagccccg cctaccgcgc tgtcacgtgg ccggagtaca tggccgtccg caagaaggcc 1020
ttcgccaccg gcggctccgc cctcaagatg gtctccaccg acgccgccgc cgccgccgac 1080
gaacacgacg acgtcgccgc cgccgccgac gtccacgcat aa 1122

<210> SEQ ID NO 129
<211> LENGTH: 373
<212> TYPE: PRT
<213> ORGANISM: Oryza sativa

<400> SEQUENCE: 129

Met Pro Thr Pro Ser His Leu Lys Asn Pro Leu Cys Phe Asp Phe Arg
1 5 10 15

Ala Ala Arg Arg Val Pro Glu Thr His Ala Trp Pro Gly Leu Asp Asp
20 25 30

His Pro Val Val Asp Gly Gly Gly Gly Gly Gly Glu Asp Ala Val Pro
35 40 45

Val Val Asp Val Gly Ala Gly Asp Ala Ala Ala Arg Val Ala Arg Ala
50 55 60

Ala Glu Gln Trp Gly Ala Phe Leu Leu Val Gly His Gly Val Pro Ala
65 70 75 80

Ala Leu Leu Ser Arg Val Glu Glu Arg Val Ala Arg Val Phe Ser Leu
85 90 95

```
Pro Ala Ser Glu Lys Met Arg Ala Val Arg Gly Pro Gly Glu Pro Cys
            100                 105                 110

Gly Tyr Gly Ser Pro Pro Ile Ser Ser Phe Phe Ser Lys Leu Met Trp
        115                 120                 125

Ser Glu Gly Tyr Thr Phe Ser Pro Ser Ser Leu Arg Ser Glu Leu Arg
    130                 135                 140

Arg Leu Trp Pro Lys Ser Gly Asp Asp Tyr Leu Leu Phe Cys Asp Val
145                 150                 155                 160

Met Glu Glu Phe His Lys Glu Met Arg Arg Leu Ala Asp Glu Leu Leu
                165                 170                 175

Arg Leu Phe Leu Arg Ala Leu Gly Leu Thr Gly Glu Glu Val Ala Gly
            180                 185                 190

Val Glu Ala Glu Arg Arg Ile Gly Glu Arg Met Thr Ala Thr Val His
        195                 200                 205

Leu Asn Trp Tyr Pro Arg Cys Pro Glu Pro Arg Arg Ala Leu Gly Leu
    210                 215                 220

Ile Ala His Thr Asp Ser Gly Phe Phe Thr Phe Val Leu Gln Ser Leu
225                 230                 235                 240

Val Pro Gly Leu Gln Leu Phe Arg Arg Gly Pro Asp Arg Trp Val Ala
                245                 250                 255

Val Pro Ala Val Ala Gly Ala Phe Val Val Asn Val Gly Asp Leu Phe
            260                 265                 270

His Ile Leu Thr Asn Gly Arg Phe His Ser Val Tyr His Arg Ala Val
        275                 280                 285

Val Asn Arg Asp Arg Asp Arg Val Ser Leu Gly Tyr Phe Leu Gly Pro
    290                 295                 300

Pro Pro Asp Ala Glu Val Ala Pro Leu Pro Glu Ala Val Pro Ala Gly
305                 310                 315                 320

Arg Ser Pro Ala Tyr Arg Ala Val Thr Trp Pro Glu Tyr Met Ala Val
                325                 330                 335

Arg Lys Lys Ala Phe Ala Thr Gly Gly Ser Ala Leu Lys Met Val Ser
            340                 345                 350

Thr Asp Ala Ala Ala Ala Ala Asp Glu His Asp Asp Val Ala Ala Ala
        355                 360                 365

Ala Asp Val His Ala
    370
```

<210> SEQ ID NO 130
<211> LENGTH: 2040
<212> TYPE: DNA
<213> ORGANISM: Oryza sativa

<400> SEQUENCE: 130

```
actactcatt ccactattgt aaagtcatag aaaaaattta tatagagaga aaaaattagt      60

gttgttattg ttactggctt tctgccagac gagacgagcg agcgcgcgag tgtgttgctc     120

tctggtcatc gtcgtcgtcg tcgcgatgcc gacgccgtcg cacttgaaga acccgctctg     180

cttcgacttc cgggcggcga ggcgggtgcc ggagacgcac gcgtggccgg ggctggacga     240

ccacccggtg gtggacggcg gcggcggcgg cggcgaggac gcggtgccgg tggtggacgt     300

cggggcgggc gacgcggcgg cgcgggtggc gcgggcggcg gagcagtggg gcgcgttcct     360

tctggtcggg cacggcgtgc cggcggcgct gctgtcgcgc gtcgaggagc gcgtcgcccg     420

cgtgttctcc ctgccggcgt cggagaagat gcgcgccgtc cgcggccccg gcgagccctg     480
```

```
cggctacggc tcgccgccca tctcctcctt cttctccaag ctcatgtggt ccgagggcta    540
caccttctcc ccttcctccc tccgctccga gctccgccgc ctctggccca agtccggcga    600
cgactacctc ctcttctggt atatatacat atatactctc ccatgcattc catgcacata    660
cactctacgt atatatctac ctctacgtat atatctacgt attgatctac gtataatata    720
cgcagtgacg tgatggagga gtttcacaag gagatgcggc ggctagccga cgagttgctg    780
aggttgttct tgagggcgct ggggctcacc ggcgaggagg tcgccggagt cgaggcggag    840
aggaggatcg gcgagaggat gacggcgacg gtgcacctca actggtaccc gaggtgcccg    900
gagccgcggc gagcgctggg gctcatcgcg cacacggact cgggcttctt caccttcgtg    960
ctccagagcc tcgtcccggg gctgcagctg ttccgtcgag ggcccgaccg gtgggtggcg   1020
gtgccggcgg tggcgggggc cttcgtcgtc aacgtcggcg acctcttcca catcctcacc   1080
aacggccgct tccacagcgt ctaccaccgc gccgtcgtga accgcgaccg cgaccgggtc   1140
tcgctcggct acttcctcgg cccgccgccg gacgccgagg tggcgccgct gccggaggcc   1200
gtgccggccg gccggagccc cgcctaccgc gctgtcacgt ggccggagta catggccgtc   1260
cgcaagaagg ccttcgccac cggcggctcc gccctcaaga tggtctccac cgacgccgcc   1320
gccgccgccg acgaacacga cgacgtcgcc gccgccgccg acgtccacgc ataagctata   1380
gctactagct acctcgatct cacgcaaaaa aaaaaagaaa caattaatag agcaaaaaaa   1440
aaaagaagag aaaatggtgg tacttgtgtt taaggtttcc tccatgcaaa atggtttgca   1500
tgcatgcatg caaagctagc atctgcagct gcaagaatta caagagcaga gaagcagaca   1560
gctagatgga gataattaat taattaatta atctaattaa gcatgcaata attaagatta   1620
ttattctgat ttcagaactg aaaaaaaaag tgtggttaat taattattgg ttaggcttaa   1680
ttttatctag atgtagaaaa agaatcaaga tcttcaagca agagagaaga ggatcgaaga   1740
agaaggaaaa gaaaacgaaa aggacatgct gtgttgtctc ttctagttgt accctggctg   1800
ctgattaagt gctttgtttt gttgctgcaa gcttgtcgtt actgattatt agttagttat   1860
gcatctaatt gattaaacta atctgtttgg cattttggct cgagctaagc tatagccagg   1920
ctggtcaatg ataggaactt gtacaattta agcaattgaa cctgatcctg tactggcatg   1980
tatgtatata tgcaagtgat gagaaccact agctagtata gctagacatg tatttgtata   2040
```

<210> SEQ ID NO 131
<211> LENGTH: 1332
<212> TYPE: DNA
<213> ORGANISM: Hordeum vulgare

<400> SEQUENCE: 131

```
acactcactc ctcaatccat ccgtctccac cattgctcgc tagctcgagc tctactagct     60
agcactgcaa agtcagccgg gccggagttg atttggtcct tgttagcttg accgatcgta    120
tacgtatcgc caggatgccg acgccgtcgc acctgagcaa ggacccgcac tacttcgact    180
tccgggcggc gcggcgggtg ccggagacac acgcgtggcc ggggctgcac gaccacccgg    240
tggtggacgg cggcggcgcg ggcggagggc cggacgcggt gccggtggtg gacatgcgcg    300
acccgtgcgc cgcggaggcg gtggcgctgg ccgcgcagga ctggggcgcc ttcctcttgc    360
agggccacgg cgtcccgttg gagctgctgg cccgcgtgga ggccgcgata gcgggcatgt    420
tcgcgctgcc ggcgtcggag aagatgcgcg ccgtgcggcg gcccggcgac tcgtgcggct    480
acgggtcgcc gcccatctcc tccttcttct ccaagtgcat gtggtccgag ggctacacct    540
tctccccggc caacctccgc tccgacctcc gcaagctctg gcccaaggcc ggccacgact    600
```

accgccactt ctgtgccgtg atggaggagt tccacaggga gatgcgcgtt ctggccgaca 660
agctgctgga gctgttcctg gtggccctcg ggctcaccgg cgagcaggtc gccgccgtcg 720
agtcggagca caagatcgcc gagaccatga ccgccacaat gcacctcaac tggtacccca 780
agtgcccgga cccgaagcga gcgctgggcc tgatcgcgca cacggactcg ggcttcttca 840
ccttcgtgct ccagagcctg gtgcccgggc tgcagctgtt ccggcacggc cccgaccgtt 900
gggtgacggt gcccgccgtg ccgggcgcca tggtcgtcaa cgtcggcgac ctcttccaca 960
tcctcaccaa tggccgcttc cacagcgtct accaccgcgc cgtcgtcaac cgcgacagcg 1020
accggatatc gctggggtac ttcctcggcc cgcccgccca cgttaaggtg gcgccgctca 1080
gggaggccct cgccggcacg cccgctgcct accgcgccgt cacgtggccc gagtacatgg 1140
gcgtgcgcaa gaaggccttc accaccggcg cctccgcgct caagatggtc gccatctcca 1200
ccgacgacgc cgccgacgtc ctccccgacg tcctctcgtc gtagatcggc gccggccatc 1260
acccggccgg ccaagagacc gatctataca aacaattagt gaacaaaaaa aaaaaaaaaa 1320
aaaaaaaaaa aa 1332

<210> SEQ ID NO 132
<211> LENGTH: 1110
<212> TYPE: DNA
<213> ORGANISM: Hordeum vulgare

<400> SEQUENCE: 132
atgccgacgc cgtcgcacct gagcaaggac ccgcactact tcgacttccg ggcggcgcgg 60
cgggtgccgg agacacacgc gtggccgggg ctgcacgacc acccggtggt ggacggcggc 120
ggcgcgggcg gagggccgga cgcggtgccg gtggtggaca tgcgcgaccc gtgcgccgcg 180
gaggcggtgg cgctggccgc gcaggactgg ggcgccttcc tcttgcaggg ccacggcgtc 240
ccgttggagc tgctggcccg cgtggaggcc gcgatagcgg gcatgttcgc gctgccggcg 300
tcggagaaga tgcgcgccgt gcggcggccc ggcgactcgt gcggctacgg gtcgccgccc 360
atctcctcct tcttctccaa gtgcatgtgg tccgagggct acaccttctc cccggccaac 420
ctccgctccg acctccgcaa gctctggccc aaggccggcc acgactaccg ccacttctgt 480
gccgtgatgg aggagttcca cagggagatg cgcgttctgg ccgacaagct gctggagctg 540
ttcctggtgg ccctcgggct caccggcgag caggtcgccg ccgtcgagtc ggagcacaag 600
atcgccgaga ccatgaccgc cacaatgcac ctcaactggt accccaagtg cccggacccg 660
aagcgagcgc tgggcctgat cgcgcacacg gactcgggct tcttcacctt cgtgctccag 720
agcctggtgc ccgggctgca gctgttccgg cacggccccg accgttgggt gacggtgccc 780
gccgtgccgg gcgccatggt cgtcaacgtc ggcgacctct tccacatcct caccaatggc 840
cgcttccaca gcgtctacca ccgcgccgtc gtcaaccgcg acagcgaccg gatatcgctg 900
gggtacttcc tcggcccgcc cgcccacgtt aaggtggcgc cgctcaggga ggccctcgcc 960
ggcacgcccg ctgcctaccg cgccgtcacg tggcccgagt acatgggcgt gcgcaagaag 1020
gccttcacca ccggcgcctc cgcgctcaag atggtcgcca tctccaccga cgacgccgcc 1080
gacgtcctcc ccgacgtcct ctcgtcgtag 1110

<210> SEQ ID NO 133
<211> LENGTH: 369
<212> TYPE: PRT
<213> ORGANISM: Hordeum vulgare

<400> SEQUENCE: 133

Met Pro Thr Pro Ser His Leu Ser Lys Asp Pro His Tyr Phe Asp Phe
1               5                   10                  15

Arg Ala Ala Arg Arg Val Pro Glu Thr His Ala Trp Pro Gly Leu His
            20                  25                  30

Asp His Pro Val Val Asp Gly Gly Gly Ala Gly Gly Gly Pro Asp Ala
        35                  40                  45

Val Pro Val Val Asp Met Arg Asp Pro Cys Ala Ala Glu Ala Val Ala
    50                  55                  60

Leu Ala Ala Gln Asp Trp Gly Ala Phe Leu Leu Gln Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
            100                 105                 110

Ser Cys Gly Tyr Gly Ser Pro Pro Ile Ser Ser Phe Phe Ser Lys Cys
        115                 120                 125

Met Trp Ser Glu Gly Tyr Thr Phe Ser Pro Ala Asn Leu Arg Ser Asp
    130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Val Leu Ala Asp Lys
                165                 170                 175

Leu Leu Glu Leu Phe Leu Val Ala Leu Gly Leu Thr Gly Glu Gln Val
            180                 185                 190

Ala Ala Val Glu Ser Glu His Lys Ile Ala Glu Thr Met Thr Ala Thr
        195                 200                 205

Met His Leu Asn Trp Tyr Pro Lys Cys Pro Asp Pro Lys Arg Ala Leu
    210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
            260                 265                 270

Leu Phe His Ile Leu Thr Asn Gly Arg Phe His Ser Val Tyr His Arg
        275                 280                 285

Ala Val Val Asn Arg Asp Ser Asp Arg Ile Ser Leu Gly Tyr Phe Leu
    290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
            340                 345                 350

Ala Ile Ser Thr Asp Asp Ala Ala Asp Val Leu Pro Asp Val Leu Ser
        355                 360                 365

Ser

<210> SEQ ID NO 134
<211> LENGTH: 1653
<212> TYPE: DNA
<213> ORGANISM: Triticum aestivum
<220> FEATURE:

<221> NAME/KEY: misc_feature
<222> LOCATION: (1594)..(1600)
<223> OTHER INFORMATION: n is a, c, g, or t
<220> FEATURE:
<221> NAME/KEY: misc_feature
<222> LOCATION: (1641)..(1641)
<223> OTHER INFORMATION: n is a, c, g, or t

<400> SEQUENCE: 134
cacgagatcc atccgtctcc accattgctc gctagctcga gctcctagct agtactgcaa 60
agtcagccgg ggagttgatt tggtccttct tggcttgacc gatcgtacgt gccgccagga 120
tgccgacgcc ggcgcacctg agcaaggacc cgcgctactt cgacttccgg gcggcgcggc 180
gggtgccgga gacgcacgcg tggcccgggc tgcacgacca ccccgtggtg gacggcagcg 240
gcgcgggcgg agggccggac gcggtgccgg tggtggacat gcgcgacccg tgcgcggcgg 300
aggcggtggc gctggcggcg caggactggg gcgccttcct cctggagggc cacggcgtcc 360
cgttggagct gctggcgcgc gtggaggccg cgatcgcggg catgttcgcg ctgccggcgt 420
cggagaagat gcgcgccgtg cggcggcccg gcgactcgtg cggctacggg tcgccgccca 480
tctcctcctt cttctccaag tgcatgtggt ccgagggcta caccttctcc ccggccaacc 540
tccgctccga cctccgcaag ctctggccca aggccggcca cgactaccgc cacttctgcg 600
ccgtgatgga ggagttccac agggagatgc gcgcgctggc cgacaagctg ctggagctgt 660
tcctggtggc cctcgggctc accggcgagc aggtcgccgc cgtcgagtcc gagcagaaga 720
tcgccgagac catgaccgcc acaatgcacc tcaactggta ccccaagtgc ccggacccga 780
agcgggcgct gggcctgatc gcgcacacgg actcgggctt cttcaccttc gtgctgcaga 840
gccttgtgcc cgggctgcag ctgttccggc acggccccga ccggtgggtg acggtgcccg 900
ccgtgccggg ggccatggtc gtcaacgtcg gcgacctctt ccagatcctc accaacggcc 960
gcttccacag cgtctaccac cgcgccgtcg tcaaccgcga cagcgaccgg atatcgctcg 1020
gctacttcct cggcccgccc gcccacgtca aggtggcgcc gctcagggag gccctggccg 1080
gcacgcccgc cgcctaccgc gccgtcacgt ggcccgagta catgggcgtg cgcaagaagg 1140
ccttcaccac cggcgcctcc gcgctcaaga tggtcgccat ctccactgac aacgacgccg 1200
ccaaccacac ggacgacctg atctcgtcgt agatcggcgc cggccatcac cggccggcca 1260
agggatcgat ctacacacac aattagtgaa caaaaaaatg ccagagatgg tgcatggtgg 1320
gctggtagct tagctgaggt agctaggagg aagagcgcgc gtgcggctgt cgttcgtgcg 1380
gctgttcccg caaaaaaaaa aaaggtttcc tccatatatg tctccatgca gaactgcaga 1440
tgctggtggt ggatgcgtcc atgcagcagg gaacgaacta attgtaagaa aatcaagcaa 1500
acttagttct acatctgtaa ttaagtatgc atgccacttg gtttaattca attcaagtgc 1560
agaaaaaatt atgatgggaa aaaaaaagac atgnnnnnnn aaaaaaaaaa aaaaaaaaaa 1620
aaaaaaaaaa aaaaaaaaaa naaaaaaaaa aaa 1653

<210> SEQ ID NO 135
<211> LENGTH: 1113
<212> TYPE: DNA
<213> ORGANISM: Triticum aestivum

<400> SEQUENCE: 135
atgccgacgc cggcgcacct gagcaaggac ccgcgctact tcgacttccg ggcggcgcgg 60
cgggtgccgg agacgcacgc gtggcccggg ctgcacgacc accccgtggt ggacggcagc 120
ggcgcgggcg gagggccgga cgcggtgccg gtggtggaca tgcgcgaccc gtgcgcggcg 180

```
gaggcggtgg cgctggcggc gcaggactgg ggcgccttcc tcctggaggg ccacggcgtc    240

ccgttggagc tgctggcgcg cgtggaggcc gcgatcgcgg gcatgttcgc gctgccggcg    300

tcggagaaga tgcgcgccgt gcggcggccc ggcgactcgt gcggctacgg gtcgccgccc    360

atctcctcct tcttctccaa gtgcatgtgg tccgagggct acaccttctc cccggccaac    420

ctccgctccg acctccgcaa gctctggccc aaggccggcc acgactaccg ccacttctgc    480

gccgtgatgg aggagttcca cagggagatg cgcgcgctgg ccgacaagct gctggagctg    540

ttcctggtgg ccctcgggct caccggcgag caggtcgccg ccgtcgagtc cgagcagaag    600

atcgccgaga ccatgaccgc cacaatgcac ctcaactggt accccaagtg cccggacccg    660

aagcgggcgc tgggcctgat cgcgcacacg gactcgggct tcttcacctt cgtgctgcag    720

agccttgtgc ccgggctgca gctgttccgg cacggccccg accggtgggt gacggtgccc    780

gccgtgccgg gggccatggt cgtcaacgtc ggcgacctct tccagatcct caccaacggc    840

cgcttccaca gcgtctacca ccgcgccgtc gtcaaccgcg acagcgaccg gatatcgctc    900

ggctacttcc tcggcccgcc cgcccacgtc aaggtggcgc cgctcaggga ggccctggcc    960

ggcacgcccg ccgcctaccg cgccgtcacg tggcccgagt acatgggcgt gcgcaagaag   1020

gccttcacca ccggcgcctc cgcgctcaag atggtcgcca tctccactga caacgacgcc   1080

gccaaccaca cggacgacct gatctcgtcg tag                                1113
```

<210> SEQ ID NO 136
<211> LENGTH: 370
<212> TYPE: PRT
<213> ORGANISM: Triticum aestivum

<400> SEQUENCE: 136

```
Met Pro Thr Pro Ala His Leu Ser Lys Asp Pro Arg Tyr Phe Asp Phe
1               5                   10                  15

Arg Ala Ala Arg Arg Val Pro Glu Thr His Ala Trp Pro Gly Leu His
            20                  25                  30

Asp His Pro Val Val Asp Gly Ser Gly Ala Gly Gly Gly Pro Asp Ala
        35                  40                  45

Val Pro Val Val Asp Met Arg Asp Pro Cys Ala Ala Glu Ala Val Ala
    50                  55                  60

Leu Ala Ala Gln Asp Trp Gly Ala Phe Leu Leu Glu Gly His Gly Val
65                  70                  75                  80

Pro Leu Glu Leu Leu Ala Arg Val Glu Ala Ala Ile Ala Gly Met Phe
                85                  90                  95

Ala Leu Pro Ala Ser Glu Lys Met Arg Ala Val Arg Arg Pro Gly Asp
            100                 105                 110

Ser Cys Gly Tyr Gly Ser Pro Pro Ile Ser Ser Phe Phe Ser Lys Cys
        115                 120                 125

Met Trp Ser Glu Gly Tyr Thr Phe Ser Pro Ala Asn Leu Arg Ser Asp
    130                 135                 140

Leu Arg Lys Leu Trp Pro Lys Ala Gly His Asp Tyr Arg His Phe Cys
145                 150                 155                 160

Ala Val Met Glu Glu Phe His Arg Glu Met Arg Ala Leu Ala Asp Lys
                165                 170                 175

Leu Leu Glu Leu Phe Leu Val Ala Leu Gly Leu Thr Gly Glu Gln Val
            180                 185                 190

Ala Ala Val Glu Ser Glu Gln Lys Ile Ala Glu Thr Met Thr Ala Thr
        195                 200                 205
```

```
Met His Leu Asn Trp Tyr Pro Lys Cys Pro Asp Pro Lys Arg Ala Leu
    210                 215                 220

Gly Leu Ile Ala His Thr Asp Ser Gly Phe Phe Thr Phe Val Leu Gln
225                 230                 235                 240

Ser Leu Val Pro Gly Leu Gln Leu Phe Arg His Gly Pro Asp Arg Trp
                245                 250                 255

Val Thr Val Pro Ala Val Pro Gly Ala Met Val Val Asn Val Gly Asp
            260                 265                 270

Leu Phe Gln Ile Leu Thr Asn Gly Arg Phe His Ser Val Tyr His Arg
        275                 280                 285

Ala Val Val Asn Arg Asp Ser Asp Arg Ile Ser Leu Gly Tyr Phe Leu
    290                 295                 300

Gly Pro Pro Ala His Val Lys Val Ala Pro Leu Arg Glu Ala Leu Ala
305                 310                 315                 320

Gly Thr Pro Ala Ala Tyr Arg Ala Val Thr Trp Pro Glu Tyr Met Gly
                325                 330                 335

Val Arg Lys Lys Ala Phe Thr Thr Gly Ala Ser Ala Leu Lys Met Val
            340                 345                 350

Ala Ile Ser Thr Asp Asn Asp Ala Ala Asn His Thr Asp Asp Leu Ile
        355                 360                 365

Ser Ser
    370


<210> SEQ ID NO 137
<211> LENGTH: 1884
<212> TYPE: DNA
<213> ORGANISM: Triticum aestivum

<400> SEQUENCE: 137

tatatataca gctccttgta cttctctcgt tcttacactc actcctcaat ccatccgtct      60

ccaccattgc tcgctagctc gagctcctag ctagtactgc aaagtcagcc ggggagttga     120

tttggtcctt cttggcttga ccgatcgtac gtgccgccag gatgccgacg ccggcgcacc     180

tgagcaagga cccgcgctac ttcgacttcc gggcggcgcg gcgggtgccg gagacgcacg     240

cgtggcccgg gctgcacgac caccccgtgg tggacggcag cggcgcgggc ggagggccgg     300

acgcggtgcc ggtggtggac atgcgcgacc cgtgcgcggc ggaggcggtg gcgctggcgg     360

cgcaggactg ggcgccttc ctcctggagg gccacggcgt cccgttggag ctgctggcgc      420

gcgtggaggc cgcgatcgcg ggcatgttcg cgctgccggc gtcggagaag atgcgcgccg     480

tgcggcggcc cggcgactcg tgcggctacg ggtcgccgcc catctcctcc ttcttctcca     540

agtgcatgtg gtccgagggc tacaccttct ccccggccaa cctccgctcc gacctccgca     600

agctctggcc caaggccggc cacgactacc gccacttctg gtacgtacgc cggccgccga     660

tgcgcatata cacgtcatag tacggcacct acctaactgg ctctggccaa ccgtccgtac     720

acacgtgaag gggcgacgtg tccgactccg accatgcatg catgcacgcg cgcgaaactt     780

gttactcctg ttctgctatg gcagcagcta gccgcgtgtg tccgttcgta ggagtagtta     840

cttacacagt tacacttacg ccgtccgtcg tgttcctcga cgtgcagcgc cgtgatggag     900

gagttccaca gggagatgcg cgcgctggcc gacaagctgc tggagctgtt cctggtggcc     960

ctcgggctca ccggcgagca ggtcgccgcc gtcgagtccg agcagaagat cgccgagacc    1020

atgaccgcca caatgcacct caactggtac gttccactac tactccagta gtacaagtac    1080

aatatataga atacaaatgg cagcagccac gacgacacgt actccaccat gcagcaaagc    1140
```

atatattgtc ggtgcggcgg ttgacacgga gttgtgtcgt gtcgttgatt cacaggtacc 1200
ccaagtgccc ggacccgaag cgggcgctgg gcctgatcgc gcacacggac tcgggcttct 1260
tcaccttcgt gctgcagagc cttgtgcccg ggctgcagct gttccggcac ggccccgacc 1320
ggtgggtgac ggtgcccgcc gtgccggggg ccatggtcgt caacgtcggc gacctcttcc 1380
agatcctcac caacggccgc ttccacagcg tctaccaccg cgccgtcgtc aaccgcgaca 1440
gcgaccggat atcgctcggc tacttcctcg gcccgcccgc ccacgtcaag gtggcgccgc 1500
tcagggaggc cctggccggc acgcccgccg cctaccgcgc cgtcacgtgg cccgagtaca 1560
tgggcgtgcg caagaaggcc ttcaccaccg gcgcctccgc gctcaagatg gtcgccatct 1620
ccactgacaa cgacgccgcc aaccacacgg acgacctgat ctcgtcgtag atcggcgccg 1680
gccatcaccg gccggccaag ggatcgatct acacacacaa ttagtgaaca aaaaaatgcc 1740
agagatggtg catggtgggc tggtagctta gctgaggtag ctaggaggaa gagcgcgcgt 1800
gcggctgtcg ttcgtgcggc tgttcccgca aaaaaaaaaa ggtttcctcc atatakgtcc 1860
ccakscaaaa tsgmaawgct gggg 1884

<210> SEQ ID NO 138
<211> LENGTH: 20
<212> TYPE: RNA
<213> ORGANISM: Artificial Sequence
<220> FEATURE:
<223> OTHER INFORMATION: suppression oligo

<400> SEQUENCE: 138
acggguucuu ccaggugugc 20

<210> SEQ ID NO 139
<211> LENGTH: 20
<212> TYPE: RNA
<213> ORGANISM: Artificial Sequence
<220> FEATURE:
<223> OTHER INFORMATION: suppression oligo

<400> SEQUENCE: 139
cacggguucu uccaggugug 20

<210> SEQ ID NO 140
<211> LENGTH: 20
<212> TYPE: RNA
<213> ORGANISM: Artificial Sequence
<220> FEATURE:
<223> OTHER INFORMATION: suppression oligo

<400> SEQUENCE: 140
cauugaccuc cccgcuggca 20

<210> SEQ ID NO 141
<211> LENGTH: 20
<212> TYPE: RNA
<213> ORGANISM: Artificial Sequence
<220> FEATURE:
<223> OTHER INFORMATION: suppression oligo

<400> SEQUENCE: 141
ccagcgggga ggucaaugcu 20

<210> SEQ ID NO 142
<211> LENGTH: 20
<212> TYPE: RNA

<213> ORGANISM: Artificial Sequence
<220> FEATURE:
<223> OTHER INFORMATION: suppression oligo

<400> SEQUENCE: 142
cccagcauug accucccgc 20

<210> SEQ ID NO 143
<211> LENGTH: 20
<212> TYPE: RNA
<213> ORGANISM: Artificial Sequence
<220> FEATURE:
<223> OTHER INFORMATION: suppression oligo

<400> SEQUENCE: 143
cgcgcucgug uacccggaca 20

<210> SEQ ID NO 144
<211> LENGTH: 20
<212> TYPE: RNA
<213> ORGANISM: Artificial Sequence
<220> FEATURE:
<223> OTHER INFORMATION: suppression oligo

<400> SEQUENCE: 144
cucccggcgc aggucgaaca 20

<210> SEQ ID NO 145
<211> LENGTH: 20
<212> TYPE: RNA
<213> ORGANISM: Artificial Sequence
<220> FEATURE:
<223> OTHER INFORMATION: suppression oligo

<400> SEQUENCE: 145
guguacccgg acacggugcc 20

<210> SEQ ID NO 146
<211> LENGTH: 20
<212> TYPE: RNA
<213> ORGANISM: Artificial Sequence
<220> FEATURE:
<223> OTHER INFORMATION: suppression oligo

<400> SEQUENCE: 146
ugcagggaag cuguccgggc 20

<210> SEQ ID NO 147
<211> LENGTH: 20
<212> TYPE: RNA
<213> ORGANISM: Artificial Sequence
<220> FEATURE:
<223> OTHER INFORMATION: suppression oligo

<400> SEQUENCE: 147
uucuuccagg ugugcgggca 20

<210> SEQ ID NO 148
<211> LENGTH: 20
<212> TYPE: RNA
<213> ORGANISM: Artificial Sequence
<220> FEATURE:
<223> OTHER INFORMATION: suppression oligo

<400> SEQUENCE: 148
agauccccgc gccauuccug 20

<210> SEQ ID NO 149
<211> LENGTH: 20
<212> TYPE: RNA
<213> ORGANISM: Artificial Sequence
<220> FEATURE:
<223> OTHER INFORMATION: suppression oligo

<400> SEQUENCE: 149
augcagggaa gcuguccggg 20

<210> SEQ ID NO 150
<211> LENGTH: 20
<212> TYPE: RNA
<213> ORGANISM: Artificial Sequence
<220> FEATURE:
<223> OTHER INFORMATION: suppression oligo

<400> SEQUENCE: 150
auuccugugg ccgcaggaag 20

<210> SEQ ID NO 151
<211> LENGTH: 20
<212> TYPE: RNA
<213> ORGANISM: Artificial Sequence
<220> FEATURE:
<223> OTHER INFORMATION: suppression oligo

<400> SEQUENCE: 151
cagcggggag gucaaugcug 20

<210> SEQ ID NO 152
<211> LENGTH: 20
<212> TYPE: RNA
<213> ORGANISM: Artificial Sequence
<220> FEATURE:
<223> OTHER INFORMATION: suppression oligo

<400> SEQUENCE: 152
caggaauggc gcggggaucu 20

<210> SEQ ID NO 153
<211> LENGTH: 20
<212> TYPE: RNA
<213> ORGANISM: Artificial Sequence
<220> FEATURE:
<223> OTHER INFORMATION: suppression oligo

<400> SEQUENCE: 153
gacuacuucg ucggcacccu 20

<210> SEQ ID NO 154
<211> LENGTH: 20
<212> TYPE: RNA
<213> ORGANISM: Artificial Sequence
<220> FEATURE:
<223> OTHER INFORMATION: suppression oligo

<400> SEQUENCE: 154
gccaggauuu cgagccaaug 20

<210> SEQ ID NO 155
<211> LENGTH: 20
<212> TYPE: RNA
<213> ORGANISM: Artificial Sequence
<220> FEATURE:

<223> OTHER INFORMATION: suppression oligo

<400> SEQUENCE: 155
ggaacauuug gagggaggcg 20

<210> SEQ ID NO 156
<211> LENGTH: 20
<212> TYPE: RNA
<213> ORGANISM: Artificial Sequence
<220> FEATURE:
<223> OTHER INFORMATION: suppression oligo

<400> SEQUENCE: 156
gggaggucaa ugcuggggcu 20

<210> SEQ ID NO 157
<211> LENGTH: 20
<212> TYPE: RNA
<213> ORGANISM: Artificial Sequence
<220> FEATURE:
<223> OTHER INFORMATION: suppression oligo

<400> SEQUENCE: 157
uuggcucgaa auccuggccg 20

<210> SEQ ID NO 158
<211> LENGTH: 20
<212> TYPE: RNA
<213> ORGANISM: Artificial Sequence
<220> FEATURE:
<223> OTHER INFORMATION: suppression oligo

<400> SEQUENCE: 158
acggguucuu ccaggugugc 20

<210> SEQ ID NO 159
<211> LENGTH: 20
<212> TYPE: RNA
<213> ORGANISM: Artificial Sequence
<220> FEATURE:
<223> OTHER INFORMATION: suppression oligo

<400> SEQUENCE: 159
cacggguucu uccaggugug 20

<210> SEQ ID NO 160
<211> LENGTH: 20
<212> TYPE: RNA
<213> ORGANISM: Artificial Sequence
<220> FEATURE:
<223> OTHER INFORMATION: suppression oligo

<400> SEQUENCE: 160
cauugaccuc cccgcuggca 20

<210> SEQ ID NO 161
<211> LENGTH: 20
<212> TYPE: RNA
<213> ORGANISM: Artificial Sequence
<220> FEATURE:
<223> OTHER INFORMATION: suppression oligo

<400> SEQUENCE: 161
ccagcgggga ggucaaugcu 20

<210> SEQ ID NO 162
<211> LENGTH: 20
<212> TYPE: RNA
<213> ORGANISM: Artificial Sequence
<220> FEATURE:
<223> OTHER INFORMATION: suppression oligo

<400> SEQUENCE: 162
cccagcauug accucccgc 20

<210> SEQ ID NO 163
<211> LENGTH: 20
<212> TYPE: RNA
<213> ORGANISM: Artificial Sequence
<220> FEATURE:
<223> OTHER INFORMATION: suppression oligo

<400> SEQUENCE: 163
cgcgcucgug uacccggaca 20

<210> SEQ ID NO 164
<211> LENGTH: 20
<212> TYPE: RNA
<213> ORGANISM: Artificial Sequence
<220> FEATURE:
<223> OTHER INFORMATION: suppression oligo

<400> SEQUENCE: 164
cucccggcgc aggucgaaca 20

<210> SEQ ID NO 165
<211> LENGTH: 20
<212> TYPE: RNA
<213> ORGANISM: Artificial Sequence
<220> FEATURE:
<223> OTHER INFORMATION: suppression oligo

<400> SEQUENCE: 165
guguacccgg acacggugcc 20

<210> SEQ ID NO 166
<211> LENGTH: 20
<212> TYPE: RNA
<213> ORGANISM: Artificial Sequence
<220> FEATURE:
<223> OTHER INFORMATION: suppression oligo

<400> SEQUENCE: 166
ugcagggaag cuguccgggc 20

<210> SEQ ID NO 167
<211> LENGTH: 20
<212> TYPE: RNA
<213> ORGANISM: Artificial Sequence
<220> FEATURE:
<223> OTHER INFORMATION: suppression oligo

<400> SEQUENCE: 167
uucuuccagg ugugcgggca 20

<210> SEQ ID NO 168
<211> LENGTH: 2488
<212> TYPE: DNA
<213> ORGANISM: Zea Mays

<400> SEQUENCE: 168

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctgtccttcg gcttccacga cggcgccgcg gcgcccgtcg tcgtggacta cttcaccggc    540
accctcggcc aagatttcga gccagtgggg tgagtaaaga agaagatggc gccgaattta    600
catttataag taggaccagc agaagcccct gcccctgggg gccttagcat tgcattcgac    660
tgatgaatac gcatggcagg cggtgtacc  agaggtactg cgaggagatg aaggagctgt    720
cgctgacgat catggagctg ctggagctga gcctgggcgt ggagcgcggc tactaccggg    780
agttcttcga ggacagccgc tccatcatgc ggtgcaacta ctacccgccg tgcccggtgc    840
cggagcgcac gctgggcacg ggcccgcact gcgaccccac ggcgctgacc atcctcctgc    900
aggacgacgt cggcgggctg gaggtcctgg tggacggcga gtggcgcccc gtccggcccg    960
tcccaggcgc catggtcatc aacatcggcg acaccttcat ggtaacgaac gaaagcgccg   1020
gctcctctgc ttttcttggc ctctttgtcc ctgccctgtg ctgctgtgca tattcattca   1080
ttcagttctc tgtggggttt tttttttgtt taattttttt ttgggatcgt atccagtgca   1140
caagggccac gccgtgcaca aatgcacaaa acgaaatctg gccgtccatt ttccatccaa   1200
cgacatgacg gcgcgggggg tttttcacaa aacagactcg gcaagctacg gaggttgcgg   1260
gagggttcat ctgcatattt acgacggccg ttggatggaa aatggacggc cagatttcgt   1320
tttgtgtatt tgtgcacggc gtggcccttg tgcactggat acgatcccat ttttttttt    1380
gccccgaatc ctagtggacc taactggaca gattacagca cgcacacgta ggcatgtcat   1440
gtagcagcac tgcagtcggg tgcagtccag tccagtcctg tccagccgcg acactgtagt   1500
acatagcgat gcaacggaga cacgcgttgg agttggttcc atctcttctc ggcggccgtg   1560
ccgaggcttc cgcggggaag ctgcgacaac agaacggacc gccgggggtg ggcaggcagc   1620
aagctccctg ttggcttgtg ccgttgcgca gcggcgggta ccggacaacg ctttcggcgg   1680
cgcgcggcct cgtcggcttc ccctgttttt gatgccgcct ctcggtgtcc ggggaccggg   1740
aggatcgatg gggcccgtgc cgtctgatcc gccacgcgag cggtcctatg cgatgcgccg   1800
cacgagcgcg ggggggccgt ggaacagtac acagctgggt cactcactca ctcatcccgc   1860
tggttgtggc tgcttggttg caacttggct cggctgtctg tctgttgccc ccgccgcgtt   1920
ttctagccgt ttccgctttg ctcgcggttt cgctggcgat ccggcacgcg gcgcccacac   1980
ccggggctgg ccccttggcc gagtgggtgg caggcacttg catgcatccg gccggtttcc   2040
cgcgaccaag ctggcccgcc gcaacaatga gagtgagacg agactttgtg tcagtgtgtg   2100
tatgtacatg tatgtctgcg cgacagccct accgtccgac acgatgattc ttgtgcactg   2160
tactgtactg tactaactcc ccccaccccc tccggtatgt aacgcatgcc atatgcaggc   2220
gctgtccaac gggcggtaca agagctgcct gcaccgcgcg gtggtgaacc ggcggcagga   2280
gcggcaatcg ctggccttct tcctgtgccc gcgcgaggac cgggtggtgc gcccgccggc   2340
cagcgccgcg ccgcggcagt acccggactt cacctgggcc gacctcatgc gcttcacgca   2400
```

gcgccactac cgcgccgaca cccgcacgct ggacgccttc acccgctggc tctcccacgg 2460
cccggcggcg gcggctccct gcacctaa 2488

<210> SEQ ID NO 169
<211> LENGTH: 2473
<212> TYPE: DNA
<213> ORGANISM: Zea Mays

<400> SEQUENCE: 169
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc ccgctggcaa ggacaaggcc 300
gacgcggcgg ccagcaaggc cggcgcggcc gtgttcgacc tgcgccggga gcccaagatc 360
cccgcgccat tcctgtggcc gcaggaagag gcgcggccgt cctcggccgc ggagctggag 420
gtgccgatgg tggacgtggg cgtgctgcgc aatggcgacc gcgcggggct gcggcgcgcc 480
gcggcgcagg tggccgcggc gtgcgcgacg cacgggttct tccaggtgtg cgggcacggc 540
gtggacgcgg cgctggggcg cgccgcgctg gacggcgcca gcgacttctt ccggctgccg 600
ctcgccgaga agcagcgcgc ccggcgcgtc cccggcaccg tgtccgggta cacgagcgcg 660
cacgccgacc ggttcgcggc caagctcccc tggaaggaga ccctgtcgtt cggctaccac 720
gacggcgccg cgtcgcctgt cgtcgtggac tacttcgtcg gcaccctcgg ccaggatttc 780
gagccaatgg ggtaagtaag gtagtaagaa ggagcgccgg tttacattta ccgcacgtcg 840
gcgtgcggtc gagtcgggac tcgggagacg tatgaacccc cgtcccgtcc catgcatgtg 900
tggcaggtgg gtgtaccaga ggtactgcga ggagatgaag gagctgtcgc tgacgatcat 960
ggagctgctg gagctgagcc tgggcgtgga gctgcgcggc tactaccggg agttcttcga 1020
ggacagccgg tccatcatgc ggtgcaacta ctacccgccg tgcccggagc cggagcgcac 1080
gctgggcacg ggcccgcact gcgaccccac ggcgctcacc atcctcctgc aggacgacgt 1140
gggcgggctg gaggtgctgg tggacggtga gtggcgcccc gtccggcccg tcccgggcgc 1200
catggtcatc aacatcggcg acaccttcat ggtaacgaaa cgaaagcgct cgctcctctg 1260
ttttccttgg ccgctcttgt cctgtgtgta tattcagttg agctctctct gtgctgttat 1320
ttcccgaatc ctagtggacc taaacgggca ggttattaca gcacgcacac gtaggcatgt 1380
catgtagcta gtacatacat agcgatgccg atgcaaatgc aatagagaca tgcgttcgag 1440
ttggttccta tctcggcggg ctacggcagg tacacgcggc cgcggcgcgc tctctctagt 1500
ctatccgcgg ccgcgcccag gccgatcgag gcttccgggg gagagttgcg acaagagaac 1560
ggaccgaggg ggtcggctag cggtagcaag ttccctgttg gtttgtggcg ttggagcgtt 1620
gcggagaggc ttgcgcggcg gcggggacgt cgacggggac gtggcgggga gacgatacga 1680
tgggtgccgg gcagggcaac gctttcggcg ggtggccgtg tccaggtgcg cgcggccttg 1740
tcggtttccc cctctcggtg tccatggccg agaaatgggt cgacgaccga gaccgacgct 1800
cggtgcggcg cccatcccgt ctgatccgcc gcgccacgcg agcggcccta tgcgatgccg 1860
cacgggcgcg gagggccgtc gcgcggagta taatgtatag tatatagtac aaggttggtt 1920
ggagtcgggt tgggttggat cgggtcaccg gtacgtggtg gctgctgttg cccccgccgt 1980

-continued ttccgcttgc acttttgtcg cggtttcgct ggcgatccgg cacgcggcgc ccacaccacg 2040
ccggggctcc aaacagctcg ggcccttggc cgtgtgggtg gcaggcactt gcacgcgtcc 2100
ggttgtcgcg gcctggcccg ccgccgggcg caccgcaaca atgagacagc ccgacacgat 2160
gattcttgtg cactgtgcta acccgcatgc catgcaggcg ctgtcgaacg ggaggtacaa 2220
gagctgcctg caccgcgcgg tggtgaacca gcggcgggcg cggcggtcgc tggccttctt 2280
cctgtgcccg cgcgaggacc gggtggtgcg cccgccggcc agtgctgcgc cgcggcgcta 2340
cccggacttc acctgggccg acctcatgcg cttcacgcag cgccactacc gcgccgacac 2400
ccgcacgctg gacgccttca cccgctggct ctcccacggc ccggcccagg cggcggcgcc 2460
tccctgcacc tag 2473

<210> SEQ ID NO 170
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 170
tcgtggacta cttcaccaag atttcgagcc 30

<210> SEQ ID NO 171
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 171
actacttcac cggcacctcg gccaagattt 30

<210> SEQ ID NO 172
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 172
actacttcac cggcaccccc tcggccaaga tt 32

<210> SEQ ID NO 173
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 173
gactacttca ccggcccctc ggccaagatt 30

<210> SEQ ID NO 174
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 174
ggactacttc accggcctcg gccaagattt 30

<210> SEQ ID NO 175
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 175
tccccggcac cgtgtgggta cacgagcgcg 30

<210> SEQ ID NO 176
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 176
tccccggcac cgtgtaccgg gtacacgagc g 31

<210> SEQ ID NO 177
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 177
tccccggcac cgtgttccgg gtacacgagc g 31

<210> SEQ ID NO 178
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 178
ccaagatttc gagccgtggg gtgagtaaag 30

<210> SEQ ID NO 179
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 179
ccaagatttc gagccaagtg ggtgagtaa ag 32

<210> SEQ ID NO 180
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 180
caagatttcg agccacgtgg ggtgagtaaa ga 32

<210> SEQ ID NO 181
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 181
cagcattgac ctcccccgct ggcaaggaca gg 32

<210> SEQ ID NO 182
<211> LENGTH: 47
<212> TYPE: DNA
<213> ORGANISM: Artificial Sequence
<220> FEATURE:
<223> OTHER INFORMATION: mutant sequence by gene editing

<400> SEQUENCE: 182
ccgcggcgcc cgtcgtcgtg gactacttca ccaagatttc gagccag 47

<210> SEQ ID NO 183
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 183
ccgcggcgcc cgtcgtcgtg gactacttca ccggcacctc ggccaagatt tcgagccag 59

<210> SEQ ID NO 184
<211> LENGTH: 62
<212> TYPE: DNA
<213> ORGANISM: Artificial Sequence
<220> FEATURE:
<223> OTHER INFORMATION: mutant sequence by gene editing

<400> SEQUENCE: 184
ccgcggcgcc cgtcgtcgtg gactacttca ccggcacccc ctcggccaag atttcgagcc 60
ag 62

<210> SEQ ID NO 185
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 185
ccgcggcgcc cgtcgtcgtg gactacttca ccggcccctc ggccaagatt tcgagccag 59

<210> SEQ ID NO 186
<211> LENGTH: 57
<212> TYPE: DNA
<213> ORGANISM: Artificial Sequence
<220> FEATURE:
<223> OTHER INFORMATION: mutant sequence by gene editing

<400> SEQUENCE: 186
ccgcggcgcc cgtcgtcgtg gactacttca ccggcctcgg ccaagatttc gagccag 57

<210> SEQ ID NO 187
<211> LENGTH: 58
<212> TYPE: DNA
<213> ORGANISM: Artificial Sequence
<220> FEATURE:
<223> OTHER INFORMATION: mutant sequence by gene editing

<400> SEQUENCE: 187
ccggcgcgtc cccggcaccg tgtgggtaca cgagcgcgca cgccgaccgg ttcgcgtc 58

<210> SEQ ID NO 188
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 188
ccggcgcgtc cccggcaccg tgtaccgggt acacgagcgc gcacgccgac cggttcgcgt 60
c 61

<210> SEQ ID NO 189
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 189
ccggcgcgtc cccggcaccg tgttccgggt acacgagcgc gcacgccgac cggttcgcgt 60
c 61

<210> SEQ ID NO 190
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 190
ctacttcacc ggcaccctcg gccaagattt cgagccgtgg ggtgagtaaa gaagaagat 59

<210> SEQ ID NO 191
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 191
ctacttcacc ggcaccctcg gccaagattt cgagccaagt ggggtgagta aagaagaaga 60
t 61

<210> SEQ ID NO 192
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 192
ctacttcacc ggcaccctcg gccaagattt cgagccacgt ggggtgagta aagaagaaga 60
t 61

<210> SEQ ID NO 193
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 193
tccccctccg cgccccaact cccagcattg acctcccccg ctggcaagga cagggccgac 60
g 61

<210> SEQ ID NO 194
<211> LENGTH: 60
<212> TYPE: DNA
<213> ORGANISM: Zea mays

<400> SEQUENCE: 194
ccgcggcgcc cgtcgtcgtg gactacttca ccggcaccct cggccaagat ttcgagccag 60

<210> SEQ ID NO 195
<211> LENGTH: 60
<212> TYPE: DNA
<213> ORGANISM: Zea mays

<400> SEQUENCE: 195
ccgcggcgcc cgtcgtcgtg gactacttca ccggcaccct cggccaagat ttcgagccag 60

<210> SEQ ID NO 196
<211> LENGTH: 60
<212> TYPE: DNA
<213> ORGANISM: Zea mays

<400> SEQUENCE: 196
ccgcggcgcc cgtcgtcgtg gactacttca ccggcaccct cggccaagat ttcgagccag 60

<210> SEQ ID NO 197
<211> LENGTH: 60
<212> TYPE: DNA
<213> ORGANISM: Zea mays

<400> SEQUENCE: 197
ccgcggcgcc cgtcgtcgtg gactacttca ccggcaccct cggccaagat ttcgagccag 60

<210> SEQ ID NO 198
<211> LENGTH: 60
<212> TYPE: DNA
<213> ORGANISM: Zea mays

<400> SEQUENCE: 198
ccgcggcgcc cgtcgtcgtg gactacttca ccggcaccct cggccaagat ttcgagccag 60

<210> SEQ ID NO 199
<211> LENGTH: 60
<212> TYPE: DNA
<213> ORGANISM: Zea mays

<400> SEQUENCE: 199
ccggcgcgtc cccggcaccg tgtccgggta cacgagcgcg cacgccgacc ggttcgcgtc 60

<210> SEQ ID NO 200
<211> LENGTH: 60
<212> TYPE: DNA
<213> ORGANISM: Zea mays

<400> SEQUENCE: 200
ccggcgcgtc cccggcaccg tgtccgggta cacgagcgcg cacgccgacc ggttcgcgtc 60

<210> SEQ ID NO 201
<211> LENGTH: 60
<212> TYPE: DNA
<213> ORGANISM: Zea mays

<400> SEQUENCE: 201
ccggcgcgtc cccggcaccg tgtccgggta cacgagcgcg cacgccgacc ggttcgcgtc 60

<210> SEQ ID NO 202
<211> LENGTH: 60
<212> TYPE: DNA
<213> ORGANISM: Zea mays

<400> SEQUENCE: 202
ctacttcacc ggcaccctcg gccaagattt cgagccagtg gggtgagtaa agaagaagat 60

<210> SEQ ID NO 203
<211> LENGTH: 60
<212> TYPE: DNA
<213> ORGANISM: Zea mays

<400> SEQUENCE: 203
ctacttcacc ggcaccctcg gccaagattt cgagccagtg gggtgagtaa agaagaagat 60

<210> SEQ ID NO 204
<211> LENGTH: 60
<212> TYPE: DNA
<213> ORGANISM: Zea mays

<400> SEQUENCE: 204
ctacttcacc ggcaccctcg gccaagattt cgagccagtg gggtgagtaa agaagaagat 60

<210> SEQ ID NO 205
<211> LENGTH: 60
<212> TYPE: DNA
<213> ORGANISM: Zea mays

<400> SEQUENCE: 205
tccccctccg cgccccaact cccagcattg acctccccgc tggcaaggac agggccgacg 60

<210> SEQ ID NO 206
<211> LENGTH: 2475
<212> TYPE: DNA
<213> ORGANISM: Artificial Sequence
<220> FEATURE:
<223> OTHER INFORMATION: mutant sequence by gene editing

<400> SEQUENCE: 206
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctgtccttcg gcttccacga cggcgccgcg gcgcccgtcg tcgtggacta cttcaccaag 540
atttcgagcc agtggggtga gtaaagaaga agatggcgcc gaatttacat ttataagtag 600
gaccagcaga agcccctgcc cctgggggcc ttagcattgc attcgactga tgaatacgca 660
tggcaggcgg gtgtaccaga ggtactgcga ggagatgaag gagctgtcgc tgacgatcat 720
ggagctgctg gagctgagcc tgggcgtgga gcgcggctac taccgggagt tcttcgagga 780

```
cagccgctcc atcatgcggt gcaactacta cccgccgtgc ccggtgccgg agcgcacgct    840

gggcacgggc ccgcactgcg accccacggc gctgaccatc ctcctgcagg acgacgtcgg    900

cgggctggag gtcctggtgg acggcgagtg gcgccccgtc cggcccgtcc caggcgccat    960

ggtcatcaac atcggcgaca ccttcatggt aacgaacgaa agcgccggct cctctgcttt   1020

tcttggcctc tttgtccctg ccctgtgctg ctgtgcatat tcattcattc agttctctgt   1080

ggggtttttt ttttgtttaa tttttttttg ggatcgtatc cagtgcacaa gggccacgcc   1140

gtgcacaaat gcacaaaacg aaatctggcc gtccattttc catccaacga catgacggcg   1200

cggggggttt ttcacaaaac agactcggca agctacggag gttgcgggag ggttcatctg   1260

catatttacg acggccgttg gatggaaaat ggacggccag atttcgtttt gtgtatttgt   1320

gcacggcgtg gcccttgtgc actggatacg atcccatttt tttttttgcc ccgaatccta   1380

gtggacctaa ctggacagat tacagcacgc acacgtaggc atgtcatgta gcagcactgc   1440

agtcgggtgc agtccagtcc agtcctgtcc agccgcgaca ctgtagtaca tagcgatgca   1500

acggagacac gcgttggagt tggttccatc tcttctcggc ggccgtgccg aggcttccgc   1560

ggggaagctg cgacaacaga acggaccgcc gggggtgggc aggcagcaag ctccctgttg   1620

gcttgtgccg ttgcgcagcg gcgggtaccg gacaacgctt tcggcggcgc gcggcctcgt   1680

cggcttcccc tgtttttgat gccgcctctc ggtgtccggg gaccgggagg atcgatgggg   1740

cccgtgccgt ctgatccgcc acgcgagcgg tcctatgcga tgcgccgcac gagcgcgggg   1800

gggccgtgga acagtacaca gctgggtcac tcactcactc atcccgctgg ttgtggctgc   1860

ttggttgcaa cttggctcgg ctgtctgtct gttgccccgg ccgcgttttc tagccgtttc   1920

cgctttgctc gcggtttcgc tggcgatccg gcacgcggcg cccacacccg gggctggccc   1980

cttggccgag tgggtggcag gcacttgcat gcatccggcc ggtttcccgc gaccaagctg   2040

gcccgccgca acaatgagag tgagacgaga ctttgtgtca gtgtgtgtat gtacatgtat   2100

gtctgcgcga cagccctacc gtccgacacg atgattcttg tgcactgtac tgtactgtac   2160

taactccccc cacccccctcc ggtatgtaac gcatgccata tgcaggcgct gtccaacggg   2220

cggtacaaga gctgcctgca ccgcgcggtg gtgaaccggc ggcaggagcg gcaatcgctg   2280

gccttcttcc tgtgcccgcg cgaggaccgg gtggtgcgcc cgccggccag cgccgcgccg   2340

cggcagtacc cggacttcac ctgggccgac ctcatgcgct tcacgcagcg ccactaccgc   2400

gccgacaccc gcacgctgga cgccttcacc cgctggctct cccacggccc ggcggcggcg   2460

gctccctgca cctaa                                                    2475
```

<210> SEQ ID NO 207
<211> LENGTH: 2487
<212> TYPE: DNA
<213> ORGANISM: Artificial Sequence
<220> FEATURE:
<223> OTHER INFORMATION: mutant sequence by gene editing

<400> SEQUENCE: 207

```
atggacgcca gcccgacccc accgctcccc ctccgcgccc caactcccag cattgacctc     60

cccgctggca aggacagggc cgacgcggcg gctaacaagg ccgcggctgt gttcgacctg    120

cgccgggagc ccaagatccc ggagccattc ctgtggccgc acgaagaggc gcggccgacc    180

tcggccgcgg agctggaggt gccggtggtg gacgtgggcg tgctgcgcaa tggcgacggc    240

gcggggctcc gccgcgccgc ggcgcaagtg gcggcggcgt gcgcgacgca cgggttcttc    300

caggtgtgcg ggcacggcgt ggacgcggcg ctggggcgcg ccgcgctgga cggcgccagc    360
```

```
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctgtccttcg gcttccacga cggcgccgcg gcgcccgtcg tcgtggacta cttcaccggc    540
acctcggcca agatttcgag ccagtggggt gagtaaagaa gaagatggcg ccgaatttac    600
atttataagt aggaccagca gaagcccctg cccctggggg ccttagcatt gcattcgact    660
gatgaatacg catggcaggc gggtgtacca gaggtactgc gaggagatga aggagctgtc    720
gctgacgatc atggagctgc tggagctgag cctgggcgtg gagcgcggct actaccggga    780
gttcttcgag gacagccgct ccatcatgcg gtgcaactac tacccgccgt gcccggtgcc    840
ggagcgcacg ctgggcacgg gcccgcactg cgaccccacg gcgctgacca tcctcctgca    900
ggacgacgtc ggcgggctgg aggtcctggt ggacggcgag tggcgccccg tccggcccgt    960
cccaggcgcc atggtcatca acatcggcga caccttcatg gtaacgaacg aaagcgccgg   1020
ctcctctgct tttcttggcc tctttgtccc tgccctgtgc tgctgtgcat attcattcat   1080
tcagttctct gtggggtttt ttttttgttt aatttttttt tgggatcgta tccagtgcac   1140
aagggccacg ccgtgcacaa atgcacaaaa cgaaatctgg ccgtccattt tccatccaac   1200
gacatgacgg cgcggggggt tttcacaaa acagactcgg caagctacgg aggttgcggg   1260
agggttcatc tgcatattta cgacggccgt tggatggaaa atggacggcc agatttcgtt   1320
ttgtgtattt gtgcacggcg tggcccttgt gcactggata cgatcccatt ttttttttg    1380
ccccgaatcc tagtggacct aactggacag attacagcac gcacacgtag gcatgtcatg   1440
tagcagcact gcagtcgggt gcagtccagt ccagtcctgt ccagccgcga cactgtagta   1500
catagcgatg caacggagac acgcgttgga gttggttcca tctcttctcg gcggccgtgc   1560
cgaggcttcc gcggggaagc tgcgacaaca gaacggaccg ccgggggtgg gcaggcagca   1620
agctccctgt tggcttgtgc cgttgcgcag cggcgggtac cggacaacgc tttcggcggc   1680
gcgcggcctc gtcggcttcc cctgtttttg atgccgcctc tcggtgtccg gggaccggga   1740
ggatcgatgg ggcccgtgcc gtctgatccg ccacgcgagc ggtcctatgc gatgcgccgc   1800
acgagcgcgg gggggccgtg gaacagtaca cagctgggtc actcactcac tcatcccgct   1860
ggttgtggct gcttggttgc aacttggctc ggctgtctgt ctgttgcccc cgccgcgttt   1920
tctagccgtt tccgctttgc tcgcggtttc gctggcgatc cggcacgcgg cgcccacacc   1980
cggggctggc cccttggccg agtgggtggc aggcacttgc atgcatccgg ccggtttccc   2040
gcgaccaagc tggcccgccg caacaatgag agtgagacga gactttgtgt cagtgtgtgt   2100
atgtacatgt atgtctgcgc gacagcccta ccgtccgaca cgatgattct tgtgcactgt   2160
actgtactgt actaactccc cccacccccct ccggtatgta acgcatgcca tatgcaggcg   2220
ctgtccaacg ggcggtacaa gagctgcctg caccgcgcgg tggtgaaccg gcggcaggag   2280
cggcaatcgc tggccttctt cctgtgcccg cgcgaggacc gggtggtgcg cccgccggcc   2340
agcgccgcgc cgcggcagta cccggacttc acctgggccg acctcatgcg cttcacgcag   2400
cgccactacc gcgccgacac ccgcacgctg gacgccttca cccgctggct ctcccacggc   2460
ccggcggcgg cggctccctg cacctaa                                        2487
```

<210> SEQ ID NO 208
<211> LENGTH: 2490
<212> TYPE: DNA
<213> ORGANISM: Artificial Sequence
<220> FEATURE:

<223> OTHER INFORMATION: mutant sequence by gene editing

<400> SEQUENCE: 208
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctgtccttcg gcttccacga cggcgccgcg gcgcccgtcg tcgtggacta cttcaccggc 540
accccctcgg ccaagatttc gagccagtgg ggtgagtaaa gaagaagatg gcgccgaatt 600
tacatttata agtaggacca gcagaagccc ctgcccctgg gggccttagc attgcattcg 660
actgatgaat acgcatggca ggcgggtgta ccagaggtac tgcgaggaga tgaaggagct 720
gtcgctgacg atcatggagc tgctggagct gagcctgggc gtggagcgcg gctactaccg 780
ggagttcttc gaggacagcc gctccatcat gcggtgcaac tactacccgc cgtgcccggt 840
gccggagcgc acgctgggca cggcccgca ctgcgacccc acggcgctga ccatcctcct 900
gcaggacgac gtcggcgggc tggaggtcct ggtggacggc gagtggcgcc ccgtccggcc 960
cgtcccaggc gccatggtca tcaacatcgg cgacaccttc atggtaacga acgaaagcgc 1020
cggctcctct gcttttcttg gcctctttgt ccctgccctg tgctgctgtg catattcatt 1080
cattcagttc tctgtggggt tttttttttg tttaattttt ttttgggatc gtatccagtg 1140
cacaagggcc acgccgtgca caaatgcaca aaacgaaatc tggccgtcca ttttccatcc 1200
aacgacatga cggcgcgggg ggtttttcac aaaacagact cggcaagcta cggaggttgc 1260
gggagggttc atctgcatat ttacgacggc cgttggatgg aaaatggacg gccagatttc 1320
gttttgtgta tttgtgcacg gcgtggccct tgtgcactgg atacgatccc attttttttt 1380
ttgccccgaa tcctagtgga cctaactgga cagattacag cacgcacacg taggcatgtc 1440
atgtagcagc actgcagtcg ggtgcagtcc agtccagtcc tgtccagccg cgacactgta 1500
gtacatagcg atgcaacgga gacacgcgtt ggagttggtt ccatctcttc tcggcggccg 1560
tgccgaggct tccgcgggga agctgcgaca acagaacgga ccgccggggg tgggcaggca 1620
gcaagctccc tgttggcttg tgccgttgcg cagcggcggg taccggacaa cgctttcggc 1680
ggcgcgcggc ctcgtcggct tcccctgttt ttgatgccgc ctctcggtgt ccggggaccg 1740
ggaggatcga tggggcccgt gccgtctgat ccgccacgcg agcggtccta tgcgatgcgc 1800
cgcacgagcg cggggggcc gtggaacagt acacagctgg gtcactcact cactcatccc 1860
gctggttgtg gctgcttggt tgcaacttgg ctcggctgtc tgtctgttgc ccccgccgcg 1920
ttttctagcc gtttccgctt tgctcgcggt ttcgctggcg atccggcacg cggcgcccac 1980
acccggggct ggccccttgg ccgagtgggt ggcaggcact tgcatgcatc cggccggttt 2040
cccgcgacca agctggcccg ccgcaacaat gagagtgaga cgagactttg tgtcagtgtg 2100
tgtatgtaca tgtatgtctg cgcgacagcc ctaccgtccg acacgatgat tcttgtgcac 2160
tgtactgtac tgtactaact ccccccaccc cctccggtat gtaacgcatg ccatatgcag 2220
gcgctgtcca acgggcggta caagagctgc ctgcaccgcg cggtggtgaa ccggcggcag 2280
gagcggcaat cgctggcctt cttcctgtgc ccgcgcgagg accgggtggt gcgcccgccg 2340
gccagcgccg cgccgcggca gtacccggac ttcacctggg ccgacctcat gcgcttcacg 2400
cagcgccact accgcgccga cacccgcacg ctggacgcct tcacccgctg gctctcccac 2460
ggcccggcgg cggcggctcc ctgcacctaa 2490

<210> SEQ ID NO 209
<211> LENGTH: 2487
<212> TYPE: DNA
<213> ORGANISM: Artificial Sequence
<220> FEATURE:
<223> OTHER INFORMATION: mutant sequence by gene editing

<400> SEQUENCE: 209
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctgtccttcg gcttccacga cggcgccgcg gcgcccgtcg tcgtggacta cttcaccggc 540
ccctcggcca agatttcgag ccagtggggt gagtaaagaa gaagatggcg ccgaatttac 600
atttataagt aggaccagca gaagcccctg cccctggggg ccttagcatt gcattcgact 660
gatgaatacg catggcaggc gggtgtacca gaggtactgc gaggagatga aggagctgtc 720
gctgacgatc atggagctgc tggagctgag cctgggcgtg gagcgcggct actaccggga 780
gttcttcgag gacagccgct ccatcatgcg gtgcaactac tacccgccgt gcccggtgcc 840
ggagcgcacg ctgggcacgg gcccgcactg cgaccccacg gcgctgacca tcctcctgca 900
ggacgacgtc ggcgggctgg aggtcctggt ggacggcgag tggcgccccg tccggcccgt 960
cccaggcgcc atggtcatca acatcggcga caccttcatg gtaacgaacg aaagcgccgg 1020
ctcctctgct tttcttggcc tctttgtccc tgccctgtgc tgctgtgcat attcattcat 1080
tcagttctct gtggggtttt ttttttgttt aatttttttt tgggatcgta tccagtgcac 1140
aagggccacg ccgtgcacaa atgcacaaaa cgaaatctgg ccgtccattt tccatccaac 1200
gacatgacgg cgcggggggt ttttcacaaa acagactcgg caagctacgg aggttgcggg 1260
agggttcatc tgcatattta cgacggccgt tggatggaaa atggacggcc agatttcgtt 1320
ttgtgtattt gtgcacggcg tggcccttgt gcactggata cgatcccatt tttttttttg 1380
ccccgaatcc tagtggacct aactggacag attacagcac gcacacgtag gcatgtcatg 1440
tagcagcact gcagtcgggt gcagtccagt ccagtcctgt ccagccgcga cactgtagta 1500
catagcgatg caacggagac acgcgttgga gttggttcca tctcttctcg gcggccgtgc 1560
cgaggcttcc gcggggaagc tgcgacaaca gaacggaccg ccgggggtgg gcaggcagca 1620
agctccctgt tggcttgtgc cgttgcgcag cggcgggtac cggacaacgc tttcggcggc 1680
gcgcggcctc gtcggcttcc cctgtttttg atgccgcctc tcggtgtccg gggaccggga 1740
ggatcgatgg ggcccgtgcc gtctgatccg ccacgcgagc ggtcctatgc gatgcgccgc 1800

```
acgagcgcgg gggggccgtg gaacagtaca cagctgggtc actcactcac tcatcccgct   1860
ggttgtggct gcttggttgc aacttggctc ggctgtctgt ctgttgcccc cgccgcgttt   1920
tctagccgtt tccgctttgc tcgcggtttc gctggcgatc cggcacgcgg cgcccacacc   1980
cggggctggc cccttggccg agtgggtggc aggcacttgc atgcatccgg ccggtttccc   2040
gcgaccaagc tggcccgccg caacaatgag agtgagacga gactttgtgt cagtgtgtgt   2100
atgtacatgt atgtctgcgc gacagcccta ccgtccgaca cgatgattct tgtgcactgt   2160
actgtactgt actaactccc cccacccccct ccggtatgta acgcatgcca tatgcaggcg   2220
ctgtccaacg ggcggtacaa gagctgcctg caccgcgcgg tggtgaaccg gcggcaggag   2280
cggcaatcgc tggccttctt cctgtgcccg cgcgaggacc gggtggtgcg cccgccggcc   2340
agcgccgcgc cgcggcagta cccggacttc acctgggccg acctcatgcg cttcacgcag   2400
cgccactacc gcgccgacac ccgcacgctg gacgccttca cccgctggct ctcccacggc   2460
ccggcggcgg cggctccctg cacctaa                                        2487
```

<210> SEQ ID NO 210
<211> LENGTH: 2485
<212> TYPE: DNA
<213> ORGANISM: Artificial Sequence
<220> FEATURE:
<223> OTHER INFORMATION: mutant sequence by gene editing

<400> SEQUENCE: 210

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
ctgtccttcg gcttccacga cggcgccgcg gcgcccgtcg tcgtggacta cttcaccggc    540
ctcggccaag atttcgagcc agtggggtga gtaaagaaga agatggcgcc gaatttacat    600
ttataagtag gaccagcaga agcccctgcc cctgggggcc ttagcattgc attcgactga    660
tgaatacgca tggcaggcgg gtgtaccaga ggtactgcga ggagatgaag gagctgtcgc    720
tgacgatcat ggagctgctg gagctgagcc tgggcgtgga gcgcggctac taccgggagt    780
tcttcgagga cagccgctcc atcatgcggt gcaactacta cccgccgtgc ccggtgccgg    840
agcgcacgct gggcacgggc ccgcactgcg accccacggc gctgaccatc ctcctgcagg    900
acgacgtcgg cgggctggag gtcctggtgg acggcgagtg gcgccccgtc cggcccgtcc    960
caggcgccat ggtcatcaac atcggcgaca ccttcatggt aacgaacgaa agcgccggct   1020
cctctgcttt tcttggcctc tttgtccctg ccctgtgctg ctgtgcatat tcattcattc   1080
agttctctgt ggggtttttt ttttgtttaa tttttttttg ggatcgtatc cagtgcacaa   1140
gggccacgcc gtgcacaaat gcacaaaacg aaatctggcc gtccattttc catccaacga   1200
catgacggcg cggggggttt ttcacaaaac agactcggca agctacggag gttgcgggag   1260
ggttcatctg catatttacg acggccgttg gatggaaaat ggacggccag atttcgtttt   1320
gtgtatttgt gcacggcgtg gcccttgtgc actggatacg atcccatttt tttttttgcc   1380
```

ccgaatccta gtggacctaa ctggacagat tacagcacgc acacgtaggc atgtcatgta 1440
gcagcactgc agtcgggtgc agtccagtcc agtcctgtcc agccgcgaca ctgtagtaca 1500
tagcgatgca acggagacac gcgttggagt tggttccatc tcttctcggc ggccgtgccg 1560
aggcttccgc ggggaagctg cgacaacaga acggaccgcc gggggtgggc aggcagcaag 1620
ctccctgttg gcttgtgccg ttgcgcagcg gcgggtaccg gacaacgctt tcggcggcgc 1680
gcggcctcgt cggcttcccc tgtttttgat gccgcctctc ggtgtccggg gaccgggagg 1740
atcgatgggg cccgtgccgt ctgatccgcc acgcgagcgg tcctatgcga tgcgccgcac 1800
gagcgcgggg gggccgtgga acagtacaca gctgggtcac tcactcactc atcccgctgg 1860
ttgtggctgc ttggttgcaa cttggctcgg ctgtctgtct gttgccccccg ccgcgttttc 1920 tagccgtttc cgctttgctc gcggtttcgc tggcgatccg gcacgcggcg cccacacccg 1980
gggctggccc cttggccgag tgggtggcag gcacttgcat gcatccggcc ggtttcccgc 2040
gaccaagctg gcccgccgca acaatgagag tgagacgaga ctttgtgtca gtgtgtgtat 2100
gtacatgtat gtctgcgcga cagccctacc gtccgacacg atgattcttg tgcactgtac 2160
tgtactgtac taactccccc cacccccctcc ggtatgtaac gcatgccata tgcaggcgct 2220
gtccaacggg cggtacaaga gctgcctgca ccgcgcggtg gtgaaccggc ggcaggagcg 2280
gcaatcgctg gccttcttcc tgtgcccgcg cgaggaccgg gtggtgcgcc cgccggccag 2340
cgccgcgccg cggcagtacc cggacttcac ctgggccgac ctcatgcgct tcacgcagcg 2400
ccactaccgc gccgacaccc gcacgctgga cgccttcacc cgctggctct cccacggccc 2460
ggcggcggcg gctccctgca cctaa 2485

<210> SEQ ID NO 211
<211> LENGTH: 2486
<212> TYPE: DNA
<213> ORGANISM: Artificial Sequence
<220> FEATURE:
<223> OTHER INFORMATION: mutant sequence by gene editing

<400> SEQUENCE: 211
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tgggtacacg agcgcgcacg ccgaccggtt cgcgtccaag ctcccctgga aggagaccct 480
gtccttcggc ttccacgacg gcgccgcggc gcccgtcgtc gtggactact tcaccggcac 540
cctcggccaa gatttcgagc cagtggggtg agtaaagaag aagatggcgc cgaatttaca 600
tttataagta ggaccagcag aagcccctgc ccctgggggc cttagcattg cattcgactg 660
atgaatacgc atggcaggcg ggtgtaccag aggtactgcg aggagatgaa ggagctgtcg 720
ctgacgatca tggagctgct ggagctgagc ctgggcgtgg agcgcggcta ctaccgggag 780
ttcttcgagg acagccgctc catcatgcgg tgcaactact acccgccgtg cccggtgccg 840
gagcgcacgc tgggcacggg cccgcactgc gaccccacgg cgctgaccat cctcctgcag 900
gacgacgtcg gcgggctgga ggtcctggtg gacggcgagt ggcgccccgt ccggcccgtc 960
ccaggcgcca tggtcatcaa catcggcgac accttcatgg taacgaacga aagcgccggc 1020
tcctctgctt ttcttggcct ctttgtccct gccctgtgct gctgtgcata ttcattcatt 1080
cagttctctg tggggttttt tttttgttta attttttttt gggatcgtat ccagtgcaca 1140
agggccacgc cgtgcacaaa tgcacaaaac gaaatctggc cgtccatttt ccatccaacg 1200
acatgacggc gcggggggtt tttcacaaaa cagactcggc aagctacgga ggttgcggga 1260
gggttcatct gcatatttac gacggccgtt ggatggaaaa tggacggcca gatttcgttt 1320
tgtgtatttg tgcacggcgt ggcccttgtg cactggatac gatcccattt tttttttgc 1380 cccgaatcct agtggaccta actggacaga ttacagcacg cacacgtagg catgtcatgt 1440
agcagcactg cagtcgggtg cagtccagtc cagtcctgtc cagccgcgac actgtagtac 1500
atagcgatgc aacggagaca cgcgttggag ttggttccat ctcttctcgg cggccgtgcc 1560
gaggcttccg cggggaagct gcgacaacag aacggaccgc cgggggtggg caggcagcaa 1620
gctccctgtt ggcttgtgcc gttgcgcagc ggcgggtacc ggacaacgct ttcggcggcg 1680
cgcggcctcg tcggcttccc ctgtttttga tgccgcctct cggtgtccgg ggaccgggag 1740
gatcgatggg gcccgtgccg tctgatccgc cacgcgagcg gtcctatgcg atgcgccgca 1800
cgagcgcggg ggggccgtgg aacagtacac agctgggtca ctcactcact catcccgctg 1860
gttgtggctg cttggttgca acttggctcg gctgtctgtc tgttgccccc gccgcgtttt 1920
ctagccgttt ccgctttgct cgcggtttcg ctggcgatcc ggcacgcggc gcccacaccc 1980
ggggctggcc ccttggccga gtgggtggca ggcacttgca tgcatccggc cggtttcccg 2040
cgaccaagct ggcccgccgc aacaatgaga gtgagacgag actttgtgtc agtgtgtgta 2100
tgtacatgta tgtctgcgcg acagccctac cgtccgacac gatgattctt gtgcactgta 2160
ctgtactgta ctaactcccc ccaccccctc cggtatgtaa cgcatgccat atgcaggcgc 2220
tgtccaacgg gcggtacaag agctgcctgc accgcgcggt ggtgaaccgg cggcaggagc 2280
ggcaatcgct ggccttcttc ctgtgcccgc gcgaggaccg ggtggtgcgc ccgccggcca 2340
gcgccgcgcc gcggcagtac ccggacttca cctgggccga cctcatgcgc ttcacgcagc 2400
gccactaccg cgccgacacc cgcacgctgg acgccttcac ccgctggctc tcccacggcc 2460
cggcggcggc ggctccctgc acctaa 2486

<210> SEQ ID NO 212
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 212
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
taccgggtac acgagcgcgc acgccgaccg gttcgcgtcc aagctcccct ggaaggagac 480

```
cctgtccttc ggcttccacg acggcgccgc ggcgcccgtc gtcgtggact acttcaccgg    540
caccctcggc caagatttcg agccagtggg gtgagtaaag aagaagatgg cgccgaattt    600
acatttataa gtaggaccag cagaagcccc tgcccctggg ggccttagca ttgcattcga    660
ctgatgaata cgcatggcag gcgggtgtac cagaggtact gcgaggagat gaaggagctg    720
tcgctgacga tcatggagct gctggagctg agcctgggcg tggagcgcgg ctactaccgg    780
gagttcttcg aggacagccg ctccatcatg cggtgcaact actacccgcc gtgcccggtg    840
ccggagcgca cgctgggcac gggcccgcac tgcgacccca cggcgctgac catcctcctg    900
caggacgacg tcggcgggct ggaggtcctg gtggacggcg agtggcgccc cgtccggccc    960
gtcccaggcg ccatggtcat caacatcggc gacaccttca tggtaacgaa cgaaagcgcc   1020
ggctcctctg cttttcttgg cctctttgtc cctgccctgt gctgctgtgc atattcattc   1080
attcagttct ctgtggggtt tttttttgt ttaattttt tttgggatcg tatccagtgc   1140
acaagggcca cgccgtgcac aaatgcacaa aacgaaatct ggccgtccat tttccatcca   1200
acgacatgac ggcgcggggg gtttttcaca aaacagactc ggcaagctac ggaggttgcg   1260
ggagggttca tctgcatatt tacgacggcc gttggatgga aaatggacgg ccagatttcg   1320
ttttgtgtat ttgtgcacgg cgtggccctt gtgcactgga tacgatccca ttttttttt   1380
tgccccgaat cctagtggac ctaactggac agattacagc acgcacacgt aggcatgtca   1440
tgtagcagca ctgcagtcgg gtgcagtcca gtccagtcct gtccagccgc gacactgtag   1500
tacatagcga tgcaacggag acacgcgttg gagttggttc catctcttct cggcggccgt   1560
gccgaggctt ccgcggggaa gctgcgacaa cagaacggac cgccgggggt gggcaggcag   1620
caagctccct gttggcttgt gccgttgcgc agcggcgggt accggacaac gctttcggcg   1680
gcgcgcggcc tcgtcggctt cccctgtttt tgatgccgcc tctcggtgtc cggggaccgg   1740
gaggatcgat ggggcccgtg ccgtctgatc cgccacgcga gcggtcctat gcgatgcgcc   1800
gcacgagcgc ggggggccg tggaacagta cacagctggg tcactcactc actcatcccg   1860
ctggttgtgg ctgcttggtt gcaacttggc tcggctgtct gtctgttgcc cccgccgcgt   1920
tttctagccg tttccgcttt gctcgcggtt tcgctggcga tccggcacgc ggcgcccaca   1980
cccggggctg gccccttggc cgagtgggtg gcaggcactt gcatgcatcc ggccggtttc   2040
ccgcgaccaa gctggcccgc cgcaacaatg agagtgagac gagactttgt gtcagtgtgt   2100
gtatgtacat gtatgtctgc gcgacagccc taccgtccga cacgatgatt cttgtgcact   2160
gtactgtact gtactaactc cccccacccc ctccggtatg taacgcatgc catatgcagg   2220
cgctgtccaa cgggcggtac aagagctgcc tgcaccgcgc ggtggtgaac cggcggcagg   2280
agcggcaatc gctggccttc ttcctgtgcc cgcgcgagga ccgggtggtg cgcccgccgg   2340
ccagcgccgc gccgcggcag tacccggact tcacctgggc cgacctcatg cgcttcacgc   2400
agcgccacta ccgcgccgac acccgcacgc tggacgcctt cacccgctgg ctctcccacg   2460
gcccggcggc ggcggctccc tgcacctaa                                     2489
```

<210> SEQ ID NO 213
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 213

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
ttccgggtac acgagcgcgc acgccgaccg gttcgcgtcc aagctcccct ggaaggagac    480
cctgtccttc ggcttccacg acggcgccgc ggcgcccgtc gtcgtggact acttcaccgg    540
caccctcggc caagatttcg agccagtggg gtgagtaaag aagaagatgg cgccgaattt    600
acatttataa gtaggaccag cagaagcccc tgcccctggg ggccttagca ttgcattcga    660
ctgatgaata cgcatggcag gcgggtgtac cagaggtact gcgaggagat gaaggagctg    720
tcgctgacga tcatggagct gctggagctg agcctgggcg tggagcgcgg ctactaccgg    780
gagttcttcg aggacagccg ctccatcatg cggtgcaact actacccgcc gtgcccggtg    840
ccggagcgca cgctgggcac gggcccgcac tgcgacccca cggcgctgac catcctcctg    900
caggacgacg tcggcgggct ggaggtcctg gtggacggcg agtggcgccc cgtccggccc    960
gtcccaggcg ccatggtcat caacatcggc gacaccttca tggtaacgaa cgaaagcgcc   1020
ggctcctctg cttttcttgg cctctttgtc cctgccctgt gctgctgtgc atattcattc   1080
attcagttct ctgtggggtt ttttttttgt ttaatttttt tttgggatcg tatccagtgc   1140
acaagggcca cgccgtgcac aaatgcacaa aacgaaatct ggccgtccat tttccatcca   1200
acgacatgac ggcgcggggg gtttttcaca aaacagactc ggcaagctac ggaggttgcg   1260
ggagggttca tctgcatatt tacgacggcc gttggatgga aaatggacgg ccagatttcg   1320
ttttgtgtat ttgtgcacgg cgtggccctt gtgcactgga tacgatccca ttttttttt    1380
tgccccgaat cctagtggac ctaactggac agattacagc acgcacacgt aggcatgtca   1440
tgtagcagca ctgcagtcgg gtgcagtcca gtccagtcct gtccagccgc gacactgtag   1500
tacatagcga tgcaacggag acacgcgttg gagttggttc catctcttct cggcggccgt   1560
gccgaggctt ccgcggggaa gctgcgacaa cagaacggac cgccgggggt gggcaggcag   1620
caagctccct gttggcttgt gccgttgcgc agcggcgggt accggacaac gctttcggcg   1680
gcgcgcggcc tcgtcggctt cccctgtttt tgatgccgcc tctcggtgtc cggggaccgg   1740
gaggatcgat ggggcccgtg ccgtctgatc cgccacgcga gcggtcctat gcgatgcgcc   1800
gcacgagcgc gggggggccg tggaacagta cacagctggg tcactcactc actcatcccg   1860
ctggttgtgg ctgcttggtt gcaacttggc tcggctgtct gtctgttgcc cccgccgcgt   1920
tttctagccg tttccgcttt gctcgcggtt tcgctggcga tccggcacgc ggcgcccaca   1980
cccggggctg gccccttggc cgagtgggtg gcaggcactt gcatgcatcc ggccggtttc   2040
ccgcgaccaa gctggcccgc cgcaacaatg agagtgagac gagactttgt gtcagtgtgt   2100
gtatgtacat gtatgtctgc gcgacagccc taccgtccga cacgatgatt cttgtgcact   2160
gtactgtact gtactaactc cccccacccc ctccggtatg taacgcatgc catatgcagg   2220
cgctgtccaa cgggcggtac aagagctgcc tgcaccgcgc ggtggtgaac cggcggcagg   2280
agcggcaatc gctggccttc ttcctgtgcc cgcgcgagga ccgggtggtg cgcccgccgg   2340
ccagcgccgc gccgcggcag tacccggact tcacctgggc cgacctcatg cgcttcacgc   2400
```

agcgccacta ccgcgccgac acccgcacgc tggacgcctt cacccgctgg ctctcccacg 2460
gcccggcggc ggcggctccc tgcacctaa 2489

<210> SEQ ID NO 214
<211> LENGTH: 2487
<212> TYPE: DNA
<213> ORGANISM: Artificial Sequence
<220> FEATURE:
<223> OTHER INFORMATION: mutant sequence by gene editing

<400> SEQUENCE: 214
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctgtccttcg gcttccacga cggcgccgcg gcgcccgtcg tcgtggacta cttcaccggc 540
accctcggcc aagatttcga gccgtggggt gagtaaagaa gaagatggcg ccgaatttac 600
atttataagt aggaccagca gaagcccctg cccctggggg ccttagcatt gcattcgact 660
gatgaatacg catggcaggc gggtgtacca gaggtactgc gaggagatga aggagctgtc 720
gctgacgatc atggagctgc tggagctgag cctgggcgtg gagcgcggct actaccggga 780
gttcttcgag gacagccgct ccatcatgcg gtgcaactac tacccgccgt gcccggtgcc 840
ggagcgcacg ctgggcacgg gcccgcactg cgaccccacg gcgctgacca tcctcctgca 900
ggacgacgtc ggcgggctgg aggtcctggt ggacggcgag tggcgccccg tccggcccgt 960
cccaggcgcc atggtcatca acatcggcga caccttcatg gtaacgaacg aaagcgccgg 1020
ctcctctgct tttcttggcc tctttgtccc tgccctgtgc tgctgtgcat attcattcat 1080
tcagttctct gtggggtttt ttttttgttt aatttttttt tgggatcgta tccagtgcac 1140
aagggccacg ccgtgcacaa atgcacaaaa cgaaatctgg ccgtccattt tccatccaac 1200
gacatgacgg cgcggggggt ttttcacaaa acagactcgg caagctacgg aggttgcggg 1260
agggttcatc tgcatattta cgacggccgt tggatggaaa atggacggcc agatttcgtt 1320
ttgtgtattt gtgcacggcg tggcccttgt gcactggata cgatcccatt tttttttttg 1380
ccccgaatcc tagtggacct aactggacag attacagcac gcacacgtag gcatgtcatg 1440
tagcagcact gcagtcgggt gcagtccagt ccagtcctgt ccagccgcga cactgtagta 1500
catagcgatg caacggagac acgcgttgga gttggttcca tctcttctcg gcggccgtgc 1560
cgaggcttcc gcggggaagc tgcgacaaca gaacggaccg ccgggggtgg gcaggcagca 1620
agctccctgt tggcttgtgc cgttgcgcag cggcgggtac cggacaacgc tttcggcggc 1680
gcgcggcctc gtcggcttcc cctgtttttg atgccgcctc tcggtgtccg gggaccggga 1740
ggatcgatgg ggcccgtgcc gtctgatccg ccacgcgagc ggtcctatgc gatgcgccgc 1800
acgagcgcgg gggggccgtg gaacagtaca cagctgggtc actcactcac tcatcccgct 1860
ggttgtggct gcttggttgc aacttggctc ggctgtctgt ctgttgcccc cgccgcgttt 1920
tctagccgtt tccgctttgc tcgcggtttc gctggcgatc cggcacgcgg cgcccacacc 1980
cggggctggc cccttggccg agtgggtggc aggcacttgc atgcatccgg ccggtttccc 2040
gcgaccaagc tggcccgccg caacaatgag agtgagacga gactttgtgt cagtgtgtgt 2100
atgtacatgt atgtctgcgc gacagcccta ccgtccgaca cgatgattct tgtgcactgt 2160
actgtactgt actaactccc cccacccccct ccggtatgta acgcatgcca tatgcaggcg 2220
ctgtccaacg ggcggtacaa gagctgcctg caccgcgcgg tggtgaaccg gcggcaggag 2280
cggcaatcgc tggccttctt cctgtgcccg cgcgaggacc gggtggtgcg cccgccggcc 2340
agcgccgcgc cgcggcagta cccggacttc acctgggccg acctcatgcg cttcacgcag 2400
cgccactacc gcgccgacac ccgcacgctg gacgccttca cccgctggct ctcccacggc 2460
ccggcggcgg cggctccctg cacctaa 2487

<210> SEQ ID NO 215
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 215
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctgtccttcg gcttccacga cggcgccgcg gcgcccgtcg tcgtggacta cttcaccggc 540
accctcggcc aagatttcga gccaagtggg gtgagtaaag aagaagatgg cgccgaattt 600
acatttataa gtaggaccag cagaagcccc tgcccctggg ggccttagca ttgcattcga 660
ctgatgaata cgcatggcag gcgggtgtac cagaggtact gcgaggagat gaaggagctg 720
tcgctgacga tcatggagct gctggagctg agcctgggcg tggagcgcgg ctactaccgg 780
gagttcttcg aggacagccg ctccatcatg cggtgcaact actacccgcc gtgcccggtg 840
ccggagcgca cgctgggcac gggcccgcac tgcgacccca cggcgctgac catcctcctg 900
caggacgacg tcggcgggct ggaggtcctg gtggacggcg agtggcgccc cgtccggccc 960
gtcccaggcg ccatggtcat caacatcggc gacaccttca tggtaacgaa cgaaagcgcc 1020
ggctcctctg cttttcttgg cctctttgtc cctgccctgt gctgctgtgc atattcattc 1080
attcagttct ctgtggggtt ttttttttgt ttaatttttt tttgggatcg tatccagtgc 1140
acaagggcca cgccgtgcac aaatgcacaa aacgaaatct ggccgtccat tttccatcca 1200
acgacatgac ggcgcggggg gtttttcaca aaacagactc ggcaagctac ggaggttgcg 1260
ggagggttca tctgcatatt tacgacggcc gttggatgga aaatggacgg ccagatttcg 1320
ttttgtgtat ttgtgcacgg cgtggccctt gtgcactgga tacgatccca ttttttttt 1380 tgccccgaat cctagtggac ctaactggac agattacagc acgcacacgt aggcatgtca 1440
tgtagcagca ctgcagtcgg gtgcagtcca gtccagtcct gtccagccgc gacactgtag 1500
tacatagcga tgcaacggag acacgcgttg gagttggttc catctcttct cggcggccgt 1560
gccgaggctt ccgcggggaa gctgcgacaa cagaacggac cgccgggggt gggcaggcag 1620
caagctccct gttggcttgt gccgttgcgc agcggcgggt accggacaac gctttcggcg 1680
gcgcgcggcc tcgtcggctt cccctgtttt tgatgccgcc tctcggtgtc cggggaccgg 1740
gaggatcgat ggggcccgtg ccgtctgatc cgccacgcga gcggtcctat gcgatgcgcc 1800
gcacgagcgc ggggggccg tggaacagta cacagctggg tcactcactc actcatcccg 1860
ctggttgtgg ctgcttggtt gcaacttggc tcggctgtct gtctgttgcc cccgccgcgt 1920
tttctagccg tttccgcttt gctcgcggtt tcgctggcga tccggcacgc ggcgcccaca 1980
cccggggctg gccccttggc cgagtgggtg gcaggcactt gcatgcatcc ggccggtttc 2040
ccgcgaccaa gctggcccgc cgcaacaatg agagtgagac gagactttgt gtcagtgtgt 2100
gtatgtacat gtatgtctgc gcgacagccc taccgtccga cacgatgatt cttgtgcact 2160
gtactgtact gtactaactc cccccacccc ctccggtatg taacgcatgc catatgcagg 2220
cgctgtccaa cgggcggtac aagagctgcc tgcaccgcgc ggtggtgaac cggcggcagg 2280
agcggcaatc gctggccttc ttcctgtgcc cgcgcgagga ccgggtggtg cgcccgccgg 2340
ccagcgccgc gccgcggcag tacccggact tcacctgggc cgacctcatg cgcttcacgc 2400
agcgccacta ccgcgccgac acccgcacgc tggacgcctt cacccgctgg ctctcccacg 2460
gcccggcggc ggcggctccc tgcacctaa 2489

<210> SEQ ID NO 216
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 216
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctgtccttcg gcttccacga cggcgccgcg gcgcccgtcg tcgtggacta cttcaccggc 540
accctcggcc aagatttcga gccacgtggg gtgagtaaag aagaagatgg cgccgaattt 600
acatttataa gtaggaccag cagaagcccc tgcccctggg ggccttagca ttgcattcga 660
ctgatgaata cgcatggcag gcgggtgtac cagaggtact gcgaggagat gaaggagctg 720
tcgctgacga tcatggagct gctggagctg agcctgggcg tggagcgcgg ctactaccgg 780
gagttcttcg aggacagccg ctccatcatg cggtgcaact actacccgcc gtgcccggtg 840
ccggagcgca cgctgggcac gggcccgcac tgcgacccca cggcgctgac catcctcctg 900
caggacgacg tcggcgggct ggaggtcctg gtggacggcg agtggcgccc cgtccggccc 960
gtcccaggcg ccatggtcat caacatcggc gacaccttca tggtaacgaa cgaaagcgcc 1020
ggctcctctg cttttcttgg cctctttgtc cctgccctgt gctgctgtgc atattcattc 1080
attcagttct ctgtggggtt tttttttgt ttaatttttt tttgggatcg tatccagtgc 1140
acaagggcca cgccgtgcac aaatgcacaa aacgaaatct ggccgtccat tttccatcca 1200
acgacatgac ggcgcggggg gtttttcaca aaacagactc ggcaagctac ggaggttgcg 1260
ggagggttca tctgcatatt tacgacggcc gttggatgga aaatggacgg ccagatttcg 1320
ttttgtgtat ttgtgcacgg cgtggccctt gtgcactgga tacgatccca ttttttttt 1380 tgccccgaat cctagtggac ctaactggac agattacagc acgcacacgt aggcatgtca 1440
tgtagcagca ctgcagtcgg gtgcagtcca gtccagtcct gtccagccgc gacactgtag 1500
tacatagcga tgcaacggag acacgcgttg gagttggttc catctcttct cggcggccgt 1560
gccgaggctt ccgcggggaa gctgcgacaa cagaacggac cgccgggggt gggcaggcag 1620
caagctccct gttggcttgt gccgttgcgc agcggcgggt accggacaac gctttcggcg 1680
gcgcgcggcc tcgtcggctt cccctgtttt tgatgccgcc tctcggtgtc cggggaccgg 1740
gaggatcgat ggggcccgtg ccgtctgatc cgccacgcga gcggtcctat gcgatgcgcc 1800
gcacgagcgc ggggggccg tggaacagta cacagctggg tcactcactc actcatcccg 1860
ctggttgtgg ctgcttggtt gcaacttggc tcggctgtct gtctgttgcc cccgccgcgt 1920
tttctagccg tttccgcttt gctcgcggtt tcgctggcga tccggcacgc ggcgcccaca 1980
cccggggctg gccccttggc cgagtgggtg gcaggcactt gcatgcatcc ggccggtttc 2040
ccgcgaccaa gctggcccgc cgcaacaatg agagtgagac gagactttgt gtcagtgtgt 2100
gtatgtacat gtatgtctgc gcgacagccc taccgtccga cacgatgatt cttgtgcact 2160
gtactgtact gtactaactc cccccacccc ctccggtatg taacgcatgc catatgcagg 2220
cgctgtccaa cgggcggtac aagagctgcc tgcaccgcgc ggtggtgaac cggcggcagg 2280
agcggcaatc gctggccttc ttcctgtgcc cgcgcgagga ccgggtggtg cgcccgccgg 2340
ccagcgccgc gccgcggcag tacccggact tcacctgggc cgacctcatg cgcttcacgc 2400
agcgccacta ccgcgccgac acccgcacgc tggacgcctt cacccgctgg ctctcccacg 2460
gcccggcggc ggcggctccc tgcacctaa 2489

<210> SEQ ID NO 217
<211> LENGTH: 2489
<212> TYPE: DNA
<213> ORGANISM: Artificial Sequence
<220> FEATURE:
<223> OTHER INFORMATION: mutant sequence by gene editing

<400> SEQUENCE: 217
atggacgcca gcccgacccc accgctcccc ctccgcgccc caactcccag cattgacctc 60
ccccgctggc aaggacaggg ccgacgcggc ggctaacaag gccgcggctg tgttcgacct 120
gcgccgggag cccaagatcc cggagccatt cctgtggccg cacgaagagg cgcggccgac 180
ctcggccgcg gagctggagg tgccggtggt ggacgtgggc gtgctgcgca atggcgacgg 240
cgcggggctc cgccgcgccg cggcgcaagt ggcggcggcg tgcgcgacgc acgggttctt 300
ccaggtgtgc gggcacggcg tggacgcggc gctggggcgc gccgcgctgg acggcgccag 360
cgacttcttc cggctgccgc tggctgagaa gcagcgggcc cggcgcgtcc ccggcaccgt 420
gtccgggtac acgagcgcgc acgccgaccg gttcgcgtcc aagctcccct ggaaggagac 480
cctgtccttc ggcttccacg acggcgccgc ggcgcccgtc gtcgtggact acttcaccgg 540
caccctcggc caagatttcg agccagtggg gtgagtaaag aagaagatgg cgccgaattt 600

```
acatttataa gtaggaccag cagaagcccc tgcccctggg ggccttagca ttgcattcga    660
ctgatgaata cgcatggcag gcgggtgtac cagaggtact gcgaggagat gaaggagctg    720
tcgctgacga tcatggagct gctggagctg agcctgggcg tggagcgcgg ctactaccgg    780
gagttcttcg aggacagccg ctccatcatg cggtgcaact actacccgcc gtgcccggtg    840
ccggagcgca cgctgggcac gggcccgcac tgcgacccca cggcgctgac catcctcctg    900
caggacgacg tcggcgggct ggaggtcctg gtggacggcg agtggcgccc cgtccggccc    960
gtcccaggcg ccatggtcat caacatcggc gacaccttca tggtaacgaa cgaaagcgcc   1020
ggctcctctg cttttcttgg cctctttgtc cctgccctgt gctgctgtgc atattcattc   1080
attcagttct ctgtggggtt tttttttgt ttaatttttt tttgggatcg tatccagtgc   1140
acaagggcca cgccgtgcac aaatgcacaa aacgaaatct ggccgtccat tttccatcca   1200
acgacatgac ggcgcggggg gtttttcaca aaacagactc ggcaagctac ggaggttgcg   1260
ggagggttca tctgcatatt tacgacggcc gttggatgga aaatggacgg ccagatttcg   1320
ttttgtgtat ttgtgcacgg cgtggccctt gtgcactgga tacgatccca ttttttttt   1380
tgccccgaat cctagtggac ctaactggac agattacagc acgcacacgt aggcatgtca   1440
tgtagcagca ctgcagtcgg gtgcagtcca gtccagtcct gtccagccgc gacactgtag   1500
tacatagcga tgcaacggag acacgcgttg gagttggttc catctcttct cggcggccgt   1560
gccgaggctt ccgcggggaa gctgcgacaa cagaacggac cgccgggggt gggcaggcag   1620
caagctccct gttggcttgt gccgttgcgc agcggcgggt accggacaac gctttcggcg   1680
gcgcgcggcc tcgtcggctt cccctgtttt tgatgccgcc tctcggtgtc cggggaccgg   1740
gaggatcgat ggggcccgtg ccgtctgatc cgccacgcga gcggtcctat gcgatgcgcc   1800
gcacgagcgc ggggggccg tggaacagta cacagctggg tcactcactc actcatcccg   1860
ctggttgtgg ctgcttggtt gcaacttggc tcggctgtct gtctgttgcc cccgccgcgt   1920
tttctagccg tttccgcttt gctcgcggtt tcgctggcga tccggcacgc ggcgcccaca   1980
cccggggctg gccccttggc cgagtgggtg gcaggcactt gcatgcatcc ggccggtttc   2040
ccgcgaccaa gctggcccgc cgcaacaatg agagtgagac gagactttgt gtcagtgtgt   2100
gtatgtacat gtatgtctgc gcgacagccc taccgtccga cacgatgatt cttgtgcact   2160
gtactgtact gtactaactc cccccacccc ctccggtatg taacgcatgc catatgcagg   2220
cgctgtccaa cgggcggtac aagagctgcc tgcaccgcgc ggtggtgaac cggcggcagg   2280
agcggcaatc gctggccttc ttcctgtgcc cgcgcgagga ccgggtggtg cgcccgccgg   2340
ccagcgccgc gccgcggcag tacccggact tcacctgggc cgacctcatg cgcttcacgc   2400
agcgccacta ccgcgccgac acccgcacgc tggacgcctt cacccgctgg ctctcccacg   2460
gcccggcggc ggcggctccc tgcacctaa                                     2489
```

<210> SEQ ID NO 218
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 218

```
tccccggcac cgtgtcgggt acacgagcgc                                      30
```

<210> SEQ ID NO 219

<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 219
tccccggcac cgtgtgggta cacgagcgcg 30

<210> SEQ ID NO 220
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 220
tccccggcac cgtgttccgg gtacacgagc 30

<210> SEQ ID NO 221
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 221
gatccccgcg ccattctgtg gccgcaggaa 30

<210> SEQ ID NO 222
<211> LENGTH: 30
<212> TYPE: DNA
<213> ORGANISM: Artificial Sequence
<220> FEATURE:
<223> OTHER INFORMATION: mutant sequence by gene editing

<400> SEQUENCE: 222
ccaggatttc gagccatggg gtaagtaagg 30

<210> SEQ ID NO 223
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 223
tcggccagga tttcgatggg gtaagtaagg t 31

<210> SEQ ID NO 224
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 224
atacccccac ccgccgacag cttccctgca ta 32

<210> SEQ ID NO 225
<211> LENGTH: 33
<212> TYPE: DNA
<213> ORGANISM: Artificial Sequence
<220> FEATURE:
<223> OTHER INFORMATION: mutant sequence by gene editing

<400> SEQUENCE: 225
atacccccac ccgccctgga cagcttccct gca 33

<210> SEQ ID NO 226
<211> LENGTH: 32
<212> TYPE: DNA
<213> ORGANISM: Artificial Sequence
<220> FEATURE:
<223> OTHER INFORMATION: mutant sequence by gene editing

<400> SEQUENCE: 226
aaataccccc acccgggaca gcttccctgc at 32

<210> SEQ ID NO 227
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 227
cagcattgac ctcccacgct ggcaaggaca a 31

<210> SEQ ID NO 228
<211> LENGTH: 31
<212> TYPE: DNA
<213> ORGANISM: Artificial Sequence
<220> FEATURE:
<223> OTHER INFORMATION: mutant sequence by gene editing

<400> SEQUENCE: 228
cagcattgac ctcccccgct ggcaaggaca a 31

<210> SEQ ID NO 229
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 229
ccggcgcgtc cccggcaccg tgtcgggtac acgagcgcgc acgccgaccg gttcgcggc 59

<210> SEQ ID NO 230
<211> LENGTH: 58
<212> TYPE: DNA
<213> ORGANISM: Artificial Sequence
<220> FEATURE:
<223> OTHER INFORMATION: mutant sequence by gene editing

<400> SEQUENCE: 230
ccggcgcgtc cccggcaccg tgtgggtaca cgagcgcgca cgccgaccgg ttcgcggc 58

<210> SEQ ID NO 231
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 231
ccggcgcgtc cccggcaccg tgttccgggt acacgagcgc gcacgccgac cggttcgcgg 60
c 61

<210> SEQ ID NO 232

<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 232
cgacctgcgc cgggagccca agatccccgc gccattctgt ggccgcagga agaggcgcg 59

<210> SEQ ID NO 233
<211> LENGTH: 59
<212> TYPE: DNA
<213> ORGANISM: Artificial Sequence
<220> FEATURE:
<223> OTHER INFORMATION: mutant sequence by gene editing

<400> SEQUENCE: 233
ctacttcgtc ggcaccctcg gccaggattt cgagccatgg ggtaagtaag gtagtaaga 59

<210> SEQ ID NO 234
<211> LENGTH: 55
<212> TYPE: DNA
<213> ORGANISM: Artificial Sequence
<220> FEATURE:
<223> OTHER INFORMATION: mutant sequence by gene editing

<400> SEQUENCE: 234
ctacttcgtc ggcaccctcg gccaggattt cgatggggta agtaaggtag taaga 55

<210> SEQ ID NO 235
<211> LENGTH: 58
<212> TYPE: DNA
<213> ORGANISM: Artificial Sequence
<220> FEATURE:
<223> OTHER INFORMATION: mutant sequence by gene editing

<400> SEQUENCE: 235
gttacaaata cccccacccg ccgacagctt ccctgcatac ttgcagctcg cacatctc 58

<210> SEQ ID NO 236
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 236
gttacaaata cccccacccg ccctggacag cttccctgca tacttgcagc tcgcacatct 60
c 61

<210> SEQ ID NO 237
<211> LENGTH: 57
<212> TYPE: DNA
<213> ORGANISM: Artificial Sequence
<220> FEATURE:
<223> OTHER INFORMATION: mutant sequence by gene editing

<400> SEQUENCE: 237
gttacaaata cccccacccg ggacagcttc cctgcatact tgcagctcgc acatctc 57

<210> SEQ ID NO 238
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 238
tccgcgcccc cactcccagc cccagcattg acctcccacg ctggcaagga caaggccgac 60
g 61

<210> SEQ ID NO 239
<211> LENGTH: 61
<212> TYPE: DNA
<213> ORGANISM: Artificial Sequence
<220> FEATURE:
<223> OTHER INFORMATION: mutant sequence by gene editing

<400> SEQUENCE: 239
tccgcgcccc cactcccagc cccagcattg acctcccccg ctggcaagga caaggccgac 60
g 61

<210> SEQ ID NO 240
<211> LENGTH: 60
<212> TYPE: DNA
<213> ORGANISM: Zea mays

<400> SEQUENCE: 240
ccggcgcgtc cccggcaccg tgtccgggta cacgagcgcg cacgccgacc ggttcgcggc 60

<210> SEQ ID NO 241
<211> LENGTH: 60
<212> TYPE: DNA
<213> ORGANISM: Zea mays

<400> SEQUENCE: 241
ccggcgcgtc cccggcaccg tgtccgggta cacgagcgcg cacgccgacc ggttcgcggc 60

<210> SEQ ID NO 242
<211> LENGTH: 60
<212> TYPE: DNA
<213> ORGANISM: Zea mays

<400> SEQUENCE: 242
ccggcgcgtc cccggcaccg tgtccgggta cacgagcgcg cacgccgacc ggttcgcggc 60

<210> SEQ ID NO 243
<211> LENGTH: 60
<212> TYPE: DNA
<213> ORGANISM: Zea mays

<400> SEQUENCE: 243
cgacctgcgc cgggagccca agatccccgc gccattcctg tggccgcagg aagaggcgcg 60

<210> SEQ ID NO 244
<211> LENGTH: 60
<212> TYPE: DNA
<213> ORGANISM: Zea mays

<400> SEQUENCE: 244
ctacttcgtc ggcaccctcg gccaggattt cgagccaatg gggtaagtaa ggtagtaaga 60

<210> SEQ ID NO 245
<211> LENGTH: 60
<212> TYPE: DNA
<213> ORGANISM: Zea mays

<400> SEQUENCE: 245
ctacttcgtc ggcaccctcg gccaggattt cgagccaatg gggtaagtaa ggtagtaaga 60

<210> SEQ ID NO 246
<211> LENGTH: 60
<212> TYPE: DNA
<213> ORGANISM: Zea mays

<400> SEQUENCE: 246
gttacaaata cccccacccg cccggacagc ttccctgcat acttgcagct cgcacatctc 60

<210> SEQ ID NO 247
<211> LENGTH: 60
<212> TYPE: DNA
<213> ORGANISM: Zea mays

<400> SEQUENCE: 247
gttacaaata cccccacccg cccggacagc ttccctgcat acttgcagct cgcacatctc 60

<210> SEQ ID NO 248
<211> LENGTH: 60
<212> TYPE: DNA
<213> ORGANISM: Zea mays

<400> SEQUENCE: 248
gttacaaata cccccacccg cccggacagc ttccctgcat acttgcagct cgcacatctc 60

<210> SEQ ID NO 249
<211> LENGTH: 60
<212> TYPE: DNA
<213> ORGANISM: Zea mays

<400> SEQUENCE: 249
tccgcgcccc cactcccagc cccagcattg acctccccgc tggcaaggac aaggccgacg 60

<210> SEQ ID NO 250
<211> LENGTH: 60
<212> TYPE: DNA
<213> ORGANISM: Zea mays

<400> SEQUENCE: 250
tccgcgcccc cactcccagc cccagcattg acctccccgc tggcaaggac aaggccgacg 60

<210> SEQ ID NO 251
<211> LENGTH: 2472
<212> TYPE: DNA
<213> ORGANISM: Artificial Sequence
<220> FEATURE:
<223> OTHER INFORMATION: mutant sequence by gene editing

<400> SEQUENCE: 251
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc ccgctggcaa ggacaaggcc 300
gacgcggcgg ccagcaaggc cggcgcggcc gtgttcgacc tgcgccggga gcccaagatc 360
cccgcgccat tcctgtggcc gcaggaagag gcgcggccgt cctcggccgc ggagctggag 420
gtgccgatgg tggacgtggg cgtgctgcgc aatggcgacc gcgcggggct gcggcgcgcc 480
gcggcgcagg tggccgcggc gtgcgcgacg cacgggttct tccaggtgtg cgggcacggc 540
gtggacgcgg cgctggggcg cgccgcgctg gacggcgcca gcgacttctt ccggctgccg 600
ctcgccgaga agcagcgcgc ccggcgcgtc cccggcaccg tgtcgggtac acgagcgcgc 660
acgccgaccg gttcgcggcc aagctcccct ggaaggagac cctgtcgttc ggctaccacg 720
acggcgccgc gtcgcctgtc gtcgtggact acttcgtcgg caccctcggc caggatttcg 780
agccaatggg gtaagtaagg tagtaagaag gagcgccggt ttacatttac cgcacgtcgg 840
cgtgcggtcg agtcgggact cgggagacgt atgaaccccc gtcccgtccc atgcatgtgt 900
ggcaggtggg tgtaccagag gtactgcgag gagatgaagg agctgtcgct gacgatcatg 960
gagctgctgg agctgagcct gggcgtggag ctgcgcggct actaccggga gttcttcgag 1020
gacagccggt ccatcatgcg gtgcaactac tacccgccgt gcccggagcc ggagcgcacg 1080
ctgggcacgg gcccgcactg cgaccccacg gcgctcacca tcctcctgca ggacgacgtg 1140
ggcgggctgg aggtgctggt ggacggtgag tggcgccccg tccggcccgt cccgggcgcc 1200
atggtcatca acatcggcga caccttcatg gtaacgaaac gaaagcgctc gctcctctgt 1260
tttccttggc cgctcttgtc ctgtgtgtat attcagttga gctctctctg tgctgttatt 1320
tcccgaatcc tagtggacct aaacgggcag gttattacag cacgcacacg taggcatgtc 1380
atgtagctag tacatacata gcgatgccga tgcaaatgca atagagacat gcgttcgagt 1440
tggttcctat ctcggcgggc tacggcaggt acacgcggcc gcggcgcgct ctctctagtc 1500
tatccgcggc cgcgcccagg ccgatcgagg cttccggggg agagttgcga caagagaacg 1560
gaccgagggg gtcggctagc ggtagcaagt tccctgttgg tttgtggcgt tggagcgttg 1620
cggagaggct tgcgcggcgg cggggacgtc gacggggacg tggcggggag acgatacgat 1680
gggtgccggg cagggcaacg ctttcggcgg gtggccgtgt ccaggtgcgc gcggccttgt 1740
cggtttcccc ctctcggtgt ccatggccga gaaatgggtc gacgaccgag accgacgctc 1800
ggtgcggcgc ccatcccgtc tgatccgccg cgccacgcga gcggccctat gcgatgccgc 1860
acgggcgcgg agggccgtcg cgcggagtat aatgtatagt atatagtaca aggttggttg 1920
gagtcgggtt gggttggatc gggtcaccgg tacgtggtgg ctgctgttgc cccegccgtt 1980 tccgcttgca cttttgtcgc ggtttcgctg gcgatccggc acgcggcgcc cacaccacgc 2040
cggggctcca aacagctcgg gcccttggcc gtgtgggtgg caggcacttg cacgcgtccg 2100
gttgtcgcgg cctggcccgc cgccgggcgc accgcaacaa tgagacagcc cgacacgatg 2160
attcttgtgc actgtgctaa cccgcatgcc atgcaggcgc tgtcgaacgg gaggtacaag 2220
agctgcctgc accgcgcggt ggtgaaccag cggcgggcgc ggcggtcgct ggccttcttc 2280
ctgtgcccgc gcgaggaccg ggtggtgcgc ccgccggcca gtgctgcgcc gcggcgctac 2340
ccggacttca cctgggccga cctcatgcgc ttcacgcagc gccactaccg cgccgacacc 2400
cgcacgctgg acgccttcac ccgctggctc tcccacggcc cggcccaggc ggcggcgcct 2460
ccctgcacct ag 2472

<210> SEQ ID NO 252
<211> LENGTH: 2471
<212> TYPE: DNA
<213> ORGANISM: Artificial Sequence
<220> FEATURE:
<223> OTHER INFORMATION: mutant sequence by gene editing

<400> SEQUENCE: 252
atgaggccgc gcctccctcc aaatgttccc tccctgcctt cgtctttgtc gttgctcgca 60

```
aactccctgt cctcccctgt tacaaatacc cccacccgcc cggacagctt ccctgcatac    120
ttgcagctcg cacatctcat ggtgtcgcag gaacgacaag agccagctgt gcctagcagc    180
agcagcagca gcgccaagcg cgcagccacg tccatggacg ccagcccggc cccgccgctc    240
ctcctccgcg cccccactcc cagccccagc attgacctcc ccgctggcaa ggacaaggcc    300
gacgcggcgg ccagcaaggc cggcgcggcc gtgttcgacc tgcgccggga gcccaagatc    360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc    540
gtggacgcgg cgctggggcg cgccgcgctg gacggcgcca gcgacttctt ccggctgccg    600
ctcgccgaga agcagcgcgc ccggcgcgtc cccggcaccg tgtgggtaca cgagcgcgca    660
cgccgaccgg ttcgcggcca agctcccctg gaaggagacc ctgtcgttcg gctaccacga    720
cggcgccgcg tcgcctgtcg tcgtggacta cttcgtcggc accctcggcc aggatttcga    780
gccaatgggg taagtaaggt agtaagaagg agcgccggtt tacatttacc gcacgtcggc    840
gtgcggtcga gtcgggactc gggagacgta tgaacccccg tcccgtccca tgcatgtgtg    900
gcaggtgggt gtaccagagg tactgcgagg agatgaagga gctgtcgctg acgatcatgg    960
agctgctgga gctgagcctg ggcgtggagc tgcgcggcta ctaccgggag ttcttcgagg   1020
acagccggtc catcatgcgg tgcaactact acccgccgtg cccggagccg gagcgcacgc   1080
tgggcacggg cccgcactgc gaccccacgg cgctcaccat cctcctgcag gacgacgtgg   1140
gcgggctgga ggtgctggtg gacggtgagt ggcgccccgt ccggcccgtc ccgggcgcca   1200
tggtcatcaa catcggcgac accttcatgg taacgaaacg aaagcgctcg ctcctctgtt   1260
ttccttggcc gctcttgtcc tgtgtgtata ttcagttgag ctctctctgt gctgttattt   1320
cccgaatcct agtggaccta aacgggcagg ttattacagc acgcacacgt aggcatgtca   1380
tgtagctagt acatacatag cgatgccgat gcaaatgcaa tagagacatg cgttcgagtt   1440
ggttcctatc tcggcgggct acggcaggta cacgcggccg cggcgcgctc tctctagtct   1500
atccgcggcc gcgcccaggc cgatcgaggc ttccggggga gagttgcgac aagagaacgg   1560
accgaggggg tcggctagcg gtagcaagtt ccctgttggt ttgtggcgtt ggagcgttgc   1620
ggagaggctt gcgcggcggc ggggacgtcg acggggacgt ggcggggaga cgatacgatg   1680
ggtgccgggc agggcaacgc tttcggcggg tggccgtgtc caggtgcgcg cggccttgtc   1740
ggtttccccc tctcggtgtc catggccgag aaatgggtcg acgaccgaga ccgacgctcg   1800
gtgcggcgcc catcccgtct gatccgccgc gccacgcgag cggccctatg cgatgccgca   1860
cgggcgcgga gggccgtcgc gcggagtata atgtatagta tatagtacaa ggttggttgg   1920
agtcgggttg ggttggatcg ggtcaccggt acgtggtggc tgctgttgcc cccgccgttt   1980
ccgcttgcac ttttgtcgcg gtttcgctgg cgatccggca cgcggcgccc acaccacgcc   2040
ggggctccaa acagctcggg cccttggccg tgtgggtggc aggcacttgc acgcgtccgg   2100
ttgtcgcggc ctggcccgcc gccgggcgca ccgcaacaat gagacagccc gacacgatga   2160
ttcttgtgca ctgtgctaac ccgcatgcca tgcaggcgct gtcgaacggg aggtacaaga   2220
gctgcctgca ccgcgcggtg gtgaaccagc ggcgggcgcg gcggtcgctg gccttcttcc   2280
tgtgcccgcg cgaggaccgg gtggtgcgcc cgccggccag tgctgcgccg cggcgctacc   2340
cggacttcac ctgggccgac ctcatgcgct tcacgcagcg ccactaccgc gccgacaccc   2400
gcacgctgga cgccttcacc cgctggctct cccacggccc ggcccaggcg gcggcgcctc   2460
```

cctgcaccta g 2471

<210> SEQ ID NO 253
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 253
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc ccgctggcaa ggacaaggcc 300
gacgcggcgg ccagcaaggc cggcgcggcc gtgttcgacc tgcgccggga gcccaagatc 360
cccgcgccat tcctgtggcc gcaggaagag gcgcggccgt cctcggccgc ggagctggag 420
gtgccgatgg tggacgtggg cgtgctgcgc aatggcgacc gcgcggggct gcggcgcgcc 480
gcggcgcagg tggccgcggc gtgcgcgacg cacgggttct tccaggtgtg cgggcacggc 540
gtggacgcgg cgctggggcg cgccgcgctg gacggcgcca gcgacttctt ccggctgccg 600
ctcgccgaga agcagcgcgc ccggcgcgtc cccggcaccg tgttccgggt acacgagcgc 660
gcacgccgac cggttcgcgg ccaagctccc ctggaaggag accctgtcgt tcggctacca 720
cgacggcgcc gcgtcgcctg tcgtcgtgga ctacttcgtc ggcaccctcg gccaggattt 780
cgagccaatg ggtaagtaa ggtagtaaga aggagcgccg gtttacattt accgcacgtc 840
ggcgtgcggt cgagtcggga ctcgggagac gtatgaaccc ccgtcccgtc ccatgcatgt 900
gtggcaggtg ggtgtaccag aggtactgcg aggagatgaa ggagctgtcg ctgacgatca 960
tggagctgct ggagctgagc ctgggcgtgg agctgcgcgg ctactaccgg gagttcttcg 1020
aggacagccg gtccatcatg cggtgcaact actacccgcc gtgcccggag ccggagcgca 1080
cgctgggcac gggcccgcac tgcgacccca cggcgctcac catcctcctg caggacgacg 1140
tgggcgggct ggaggtgctg gtggacggtg agtggcgccc cgtccggccc gtcccgggcg 1200
ccatggtcat caacatcggc gacaccttca tggtaacgaa acgaaagcgc tcgctcctct 1260
gttttccttg gccgctcttg tcctgtgtgt atattcagtt gagctctctc tgtgctgtta 1320
tttcccgaat cctagtggac ctaaacgggc aggttattac agcacgcaca cgtaggcatg 1380
tcatgtagct agtacataca tagcgatgcc gatgcaaatg caatagagac atgcgttcga 1440
gttggttcct atctcggcgg gctacggcag gtacacgcgg ccgcggcgcg ctctctctag 1500
tctatccgcg gccgcgccca ggccgatcga ggcttccggg ggagagttgc gacaagagaa 1560
cggaccgagg gggtcggcta gcggtagcaa gttccctgtt ggtttgtggc gttggagcgt 1620
tgcggagagg cttgcgcggc ggcggggacg tcgacgggga cgtggcgggg agacgatacg 1680
atgggtgccg ggcagggcaa cgctttcggc gggtggccgt gtccaggtgc gcgcggcctt 1740
gtcggtttcc ccctctcggt gtccatggcc gagaaatggg tcgacgaccg agaccgacgc 1800
tcggtgcggc gcccatcccg tctgatccgc cgcgccacgc gagcggccct atgcgatgcc 1860
gcacgggcgc ggagggccgt cgcgcggagt ataatgtata gtatatagta caaggttggt 1920
tggagtcggg ttgggttgga tcgggtcacc ggtacgtggt ggctgctgtt gcccccgccg 1980
tttccgcttg cacttttgtc gcggtttcgc tggcgatccg gcacgcggcg cccacaccac 2040
gccggggctc caaacagctc gggcccttgg ccgtgtgggt ggcaggcact tgcacgcgtc 2100
cggttgtcgc ggcctggccc gccgccgggc gcaccgcaac aatgagacag cccgacacga 2160
tgattcttgt gcactgtgct aacccgcatg ccatgcaggc gctgtcgaac gggaggtaca 2220
agagctgcct gcaccgcgcg gtggtgaacc agcggcgggc gcggcggtcg ctggccttct 2280
tcctgtgccc gcgcgaggac cgggtggtgc gcccgccggc cagtgctgcg ccgcggcgct 2340
acccggactt cacctgggcc gacctcatgc gcttcacgca gcgccactac cgcgccgaca 2400
cccgcacgct ggacgccttc acccgctggc tctcccacgg cccggcccag gcggcggcgc 2460
ctccctgcac ctag 2474

<210> SEQ ID NO 254
<211> LENGTH: 2472
<212> TYPE: DNA
<213> ORGANISM: Artificial Sequence
<220> FEATURE:
<223> OTHER INFORMATION: mutant sequence by gene editing

<400> SEQUENCE: 254
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc ccgctggcaa ggacaaggcc 300
gacgcggcgg ccagcaaggc cggcgcggcc gtgttcgacc tgcgccggga gcccaagatc 360
cccgcgccat tctgtggccg caggaagagg cgcggccgtc ctcggccgcg gagctggagg 420
tgccgatggt ggacgtgggc gtgctgcgca atggcgaccg cgcggggctg cggcgcgccg 480
cggcgcaggt ggccgcggcg tgcgcgacgc acgggttctt ccaggtgtgc gggcacggcg 540
tggacgcggc gctggggcgc gccgcgctgg acggcgccag cgacttcttc cggctgccgc 600
tcgccgagaa gcagcgcgcc cggcgcgtcc ccggcaccgt gtccgggtac acgagcgcgc 660
acgccgaccg gttcgcggcc aagctcccct ggaaggagac cctgtcgttc ggctaccacg 720
acggcgccgc gtcgcctgtc gtcgtggact acttcgtcgg caccctcggc caggatttcg 780
agccaatggg gtaagtaagg tagtaagaag gagcgccggt ttacatttac cgcacgtcgg 840
cgtgcggtcg agtcgggact cgggagacgt atgaaccccc gtcccgtccc atgcatgtgt 900
ggcaggtggg tgtaccagag gtactgcgag gagatgaagg agctgtcgct gacgatcatg 960
gagctgctgg agctgagcct gggcgtggag ctgcgcggct actaccggga gttcttcgag 1020
gacagccggt ccatcatgcg gtgcaactac tacccgccgt gcccggagcc ggagcgcacg 1080
ctgggcacgg gcccgcactg cgaccccacg gcgctcacca tcctcctgca ggacgacgtg 1140
ggcgggctgg aggtgctggt ggacggtgag tggcgccccg tccggcccgt cccgggcgcc 1200
atggtcatca acatcggcga caccttcatg gtaacgaaac gaaagcgctc gctcctctgt 1260
tttccttggc cgctcttgtc ctgtgtgtat attcagttga gctctctctg tgctgttatt 1320
tcccgaatcc tagtggacct aaacgggcag gttattacag cacgcacacg taggcatgtc 1380
atgtagctag tacatacata gcgatgccga tgcaaatgca atagagacat gcgttcgagt 1440
tggttcctat ctcggcgggc tacggcaggt acacgcggcc gcggcgcgct ctctctagtc 1500
tatccgcggc cgcgcccagg ccgatcgagg cttccggggg agagttgcga caagagaacg 1560
gaccgagggg gtcggctagc ggtagcaagt tccctgttgg tttgtggcgt tggagcgttg 1620
cggagaggct tgcgcggcgg cggggacgtc gacggggacg tggcggggag acgatacgat 1680
gggtgccggg cagggcaacg ctttcggcgg gtggccgtgt ccaggtgcgc gcggccttgt 1740
cggtttcccc ctctcggtgt ccatggccga gaaatgggtc gacgaccgag accgacgctc 1800
ggtgcggcgc ccatcccgtc tgatccgccg cgccacgcga gcggccctat gcgatgccgc 1860
acgggcgcgg agggccgtcg cgcggagtat aatgtatagt atatagtaca aggttggttg 1920
gagtcgggtt gggttggatc gggtcaccgg tacgtggtgg ctgctgttgc cccgccgtt 1980 tccgcttgca cttttgtcgc ggtttcgctg gcgatccggc acgcggcgcc cacaccacgc 2040
cggggctcca aacagctcgg gcccttggcc gtgtgggtgg caggcacttg cacgcgtccg 2100
gttgtcgcgg cctggcccgc cgccgggcgc accgcaacaa tgagacagcc cgacacgatg 2160
attcttgtgc actgtgctaa cccgcatgcc atgcaggcgc tgtcgaacgg gaggtacaag 2220
agctgcctgc accgcgcggt ggtgaaccag cggcgggcgc ggcggtcgct ggccttcttc 2280
ctgtgcccgc gcgaggaccg ggtggtgcgc ccgccggcca gtgctgcgcc gcggcgctac 2340
ccggacttca cctgggccga cctcatgcgc ttcacgcagc gccactaccg cgccgacacc 2400
cgcacgctgg acgccttcac ccgctggctc tcccacggcc cggcccaggc ggcggcgcct 2460
ccctgcacct ag 2472

<210> SEQ ID NO 255
<211> LENGTH: 2472
<212> TYPE: DNA
<213> ORGANISM: Artificial Sequence
<220> FEATURE:
<223> OTHER INFORMATION: mutant sequence by gene editing

<400> SEQUENCE: 255
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc ccgctggcaa ggacaaggcc 300
gacgcggcgg ccagcaaggc cggcgcggcc gtgttcgacc tgcgccggga gcccaagatc 360
cccgcgccat tcctgtggcc gcaggaagag gcgcggccgt cctcggccgc ggagctggag 420
gtgccgatgg tggacgtggg cgtgctgcgc aatggcgacc gcgcggggct gcggcgcgcc 480
gcggcgcagg tggccgcggc gtgcgcgacg cacgggttct tccaggtgtg cgggcacggc 540
gtggacgcgg cgctggggcg cgccgcgctg gacggcgcca gcgacttctt ccggctgccg 600
ctcgccgaga agcagcgcgc ccggcgcgtc cccggcaccg tgtccgggta cacgagcgcg 660
cacgccgacc ggttcgcggc caagctcccc tggaaggaga ccctgtcgtt cggctaccac 720
gacggcgccg cgtcgcctgt cgtcgtggac tacttcgtcg gcaccctcgg ccaggatttc 780
gagccatggg gtaagtaagg tagtaagaag gagcgccggt ttacatttac cgcacgtcgg 840
cgtgcggtcg agtcgggact cgggagacgt atgaaccccc gtcccgtccc atgcatgtgt 900
ggcaggtggg tgtaccagag gtactgcgag gagatgaagg agctgtcgct gacgatcatg 960
gagctgctgg agctgagcct gggcgtggag ctgcgcggct actaccggga gttcttcgag 1020
gacagccggt ccatcatgcg gtgcaactac tacccgccgt gcccggagcc ggagcgcacg 1080

```
ctgggcacgg gcccgcactg cgaccccacg gcgctcacca tcctcctgca ggacgacgtg   1140
ggcgggctgg aggtgctggt ggacggtgag tggcgccccg tccggcccgt cccgggcgcc   1200
atggtcatca acatcggcga caccttcatg gtaacgaaac gaaagcgctc gctcctctgt   1260
tttccttggc cgctcttgtc ctgtgtgtat attcagttga gctctctctg tgctgttatt   1320
tcccgaatcc tagtggacct aaacgggcag gttattacag cacgcacacg taggcatgtc   1380
atgtagctag tacatacata gcgatgccga tgcaaatgca atagagacat gcgttcgagt   1440
tggttcctat ctcggcgggc tacggcaggt acacgcggcc gcggcgcgct ctctctagtc   1500
tatccgcggc cgcgcccagg ccgatcgagg cttccggggg agagttgcga caagagaacg   1560
gaccgagggg gtcggctagc ggtagcaagt tccctgttgg tttgtggcgt tggagcgttg   1620
cggagaggct tgcgcggcgg cggggacgtc gacggggacg tggcggggag acgatacgat   1680
gggtgccggg cagggcaacg ctttcggcgg gtggccgtgt ccaggtgcgc gcggccttgt   1740
cggtttcccc ctctcggtgt ccatggccga gaaatgggtc gacgaccgag accgacgctc   1800
ggtgcggcgc ccatcccgtc tgatccgccg cgccacgcga gcggccctat gcgatgccgc   1860
acgggcgcgg agggccgtcg cgcggagtat aatgtatagt atatagtaca aggttggttg   1920
gagtcgggtt gggttggatc gggtcaccgg tacgtggtgg ctgctgttgc ccccgccgtt   1980
tccgcttgca cttttgtcgc ggtttcgctg gcgatccggc acgcggcgcc cacaccacgc   2040
cggggctcca aacagctcgg gcccttggcc gtgtgggtgg caggcacttg cacgcgtccg   2100
gttgtcgcgg cctggcccgc cgccgggcgc accgcaacaa tgagacagcc cgacacgatg   2160
attcttgtgc actgtgctaa cccgcatgcc atgcaggcgc tgtcgaacgg gaggtacaag   2220
agctgcctgc accgcgcggt ggtgaaccag cggcgggcgc ggcggtcgct ggccttcttc   2280
ctgtgcccgc gcgaggaccg ggtggtgcgc ccgccggcca gtgctgcgcc gcggcgctac   2340
ccggacttca cctgggccga cctcatgcgc ttcacgcagc gccactaccg cgccgacacc   2400
cgcacgctgg acgccttcac ccgctggctc tcccacggcc cggcccaggc ggcggcgcct   2460
ccctgcacct ag                                                       2472
```

<210> SEQ ID NO 256
<211> LENGTH: 2468
<212> TYPE: DNA
<213> ORGANISM: Artificial Sequence
<220> FEATURE:
<223> OTHER INFORMATION: mutant sequence by gene editing

<400> SEQUENCE: 256

```
atgaggccgc gcctccctcc aaatgttccc tccctgcctt cgtctttgtc gttgctcgca     60
aactccctgt cctcccctgt tacaaatacc cccacccgcc cggacagctt ccctgcatac    120
ttgcagctcg cacatctcat ggtgtcgcag gaacgacaag agccagctgt gcctagcagc    180
agcagcagca gcgccaagcg cgcagccacg tccatggacg ccagcccggc cccgccgctc    240
ctcctccgcg cccccactcc cagccccagc attgacctcc ccgctggcaa ggacaaggcc    300
gacgcggcgg ccagcaaggc cggcgcggcc gtgttcgacc tgcgccggga gcccaagatc    360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc    540
gtggacgcgg cgctggggcg cgccgcgctg gacggcgcca gcgacttctt ccggctgccg    600
ctcgccgaga agcagcgcgc ccggcgcgtc cccggcaccg tgtccgggta cacgagcgcg    660
```

```
cacgccgacc ggttcgcggc caagctcccc tggaaggaga ccctgtcgtt cggctaccac    720

gacggcgccg cgtcgcctgt cgtcgtggac tacttcgtcg gcaccctcgg ccaggatttc    780

gatggggtaa gtaaggtagt aagaaggagc gccggtttac atttaccgca cgtcggcgtg    840

cggtcgagtc gggactcggg agacgtatga acccccgtcc cgtcccatgc atgtgtggca    900

ggtgggtgta ccagaggtac tgcgaggaga tgaaggagct gtcgctgacg atcatggagc    960

tgctggagct gagcctgggc gtggagctgc gcggctacta ccgggagttc ttcgaggaca   1020

gccggtccat catgcggtgc aactactacc cgccgtgccc ggagccggag cgcacgctgg   1080

gcacgggccc gcactgcgac ccacggcgc tcaccatcct cctgcaggac gacgtgggcg   1140

ggctggaggt gctggtggac ggtgagtggc gccccgtccg gcccgtcccg ggcgccatgg   1200

tcatcaacat cggcgacacc ttcatggtaa cgaaacgaaa gcgctcgctc ctctgttttc   1260

cttggccgct cttgtcctgt gtgtatattc agttgagctc tctctgtgct gttatttccc   1320

gaatcctagt ggacctaaac gggcaggtta ttacagcacg cacacgtagg catgtcatgt   1380

agctagtaca tacatagcga tgccgatgca aatgcaatag agacatgcgt tcgagttggt   1440

tcctatctcg gcgggctacg gcaggtacac gcggccgcgg cgcgctctct ctagtctatc   1500

cgcggccgcg cccaggccga tcgaggcttc cgggggagag ttgcgacaag agaacggacc   1560

gagggggtcg gctagcggta gcaagttccc tgttggtttg tggcgttgga gcgttgcgga   1620

gaggcttgcg cggcggcggg gacgtcgacg gggacgtggc ggggagacga tacgatgggt   1680

gccgggcagg gcaacgcttt cggcgggtgg ccgtgtccag gtgcgcgcgg ccttgtcggt   1740

ttccccctct cggtgtccat ggccgagaaa tgggtcgacg accgagaccg acgctcggtg   1800

cggcgcccat cccgtctgat ccgccgcgcc acgcgagcgg ccctatgcga tgccgcacgg   1860

gcgcggaggg ccgtcgcgcg gagtataatg tatagtatat agtacaaggt tggttggagt   1920

cgggttgggt tggatcgggt caccggtacg tggtggctgc tgttgccccc gccgtttccg   1980

cttgcacttt tgtcgcggtt tcgctggcga tccggcacgc ggcgcccaca ccacgccggg   2040

gctccaaaca gctcgggccc ttggccgtgt gggtggcagg cacttgcacg cgtccggttg   2100

tcgcggcctg gcccgccgcc gggcgcaccg caacaatgag acagcccgac acgatgattc   2160

ttgtgcactg tgctaacccg catgccatgc aggcgctgtc gaacgggagg tacaagagct   2220

gcctgcaccg cgcggtggtg aaccagcggc gggcgcggcg gtcgctggcc ttcttcctgt   2280

gcccgcgcga ggaccgggtg gtgcgcccgc cggccagtgc tgcgccgcgg cgctacccgg   2340

acttcacctg ggccgacctc atgcgcttca cgcagcgcca ctaccgcgcc gacacccgca   2400

cgctggacgc cttcacccgc tggctctccc acggcccggc ccaggcggcg gcgcctccct   2460

gcacctag                                                            2468
```

```
<210> SEQ ID NO 257
<211> LENGTH: 2471
<212> TYPE: DNA
<213> ORGANISM: Artificial Sequence
<220> FEATURE:
<223> OTHER INFORMATION: mutant sequence by gene editing

<400> SEQUENCE: 257

atgaggccgc gcctccctcc aaatgttccc tccctgcctt cgtctttgtc gttgctcgca     60

aactccctgt cctcccctgt tacaaatacc cccacccgcc gacagcttcc ctgcatactt    120

gcagctcgca catctcatgg tgtcgcagga acgacaagag ccagctgtgc ctagcagcag    180
```

-continued

```
cagcagcagc gccaagcgcg cagccacgtc catggacgcc agcccggccc cgccgctcct    240
cctccgcgcc cccactccca gccccagcat tgacctcccc gctggcaagg acaaggccga    300
cgcggcggcc agcaaggccg gcgcggccgt gttcgacctg cgccgggagc ccaagatccc    360
cgcgccattc ctgtggccgc aggaagaggc gcggccgtcc tcggccgcgg agctggaggt    420
gccgatggtg gacgtgggcg tgctgcgcaa tggcgaccgc gcggggctgc ggcgcgccgc    480
ggcgcaggtg gccgcggcgt gcgcgacgca cgggttcttc caggtgtgcg ggcacggcgt    540
ggacgcggcg ctggggcgcg ccgcgctgga cggcgccagc gacttcttcc ggctgccgct    600
cgccgagaag cagcgcgccc ggcgcgtccc cggcaccgtg tccgggtaca cgagcgcgca    660
cgccgaccgg ttcgcggcca agctcccctg gaaggagacc ctgtcgttcg gctaccacga    720
cggcgccgcg tcgcctgtcg tcgtggacta cttcgtcggc accctcggcc aggatttcga    780
gccaatgggg taagtaaggt agtaagaagg agcgccggtt tacatttacc gcacgtcggc    840
gtgcggtcga gtcgggactc gggagacgta tgaacccccg tcccgtccca tgcatgtgtg    900
gcaggtgggt gtaccagagg tactgcgagg agatgaagga gctgtcgctg acgatcatgg    960
agctgctgga gctgagcctg ggcgtggagc tgcgcggcta ctaccgggag ttcttcgagg   1020
acagccggtc catcatgcgg tgcaactact acccgccgtg cccggagccg gagcgcacgc   1080
tgggcacggg cccgcactgc gaccccacgg cgctcaccat cctcctgcag gacgacgtgg   1140
gcgggctgga ggtgctggtg gacggtgagt ggcgccccgt ccggcccgtc ccgggcgcca   1200
tggtcatcaa catcggcgac accttcatgg taacgaaacg aaagcgctcg ctcctctgtt   1260
ttccttggcc gctcttgtcc tgtgtgtata ttcagttgag ctctctctgt gctgttattt   1320
cccgaatcct agtggaccta aacgggcagg ttattacagc acgcacacgt aggcatgtca   1380
tgtagctagt acatacatag cgatgccgat gcaaatgcaa tagagacatg cgttcgagtt   1440
ggttcctatc tcggcgggct acggcaggta cacgcggccg cggcgcgctc tctctagtct   1500
atccgcggcc gcgcccaggc cgatcgaggc ttccgggggga gagttgcgac aagagaacgg   1560
accgaggggg tcggctagcg gtagcaagtt ccctgttggt ttgtggcgtt ggagcgttgc   1620
ggagaggctt gcgcggcggc ggggacgtcg acggggacgt ggcggggaga cgatacgatg   1680
ggtgccgggc agggcaacgc tttcggcggg tggccgtgtc caggtgcgcg cggccttgtc   1740
ggtttccccc tctcggtgtc catggccgag aaatgggtcg acgaccgaga ccgacgctcg   1800
gtgcggcgcc catcccgtct gatccgccgc gccacgcgag cggccctatg cgatgccgca   1860
cgggcgcgga gggccgtcgc gcggagtata atgtatagta tatagtacaa ggttggttgg   1920
agtcgggttg ggttggatcg ggtcaccggt acgtggtggc tgctgttgcc cccgccgttt   1980
ccgcttgcac ttttgtcgcg gtttcgctgg cgatccggca cgcggcgccc acaccacgcc   2040
ggggctccaa acagctcggg cccttggccg tgtgggtggc aggcacttgc acgcgtccgg   2100
ttgtcgcggc ctggcccgcc gccgggcgca ccgcaacaat gagacagccc gacacgatga   2160
ttcttgtgca ctgtgctaac ccgcatgcca tgcaggcgct gtcgaacggg aggtacaaga   2220
gctgcctgca ccgcgcggtg gtgaaccagc ggcgggcgcg gcggtcgctg gccttcttcc   2280
tgtgcccgcg cgaggaccgg gtggtgcgcc cgccggccag tgctgcgccg cggcgctacc   2340
cggacttcac ctgggccgac ctcatgcgct tcacgcagcg ccactaccgc gccgacaccc   2400
gcacgctgga cgccttcacc cgctggctct cccacggccc ggcccaggcg gcggcgcctc   2460
cctgcaccta g                                                         2471
```

<210> SEQ ID NO 258
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 258
atgaggccgc gcctccctcc aaatgttccc tccctgcctt cgtctttgtc gttgctcgca 60
aactccctgt cctcccctgt tacaaatacc cccacccgcc ctggacagct tccctgcata 120
cttgcagctc gcacatctca tggtgtcgca ggaacgacaa gagccagctg tgcctagcag 180
cagcagcagc agcgccaagc gcgcagccac gtccatggac gccagcccgg ccccgccgct 240
cctcctccgc gcccccactc ccagccccag cattgacctc cccgctggca aggacaaggc 300
cgacgcggcg gccagcaagg ccggcgcggc cgtgttcgac ctgcgccggg agcccaagat 360
ccccgcgcca ttcctgtggc cgcaggaaga ggcgcggccg tcctcggccg cggagctgga 420
ggtgccgatg gtggacgtgg gcgtgctgcg caatggcgac cgcgcggggc tgcggcgcgc 480
cgcggcgcag gtggccgcgg cgtgcgcgac gcacgggttc ttccaggtgt gcgggcacgg 540
cgtggacgcg gcgctggggc gcgccgcgct ggacggcgcc agcgacttct tccggctgcc 600
gctcgccgag aagcagcgcg cccggcgcgt ccccggcacc gtgtccgggt acacgagcgc 660
gcacgccgac cggttcgcgg ccaagctccc ctggaaggag accctgtcgt tcggctacca 720
cgacggcgcc gcgtcgcctg tcgtcgtgga ctacttcgtc ggcaccctcg gccaggattt 780
cgagccaatg ggtaagtaa ggtagtaaga aggagcgccg gtttacattt accgcacgtc 840
ggcgtgcggt cgagtcggga ctcgggagac gtatgaaccc ccgtcccgtc ccatgcatgt 900
gtggcaggtg ggtgtaccag aggtactgcg aggagatgaa ggagctgtcg ctgacgatca 960
tggagctgct ggagctgagc ctgggcgtgg agctgcgcgg ctactaccgg gagttcttcg 1020
aggacagccg gtccatcatg cggtgcaact actacccgcc gtgcccggag ccggagcgca 1080
cgctgggcac gggcccgcac tgcgacccca cggcgctcac catcctcctg caggacgacg 1140
tgggcgggct ggaggtgctg gtggacggtg agtggcgccc cgtccggccc gtcccgggcg 1200
ccatggtcat caacatcggc gacaccttca tggtaacgaa acgaaagcgc tcgctcctct 1260
gttttccttg gccgctcttg tcctgtgtgt atattcagtt gagctctctc tgtgctgtta 1320
tttcccgaat cctagtggac ctaaacgggc aggttattac agcacgcaca cgtaggcatg 1380
tcatgtagct agtacataca tagcgatgcc gatgcaaatg caatagagac atgcgttcga 1440
gttggttcct atctcggcgg gctacggcag gtacacgcgg ccgcggcgcg ctctctctag 1500
tctatccgcg gccgcgccca ggccgatcga ggcttccggg ggagagttgc gacaagagaa 1560
cggaccgagg gggtcggcta gcggtagcaa gttccctgtt ggtttgtggc gttggagcgt 1620
tgcggagagg cttgcgcggc ggcggggacg tcgacgggga cgtggcgggg agacgatacg 1680
atgggtgccg ggcagggcaa cgctttcggc gggtggccgt gtccaggtgc gcgcggcctt 1740
gtcggtttcc ccctctcggt gtccatggcc gagaaatggg tcgacgaccg agaccgacgc 1800
tcggtgcggc gcccatcccg tctgatccgc cgcgccacgc gagcggccct atgcgatgcc 1860
gcacgggcgc ggagggccgt cgcgcggagt ataatgtata gtatatagta caaggttggt 1920
tggagtcggg ttgggttgga tcgggtcacc ggtacgtggt ggctgctgtt gcccccgccg 1980
tttccgcttg cacttttgtc gcggtttcgc tggcgatccg gcacgcggcg cccacaccac 2040
gccggggctc caaacagctc gggcccttgg ccgtgtgggt ggcaggcact tgcacgcgtc 2100
cggttgtcgc ggcctggccc gccgccgggc gcaccgcaac aatgagacag cccgacacga 2160
tgattcttgt gcactgtgct aacccgcatg ccatgcaggc gctgtcgaac gggaggtaca 2220
agagctgcct gcaccgcgcg gtggtgaacc agcggcgggc gcggcggtcg ctggccttct 2280
tcctgtgccc gcgcgaggac cgggtggtgc gcccgccggc cagtgctgcg ccgcggcgct 2340
acccggactt cacctgggcc gacctcatgc gcttcacgca gcgccactac cgcgccgaca 2400
cccgcacgct ggacgccttc acccgctggc tctcccacgg cccggcccag gcggcggcgc 2460
ctccctgcac ctag 2474

<210> SEQ ID NO 259
<211> LENGTH: 2470
<212> TYPE: DNA
<213> ORGANISM: Artificial Sequence
<220> FEATURE:
<223> OTHER INFORMATION: mutant sequence by gene editing

<400> SEQUENCE: 259
atgaggccgc gcctccctcc aaatgttccc tccctgcctt cgtctttgtc gttgctcgca 60
aactccctgt cctcccctgt tacaaatacc cccacccggg acagcttccc tgcatacttg 120
cagctcgcac atctcatggt gtcgcaggaa cgacaagagc cagctgtgcc tagcagcagc 180
agcagcagcg ccaagcgcgc agccacgtcc atggacgcca gcccggcccc gccgctcctc 240
ctccgcgccc ccactcccag ccccagcatt gacctccccg ctggcaagga caaggccgac 300
gcggcggcca gcaaggccgg cgcggccgtg ttcgacctgc gccgggagcc caagatcccc 360
gcgccattcc tgtggccgca ggaagaggcg cggccgtcct cggccgcgga gctggaggtg 420
ccgatggtgg acgtgggcgt gctgcgcaat ggcgaccgcg cggggctgcg gcgcgccgcg 480
gcgcaggtgg ccgcggcgtg cgcgacgcac gggttcttcc aggtgtgcgg gcacggcgtg 540
gacgcggcgc tggggcgcgc cgcgctggac ggcgccagcg acttcttccg gctgccgctc 600
gccgagaagc agcgcgcccg gcgcgtcccc ggcaccgtgt ccgggtacac gagcgcgcac 660
gccgaccggt tcgcggccaa gctcccctgg aaggagaccc tgtcgttcgg ctaccacgac 720
ggcgccgcgt cgcctgtcgt cgtggactac ttcgtcggca ccctcggcca ggatttcgag 780
ccaatggggt aagtaaggta gtaagaagga gcgccggttt acatttaccg cacgtcggcg 840
tgcggtcgag tcgggactcg ggagacgtat gaaccccccgt cccgtcccat gcatgtgtgg 900
caggtgggtg taccagaggt actgcgagga gatgaaggag ctgtcgctga cgatcatgga 960
gctgctggag ctgagcctgg gcgtggagct gcgcggctac taccgggagt tcttcgagga 1020
cagccggtcc atcatgcggt gcaactacta cccgccgtgc ccggagccgg agcgcacgct 1080
gggcacgggc ccgcactgcg accccacggc gctcaccatc ctcctgcagg acgacgtggg 1140
cgggctggag gtgctggtgg acggtgagtg gcgccccgtc cggcccgtcc cgggcgccat 1200
ggtcatcaac atcggcgaca ccttcatggt aacgaaacga aagcgctcgc tcctctgttt 1260
tccttggccg ctcttgtcct gtgtgtatat tcagttgagc tctctctgtg ctgttatttc 1320
ccgaatccta gtggacctaa acgggcaggt tattacagca cgcacacgta ggcatgtcat 1380
gtagctagta catacatagc gatgccgatg caaatgcaat agagacatgc gttcgagttg 1440
gttcctatct cggcgggcta cggcaggtac acgcggccgc ggcgcgctct ctctagtcta 1500
tccgcggccg cgcccaggcc gatcgaggct tccgggggag agttgcgaca agagaacgga 1560
ccgagggggt cggctagcgg tagcaagttc cctgttggtt tgtggcgttg gagcgttgcg 1620
gagaggcttg cgcggcggcg gggacgtcga cggggacgtg gcggggagac gatacgatgg 1680
gtgccgggca gggcaacgct ttcggcgggt ggccgtgtcc aggtgcgcgc ggccttgtcg 1740 gtttcccccct ctcggtgtcc atggccgaga aatgggtcga cgaccgagac cgacgctcgg 1800
tgcggcgccc atcccgtctg atccgccgcg ccacgcgagc ggccctatgc gatgccgcac 1860
gggcgcggag ggccgtcgcg cggagtataa tgtatagtat atagtacaag gttggttgga 1920
gtcgggttgg gttggatcgg gtcaccggta cgtggtggct gctgttgccc ccgccgtttc 1980
cgcttgcact tttgtcgcgg tttcgctggc gatccggcac gcggcgccca caccacgccg 2040
gggctccaaa cagctcgggc ccttggccgt gtgggtggca ggcacttgca cgcgtccggt 2100
tgtcgcggcc tggcccgccg ccgggcgcac cgcaacaatg agacagcccg acacgatgat 2160
tcttgtgcac tgtgctaacc cgcatgccat gcaggcgctg tcgaacggga ggtacaagag 2220
ctgcctgcac cgcgcggtgg tgaaccagcg gcgggcgcgg cggtcgctgg ccttcttcct 2280
gtgcccgcgc gaggaccggg tggtgcgccc gccggccagt gctgcgccgc ggcgctaccc 2340
ggacttcacc tgggccgacc tcatgcgctt cacgcagcgc cactaccgcg ccgacacccg 2400
cacgctggac gccttcaccc gctggctctc ccacggcccg gcccaggcgg cggcgcctcc 2460
ctgcacctag 2470

<210> SEQ ID NO 260
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 260
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc cacgctggca aggacaaggc 300
cgacgcggcg gccagcaagg ccggcgcggc cgtgttcgac ctgcgccggg agcccaagat 360
ccccgcgcca ttcctgtggc cgcaggaaga ggcgcggccg tcctcggccg cggagctgga 420
ggtgccgatg gtggacgtgg gcgtgctgcg caatggcgac cgcgcggggc tgcggcgcgc 480
cgcggcgcag gtggccgcgg cgtgcgcgac gcacgggttc ttccaggtgt gcgggcacgg 540
cgtggacgcg gcgctggggc gcgccgcgct ggacggcgcc agcgacttct tccggctgcc 600
gctcgccgag aagcagcgcg cccggcgcgt ccccggcacc gtgtccgggt acacgagcgc 660
gcacgccgac cggttcgcgg ccaagctccc ctggaaggag accctgtcgt tcggctacca 720
cgacggcgcc gcgtcgcctg tcgtcgtgga ctacttcgtc ggcaccctcg gccaggattt 780
cgagccaatg gggtaagtaa ggtagtaaga aggagcgccg gtttacattt accgcacgtc 840
ggcgtgcggt cgagtcggga ctcgggagac gtatgaaccc ccgtcccgtc ccatgcatgt 900
gtggcaggtg ggtgtaccag aggtactgcg aggagatgaa ggagctgtcg ctgacgatca 960
tggagctgct ggagctgagc ctgggcgtgg agctgcgcgg ctactaccgg gagttcttcg 1020
aggacagccg gtccatcatg cggtgcaact actacccgcc gtgcccggag ccggagcgca 1080
cgctgggcac gggcccgcac tgcgacccca cggcgctcac catcctcctg caggacgacg 1140
tgggcgggct ggaggtgctg gtggacggtg agtggcgccc cgtccggccc gtcccgggcg 1200
ccatggtcat caacatcggc gacaccttca tggtaacgaa acgaaagcgc tcgctcctct 1260
gttttccttg gccgctcttg tcctgtgtgt atattcagtt gagctctctc tgtgctgtta 1320
tttcccgaat cctagtggac ctaaacgggc aggttattac agcacgcaca cgtaggcatg 1380
tcatgtagct agtacataca tagcgatgcc gatgcaaatg caatagagac atgcgttcga 1440
gttggttcct atctcggcgg gctacggcag gtacacgcgg ccgcggcgcg ctctctctag 1500
tctatccgcg gccgcgccca ggccgatcga ggcttccggg ggagagttgc gacaagagaa 1560
cggaccgagg gggtcggcta gcggtagcaa gttccctgtt ggtttgtggc gttggagcgt 1620
tgcggagagg cttgcgcggc ggcggggacg tcgacgggga cgtggcgggg agacgatacg 1680
atgggtgccg ggcagggcaa cgctttcggc gggtggccgt gtccaggtgc gcgcggcctt 1740
gtcggtttcc ccctctcggt gtccatggcc gagaaatggg tcgacgaccg agaccgacgc 1800
tcggtgcggc gcccatcccg tctgatccgc cgcgccacgc gagcggccct atgcgatgcc 1860
gcacgggcgc ggagggccgt cgcgcggagt ataatgtata gtatatagta caaggttggt 1920
tggagtcggg ttgggttgga tcgggtcacc ggtacgtggt ggctgctgtt gcccccgccg 1980
tttccgcttg cacttttgtc gcggtttcgc tggcgatccg gcacgcggcg cccacaccac 2040
gccggggctc caaacagctc gggcccttgg ccgtgtgggt ggcaggcact tgcacgcgtc 2100
cggttgtcgc ggcctggccc gccgccgggc gcaccgcaac aatgagacag cccgacacga 2160
tgattcttgt gcactgtgct aacccgcatg ccatgcaggc gctgtcgaac gggaggtaca 2220
agagctgcct gcaccgcgcg gtggtgaacc agcggcgggc gcggcggtcg ctggccttct 2280
tcctgtgccc gcgcgaggac cgggtggtgc gcccgccggc cagtgctgcg ccgcggcgct 2340
acccggactt cacctgggcc gacctcatgc gcttcacgca gcgccactac cgcgccgaca 2400
cccgcacgct ggacgccttc acccgctggc tctcccacgg cccggcccag gcggcggcgc 2460
ctccctgcac ctag 2474

<210> SEQ ID NO 261
<211> LENGTH: 2474
<212> TYPE: DNA
<213> ORGANISM: Artificial Sequence
<220> FEATURE:
<223> OTHER INFORMATION: mutant sequence by gene editing

<400> SEQUENCE: 261
atgaggccgc gcctccctcc aaatgttccc tccctgcctt cgtctttgtc gttgctcgca 60
aactccctgt cctcccctgt tacaaatacc cccacccgcc cggacagctt ccctgcatac 120
ttgcagctcg cacatctcat ggtgtcgcag gaacgacaag agccagctgt gcctagcagc 180
agcagcagca gcgccaagcg cgcagccacg tccatggacg ccagcccggc cccgccgctc 240
ctcctccgcg cccccactcc cagccccagc attgacctcc cccgctggca aggacaaggc 300
cgacgcggcg gccagcaagg ccggcgcggc cgtgttcgac ctgcgccggg agcccaagat 360
ccccgcgcca ttcctgtggc cgcaggaaga ggcgcggccg tcctcggccg cggagctgga 420
ggtgccgatg gtggacgtgg gcgtgctgcg caatggcgac cgcgcggggc tgcggcgcgc 480
cgcggcgcag gtggccgcgg cgtgcgcgac gcacgggttc ttccaggtgt gcgggcacgg 540
cgtggacgcg gcgctggggc gcgccgcgct ggacggcgcc agcgacttct tccggctgcc 600
gctcgccgag aagcagcgcg cccggcgcgt ccccggcacc gtgtccgggt acacgagcgc 660
gcacgccgac cggttcgcgg ccaagctccc ctggaaggag accctgtcgt tcggctacca 720
cgacggcgcc gcgtcgcctg tcgtcgtgga ctacttcgtc ggcaccctcg gccaggattt 780

```
cgagccaatg gggtaagtaa ggtagtaaga aggagcgccg gtttacattt accgcacgtc    840
ggcgtgcggt cgagtcggga ctcgggagac gtatgaaccc ccgtcccgtc ccatgcatgt    900
gtggcaggtg ggtgtaccag aggtactgcg aggagatgaa ggagctgtcg ctgacgatca    960
tggagctgct ggagctgagc ctgggcgtgg agctgcgcgg ctactaccgg gagttcttcg   1020
aggacagccg gtccatcatg cggtgcaact actacccgcc gtgcccggag ccggagcgca   1080
cgctgggcac gggcccgcac tgcgacccca cggcgctcac catcctcctg caggacgacg   1140
tgggcgggct ggaggtgctg gtggacggtg agtggcgccc cgtccggccc gtcccgggcg   1200
ccatggtcat caacatcggc gacaccttca tggtaacgaa acgaaagcgc tcgctcctct   1260
gttttccttg gccgctcttg tcctgtgtgt atattcagtt gagctctctc tgtgctgtta   1320
tttcccgaat cctagtggac ctaaacgggc aggttattac agcacgcaca cgtaggcatg   1380
tcatgtagct agtacataca tagcgatgcc gatgcaaatg caatagagac atgcgttcga   1440
gttggttcct atctcggcgg gctacggcag gtacacgcgg ccgcggcgcg ctctctctag   1500
tctatccgcg gccgcgccca ggccgatcga ggcttccggg ggagagttgc gacaagagaa   1560
cggaccgagg gggtcggcta gcggtagcaa gttccctgtt ggtttgtggc gttggagcgt   1620
tgcggagagg cttgcgcggc ggcggggacg tcgacgggga cgtggcgggg agacgatacg   1680
atgggtgccg ggcagggcaa cgctttcggc gggtggccgt gtccaggtgc gcgcggcctt   1740
gtcggtttcc ccctctcggt gtccatggcc gagaaatggg tcgacgaccg agaccgacgc   1800
tcggtgcggc gcccatcccg tctgatccgc cgcgccacgc gagcggccct atgcgatgcc   1860
gcacgggcgc ggagggccgt cgcgcggagt ataatgtata gtatatagta caaggttggt   1920
tggagtcggg ttgggttgga tcgggtcacc ggtacgtggt ggctgctgtt gcccccgccg   1980
tttccgcttg cacttttgtc gcggtttcgc tggcgatccg gcacgcggcg cccacaccac   2040
gccggggctc caaacagctc gggcccttgg ccgtgtgggt ggcaggcact tgcacgcgtc   2100
cggttgtcgc ggcctggccc gccgccgggc gcaccgcaac aatgagacag cccgacacga   2160
tgattcttgt gcactgtgct aacccgcatg ccatgcaggc gctgtcgaac gggaggtaca   2220
agagctgcct gcaccgcgcg gtggtgaacc agcggcgggc gcggcggtcg ctggccttct   2280
tcctgtgccc gcgcgaggac cgggtggtgc gcccgccggc cagtgctgcg ccgcggcgct   2340
acccggactt cacctgggcc gacctcatgc gcttcacgca gcgccactac cgcgccgaca   2400
cccgcacgct ggacgccttc acccgctggc tctcccacgg cccggcccag gcggcggcgc   2460
ctccctgcac ctag                                                      2474
```

METHODS AND COMPOSITIONS FOR INCREASING HARVESTABLE YIELD VIA EDITING GA20 OXIDASE GENES TO GENERATE SHORT STATURE PLANTS

CROSS-REFERENCE TO RELATED APPLICATIONS

This application is a U.S. National Stage of International Application No. PCT/US2019/018131, filed Feb. 15, 2019, which claims the benefit of U.S. Provisional Application No. 62/631,412, filed Feb. 15, 2018, and U.S. Provisional Application No. 62/710,302, filed Feb. 16, 2018, all of which are incorporated by reference in their entireties herein.

SUBMISSION OF SEQUENCE LISTING ON ASCII TEXT

The content of the following submission on ASCII text file is incorporated herein by reference in its entirety: a computer readable form (CRF) of the Sequence Listing (file name: 777052058630SUBSEQLIST.TXT, date recorded: Jul. 10, 2023, size: 392,290 bytes).

BACKGROUND

The present disclosure relates to compositions and methods for improving traits, such as lodging resistance and increased yield in corn.

Gibberellins (gibberellic acids or GAs) are plant hormones that regulate a number of major plant growth and developmental processes. Manipulation of GA levels in semi-dwarf wheat, rice and sorghum plant varieties led to increased yield and reduced lodging in these cereal crops during the 20$^{th}$ century, which was largely responsible for the Green Revolution. However, successful yield gains in other cereal crops, such as corn, have not been realized through manipulation of the GA pathway. Indeed, some mutations in the GA pathway genes have been associated with various off-types in corn that are incompatible with yield, which has led researchers away from finding semi-dwarf, high-yielding corn varieties via manipulation of the GA pathway.

There continues to be a need in the art for the development of monocot or cereal crop plants, such as corn, having increased yield and/or resistance to lodging.

SUMMARY

In an aspect, the present disclosure provides a modified corn plant having a reduced plant height relative to a wild type control plant, and (i) an increased stem or stalk diameter relative to a wild type control plant, (ii) improved lodging resistance relative to a wild type control plant, or (iii) improved drought tolerance relative to a wild type control plant.

In another aspect, the present disclosure provides a modified corn plant, or plant part thereof, comprising a homozygous mutant GA20 oxidase_3 gene and a homozygous mutant GA20 oxidase_5 gene.

In another aspect, the present disclosure provides a modified corn plant, or plant part thereof, comprising homozygous mutant alleles at an endogenous GA20 oxidase_3 locus and homozygous mutant alleles at an endogenous GA20 oxidase_5 locus.

In an aspect, the present disclosure provides a method of making a modified corn plant, or plant part thereof, comprising: (a) crossing a first corn plant comprising a mutant allele of the GA20 oxidase_3 locus with a second plant comprising a mutant allele of the GA20 oxidase_5 locus; and (b) selecting a progeny corn plant, or plant part thereof, from the cross in step (a) that is homozygous for one or more mutant alleles of the GA20 oxidase_3 locus and homozygous for one or more mutant alleles of the GA20 oxidase 5 locus.

In another aspect, the present disclosure provides a method of making a modified corn plant, or plant part thereof, comprising: (a) crossing a first corn plant comprising a mutant allele of the GA20 oxidase_3 locus and a mutant allele of the GA20 oxidase_5 locus with a second plant; and (b) selecting a progeny corn plant, or plant part thereof, from the cross in step (a) that is homozygous for one or more mutant alleles of the GA20 oxidase_3 locus and homozygous for one or more mutant alleles of the GA20 oxidase 5 locus.

BRIEF DESCRIPTION OF THE DRAWINGS

FIG. 1 shows plant heights of inbred mutant plants having edited mutant GA20 oxidase_3 and/or GA20 oxidase_5 genes in comparison to inbred wild-type control plants and plants expressing a GA20 oxidase suppression construct.

DETAILED DESCRIPTION

To facilitate understanding of the disclosure, several terms and abbreviations as used herein are defined below as follows:

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

The term "about" as used herein, is intended to qualify the numerical values that it modifies, denoting such a value as variable within a margin of error. When no particular margin of error, such as a standard deviation to a mean value, is recited, the term "about" should be understood to mean that range which would encompass the recited value and the range which would be included by rounding up or down to that figure, taking into account significant figures.

As used herein, "locus" is a chromosomal locus or region where a polymorphic nucleic acid, trait determinant, gene, or marker is located. A "locus" can be shared by two homologous chromosomes to refer to their corresponding locus or region. As used herein, "allele" refers to an alternative nucleic acid sequence of a gene or at a particular locus (e.g., a nucleic acid sequence of a gene or locus that is different than other alleles for the same gene or locus). Such an allele can be considered (i) wild-type or (ii) mutant if one or more mutations or edits are present in the nucleic acid sequence of the mutant allele relative to the wild-type allele. A mutant allele for a gene may have a reduced or eliminated activity or expression level for the gene relative to the wild-type allele. For diploid organisms such as corn, a first allele can occur on one chromosome, and a second allele can occur at the same locus on a second homologous chromosome. If one allele at a locus on one chromosome of a plant is a mutant allele and the other corresponding allele on the homologous chromosome of the plant is wild-type, then the plant is described as being heterozygous for the mutant allele. However, if both alleles at a locus are mutant alleles, then the plant is described as being homozygous for the mutant alleles. A plant homozygous for mutant alleles at a locus may comprise the same mutant allele or different mutant alleles if heteroallelic or biallelic.

As used herein, a “wild-type gene” or “wild-type allele” refers to a gene or allele having a sequence or genotype that is most common in a particular plant species, or another sequence or genotype with natural variations, polymorphisms, or other silent mutations relative to the most common sequence or genotype that do not significantly impact the expression and activity of the gene or allele. Indeed, a “wild-type” gene or allele contains no variation, polymorphism, or any other type of mutation that substantially affects the normal function, activity, expression, or phenotypic consequence of the gene or allele.

The terms “percent identity” or “percent identical” as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. For purposes of calculating “percent identity” between DNA and RNA sequences, a uracil (U) of a RNA sequence is considered identical to a thymine (T) of a DNA sequence. If the window of comparison is defined as a region of alignment between two or more sequences (i.e., excluding nucleotides at the 5' and 3' ends of aligned polynucleotide sequences, or amino acids at the N-terminus and C-terminus of aligned protein sequences, that are not identical between the compared sequences), then the “percent identity” may also be referred to as a “percent alignment identity”. If the “percent identity” is being calculated in relation to a reference sequence without a particular comparison window being specified, then the percent identity is determined by dividing the number of matched positions over the region of alignment by the total length of the reference sequence. Accordingly, for purposes of the present disclosure, when two sequences (query and subject) are optimally aligned (with allowance for gaps in their alignment), the “percent identity” for the query sequence is equal to the number of identical positions between the two sequences divided by the total number of positions in the query sequence over its length (or a comparison window), which is then multiplied by 100%.

It is recognized that residue positions of proteins that are not identical often differ by conservative amino acid substitutions, where amino acid residues are substituted for other amino acid residues with similar size and chemical properties (e.g., charge, hydrophobicity, polarity, etc.), and therefore may not change the functional properties of the molecule. When sequences differ in conservative substitutions, the percent sequence similarity may be adjusted upwards to correct for the conservative nature of the non-identical substitution(s). Sequences that differ by such conservative substitutions are said to have “sequence similarity” or “similarity.” Thus, “percent similarity” or “percent similar” as used herein in reference to two or more protein sequences is calculated by (i) comparing two optimally aligned protein sequences over a window of comparison, (ii) determining the number of positions at which the same or similar amino acid residue occurs in both sequences to yield the number of matched positions, (iii) dividing the number of matched positions by the total number of positions in the window of comparison (or the total length of the reference or query protein if a window of comparison is not specified), and then (iv) multiplying this quotient by 100% to yield the percent similarity. Conservative amino acid substitutions for proteins are known in the art.

For optimal alignment of sequences to calculate their percent identity or similarity, various pair-wise or multiple sequence alignment algorithms and programs are known in the art, such as ClustalW, or Basic Local Alignment Search Tool® (BLAST®), etc., that may be used to compare the sequence identity or similarity between two or more nucleotide or protein sequences. Although other alignment and comparison methods are known in the art, the alignment between two sequences (including the percent identity ranges described above) may be as determined by the ClustalW or BLAST® algorithm, see, e.g., Chenna R. et al., “Multiple sequence alignment with the Clustal series of programs,” *Nucleic Acids Research* 31: 3497-3500 (2003); Thompson J D et al., “Clustal W: Improving the sensitivity of progressive multiple sequence alignment through sequence weighting, position-specific gap penalties and weight matrix choice,” *Nucleic Acids Research* 22: 4673-4680 (1994); and Larkin M A et al., “Clustal W and Clustal X version 2.0,” *Bioinformatics* 23: 2947-48 (2007); and Altschul, S. F., Gish, W., Miller, W., Myers, E. W. & Lipman, D. J. (1990) “Basic local alignment search tool.” *J. Mol. Biol.* 215:403-410 (1990), the entire contents and disclosures of which are incorporated herein by reference.

The terms “percent complementarity” or “percent complementary”, as used herein in reference to two nucleotide sequences, is similar to the concept of percent identity but refers to the percentage of nucleotides of a query sequence that optimally base-pair or hybridize to nucleotides of a subject sequence when the query and subject sequences are linearly arranged and optimally base paired without secondary folding structures, such as loops, stems or hairpins. Such a percent complementarity may be between two DNA strands, two RNA strands, or a DNA strand and a RNA strand. The “percent complementarity” is calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences may be determined based on the known pairings of nucleotide bases, such as G-C, A-T, and A-U, through hydrogen bonding. If the “percent complementarity” is being calculated in relation to a reference sequence without specifying a particular comparison window, then the percent identity is determined by dividing the number of complementary positions between the two linear sequences by the total length of the reference sequence. Thus, for purposes of the present disclosure, when two sequences (query and subject) are optimally base-paired (with allowance for mismatches or non-base-paired nucleotides but without folding or secondary structures), the “percent complementarity” for the query sequence is equal to the number of base-paired positions between the two sequences divided by the total number of positions in the query sequence over its length (or by the number of positions in the query sequence over a comparison window), which is then multiplied by 100%.

As used herein, "modified" in the context of a plant, plant seed, plant part, plant cell, and/or plant genome, refers to a plant, plant seed, plant part, plant cell, and/or plant genome comprising an engineered change in the expression level and/or coding sequence of one or more GA oxidase gene(s) relative to a wild-type or control plant, plant seed, plant part, plant cell, and/or plant genome, such as via a genome editing event or mutation affecting (e.g., reducing or eliminating) the expression level or activity of one or more endogenous GA3 and/or GA20 oxidase genes. Indeed, the term "modified" may further refer to a plant, plant seed, plant part, plant cell, and/or plant genome having one or more mutations affecting expression of one or more endogenous GA oxidase genes, such as one or more endogenous GA3 and/or GA20 oxidase genes, introduced through chemical mutagenesis, transposon insertion or excision, or any other known mutagenesis technique, or introduced through genome editing. For clarity, therefore, a modified plant, plant seed, plant part, plant cell, and/or plant genome includes a mutated and/or edited plant, plant seed, plant part, plant cell, and/or plant genome having a modified expression level, expression pattern, and/or coding sequence of one or more GA oxidase gene(s) relative to a wild-type or control plant, plant seed, plant part, plant cell, and/or plant genome. Modified plants may be homozygous or heterozygous for any given mutation or edit, and/or may be bi-allelic at a GA oxidase gene locus. A modified plant is bi-allelic for a GA oxidase gene if each copy of the GA oxidase gene is modified by a different allele (i.e., different mutation(s) and/or edit(s)), wherein each allele lowers the expression level and/or activity of the GA oxidase gene. Modified plants or seeds may contain various molecular changes that affect expression of GA oxidase gene(s), such as GA3 and/or GA20 oxidase gene(s), including genetic and/or epigenetic modifications. Modified plants, plant parts, seeds, etc., may have been subjected to mutagenesis, genome editing or site-directed integration (e.g., without being limiting, via methods using site-specific nucleases), genetic transformation (e.g., without being limiting, via methods of *Agrobacterium* transformation or microprojectile bombardment), or a combination thereof. Such "modified" plants, plant seeds, plant parts, and plant cells include plants, plant seeds, plant parts, and plant cells that are offspring or derived from "modified" plants, plant seeds, plant parts, and plant cells that retain the molecular change (e.g., change in expression level and/or activity) to the one or more GA oxidase genes. A modified seed provided herein may give rise to a modified plant provided herein. A modified plant, plant seed, plant part, plant cell, or plant genome provided herein may comprise a recombinant DNA construct or vector or genome edit as provided herein. A "modified plant product" may be any product made from a modified plant, plant part, plant cell, or plant chromosome provided herein, or any portion or component thereof.

As used herein, the term "homozygous" refers to a genotype comprising two identical alleles at a given locus in a diploid genome, or a genotype comprising two non-identical mutant alleles at a given locus in a diploid genome. The latter genotype comprising two non-identical mutant alleles is also referred to as being heteroallelic or transheterozygous, or as a heteroallelic combination. As used herein, "heterozygous" describes a genotype comprising a mutant allele and a wild-type allele at a given locus in a diploid genome.

As used herein, the term "control plant" (or likewise a "control" plant seed, plant part, plant cell and/or plant genome) refers to a plant (or plant seed, plant part, plant cell and/or plant genome) that is used for comparison to a modified plant (or modified plant seed, plant part, plant cell and/or plant genome) and has the same or similar genetic background (e.g., same parental lines, hybrid cross, inbred line, testers, etc.) as the modified plant (or plant seed, plant part, plant cell and/or plant genome), except for a genome editing event(s) affecting one or more GA oxidase genes. For example, a control plant may be an inbred line that is the same as the inbred line used to make the modified plant, or a control plant may be the product of the same hybrid cross of inbred parental lines as the modified plant, except for the absence in the control plant of any genome editing event(s) affecting one or more GA oxidase genes. Similarly, an unmodified control plant refers to a plant that shares a substantially similar or essentially identical genetic background as a modified plant, but without the one or more engineered changes to the genome (e.g., transgene, mutation or edit) of the modified plant. For purposes of comparison to a modified plant, plant seed, plant part, plant cell and/or plant genome, a "wild-type plant" (or likewise a "wild-type" plant seed, plant part, plant cell and/or plant genome) refers to a non-transgenic and non-genome edited control plant, plant seed, plant part, plant cell and/or plant genome. As used herein, a "control" plant, plant seed, plant part, plant cell and/or plant genome may also be a plant, plant seed, plant part, plant cell and/or plant genome having a similar (but not the same or identical) genetic background to a modified plant, plant seed, plant part, plant cell and/or plant genome, if deemed sufficiently similar for comparison of the characteristics or traits to be analyzed.

As used herein, a "target site" for genome editing refers to the location of a polynucleotide sequence within a plant genome that is bound and cleaved by a site-specific nuclease introducing a double stranded break (or single-stranded nick) into the nucleic acid backbone of the polynucleotide sequence and/or its complementary DNA strand. A target site may comprise at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. A "target site" for a RNA-guided nuclease may comprise the sequence of either complementary strand of a double-stranded nucleic acid (DNA) molecule or chromosome at the target site. A site-specific nuclease may bind to a target site, such as via a non-coding guide RNA (e.g., without being limiting, a CRISPR RNA (crRNA) or a single-guide RNA (sgRNA) as described further below). A non-coding guide RNA provided herein may be complementary to a target site (e.g., complementary to either strand of a double-stranded nucleic acid molecule or chromosome at the target site). It will be appreciated that perfect identity or complementarity may not be required for a non-coding guide RNA to bind or hybridize to a target site. For example, at least 1, at least 2, at least 3, at least 4, at least 5, at least 6, at least 7, or at least 8 mismatches (or more) between a target site and a non-coding RNA may be tolerated. A "target site" also refers to the location of a polynucleotide sequence within a plant genome that is bound and cleaved by another site-specific nuclease that may not be guided by a non-coding RNA molecule, such as a meganuclease, zinc finger nuclease (ZFN), or a transcription activator-like effector nuclease (TALEN), to introduce a double stranded break (or single-stranded nick) into the polynucleotide sequence and/or its complementary DNA strand. As used herein, a "target region" or a "targeted region" refers to a polynucleotide sequence or region that is flanked by two or more target sites. Without being limiting, in some embodiments a target region may be subjected to a mutation, deletion, insertion or inversion. As used herein, "flanked" when used to describe a target region of a polynucleotide sequence or molecule, refers to two or more target sites of the polynucleotide sequence or molecule surrounding the target region, with one target site on each side of the target region. Apart from genome editing, the term "target site" may also be used in the context of gene suppression to refer to a portion of a mRNA molecule (e.g., a "recognition site") that is complementary to at least a portion of a non-coding RNA molecule (e.g., a miRNA, siRNA, etc.) encoded by a suppression construct.

The co-pending PCT Application No. PCT/US2017/047405 and U.S. application Ser. No. 15/679,699, both filed on Aug. 17, 2017, are incorporated herein by reference in their entirety.

Most grain producing grasses, such as wheat, rice and sorghum, produce both male and female structures within each floret of the panicle (i.e., they have a single reproductive structure). However, corn or maize is unique among the grain-producing grasses in that it forms separate male (tassel) and female (ear) inflorescences. Corn produces completely sexually dimorphic reproductive structures by selective abortion of male organs (anthers) in florets of the ear, and female organs (ovules) in the florets of the tassel within early stages of development. Precisely regulated gibberellin synthesis and signaling is critical to regulation of this selective abortion process, with the female reproductive ear being most sensitive to disruptions in the GA pathway. Indeed, the "anther ear" phenotype is the most common reproductive phenotype in GA corn mutants.

In contrast to corn, mutations in the gibberellin synthesis or signaling pathways that led to the "Green Revolution" in wheat, rice and sorghum had little impact on their reproductive structures because these crop species do not undergo the selective abortion process of the grain bearing panicle during development, and thus are not sensitive to disruptions in GA levels. The same mutations have not been utilized in corn because disruption of the GA synthesis and signaling pathway has repeatedly led to dramatic distortion and masculinization of the ear ("anther ear") and sterility (disrupted anther and microspore development) in the tassel, in addition to extreme dwarfing in some cases. See, e.g., Chen, Y. et al., "The Maize DWARF1 Encodes a Gibberellin 3-Oxidase and Is Dual Localized to the Nucleus and Cytosol," *Plant Physiology* 166: 2028-2039 (2014). These GA mutant phenotypes (off-types) in corn led to significant reductions in kernel production and a reduction in yield. Furthermore, production of anthers within the ear increases the likelihood of fungal or insect infections, which reduces the quality of the grain that is produced on those mutant ears. Forward breeding to develop semi-dwarf lines of corn has not been successful, and the reproductive off-types (as well as the extreme dwarfing) of GA mutants have been challenging to overcome. Thus, the same mutations in the GA pathway that led to the Green Revolution in other grasses have not yet been successful in corn.

Despite these prior difficulties in achieving higher grain yields in corn through manipulation of the GA pathway, the present inventors have discovered a way to manipulate GA levels in corn plants in a manner that reduces overall plant height and stem internode length and increases resistance to lodging, but does not cause the reproductive off-types previously associated with mutations of the GA pathway in corn. Further evidence indicates that these short stature or semi-dwarf corn plants may also have one or more additional traits, including increased stem diameter, reduced green snap, deeper roots, increased leaf area, earlier canopy closure, higher stomatal conductance, lower ear height, increased foliar water content, improved drought tolerance, increased nitrogen use efficiency, increased water use efficiency, reduced anthocyanin content and area in leaves under normal or nitrogen or water limiting stress conditions, increased ear weight, increased kernel number, increased kernel weight, increased yield, and/or increased harvest index.

According to embodiments of the present disclosure, modified corn plants are provided that have at least one beneficial agronomic trait and at least one female reproductive organ or ear that is substantially or completely free of off-types. The beneficial agronomic trait may include, for example, shorter plant height, shorter internode length in one or more internode(s), larger (thicker) stem or stalk diameter, increased lodging resistance, improved drought tolerance, increased nitrogen use efficiency, increased water use efficiency, deeper roots, larger leaf area, earlier canopy closure, and/or increased harvestable yield. Off-types may include male (tassel or anther) sterility, reduced kernel or seed number, and/or the presence of one or more masculinized or male (or male-like) reproductive structures in the female organ or ear (e.g., anther ear) of the plant. A modified corn plant is provided herein that lacks significant off-types in the reproductive tissues of the plant. Such a modified corn plant may have a female reproductive organ or ear that appears normal relative to a control or wild-type plant. Indeed, modified corn plants are provided that comprise at least one reproductive organ or ear that does not have or exhibit, or is substantially or completely free of, off-types including male sterility, reduced kernel or seed number, and/or masculinized structure(s) in one or more female organs or ears. As used herein, a female organ or ear of a plant, such as corn, is "substantially free" of male reproductive structures if male reproductive structures are absent or nearly absent in the female organ or ear of the plant based on visual inspection of the female organ or ear at later reproductive stages. A female organ or ear of a plant, such as corn, is "completely free" of mature male reproductive structures if male reproductive structures are absent or not observed or observable in the female organ or ear of the plant, such as a corn plant, by visual inspection of the female organ or ear at later reproductive stages. A female organ or ear of a plant, such as corn, without significant off-types and substantially free of male reproductive structures in the ear may have a number of kernels or seeds per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the number of kernels or seeds per female organ or ear of a wild-type or control plant. Likewise, a female organ or ear of a plant, such as corn, without significant off-types and substantially free of male reproductive structures in the ear may have an average kernel or seed weight per female organ or ear of the plant that is at least 90%, at least 95%, at least 96%, at least 97%, at least 98%, at least 99%, at least 99.5%, at least 99.6%, at least 99.7%, at least 99.8%, or at least 99.9% of the average kernel or seed weight per female organ or ear of a wild-type or control plant. A female organ or ear of a plant, such as corn, that is completely free of mature male reproductive structures may have a number of kernels or seeds per female organ or ear of the plant that is about the same as a wild-type or control plant. In other words, the reproductive development of the female organ or ear of the plant may be normal or substantially normal. However, the number of seeds or kernels per female organ or ear may depend on other factors that affect resource utilization and development of the plant. Indeed, the number of kernels or seeds per female organ or ear of the plant, and/or the kernel or seed weight per female organ or ear of the plant, may be about the same or greater than a wild-type or control plant.

The plant hormone gibberellin plays an important role in a number of plant developmental processes including germination, cell elongation, flowering, embryogenesis and seed development. Certain biosynthetic enzymes (e.g., GA20 oxidase and GA3 oxidase) and catabolic enzymes (e.g., GA2 oxidase) in the GA pathway are critical to affecting active GA levels in plant tissues.

Several of the GA oxidases in cereal plants consist of a family of related GA oxidase genes. For example, corn has a family of at least nine GA20 oxidase genes that includes GA20 oxidase 1, GA20 oxidase 2, GA20 oxidase 3, GA20 oxidase 4, GA20 oxidase 5, GA20 oxidase_6, GA20 oxidase_7, GA20 oxidase_8, and GA20 oxidase_9. However, there are only two GA3 oxidases in corn, GA3_oxidase_1 and GA3 oxidase_2. The DNA and protein sequences by SEQ ID NOs for each of these GA20 oxidase genes are provided in Table 1.

TABLE 1

DNA and protein sequences by sequence identifier for GA20 oxidase genes in corn.

| GA20 oxidase Gene | cDNA | Coding Sequence (CDS) | Protein |
|---|---|---|---|
| GA20 oxidase_1 | SEQ ID NO: 1 | SEQ ID NO: 2 | SEQ ID NO: 3 |
| GA20 oxidase_2 | SEQ ID NO: 4 | SEQ ID NO: 5 | SEQ ID NO: 6 |
| GA20 oxidase_3 | SEQ ID NO: 7 | SEQ ID NO: 8 | SEQ ID NO: 9 |
| GA20 oxidase_4 | SEQ ID NO: 10 | SEQ ID NO: 11 | SEQ ID NO: 12 |
| GA20 oxidase_5 | SEQ ID NO: 13 | SEQ ID NO: 14 | SEQ ID NO: 15 |
| GA20 oxidase_6 | SEQ ID NO: 16 | SEQ ID NO: 17 | SEQ ID NO: 18 |
| GA20 oxidase_7 | SEQ ID NO: 19 | SEQ ID NO: 20 | SEQ ID NO: 21 |
| GA20 oxidase_8 | SEQ ID NO: 22 | SEQ ID NO: 23 | SEQ ID NO: 24 |
| GA20 oxidase_9 | SEQ ID NO: 25 | SEQ ID NO: 26 | SEQ ID NO: 27 |

The genomic DNA sequence of GA20 oxidase_3 is provided in SEQ ID NO: 34, and the genomic DNA sequence of GA20 oxidase_5 is provided in SEQ ID NO: 35. For the GA20 oxidase_3 gene, SEQ ID NO: 34 provides 3000 nucleotides upstream of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 34 also provides 3000 nucleotides downstream of the end of the 3'-UTR (nucleotides 5801-8800). For the GA20 oxidase_5 gene, SEQ ID NO: 35 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 35 also provides 3000 nucleotides downstream of the end of the 3'-UTR (nucleotides 5860-8859).

A modified plant, plant part, cell, or explant provided herein may be of an elite variety or an elite line. An elite variety or an elite line refers to a variety that has resulted from breeding and selection for superior agronomic performance. A edited plant, cell, or explant provided herein may be a hybrid plant, cell, or explant. As used herein, a "hybrid" is created by crossing two plants from different varieties, lines, inbreds, or species, such that the progeny comprises genetic material from each parent. Skilled artisans recognize that higher order hybrids can be generated as well. For example, a first hybrid can be made by crossing Variety A with Variety B to create a A×B hybrid, and a second hybrid can be made by crossing Variety C with Variety D to create an C×D hybrid. The first and second hybrids can be further crossed to create the higher order hybrid (A×B)×(C×D) comprising genetic information from all four parent varieties.

Targeted mutations in the genome of a plant can be made by introducing a double strand break (DSB) or nick. According to this approach, mutations, such as deletions, insertions, inversions and/or substitutions may be introduced at a target site via imperfect repair of the DSB or nick to produce a knock-out or knock-down of a GA oxidase gene. Such mutations may be generated by imperfect repair of the targeted locus even without the use of a donor template molecule. A "knock-out" of a GA oxidase gene may be achieved by inducing a DSB or nick at or near the endogenous locus of the GA oxidase gene that results in non-expression of the GA oxidase protein or expression of a non-functional protein, whereas a "knock-down" of a GA oxidase gene may be achieved in a similar manner by inducing a DSB or nick at or near the endogenous locus of the GA oxidase gene that is repaired imperfectly at a site that does not affect the coding sequence of the GA oxidase gene in a manner that would eliminate the function of the encoded GA oxidase protein. For example, the site of the DSB or nick within the endogenous locus may be in the upstream or 5' region of the GA oxidase gene (e.g., a promoter and/or enhancer sequence) to affect or reduce its level of expression. Similarly, such targeted knock-out or knock-down mutations of a GA oxidase gene may be generated with a donor template molecule to direct a particular or desired mutation at or near the target site via repair of the DSB or nick. The donor template molecule may comprise a homologous sequence with or without an insertion sequence and comprising one or more mutations, such as one or more deletions, insertions, inversions and/or substitutions, relative to the targeted genomic sequence at or near the site of the DSB or nick. For example, targeted knock-out mutations of a GA oxidase gene may be achieved by deleting or inverting at least a portion of the gene or by introducing a frame shift or premature stop codon into the coding sequence of the gene. A deletion of a portion of a GA oxidase gene may also be introduced by generating DSBs or nicks at two target sites and causing a deletion of the intervening target region flanked by the target sites.

A site-specific nuclease provided herein may be selected from the group consisting of a zinc-finger nuclease (ZFN), a meganuclease, an RNA-guided endonuclease, a TALE-endonuclease (TALEN), a recombinase, a transposase, or any combination thereof. See, e.g., Khandagale, K. et al., "Genome editing for targeted improvement in plants," *Plant Biotechnol Rep* 10: 327-343 (2016); and Gaj, T. et al., "ZFN, TALEN and CRISPR/Cas-based methods for genome engineering," *Trends Biotechnol.* 31(7): 397-405 (2013), the contents and disclosures of which are incorporated herein by reference. A recombinase may be a serine recombinase attached to a DNA recognition motif, a tyrosine recombinase attached to a DNA recognition motif or other recombinase enzyme known in the art. A recombinase or transposase may be a DNA transposase or recombinase attached to a DNA binding domain. A tyrosine recombinase attached to a DNA recognition motif may be selected from the group consisting of a Cre recombinase, a Flp recombinase, and a Tnp1 recombinase. According to some embodiments, a Cre recombinase or a Gin recombinase provided herein is tethered to a zinc-finger DNA binding domain. In another embodiment, a serine recombinase attached to a DNA recognition motif provided herein is selected from the group consisting of a PhiC31 integrase, an R4 integrase, and a TP-901 integrase. In another embodiment, a DNA transposase attached to a DNA binding domain provided herein is selected from the group consisting of a TALE-piggyBac and TALE-Mutator.

According to embodiments of the present disclosure, an RNA-guided endonuclease may be selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, and homologs or modified versions thereof, Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo) and homologs or modified versions thereof. According to some embodiments, an RNA-guided endonuclease may be a Cas9 or Cpf1 enzyme.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1. In another aspect, a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx1 0, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, an RNA-guided nuclease provided herein is selected from the group consisting of a Cas9 or a Cpf1. In another aspect, an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, CasX, CasY, a homolog thereof, or a modified version thereof. In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

For RNA-guided endonucleases, a guide RNA (gRNA) molecule is further provided to direct the endonuclease to a target site in the genome of the plant via base-pairing or hybridization to cause a DSB or nick at or near the target site. The gRNA may be transformed or introduced into a plant cell or tissue (perhaps along with a nuclease, or nuclease-encoding DNA molecule, construct or vector) as a gRNA molecule, or as a recombinant DNA molecule, construct or vector comprising a transcribable DNA sequence encoding the guide RNA operably linked to a plant-expressible promoter. As understood in the art, a "guide RNA" may comprise, for example, a CRISPR RNA (crRNA), a single-chain guide RNA (sgRNA), or any other RNA molecule that may guide or direct an endonuclease to a specific target site in the genome. A "single-chain guide RNA" (or "sgRNA") is a RNA molecule comprising a crRNA covalently linked a tracrRNA by a linker sequence, which may be expressed as a single RNA transcript or molecule. The guide RNA comprises a guide or targeting sequence that is identical or complementary to a target site within the plant genome, such as at or near a GA oxidase gene. A protospacer-adjacent motif (PAM) may be present in the genome immediately adjacent and upstream to the 5' end of the genomic target site sequence complementary to the targeting sequence of the guide RNA—i.e., immediately downstream (3') to the sense (+) strand of the genomic target site (relative to the targeting sequence of the guide RNA) as known in the art. See, e.g., Wu, X. et al., "Target specificity of the CRISPR-Cas9 system," *Quant Biol.* 2(2): 59-70 (2014), the content and disclosure of which is incorporated herein by reference. The genomic PAM sequence on the sense (+) strand adjacent to the target site (relative to the targeting sequence of the guide RNA) may comprise 5'-NGG-3'. However, the corresponding sequence of the guide RNA (i.e., immediately downstream (3') to the targeting sequence of the guide RNA) may generally not be complementary to the genomic PAM sequence. The guide RNA may typically be a non-coding RNA molecule that does not encode a protein. The guide sequence of the guide RNA may be at least 10 nucleotides in length, such as 12-40 nucleotides, 12-30 nucleotides, 12-20 nucleotides, 12-35 nucleotides, 12-30 nucleotides, 15-30 nucleotides, 17-30 nucleotides, or 17-25 nucleotides in length, or about 12, 13, 14, 15, 16, 17, 18, 19, 20, 21, 22, 23, 24, 25 or more nucleotides in length. The guide sequence may be at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of a DNA sequence at the genomic target site.

In an aspect, the GA20 oxidase_3 gene is edited via a genome editing technique. For genome editing at or near the GA20 oxidase_3 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 34 or a sequence complementary thereto (e.g., 12, 13, 14, 15, 16, 17, 18, 19, 20, 21, 22, 23, 24, 25 or more consecutive nucleotides of SEQ ID NO: 34 or a sequence complementary thereto). For genome editing at or near the GA20 oxidase_5 gene with an RNA-guided endonuclease, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides of SEQ ID NO: 35 or a sequence complementary thereto (e.g., 10, 11, 12, 13, 14, 15, 16, 17, 18, 19, 20, 21, 22, 23, 24, 25 or more consecutive nucleotides of SEQ ID NO: 35 or a sequence complementary thereto). As used herein, the term "consecutive" in reference to a polynucleotide or protein sequence means without deletions or gaps in the sequence.

For knockdown (and possibly knockout) mutations through genome editing, an RNA-guided endonuclease may be targeted to an upstream or downstream sequence, such as a promoter and/or enhancer sequence, or an intron, 5'UTR, and/or 3'UTR sequence of a GA20 oxidase_3 or GA20 oxidase_5 gene to mutate one or more promoter and/or regulatory sequences of the gene and affect or reduce its level of expression. For knockdown (and possibly knockout) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3096 of SEQ ID NO: 34, the nucleotide sequence range 3666-3775 of SEQ ID NO: 34, the nucleotide sequence range 4098-5314 of SEQ ID NO: 34, the nucleotide sequence range 5585-5800 of SEQ ID NO: 34, or the nucleotide sequence range 5801-8800 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3096, 3666-3775, 4098-5314, 5585-5800, 5801-8800, or 5585-8800 of SEQ ID NO: 34, or a sequence complementary thereto).

For knockdown (and possibly knockout) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 1-3000 of SEQ ID NO: 35, the nucleotide sequence range 1-3000 of SEQ ID NO: 35, the nucleotide sequence range 3792-3906 of SEQ ID NO: 35, the nucleotide sequence range 4476-5197 of SEQ ID NO: 35, or the nucleotide sequence range 5860-8859 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 1-3000, 3792-3906, 4476-5197, or 5860-8859 of SEQ ID NO: 35, or a sequence complementary thereto).

For knockout (and possibly knockdown) mutations through genome editing, an RNA-guided endonuclease may be targeted to a coding and/or intron sequence of a GA20 oxidase_3 or GA20 oxidase_5 gene to potentially eliminate expression and/or activity of a functional GA oxidase protein from the gene. However, a knockout of a GA oxidase gene expression may also be achieved in some cases by targeting the upstream and/or 5'UTR sequence(s) of the gene, or other sequences at or near the genomic locus of the gene. Thus, a knockout of a GA oxidase gene expression may be achieved by targeting a genomic sequence at or near the site or locus of a targeted GA20 oxidase_3 or GA20 oxidase_5 gene, an upstream or downstream sequence, such as a promoter and/or enhancer sequence, or an intron, 5'UTR, and/or 3'UTR sequence, of a GA20 oxidase_3 or GA20 oxidase_5 gene, as described above for knockdown of a GA20 oxidase_3 or GA20 oxidase_5 gene.

For knockout (and possibly knockdown) of the GA20 oxidase_3 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3097-5584 of SEQ ID NO: 34, the nucleotide sequence range 3097-3665 of SEQ ID NO: 34, the nucleotide sequence range 3776-4097 of SEQ ID NO: 34, or the nucleotide sequence range 5315-5584 of SEQ ID NO: 34, or a sequence complementary thereto (e.g., 10, 11, 12, 13, 14, 15, 16, 17, 18, 19, 20, 21, 22, 23, 24, 25 or more consecutive nucleotides within the nucleotide sequence range 3097-5584, 3097-3665, 3097-3775, 3665-4097, 3776-4097, 3776-5314, 4098-5584, or 5315-5584 of SEQ ID NO: 34, or a sequence complementary thereto).

For knockout (and possibly knockdown) of the GA20 oxidase_5 gene in corn, a guide RNA may be used comprising a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, at least 21, at least 22, at least 23, at least 24, at least 25, or more consecutive nucleotides within the nucleotide sequence range 3001-5473 of SEQ ID NO: 35, the nucleotide sequence range 3001-3791 of SEQ ID NO: 35, the nucleotide sequence range 3907-4475 of SEQ ID NO: 35, or the nucleotide sequence range 5198-5473 of SEQ ID NO: 35, or a sequence complementary thereto (e.g., 10, 11, 12, 13, 14, 15, 16, 17, 18, 19, 20, 21, 22, 23, 24, 25 or more consecutive nucleotides within the nucleotide sequence range 3001-5473, 3001-3791, 3001-3906, 3792-4475, 3907-4475, 3907-5197, 4476-5473, or 5198-5473 of SEQ ID NO: 35, or a sequence complementary thereto).

According to some embodiments, a guide RNA for targeting an endogenous GA20 oxidase_3 and/or GA20 oxidase_5 gene is provided, which may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 138-167. According to some embodiments, a guide RNA for targeting both of the endogenous GA20 oxidase_3 and GA20 oxidase_5 genes is provided, which may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of SEQ ID NO: 34, and at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of SEQ ID NO: 35. According to some embodiments, a guide RNA for targeting both of the endogenous GA20 oxidase_3 and GA20 oxidase_5 genes is provided, which may comprise a guide sequence that is at least 90%, at least 95%, at least 96%, at least 97%, at least 99% or 100% identical or complementary to at least 10, at least 11, at least 12, at least 13, at least 14, at least 15, at least 16, at least 17, at least 18, at least 19, at least 20, or at least 21 consecutive nucleotides of any one or more of SEQ ID NOs: 158-167.

In addition to the guide sequence, a guide RNA may further comprise one or more other structural or scaffold sequence(s), which may bind or interact with an RNA-guided endonuclease. Such scaffold or structural sequences may further interact with other RNA molecules (e.g., tracrRNA). Methods and techniques for designing targeting constructs and guide RNAs for genome editing and site-directed integration at a target site within the genome of a plant using an RNA-guided endonuclease are known in the art.

According to some embodiments, recombinant DNA constructs and vectors are provided comprising a polynucleotide sequence encoding a site-specific nuclease, such as a zinc-finger nuclease (ZFN), a meganuclease, an RNA-guided endonuclease, a TALE-endonuclease (TALEN), a recombinase, or a transposase, wherein the coding sequence is operably linked to a plant expressible promoter. For RNA-guided endonucleases, recombinant DNA constructs and vectors are further provided comprising a polynucleotide sequence encoding a guide RNA, wherein the guide RNA comprises a guide sequence of sufficient length having a percent identity or complementarity to a target site within the genome of a plant, such as at or near a targeted GA oxidase gene. According to some embodiments, a polynucleotide sequence of a recombinant DNA construct and vector that encodes a site-specific nuclease or a guide RNA may be operably linked to a plant expressible promoter, such as an inducible promoter, a constitutive promoter, a tissue-specific promoter, etc.

In another aspect, the present disclosure provides a modified corn plant, or plant part thereof, comprising a homozygous mutant GA20 oxidase_3 gene and a homozygous mutant GA20 oxidase_5 gene. In an aspect, a homozygous mutant GA20 oxidase_3 gene, a homozygous mutant GA20 oxidase_5 gene, or both comprise a heteroallelic combination of mutant alleles or two identical mutant alleles. In an aspect, a homozygous mutant GA20 oxidase_3 gene, a homozygous mutant GA20 oxidase_5 gene, or both comprise a mutation in a sequence region selected from the group consisting of promoter, 5' UTR, first exon, first intron, second exon, second intron, third exon, 3' UTR, terminator, and any combination thereof. In an aspect, a homozygous mutant GA20 oxidase_3 gene, a homozygous mutant GA20 oxidase_5 gene, or both comprise one or more mutation types selected from the group consisting of a nonsense mutation, a missense mutation, a frameshift mutation, a splice-site mutation, and any combination thereof. In an aspect, a homozygous mutant GA20 oxidase_3 gene, a homozygous mutant GA20 oxidase_5 gene, or both result in one or more of the following: a protein truncation, a non-translatable transcript, a non-functional protein, a premature stop codon, and any combination thereof. In an aspect, a homozygous mutant GA20 oxidase_3 gene, a homozygous mutant GA20 oxidase_5 gene, or both comprise a mutation selected from the group consisting of a substitution, a deletion, an insertion, a duplication, and an inversion of one or more nucleotides relative to a wild-type GA20 oxidase_3 gene. In an aspect, a mutant GA20 oxidase_3 gene, a homozygous mutant GA20 oxidase_5 gene, or both comprise a null allele.

In another aspect, the present disclosure provides a modified corn plant, or plant part thereof, comprising homozygous mutant alleles at an endogenous GA20 oxidase_3 locus and homozygous mutant alleles at an endogenous GA20 oxidase_5 locus. In an aspect, homozygous mutant alleles at the endogenous GA20 oxidase_3 locus, homozygous mutant alleles at the endogenous GA20 oxidase_5 locus, or both comprise a heteroallelic combination or two identical mutant alleles. In an aspect, a modified plant comprises a homozygous GA20 oxidase_3 locus comprising a heteroallelic combination of mutant alleles and a homozygous GA20 oxidase_5 locus comprising a heteroallelic combination of mutant alleles. In another aspect, a modified plant comprises a homozygous GA20 oxidase_3 locus comprising a heteroallelic combination of mutant alleles and a homozygous GA20 oxidase_5 locus comprising two identical mutant alleles. In an aspect, a modified plant comprises a homozygous GA20 oxidase_3 locus comprising two identical mutant alleles and a homozygous GA20 oxidase_5 locus comprising a heteroallelic combination of mutant alleles. In another aspect, a modified plant comprises a homozygous GA20 oxidase_3 locus comprising two identical mutant alleles and a homozygous GA20 oxidase_5 locus comprising two identical mutant alleles.

In an aspect, a GA20 oxidase_3 locus or gene comprises a sequence sharing at least 80%, at least 85%, at least 90%, at least 95%, at least 99%, or at least 99.5% sequence identity to SEQ ID No. 34 or 168. In an aspect, a GA20 oxidase_5 locus or gene comprises a sequence sharing at least 80%, at least 85%, at least 90%, at least 95%, at least 99%, or at least 99.5% sequence identity to SEQ ID No. 35 or 169.

In an aspect, a GA20 oxidase_3 or GA20 oxidase_5 mutation (mutant gene or mutant allele) comprises a mutation type selected from the group consisting of a nonsense mutation, a missense mutation, a frameshift mutation, and a splice-site mutation. In an aspect, a GA20 oxidase_3 or GA20 oxidase_5 mutation (or mutant allele) results in a truncated mRNA or polypeptide, or results in a non-translatable mRNA molecule. A missense mutation is a change in one DNA base pair that results in the substitution of one amino acid for another in the protein made by a gene. A nonsense mutation is also a change in one DNA base pair. Instead of substituting one amino acid for another, however, the altered DNA sequence prematurely signals the cell to stop building a protein. This type of mutation results in a shortened protein that may function improperly or not at all. A frameshift mutation occurs when the addition or loss of DNA bases changes a gene's reading frame. A frameshift mutation shifts the grouping of these bases and changes the code for amino acids. The resulting protein, even if made, is usually nonfunctional. Insertions, deletions, and duplications can all be frameshift mutations. In another aspect, a GA20 oxidase_3 or GA20 oxidase_5 mutation (mutant gene or mutant allele) can comprise a silent mutation which does not change an encoded amino acid sequence, but can affect mRNA transcript expression, stability or protein translation efficiency, or otherwise contribute to reduced enzyme activity, relative to a corresponding wild type GA20 oxidase_3 or GA20 oxidase_5 gene. In a further aspect, a GA20 oxidase_3 or GA20 oxidase_5 mutation (mutant gene or mutant allele) can comprise a mutation or edit at or around the TATA box or other promoter elements that affect gene transcription. In an aspect, a GA20 oxidase_3 mutation or allele in a modified corn plant is a recessive mutation or allele. In an aspect, a GA20 oxidase_3 mutation or allele in a modified corn plant is a dominant mutation or allele. In an aspect, a GA20 oxidase_5 mutation or allele in a modified corn plant is a recessive mutation or allele. In an aspect, a GA20 oxidase_5 mutation or allele in a modified corn plant is a dominant mutation or allele.

In an aspect, a GA20 oxidase_3 or GA20 oxidase_5 mutation (or mutant allele) comprises a mutation in a GA20 oxidase_3 or GA20 oxidase_5 sequence region selected from the group consisting of a promoter, 5' UTR, first exon, first intron, second exon, second intron, third exon, 3' UTR, and terminator. In an aspect, a GA20 oxidase_3 or GA20 oxidase_5 mutation (or mutant allele) comprises a mutation in the first or second exon of the GA20 oxidase_3 or GA20 oxidase_5 gene.

In an aspect, a mutant GA20 oxidase_3 or GA20 oxidase_5 allele exhibits an at least 30%, at least 40%, at least 50%, at least 60%, at least 70%, at least 80%, at least 90%, at least 95%, or 100% reduction of expression or enzymatic activity relative to an unmodified, wild-type GA20 oxidase_3 or GA20 oxidase_5 gene allele. In another aspect, a mutant GA20 oxidase_3 or GA20 oxidase_5 allele comprises a mutation in a sequence region selected from the group consisting of a promoter, 5' UTR, first exon, first intron, second exon, second intron, third exon, 3' UTR, terminator, and any combination thereof. In another aspect, a mutant GA20 oxidase_3 or GA20 oxidase_5 allele comprises one or more mutation types selected from the group consisting of a nonsense mutation, a missense mutation, a frameshift mutation, a splice-site mutation, and any combination thereof. In another aspect, a mutant GA20 oxidase_3 or GA20 oxidase_5 allele results in one or more of the following: a protein truncation, a non-translatable transcript, a non-functional protein, a premature stop codon, and any combination thereof. In another aspect, a mutant GA20 oxidase_3 or GA20 oxidase_5 allele comprises a mutation selected from the group consisting of a substitution, a deletion, an insertion, a duplication, and an inversion of one or more nucleotides relative to a wild-type GA20 oxidase_3 gene. In another aspect, a mutant GA20 oxidase_3 or GA20 oxidase_5 allele comprises one or more mutations in the first exon. In another aspect, a mutant GA20 oxidase_3 or GA20 oxidase_5 allele comprises one or more mutations in the second exon.

In an aspect, a modified corn plant, or plant part thereof, comprises a first mutation comprising one or more alleles, as a pair of two identical alleles or a heteroallelic combination, selected from the group consisting of: a deletion of 13 bases starting at 536; a deletion of base 542; an insertion of CC at base 542; a deletion of base 541; a deletion of 3 nt starting at base 540; a deletion of 2 bases starting at base 422; an insertion of an A at base 422; an insertion of a T at base 422; a deletion of base 564; an insertion of an A at base 564; an insertion of a C at base 565; and an insertion of a C at base 63; wherein the base numbering is based on SEQ ID No. 168 and counted from the first nucleotide of SEQ ID NO: 168 in the 5' to 3' direction. In another aspect, a modified corn plant, or plant part thereof, comprises a first mutation comprising one or more alleles, as a pair of two identical alleles or a heteroallelic combination, selected from the group consisting of: a deletion of base 644; a deletion of 2 bases starting at base 644; an insertion of a T at base 644; a deletion of base 372; a deletion of base 786; a deletion of 5 bases starting at base 786; a deletion of 2 bases starting at base 101; an insertion of a T at base base 102; a deletion of 3 bases starting at base 99; an insertion of an A at base 282; and an insertion of a C at base 282; wherein the base numbering is based on SEQ ID No. 169 and counted from the first nucleotide of SEQ ID NO: 169 in the 5' to 3' direction. In an aspect, a modified corn plant, or plant part thereof, comprises a first mutation identified by one or more of SEQ ID Nos.: 170 to 193 and 206 to 217 relative to the corresponding reference sequence in SEQ ID No: 168. In an aspect, a modified corn plant, or plant part thereof, comprises a first mutation identified by one or more of SEQ ID Nos.: 218 to 239 and 251 to 261 relative to the corresponding reference sequence in SEQ ID No: 169. In an aspect, the present disclosure provides a progeny plant of one or more plants listed in Table 5 or 6. In another aspect, also provided is a progeny plant of any one of plant Nos. 17 to 31 in Table 6. In a further aspect, a plant is provided from a cross or hybridization of one or more plants listed in Table 5 or 6.

In an aspect, a modified corn plant described here has a shorter plant height and/or improved lodging resistance relative to an unmodified control plant. In an aspect, a modified corn plant is at least 10%, at least 20%, at least 25%, at least 30%, at least 35%, or at least 40% shorter than an unmodified control plant. In another aspect, a modified corn plant has a stalk or stem diameter at one or more stem internodes is at least 5%, at least 10%, at least 15%, at least 20%, at least 25%, at least 30%, at least 35%, or at least 40% greater than the stalk or stem diameter at the same one or more internodes of an unmodified control plant. In an aspect, a modified corn plant has a stalk or stem diameter at one or more of the first, second, third, and/or fourth internode below the ear is at least 5%, at least 10%, at least 15%, at least 20%, at least 25%, at least 30%, at least 35%, or at least 40% greater than the same internode of an unmodified control plant. In another aspect, the level of one or more active GAs in at least one internode tissue of the stem or stalk of a modified corn plant is at least 5%, at least 10%, at least 15%, at least 20%, at least 25%, at least 30%, at least 35%, or at least 40% lower than the same internode tissue of an unmodified control plant. In an aspect, the level of one or more active GAs in at least one internode tissue of the stem or stalk of a modified corn plant is lower than the same internode tissue of an unmodified control plant.

In another aspect, a modified corn plant does not have any significant off-types in at least one female organ or ear. In an aspect, a modified corn plant exhibits essentially no reproductive abnormality. In a further aspect, an off-type or reproductive abnormality is selected from the group consisting of male (tassel or anther) sterility, reduced kernel or seed number, and the presence of one or more masculinized or male (or male-like) reproductive structures in the female organ or ear (e.g., anther ear).

In another aspect, a modified corn plant comprises one or more traits, relative to an unmodified control plant, selected from the group consisting of shorter plant height, increased stalk/stem diameter, improved lodging resistance, reduced green snap, deeper roots, increased leaf area, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions, increased ear weight, increased harvest index, increased yield, increased seed number, increased seed weight, and increased prolificacy.

In an aspect, a modified corn plant is an inbred. In another aspect, a modified corn plant is a hybrid. In an aspect, a modified corn plant is a plant modified by a targeted genome editing technique.

According to some embodiments, a recombinant DNA construct or vector may comprise a first polynucleotide sequence encoding a site-specific nuclease and a second polynucleotide sequence encoding a guide RNA that may be introduced into a plant cell together via plant transformation techniques. Alternatively, two recombinant DNA constructs or vectors may be provided including a first recombinant DNA construct or vector and a second DNA construct or vector that may be introduced into a plant cell together or sequentially via plant transformation techniques, wherein the first recombinant DNA construct or vector comprises a polynucleotide sequence encoding a site-specific nuclease and the second recombinant DNA construct or vector comprises a polynucleotide sequence encoding a guide RNA. According to some embodiments, a recombinant DNA construct or vector comprising a polynucleotide sequence encoding a site-specific nuclease may be introduced via plant transformation techniques into a plant cell that already comprises (or is transformed with) a recombinant DNA construct or vector comprising a polynucleotide sequence encoding a guide RNA. Alternatively, a recombinant DNA construct or vector comprising a polynucleotide sequence encoding a guide RNA may be introduced via plant transformation techniques into a plant cell that already comprises (or is transformed with) a recombinant DNA construct or vector comprising a polynucleotide sequence encoding a site-specific nuclease. According to yet further embodiments, a first plant comprising (or transformed with) a recombinant DNA construct or vector comprising a polynucleotide sequence encoding a site-specific nuclease may be crossed with a second plant comprising (or transformed with) a recombinant DNA construct or vector comprising a polynucleotide sequence encoding a guide RNA. Such recombinant DNA constructs or vectors may be transiently transformed into a plant cell or stably transformed or integrated into the genome of a plant cell.

In an aspect, vectors comprising polynucleotides encoding a site-specific nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In an aspect, vectors comprising polynucleotides encoding a Cas9 nuclease, and optionally one or more, two or more, three or more, or four or more gRNAs are provided to a plant cell by transformation methods known in the art (e.g., without being limiting, particle bombardment, PEG-mediated protoplast transfection or *Agrobacterium*-mediated transformation). In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

Several site-specific nucleases, such as recombinases, zinc finger nucleases (ZFNs), meganucleases, and TALENs, are not RNA-guided and instead rely on their protein structure to determine their target site for causing the DSB or nick, or they are fused, tethered or attached to a DNA-binding protein domain or motif. The protein structure of the site-specific nuclease (or the fused/attached/tethered DNA binding domain) may target the site-specific nuclease to the target site. According to many of these embodiments, non-RNA-guided site-specific nucleases, such as recombinases, zinc finger nucleases (ZFNs), meganucleases, and TALENs, may be designed, engineered and constructed according to known methods to target and bind to a target site at or near the genomic locus of an endogenous GA oxidase gene of a corn plant, such as the GA20 oxidase_3 gene or the GA20 oxidase_5 gene in corn, to create a DSB or nick at such genomic locus to knockout or knockdown expression of the GA oxidase gene via repair of the DSB or nick. For example, an engineered site-specific nuclease, such as a recombinase, zinc finger nuclease (ZFN), meganuclease, or TALEN, may be designed to target and bind to (i) a target site within the genome of a plant corresponding to a sequence within SEQ ID NO: 34, or its complementary sequence, to create a DSB or nick at the genomic locus for the GA20 oxidase_3 gene, (ii) a target site within the genome of a plant corresponding to a sequence within SEQ ID NO: 35, or its complementary sequence, to create a DSB or nick at the genomic locus for the GA20 oxidase_5 gene, and/or (iii) a target site within the genome of a plant corresponding to a sequence within SEQ ID NO: 38, or its complementary sequence, to create a DSB or nick at the genomic locus for the GA20 oxidase_4 gene, which may then lead to the creation of a mutation or insertion of a sequence at the site of the DSB or nick, through cellular repair mechanisms, which may be guided by a donor molecule or template.

In an aspect, a targeted genome editing technique described herein may comprise the use of a recombinase. In some embodiments, a tyrosine recombinase attached, etc., to a DNA recognition domain or motif may be selected from the group consisting of a Cre recombinase, a Flp recombinase, and a Tnp1 recombinase. In an aspect, a Cre recombinase or a Gin recombinase provided herein may be tethered to a zinc-finger DNA binding domain. The Flp-FRT site-directed recombination system may come from the 2μ plasmid from the baker's yeast *Saccharomyces cerevisiae*. In this system, Flp recombinase (flippase) may recombine sequences between flippase recognition target (FRT) sites. FRT sites comprise 34 nucleotides. Flp may bind to the "arms" of the FRT sites (one arm is in reverse orientation) and cleaves the FRT site at either end of an intervening nucleic acid sequence. After cleavage, Flp may recombine nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase may recombine a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

ZFNs are synthetic proteins consisting of an engineered zinc finger DNA-binding domain fused to a cleavage domain (or a cleavage half-domain), which may be derived from a restriction endonuclease (e.g., FokI). The DNA binding domain may be canonical (C2H2) or non-canonical (e.g., C3H or C4). The DNA-binding domain can comprise one or more zinc fingers (e.g., 2, 3, 4, 5, 6, 7, 8, 9 or more zinc fingers) depending on the target site. Multiple zinc fingers in a DNA-binding domain may be separated by linker sequence(s). ZFNs can be designed to cleave almost any stretch of double-stranded DNA by modification of the zinc finger DNA-binding domain. ZFNs form dimers from monomers composed of a non-specific DNA cleavage domain (e.g., derived from the FokI nuclease) fused to a DNA-binding domain comprising a zinc finger array engineered to bind a target site DNA sequence. The DNA-binding domain of a ZFN may typically be composed of 3-4 (or more) zinc-fingers. The amino acids at positions −1, +2, +3, and +6 relative to the start of the zinc finger α-helix, which contribute to site-specific binding to the target site, can be changed and customized to fit specific target sequences. The other amino acids may form a consensus backbone to generate ZFNs with different sequence specificities. Methods and rules for designing ZFNs for targeting and binding to specific target sequences are known in the art. See, e.g., US Patent App. Nos. 2005/0064474, 2009/0117617, and 2012/0142062, the contents and disclosures of which are incorporated herein by reference. The FokI nuclease domain may require dimerization to cleave DNA and therefore two ZFNs with their C-terminal regions are needed to bind opposite DNA strands of the cleavage site (separated by 5-7 bp). The ZFN monomer can cut the target site if the two-ZF-binding sites are palindromic. A ZFN, as used herein, is broad and includes a monomeric ZFN that can cleave double stranded DNA without assistance from another ZFN. The term ZFN may also be used to refer to one or both members of a pair of ZFNs that are engineered to work together to cleave DNA at the same site.

Without being limited by any scientific theory, because the DNA-binding specificities of zinc finger domains can be re-engineered using one of various methods, customized ZFNs can theoretically be constructed to target nearly any target sequence (e.g., at or near a GA oxidase gene in a plant genome). Publicly available methods for engineering zinc finger domains include Context-dependent Assembly (CoDA), Oligomerized Pool Engineering (OPEN), and Modular Assembly. In an aspect, a method and/or composition provided herein comprises one or more, two or more, three or more, four or more, or five or more ZFNs. In another aspect, a ZFN provided herein is capable of generating a targeted DSB or nick. In an aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection, or *Agrobacterium*-mediated transformation). The ZFNs may be introduced as ZFN proteins, as polynucleotides encoding ZFN proteins, and/or as combinations of proteins and protein-encoding polynucleotides.

Meganucleases, which are commonly identified in microbes, such as the LAGLIDADG family of homing endonucleases, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). According to some embodiments, a meganuclease may comprise a scaffold or base enzyme selected from the group consisting of I-CreI, I-CeuI, I-MsoI, I-SceI, I-AniI, and I-DmoI. The engineering of meganucleases can be more challenging than ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity. Thus, a meganuclease may be selected or engineered to bind to a genomic target sequence in a plant, such as at or near the genomic locus of a GA oxidase gene. In an aspect, a method and/or composition provided herein comprises one or more, two or more, three or more, four or more, or five or more meganucleases. In another aspect, a meganuclease provided herein is capable of generating a targeted DSB. In an aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

TALENs are artificial restriction enzymes generated by fusing the transcription activator-like effector (TALE) DNA binding domain to a nuclease domain (e.g., FokI). When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In some aspects, the nuclease is selected from a group consisting of PvuII, MutH, TevI, FokI, AlwI, MlyI, SbfI, SdaI, StsI, CleDORF, Clo051, and Pept071. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also refers to one or both members of a pair of TALENs that work together to cleave DNA at the same site.

Transcription activator-like effectors (TALEs) can be engineered to bind practically any DNA sequence, such as at or near the genomic locus of a GA oxidase gene in a plant. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One*. 8: e82539). MutH is capable of introducing strand-specific nicks in DNA (see Gabsalilow et al. 2013. *Nucleic Acids Research*. 41: e83). TevI introduces double-stranded breaks in DNA at targeted sites (see Beurdeley et al., 2013. *Nature Communications*. 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122.; Cermak et al., *Nucleic Acids Research* (2011). 39:e82; and tale-nt.cac.cornell.edu/about. In an aspect, a method and/or composition provided herein comprises one or more, two or more, three or more, four or more, or five or more TALENs. In another aspect, a TALEN provided herein is capable of generating a targeted DSB. In an aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation). See, e.g., US Patent App. Nos. 2011/0145940, 2011/0301073, and 2013/0117869, the contents and disclosures of which are incorporated herein by reference.

As used herein, a "targeted genome editing technique" refers to any method, protocol, or technique that allows the precise and/or targeted editing of a specific location in a genome of a plant (i.e., the editing is largely or completely non-random) using a site-specific nuclease, such as a meganuclease, a zinc-finger nuclease (ZFN), an RNA-guided endonuclease (e.g., the CRISPR/Cas9 system), a TALE-endonuclease (TALEN), a recombinase, or a transposase. As used herein, "editing" or "genome editing" refers to generating a targeted mutation, deletion, inversion or substitution of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides of an endogenous plant genome nucleic acid sequence. As used herein, "editing" or "genome editing" also encompasses the targeted insertion or site-directed integration of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 750, at least 1000, at least 1500, at least 2000, at least 2500, at least 3000, at least 4000, at least 5000, at least 10,000, or at least 25,000 nucleotides into the endogenous genome of a plant. An "edit" or "genomic edit" in the singular refers to one such targeted mutation, deletion, inversion, substitution or insertion, whereas "edits" or "genomic edits" refers to two or more targeted mutation(s), deletion(s), inversion(s), substitution(s) and/or insertion(s), with each "edit" being introduced via a targeted genome editing technique.

In an aspect, targeted gene editing approaches are used to modify the sequence of the promoter and/or regulatory region(s) of one or more of the GA20 oxidase_3 and/or GA20 oxidase_5 genes to knock-down or knock-out expression of these gene(s), such as through targeted deletions, insertions, mutations, or other sequence changes. Indeed, the promoter and/or regulatory region(s) or sequence(s), or the 5'-UTR, 3'UTR, and/or intron sequence(s), of one or more of the GA20 oxidase_3 and/or GA20 oxidase_5 genes may be largely deleted or mutated. Alternatively, all or a portion of the coding (exon), 5-UTR, 3'UTR, and/or intron sequence(s) of one or more of the GA20 oxidase_3 and/or GA20 oxidase_5 genes may be edited, deleted, mutated, or otherwise modified to knock-down or knock-out expression or activity of these gene(s). Such targeted modifications to the GA20 oxidase_3 and/or GA20 oxidase_5 gene loci may be achieved using any suitable genome editing technology known in the art, such as via repair of a double strand break (DSB) or nick introduced by a site-specific nuclease, such as, for example, a zinc-finger nuclease, an engineered or native meganuclease, a TALE-endonuclease, or an RNA-guided endonuclease (e.g., Cas9 or Cpf1). Such repair of the DSB or nick may introduce spontaneous or stochastic deletions, additions, mutations, etc., at the targeted site where the DSB or nick was introduced, or repair of the site may involve the use of a donor template molecule to direct or cause a preferred or specific deletion, addition, mutation, etc., at the targeted site.

For purposes of the present disclosure, a "plant" includes an explant, plant part, seedling, plantlet or whole plant at any stage of regeneration or development. As used herein, a "plant part" may refer to any organ or intact tissue of a plant, such as a meristem, shoot organ/structure (e.g., leaf, stem or node), root, flower or floral organ/structure (e.g., bract, sepal, petal, stamen, carpel, anther and ovule), seed (e.g., embryo, endosperm, and seed coat), fruit (e.g., the mature ovary), propagule, or other plant tissues (e.g., vascular tissue, dermal tissue, ground tissue, and the like), or any portion thereof. Plant parts of the present disclosure may be viable, nonviable, regenerable, and/or non-regenerable. A "propagule" may include any plant part that can grow into an entire plant.

According to some embodiments, a modified plant may be planted at a density in the field (plants per land/field area) that is at least 5%, 10%, 15%, 20%, 25%, 50%, 75%, 100%, 125%, 150%, 175%, 200%, 225%, or 250% higher than the normal planting density for that crop plant according to standard agronomic practices. A modified plant may be planted at a density in the field of at least 38,000 plants per acre, at least 40,000 plants per acre, at least 42,000 plants per acre, at least 44,000 plants per acre, at least 45,000 plants per acre, at least 46,000 plants per acre, at least 48,000 plants per acre, 50,000 plants per acre, at least 52,000 plants per acre, at least 54,000 per acre, or at least 56,000 plants per acre. As an example, corn plants may be planted at a higher density, such as in a range from about 38,000 plants per acre to about 60,000 plants per acre, or about 40,000 plants per acre to about 58,000 plants per acre, or about 42,000 plants per acre to about 58,000 plants per acre, or about 40,000 plants per acre to about 45,000 plants per acre, or about 45,000 plants per acre to about 50,000 plants per acre, or about 50,000 plants per acre to about 58,000 plants per acre, or about 52,000 plants per acre to about 56,000 plants per acre, or about 38,000 plants per acre, about 42,000 plant per acre, about 46,000 plant per acre, or about 48,000 plants per acre, about 50,000 plants per acre, or about 52,000 plants per acre, or about 54,000 plant per acre, as opposed to a standard density range, such as about 18,000 plants per acre to about 38,000 plants per acre.

According to embodiments of the present disclosure, a modified corn plant(s) is/are provided that comprise (i) a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or (ii) an average stem or stalk diameter of at least 18 mm, at least 18.5 mm, at least 19 mm, at least 19.5 mm, at least 20 mm, at least 20.5 mm, at least 21 mm, at least 21.5 mm, or at least 22 mm. Stated a different way, a modified corn plant(s) is/are provided that comprise a plant height of less than 2000 mm, less than 1950 mm, less than 1900 mm, less than 1850 mm, less than 1800 mm, less than 1750 mm, less than 1700 mm, less than 1650 mm, less than 1600 mm, less than 1550 mm, less than 1500 mm, less than 1450 mm, less than 1400 mm, less than 1350 mm, less than 1300 mm, less than 1250 mm, less than 1200 mm, less than 1150 mm, less than 1100 mm, less than 1050 mm, or less than 1000 mm, and/or an average stem or stalk diameter that is greater than 18 mm, greater than 18.5 mm, greater than 19 mm, greater than 19.5 mm, greater than 20 mm, greater than 20.5 mm, greater than 21 mm, greater than 21.5 mm, or greater than 22 mm. Any such plant height trait or range that is expressed in millimeters (mm) may be converted into a different unit of measurement based on known conversions (e.g., one inch is equal to 2.54 cm or 25.4 millimeters, and millimeters (mm), centimeters (cm) and meters (m) only differ by one or more powers of ten). Thus, any measurement provided herein is further described in terms of any other comparable units of measurement according to known and established conversions. However, the exact plant height and/or stem diameter of a modified corn plant may depend on the environment and genetic background. Thus, the change in plant height and/or stem diameter of a modified corn plant may instead be described in terms of a minimum difference or percent change relative to a control plant. A modified corn plant may further comprise at least one ear that is substantially free of male reproductive tissues or structures or other off-types.

According to embodiments of the present disclosure, modified corn plants are provided that comprise a plant height during late vegetative and/or reproductive stages of development (e.g., at R3 stage) of between 1000 mm and 1800 mm, between 1000 mm and 1700 mm, between 1050 mm and 1700 mm, between 1100 mm and 1700 mm, between 1150 mm and 1700 mm, between 1200 mm and 1700 mm, between 1250 mm and 1700 mm, between 1300 mm and 1700 mm, between 1350 mm and 1700 mm, between 1400 mm and 1700 mm, between 1450 mm and 1700 mm, between 1000 mm and 1500 mm, between 1050 mm and 1500 mm, between 1100 mm and 1500 mm, between 1150 mm and 1500 mm, between 1200 mm and 1500 mm, between 1250 mm and 1500 mm, between 1300 mm and 1500 mm, between 1350 mm and 1500 mm, between 1400 mm and 1500 mm, between 1450 mm and 1500 mm, between 1000 mm and 1600 mm, between 1100 mm and 1600 mm, between 1200 mm and 1600 mm, between 1300 mm and 1600 mm, between 1350 mm and 1600 mm, between 1400 mm and 1600 mm, between 1450 mm and 1600 mm, of between 1000 mm and 2000 mm, between 1200 mm and 2000 mm, between 1200 mm and 1800 mm, between 1300 mm and 1700 mm, between 1400 mm and 1700 mm, between 1400 mm and 1600 mm, between 1400 mm and 1700 mm, between 1400 mm and 1800 mm, between 1400 mm and 1900 mm, between 1400 mm and 2000 mm, or between 1200 mm and 2500 mm, and/or an average stem diameter of between 17.5 mm and 22 mm, between 18 mm and 22 mm, between 18.5 and 22 mm, between 19 mm and 22 mm, between 19.5 mm and 22 mm, between 20 mm and 22 mm, between 20.5 mm and 22 mm, between 21 mm and 22 mm, between 21.5 mm and 22 mm, between 17.5 mm and 21 mm, between 17.5 mm and 20 mm, between 17.5 mm and 19 mm, between 17.5 mm and 18 mm, between 18 mm and 21 mm, between 18 mm and 20 mm, or between 18 mm and 19 mm. A modified corn plant may be substantially free of off-types, such as male reproductive tissues or structures in one or more ears of the modified corn plant.

According to embodiments of the present disclosure, modified corn plants are provided that have (i) a plant height that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the height of a wild-type or control plant, and/or (ii) a stem or stalk diameter that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the stem diameter of the wild-type or control plant. According to embodiments of the present disclosure, a modified corn plant may have a reduced plant height that is no more than 20%, 25%, 30%, 35%, 40%, 45%, 50%, 55%, or 60% shorter than the height of a wild-type or control plant, and/or a stem or stalk diameter that is less than (or not more than) 10%, 15%, 20%, 25%, 30%, 35%, 40%, 45%, 50%, 55%, 60%, 65%, 70%, 75%, 80%, 85%, 90%, 95%, or 100% greater than the stem or stalk diameter of a wild-type or control plant. For example, a modified plant may have (i) a plant height that is at least 10%, at least 15%, or at least 20% less or shorter (i.e., greater than or equal to 10%, 15%, or 20% shorter), but not greater or more than 50% shorter, than a wild type or control plant, and/or (ii) a stem or stalk diameter that is that is at least 5%, at least 10%, or at least 15% greater, but not more than 30%, 35%, or 40% greater, than a wild type or control plant. For clarity, the phrases "at least 20% shorter" and "greater than or equal to 20% shorter" would exclude, for example, 10% shorter. Likewise for clarity, the phrases "not greater than 50% shorter", "no more than 50% shorter" and "not more than 50% shorter" would exclude 60% shorter; the phrase "at least 5% greater" would exclude 2% greater; and the phrases "not more than 30% greater" and "no more than 30% greater" would exclude 40% greater.

According to embodiments of the present disclosure, modified corn plants are provided that comprise a height between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the height of a wild-type or control plant, and/or a stem or stalk diameter that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, between 50% and 75%, between 8% and 20%, or between 8% and 15% greater than the stem or stalk diameter of the wild-type or control plant.

According to embodiments of the present disclosure, modified corn plants are provided that comprise an average internode length (or a minus-2 internode length and/or minus-4 internode length relative to the position of the ear) that is at least 5%, at least 10%, at least 15%, at least 20%, at least 25%, at least 30%, at least 35%, at least 40%, at least 45%, at least 50%, at least 55%, at least 60%, at least 65%, at least 70%, or at least 75% less than the same or average internode length of a wild-type or control plant. The "minus-2 internode" of a corn plant refers to the second internode below the ear of the plant, and the "minus-4 internode" of a corn plant refers to the fourth internode below the ear of the plant According to many embodiments, modified corn plants are provided that have an average internode length (or a minus-2 internode length and/or minus-4 internode length relative to the position of the ear) that is between 5% and 75%, between 5% and 50%, between 10% and 70%, between 10% and 65%, between 10% and 60%, between 10% and 55%, between 10% and 50%, between 10% and 45%, between 10% and 40%, between 10% and 35%, between 10% and 30%, between 10% and 25%, between 10% and 20%, between 10% and 15%, between 10% and 10%, between 10% and 75%, between 25% and 75%, between 10% and 50%, between 20% and 50%, between 25% and 50%, between 30% and 75%, between 30% and 50%, between 25% and 50%, between 15% and 50%, between 20% and 50%, between 25% and 45%, or between 30% and 45% less than the same or average internode length of a wild-type or control plant.

According to embodiments of the present disclosure, modified corn plants are provided that comprise an ear weight (individually or on average) that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than the ear weight of a wild-type or control plant. A modified corn plant provided herein may comprise an ear weight that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 25% and 75%, between 25% and 50%, or between 50% and 75% greater than the ear weight of a wild-type or control plant.

According to embodiments of the present disclosure, modified corn plants are provided that have a harvest index of at least 0.57, at least 0.58, at least 0.59, at least 0.60, at least 0.61, at least 0.62, at least 0.63, at least 0.64, or at least 0.65 (or greater). A modified corn plant may comprise a harvest index of between 0.57 and 0.65, between 0.57 and 0.64, between 0.57 and 0.63, between 0.57 and 0.62, between 0.57 and 0.61, between 0.57 and 0.60, between 0.57 and 0.59, between 0.57 and 0.58, between 0.58 and 0.65, between 0.59 and 0.65, or between 0.60 and 0.65. A modified corn plant may have a harvest index that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, at least 25%, at least 30%, at least 35%, at least 40%, at least 45%, or at least 50% greater than the harvest index of a wild-type or control plant. A modified corn plant may have a harvest index that is between 1% and 45%, between 1% and 40%, between 1% and 35%, between 1% and 30%, between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 30%, or between 5% and 40% greater than the harvest index of a wild-type or control plant.

According to embodiments of the present disclosure, modified corn plants are provided that have an increase in harvestable yield of at least 1 bushel per acre, at least 2 bushels per acre, at least 3 bushels per acre, at least 4 bushels per acre, at least 5 bushels per acre, at least 6 bushels per acre, at least 7 bushels per acre, at least 8 bushels per acre, at least 9 bushels per acre, or at least 10 bushels per acre, relative to a wild-type or control plant. A modified corn plant may have an increase in harvestable yield between 1 and 10, between 1 and 8, between 2 and 8, between 2 and 6, between 2 and 5, between 2.5 and 4.5, or between 3 and 4 bushels per acre. A modified corn plant may have an increase in harvestable yield that is at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 20%, or at least 25% greater than the harvestable yield of a wild-type or control plant. A modified corn plant may have a harvestable yield that is between 1% and 25%, between 1% and 20%, between 1% and 15%, between 1% and 14%, between 1% and 13%, between 1% and 12%, between 1% and 11%, between 1% and 10%, between 1% and 9%, between 1% and 8%, between 1% and 7%, between 1% and 6%, between 1% and 5%, between 1% and 4%, between 1% and 3%, between 1% and 2%, between 5% and 15%, between 5% and 20%, between 5% and 25%, between 2% and 10%, between 2% and 9%, between 2% and 8%, between 2% and 7%, between 2% and 6%, between 2% and 5%, or between 2% and 4% greater than the harvestable yield of a wild-type or control plant.

According to embodiments of the present disclosure, a modified corn plant is provided that has a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a wild-type or control plant. A modified corn plant may have a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a wild-type or control plant. Further provided are populations of corn plants having increased lodging resistance and a reduced lodging frequency. Populations of modified corn plants are provided having a lodging frequency that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% less or lower than a population of wild-type or control plants. A population of modified corn plants may comprise a lodging frequency that is between 5% and 100%, between 5% and 95%, between 5% and 90%, between 5% and 85%, between 5% and 80%, between 5% and 75%, between 5% and 70%, between 5% and 65%, between 5% and 60%, between 5% and 55%, between 5% and 50%, between 5% and 45%, between 5% and 40%, between 5% and 35%, between 5% and 30%, between 5% and 25%, between 5% and 20%, between 5% and 15%, between 5% and 10%, between 10% and 100%, between 10% and 75%, between 10% and 50%, between 10% and 40%, between 10% and 30%, between 10% and 20%, between 25% and 75%, between 25% and 50%, or between 50% and 75% less or lower than a population of wild-type or control plants, which may be expressed as an average over a specified number of plants or crop area of equal density.

According to embodiments of the present disclosure, modified corn plants are provided having a significantly reduced or decreased plant height (e.g., 2000 mm or less) and a significantly increased stem diameter (e.g., 18 mm or more), relative to a wild-type or control plant. According to these embodiments, the decrease or reduction in plant height and increase in stem diameter may be within any of the height, diameter or percentage ranges recited herein. Such modified corn plants having a reduced plant height and increased stem diameter relative to a wild-type or control plant may be transformed with a transcribable DNA sequence encoding a non-coding RNA molecule that targets at least one GA20 oxidase gene for suppression. Modified corn plants having a significantly reduced plant height and/or a significantly increased stem diameter relative to a wild-type or control plant may further have at least one ear that is substantially free of male reproductive tissues or structures and/or other off-types. Modified corn plants having a significantly reduced plant height and/or an increased stem diameter relative to a wild-type or control plant may have reduced activity of one or more GA20 oxidase and/or GA3 oxidase gene(s) in one or more tissue(s) of the plant, such as one or more vascular and/or leaf tissue(s) of the plant, relative to the same tissue(s) of the wild-type or control plant. According to many embodiments, modified corn plants may comprise at least one polynucleotide or transcribable DNA sequence encoding a non-coding RNA molecule operably linked to a promoter, which may be a constitutive, tissue-specific or tissue-preferred promoter, wherein the non-coding RNA molecule targets at least one GA20 oxidase for suppression as provided herein. The non-coding RNA molecule may be a miRNA, siRNA, or miRNA or siRNA precursor molecule. According to some embodiments, modified corn plants having a significantly reduced plant height and/or an increased stem diameter relative to a wild-type or control plant may further have an increased harvest index and/or increased lodging resistance relative to the wild-type or control plant.

Modified corn plants having a significantly reduced plant height and/or a significantly increased stem diameter relative to a wild-type or control plant may comprise a mutation (e.g., an insertion, deletion, substitution, etc.) in a GA oxidase gene introduced through a gene editing technology or other mutagenesis technique, wherein expression of the GA oxidase gene is reduced or eliminated in one or more tissues of the modified plant. Such modified corn plants having a reduced plant height and/or an increased stem diameter relative to a wild-type or control plant may further have an increased harvest index and/or increased lodging resistance relative to the wild-type or control plant. Such modified corn plants may be substantially free of off-types, such as male reproductive tissues or structures and/or other off-types in at least one ear of the modified plants. Plant mutagenesis techniques (excluding genome editing) may include chemical mutagenesis (i.e., treatment with a chemical mutagen, such as an azide, hydroxylamine, nitrous acid, acridine, nucleotide base analog, or alkylating agent—e.g., EMS (ethylmethane sulfonate), MNU (N-methyl-N-nitrosourea), etc.), physical mutagenesis (e.g., gamma rays, X-rays, UV, ion beam, other forms of radiation, etc.), and insertional mutagenesis (e.g., transposon or T-DNA insertion). Plants or various plant parts, plant tissues or plant cells may be subjected to mutagenesis. Treated plants may be reproduced to collect seeds or produce a progeny plant, and treated plant parts, plant tissues or plant cells may be developed or regenerated into plants or other plant tissues. Mutations generated with chemical or physical mutagenesis techniques may include a frameshift, missense or nonsense mutation leading to loss of function or expression of a targeted gene, such as a GA3 or GA20 oxidase gene.

One method for mutagenesis of a gene is called "TILLING" (for targeting induced local lesions in genomes), in which mutations are created in a plant cell or tissue, preferably in the seed, reproductive tissue or germline of a plant, for example, using a mutagen, such as an EMS treatment. The resulting plants are grown and self-fertilized, and the progeny are used to prepare DNA samples. PCR amplification and sequencing of a nucleic acid sequence of a GA oxidase gene may be used to identify whether a mutated plant has a mutation in the GA oxidase gene. Plants having mutations in the GA oxidase gene may then be tested for an altered trait, such as reduced plant height. Alternatively, mutagenized plants may be tested for an altered trait, such as reduced plant height, and then PCR amplification and sequencing of a nucleic acid sequence of a GA oxidase gene may be used to determine whether a plant having the altered trait also has a mutation in the GA oxidase gene. See, e.g., Colbert et al., 2001, *Plant Physiol* 126:480-484; and McCallum et al., 2000, *Nature Biotechnology* 18:455-457. TILLING can be used to identify mutations that alter the expression a gene or the activity of proteins encoded by a gene, which may be used to introduce and select for a targeted mutation in a GA oxidase gene of a corn plant.

Corn plants that have been subjected to a mutagenesis or genome editing treatment may be screened and selected based on an observable phenotype (e.g., any phenotype described herein, such as shorter plant height, increased stem/stalk diameter, etc.), or using a selection agent with a selectable marker (e.g., herbicide, etc.), a screenable marker, or a molecular technique (e.g., lower GA levels, lower GA oxidase transcript or protein levels, presence of transgene or transcribable sequence, etc.). Such screening and/or selecting techniques may be used to identify and select plants having a mutation in a GA oxidase gene that leads to a desirable plant phenotype.

According to embodiments of the present disclosure, a population of modified corn plants are provided, wherein the population of modified corn plants have an average plant height that is significantly less, and/or an average stem or stalk diameter that is significantly more, than a population of wild-type or control plants. The population of modified corn plants may share ancestry with a single modified corn plant. Modified corn plants within a population of modified corn plants may generally comprise at least one ear that is substantially free of male reproductive tissues or structures and/or other off-types. A population of modified corn plants may have increased lodging resistance on average or per number of plants or field area than a population of wild-type or control plants. The population of modified corn plants may have a lodging frequency that is at least 5%, at least 10%, at least 20%, at least 30%, at least 40%, at least 50%, at least 60%, at least 70% at least 80%, at least 90%, or 100% less (or lower) than a population of control corn plants. A population of modified corn plants may have a harvest index of at least 0.57 or greater.

According to embodiments of the present invention, modified corn plants are provided having a reduced gibberellin content (in active form) in at least the stem and internode tissue(s), such as the stem, internode, leaf and/or vascular tissue(s), as compared to the same tissue(s) of wild-type or control plants. According to many embodiments, modified corn plants are provided having a significantly reduced plant height and/or a significantly increased stem diameter relative to wild-type or control plants, wherein the modified corn plants further have significantly reduced or decreased level(s) of active gibberellins or active GAs (e.g., one or more of GA1, GA3, GA4, and/or GA7) in one or more stem, internode, leaf and/or vascular tissue(s), relative to the same tissue(s) of the wild-type or control plants. For example, the level of one or more active GAs in the stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn plant may comprise an active gibberellin (GA) level(s) (e.g., one or more of GA1, GA3, GA4, and/or GA7) in one or more stem, internode, leaf and/or vascular tissue(s) that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or (or lower) than in the same tissue(s) of a wild-type or control corn plant. A modified corn plant having a reduced active gibberellin (GA) level(s) in one or more stem, internode, leaf and/or vascular tissue(s) may further be substantially free of off-types, such as male reproductive tissues or structures and/or other off-types in at least one ear of a modified corn plant.

According to embodiments of the present disclosure, modified corn plants are provided having a significantly reduced or eliminated expression level of one or more GA3 oxidase and/or GA20 oxidase gene transcript(s) and/or protein(s) in one or more tissue(s), such as one or more stem, internode, leaf and/or vascular tissue(s), of the modified plants, as compared to the same tissue(s) of wild-type or control plants. According to many embodiments, a modified corn plant is provided comprising a significantly reduced plant height and/or a significantly increased stem diameter relative to wild-type or control plants, wherein the modified corn plant has a significantly reduced or eliminated expression level of one or more GA20 oxidase and/or GA3 oxidase gene transcript(s) and/or protein(s) in one or more tissues, such as one or more stem, internode, leaf and/or vascular tissue(s), of the modified plant, as compared to the same tissue(s) of a wild-type or control corn plant. For example, a modified corn plant has a significantly reduced or eliminated expression level of a GA20 oxidase_3 and/or GA20 oxidase_5 gene transcript(s) and/or protein(s), and/or a significantly reduced or eliminated expression level of a GA3 oxidase_1 and/or GA3 oxidase_2 gene transcript(s) and/or protein(s), in the whole modified plant, or in one or more stem, internode, leaf and/or vascular tissue(s) of the modified plant, as compared to the same tissue(s) of a wild-type or control plant. For example, the level of one or more GA3 oxidase and/or GA20 oxidase gene transcript(s) and/or protein(s), or one or more GA oxidase (or GA oxidase-like) gene transcript(s) and/or protein(s), in one or more stem, internode, leaf and/or vascular tissue(s) of a modified corn plant may be at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% less or lower than in the same tissue(s) of a wild-type or control corn plant.

According to some embodiments, a modified corn plant may comprise level(s) of one or more GA3 oxidase and/or GA20 oxidase gene transcript(s) and/or protein(s), or one or more GA oxidase (or GA oxidase-like) gene transcript(s) and/or protein(s), in the whole plant, or in one or more stem, internode, leaf and/or vascular tissue(s), that is between 5% and 50%, between 10% and 100%, between 20% and 100%, between 30% and 100%, between 40% and 100%, between 50% and 100%, between 60% and 100%, between 70% and 100%, between 80% and 100%, between 80% and 90%, between 10% and 90%, between 10% and 80%, between 10% and 70%, between 10% and 60%, between 10% and 50%, between 10% and 40%, between 10% and 30%, between 10% and 20%, between 50% and 100%, between 20% and 90%, between 20% and 80%, between 20% and 70%, between 20% and 60%, between 20% and 50%, between 20% and 40%, between 20% and 40%, between 20% and 30%, between 30% and 90%, between 30% and 80%, between 30% and 70%, between 30% and 60%, between 30% and 50%, between 30% and 40%, between 40% and 90% between 40% and 80%, between 40% and 70%, between 40% and 60%, between 40% and 50%, between 50% and 90%, between 50% and 80%, between 50% and 70%, between 50% and 60%, between 60% and 90%, between 60% and 80%, between 60% and 70%, between 70% and 90%, or between 70% and 80% less or lower than in the same tissue(s) of a wild-type or control corn plant. A modified corn plant having a reduced or eliminated expression level of at least one GA20 oxidase and/or GA3 oxidase gene(s) in one or more tissue(s), may also be substantially free of off-types, such as male reproductive tissues or structures and/or other off-types in at least one ear of the modified corn plant.

Methods and techniques are provided for screening for, and/or identifying, cells or plants, etc., for the presence of targeted edits or transgenes, and selecting cells or plants comprising targeted edits or transgenes, which may be based on one or more phenotypes or traits, or on the presence or absence of a molecular marker or polynucleotide or protein sequence in the cells or plants. Nucleic acids can be isolated and detected using techniques known in the art. For example, nucleic acids can be isolated and detected using, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis. Any method known in the art may be used to screen for, and/or identify, cells, plants, etc., having a transgene or genome edit in its genome, which may be based on any suitable form of visual observation, selection, molecular technique, etc.

In some embodiments, methods are provided for detecting recombinant nucleic acids and/or polypeptides in plant cells. For example, nucleic acids may be detected using hybridization probes or through production of amplicons using PCR with primers as known in the art. Hybridization between nucleic acids is discussed in Sambrook et al. (1989, Molecular Cloning: A Laboratory Manual, 2nd Ed., Cold Spring Harbor Laboratory Press, Cold Spring Harbor, NY). Polypeptides can be detected using antibodies. Techniques for detecting polypeptides using antibodies include enzyme linked immunosorbent assays (ELISAs), Western blots, immunoprecipitations, immunofluorescence, and the like. An antibody provided herein may be a polyclonal antibody or a monoclonal antibody. An antibody having specific binding affinity for a polypeptide provided herein can be generated using methods known in the art. An antibody or hybridization probe may be attached to a solid support, such as a tube, plate or well, using methods known in the art.

Detection (e.g., of an amplification product, of a hybridization complex, of a polypeptide) can be accomplished using detectable labels that may be attached or associated with a hybridization probe or antibody. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified or edited plants or plant cells can be through any methodologies known to those skilled in the art of molecular biology. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina®, PacBio®, Ion Torrent™, etc.) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known in the art.

EXAMPLES

Example 1. Phenotypic Observations of Corn Plants Having an Edited GA20 Oxidase_3 or GA20 Oxidase_5 Gene Several genome-edited mutations were created in the endogenous GA20 oxidase_3 and GA20 oxidase_5 genes in corn plants to test for the phenotypic effect of knocking out each of these genes. A series of ten single-chain guide RNA (sgRNAs) encoding targeting constructs were created for each of the GA20 oxidase_3 and GA20 oxidase_5 genes that target different positions along the genomic sequence for each gene. An additional series of ten sgRNAs were created that each target both of the GA20 oxidase_3 and GA20 oxidase_5 genes, at similar or different positions along the genomic sequence for each gene. Targeted genome edits were made by delivering the sgRNA along with expression of a Cas9 protein to corn explants to cause a DSB or nick to occur at or near the genomic target site for the gRNA, which may then be imperfectly repaired to introduce a mutation at or near the target site. The presence of a mutation was subsequently confirmed by RFLP analysis and/or sequencing of plants. Table 2 below provides a list of the guide RNA (gRNA) constructs that were tested, which may be used for genome editing of one or both of the GA20 oxidase_3 and GA20 oxidase_5 gene(s) with a RNA-guided endonuclease. These guide RNA constructs are generally designed to target the coding sequences of the GA20 oxidase_3 and/or GA20 oxidase_5 genes, but some of the joint targeting constructs may instead target a UTR sequence of one of the two genes. These gRNAs may be used with a suitable endonuclease to produce a double stranded break (DSB) or nick in the genome at or near the genomic target site of the respective gRNA, which may be imperfectly repaired to produce a mutation (e.g., an insertion, deletion, substitution, etc.). Plants homozygous for an edited GA20 oxidase_3 gene or homozygous for an edited GA20 oxidase_5 gene were generated from a few of the constructs (see bold text). Events were also generated from constructs targeting both genes for editing. For the constructs jointly targeting the GA20 oxidase_3 and GA20 oxidase_5 genes, the coding sequence (CDS) coordinates are provided in reference to one of the two genes as indicated in parenthesis. Table 2 further shows which constructs produced gene editing events, whether those events were homozygous or heterozygous in the R0 plants, and the ±numbers in parenthesis indicate the likely sequence change with the mutation (e.g., +1 means an insertion of 1 nucleotide, −1 means a deletion of 1 nucleotide, etc., and larger or more complicated Indels are labeled "del." or insert."). For joint targeting of GA20 oxidase_3 and GA20 oxidase_5 genes, the identity of the mutated gene is also provided in parenthesis. R0 plants homozygous for an edited GA20 oxidase_3 or GA20 oxidase_5 gene did not have an observable short stature, semi-dwarf phenotype and had a normal plant height relative to control plants (See constructs GA20 oxidase_3-D and GA20 oxidase_3-G, and constructs GA20 oxidase_5-B and GA20 oxidase_5-G in Table 2), indicating that knockout of only one of these genes is not sufficient to produce the semi-dwarf phenotype.

TABLE 2

Guide RNAs (gRNAs) targeting GA20 oxidase_3 and GA oxidase_5 genes for editing.

| gRNA Gene Target | gRNA Targeting Sequence (SEQ ID NO) | Gene CDS coordinates | R0 Plants Generated |
|---|---|---|---|
| GA20 oxidase_3-A | 138 | 552-572 | — |
| GA20 oxidase_3-B | 139 | 879-899 | — |
| GA20 oxidase_3-C | 140 | 147-167 | — |
| GA20 oxidase_3-D | 141 | 526-546 | 1. homozygous (−1)<br>2. heterozygous (−1)<br>3. bi-allelic (−2, +1) |
| GA20 oxidase_3-E | 142 | 446-466 | — |
| GA20 oxidase_3-F | 143 | 2227-2247 | — |
| GA20 oxidase_3-G | 144 | 548-568 | 1. homozygous (+1)<br>2. heterozygous (−1)<br>3. bi-allelic (+1, −1) |
| GA20 oxidase_3-H | 145 | 547-567 | — |
| GA20 oxidase_3-I | 146 | 43-63 | — |
| GA20 oxidase_3-J | 147 | 548-567 | — |
| GA20 oxidase_5-A | 148 | 356-376 (+) | 1. heterozygous (−1) |
| GA20 oxidase_5-B | 149 | 99-119 | 1. homozygous (−1)<br>2. heterozygous (+1)<br>3. heterozygous (+1, −7)<br>4. heterozygous (−3, −1) |
| GA20 oxidase_5-C | 150 | 369-389 | — |
| GA20 oxidase_5-D | 151 | 48-68 | — |
| GA20 oxidase_5-E | 152 | 356-376 (−) | — |
| GA20 oxidase_5-F | 153 | 748-768 | 1. heterozygous (−1, +1) |
| GA20 oxidase_5-G | 154 | 770-790 | 1. homozygous (−1)<br>2. homozygous (−1) |
| GA20 oxidase_5-H | 155 | 10-30 | — |
| GA20 oxidase_5-I | 156 | 262-282 | — |
| GA20 oxidase_5-J | 157 | 768-788 | — |
| GA20 oxidase_3/5-A | 158 | 290 . . . 310<br>(GA20 Ox_3) | — |
| GA20 oxidase_3/5-B | 159 | 289 . . . 309<br>(GA20 Ox_3) | — |
| GA20 oxidase_3/5-C | 160 | 270 . . . 290<br>(GA20 Ox_5) | — |
| GA20 oxidase_3/5-D | 161 | 49 . . . 69<br>(GA20 Ox_3) | — |
| GA20 oxidase_3/5-E | 162 | 265 . . . 285<br>(GA20 Ox_5) | 1. heterozygous (Ox5, +1) |
| GA20 oxidase_3/5-F | 163 | 419 . . . 439<br>(GA20 Ox_3) | 1. hetero (Ox3, +1, −1)<br>hetero (Ox5, +1, del.)<br>2. hetero (Ox3, +1, del.)<br>hetero (Ox5, +1) |
| GA20 oxidase_3/5-G | 164 | 110 . . . 130<br>(GA20 Ox_3) | — |
| GA20 oxidase_3/5-H | 165 | 634 . . . 654<br>(GA20 Ox_5) | — |
| GA20 oxidase_3/5-I | 166 | 98 . . . 118<br>(GA20 Ox_5) | — |
| GA20 oxidase_3/5-J | 167 | 517 . . . 537<br>(GA20 Ox_5) | — |

Example 2. Identification of Corn Plants Having Various Combinations of Edited GA20 Oxidase_3 and GA20 Oxidase_5 Mutant Alleles Corn plants were edited as described in Example 1 via a CRISPR/Cas9 based approach using guide RNAs (gRNAs) that target one of GA20 oxidase_3 and GA20 oxidase_5 genes specifically or target both of these two genes simultaneously (see Table 2). In total, 30 gRNA constructs were transformed into corn. Leaf samples from R0 plants were collected and analyzed for InDels by a Fragment Length Analysis (FLA) assay. Putative mutant alleles identified by FLA were sequenced using gene specific primers and standard deep sequencing protocols to confirmed the mutation (s). Table 3 provides a list of 12 edited mutant alleles in the GA20 oxidase_3 gene (ga20ox3-1 to ga20ox3-12) and their sequences. Table 4 provides a list of 11 edited mutant alleles in the GA20 oxidase_5 gene (ga20ox5-1 to ga20ox5-11) and their sequences. R0 plants with mutation(s) in either GA20 oxidase_3 or GA20 oxidase_5, or in both of those genes, were selfed to produce R1 plants.

R1 seeds from multiple R0 plants were planted and sampled again to confirm mutation(s) using FLA and standard sequencing protocols. Table 5 provides a list of R1 plants having mutations in GA20 oxidase_3, GA20 oxidase_5, or both genes. Table 5 also shows plant height and internode length (ear minus 2) of R1 plants measured at the R3 stage. Plant height were measured at R2/R3 growth stage from the soil line to the base of highest collared leaf. R1 plants that are homozygous or heterozygous for a mutation in the gene of interest (GA20 oxidase_3 and/or GA20 oxidase_5) were identified through sequencing and further selfed to produce R2 plants. Genotypes of the R2 plants were again determined by FLA and sequencing. Table 6 provides a list of R2 plants having mutations in GA20 oxidase_3, GA20 oxidase_5, or both genes, and their plant height at the R2/R3 stage. Table 6 also provides corresponding characterization of unedited reference control plants (wild-type inbred plants, shown as WT) and transgenic inbred corn plants having an artificial microRNA suppression construct targeting the GA20 oxidase_3 and GA20 oxidase_5 genes for suppression (SUP_GA20Ox3&Ox5 ("SUP_Ox3&Ox5")).

On average, R2 plants containing homozygous mutant alleles of both GA20 oxidase_3 and GA20 oxidase_5 genes (i.e., double homozygous) showed a semi-dwarf phenotype (about 27.5% reduction in plant height relative to control) with altered plant architecture similar to SUP_Ox3&Ox5 plants (comparing Homo_ox3/Homo_ox5 and SUP_Ox3&Ox5 plants in Table 7 and FIG. 1). Homozygous single ga20ox3 mutants and homozygous single ga20ox5 mutants exhibited a slight reduction (about 10-11%) in average plant height (at the R3 stage) relative to unedited reference control plants (WT inbred). In addition, corn plants with homozygous ga20ox3 mutations and heterozygous for a ga20ox5 mutation (i.e., Homo_ox3/Het_ox5 in Table 7 and FIG. 1) exhibited a moderate reduction (about 19.1%) in average plant height (at the R3 stage) relative to unedited reference control plants (WT inbred). Homo_ox3/Het_ox5 plants were slightly taller than double homozygous ga20ox3 ga20ox5 plants (Homo_ox3/Homo_ox5). Given that corn is a diploid organism, CRISPR-mediated gene editing can result in biallelic mutations in R0 plants (also known as a biallelic mutant combination or transheterozygous mutations). For simplicity, a biallelic mutant at a particular locus is treated as a homozygous mutant at that locus for genotype description and plant height calculation purposes. Detailed mutant genotypes (including biallelic mutants) are provided in Tables 18 and 19 for R1 and R2 generation plants, respectively. Both double homozygous ga20ox3/ga20ox5 mutants, and homozygous/heterozygous mutant combinations (e.g., Homo_ox3/Het_ox5 or Het_ox3/Homo_ox5) also resulted in shorter, semi-dwarf plants, although plant heights in homozygous/heterozygous mutant combinations were not reduced as much as the double homozygous ga20ox3/ga20ox5 mutant plants.

TABLE 3

A list of 12 edited mutant alleles in GA20 oxidase_3 (ga20ox3-1 to ga20ox3-12) and their sequences. The gRNA IDs shown here correspond to those in Table 2.

| Gene Locus | Mutant allele | SEQ ID for Mutant Allele Sequence (~30 nt flanking edits) | SEQ ID for Mutant Allele Sequence (~60 nt flanking edits) | SEQ ID for Wild-type Reference Sequence (~60 nt flanking edits) | SEQ ID for Mutant Allele Sequence (genomic coding DNA) | Allele Description (EDIT @ genomic coding DNA coordinate, based on SEQ ID No. 168) | Edit Position | gRNA ID |
|---|---|---|---|---|---|---|---|---|
| GA20ox3 | ga20ox3-1 | 170 | 182 | 194 | 206 | Deletion of 13 bases starting at 536 | first exon | GA20ox3_d |
| GA20ox3 | ga20ox3-2 | 171 | 183 | 195 | 207 | Deletion of base 542 | first exon | GA20ox3_d |
| GA20ox3 | ga20ox3-3 | 172 | 184 | 196 | 208 | Insertion of CC at base 542 | first exon | GA20ox3_d |
| GA20ox3 | ga20ox3-4 | 173 | 185 | 197 | 209 | Deletion of base 541 | first exon | GA20ox3_d |
| GA20ox3 | ga20ox3-5 | 174 | 186 | 198 | 210 | Deletion of 3 nt starting at base 540 | first exon | GA20ox3_d |
| GA20ox3 | ga20ox3-6 | 175 | 187 | 199 | 211 | Deletion of 2 bases starting at base 422 | first exon | GA20ox3_5_f |
| GA20ox3 | ga20ox3-7 | 176 | 188 | 200 | 212 | Insertion of an A at base 422 | first exon | GA20ox3_5_f |
| GA20ox3 | ga20ox3-8 | 177 | 189 | 201 | 213 | Insertion of a T at base 422 | first exon | GA20ox3_5_f |
| GA20ox3 | ga20ox3-9 | 178 | 190 | 202 | 214 | Deletion of base 564 | first exon | GA20ox3_g |
| GA20ox3 | ga20ox3-10 | 179 | 191 | 203 | 215 | Insertion of an A at base 564 | first exon | GA20ox3_g |
| GA20ox3 | ga20ox3-11 | 180 | 192 | 204 | 216 | Insertion of a C at base 565 | first exon | GA20ox3_g |
| GA20ox3 | ga20ox3-12 | 181 | 193 | 205 | 217 | Insertion of a C at base 63 | first exon | GA20ox3_5_e |

TABLE 4

A list of 11 edited mutant alleles in GA20 oxidase_5 (ga20ox5-1 to ga20ox5-11) and their sequences. The gRNA IDs shown here correspond to those in Table 2.

| Gene Locus | Mutant Allele | SEQ ID for Mutant Allele Sequence (~30 nt flanking edits) | SEQ ID for Mutant Allele Sequence (~60 nt flanking edits) | SEQ ID for Wild-type Reference Sequence (~60 nt flanking edits) | SEQ ID for Mutant Allele Sequence (genomic coding DNA) | Allele description (EDIT @ genomic coding DNA coordinate, based on SEQ ID No. 169) | Edit Position | gRNA ID |
|---|---|---|---|---|---|---|---|---|
| GA20ox5 | ga20ox5-1 | 218 | 229 | 240 | 251 | Deletion of base 644 | first exon | GA20ox3_5_f |
| GA20ox5 | ga20ox5-2 | 219 | 230 | 241 | 252 | Deletion of 2 bases starting at base 644 | first exon | GA20ox3_5_f |
| GA20ox5 | ga20ox5-3 | 220 | 231 | 242 | 253 | Insertion of a T at base 644 | first exon | GA20ox3_5_f |
| GA20ox5 | ga20ox5-4 | 221 | 232 | 243 | 254 | Deletion of base 372 | first exon | GA20ox5_a |
| GA20ox5 | ga20ox5-5 | 222 | 233 | 244 | 255 | Deletion of base 786 | first exon | GA2ox5_g |
| GA20ox5 | ga20ox5-6 | 223 | 234 | 245 | 256 | Deletion of 5 bases starting at base 786 | first exon | GA2ox5_g |
| GA20ox5 | ga20ox5-7 | 224 | 235 | 246 | 257 | Deletion of 2 bases starting at base 101 | first exon | GA20ox5_b |
| GA20ox5 | ga20ox5-8 | 225 | 236 | 247 | 258 | Insertion of a T at base base 102 | first exon | GA20ox5_b |
| GA20ox5 | ga20ox5-9 | 226 | 237 | 248 | 259 | Deletion of 3 bases starting at base 99 | first exon | GA20ox5_b |
| GA20ox5 | ga20ox5-10 | 227 | 238 | 249 | 260 | Insertion of an A at base 282 | first exon | GA20ox3_5_e |
| GA20ox5 | ga20ox5-11 | 228 | 239 | 250 | 261 | Insertion of a C at base 282 | first exon | GA20ox3_5_e |

TABLE 5

A list of R1 plants having mutations in GA20 oxidase_3, GA20 oxidase_5, or both genes.

| Plant No. | Plant Genotype | Plant Height (inches) | Internode Length (cm) | GA20ox3 Genotype | GA20ox5 Genotype | ga20ox3 Allele(s) | ga20ox5 Allele(s) | Generation | gRNA |
|---|---|---|---|---|---|---|---|---|---|
| 1 | single homo ga20ox5 | 58.74 | 12 | WT | Biallelic deletion −1, deletion −5, | none | ga20ox5-6, ga20ox5-5 | R1 | GA20ox5_g |
| 2 | single homo ga20ox5 | 51.65 | 10 | WT | Biallelic deletion −1, deletion −5, | none | ga20ox5-6, ga20ox5-5 | R1 | GA20ox5_g |
| 3 | single homo ga20ox5 | 57.49 | 10.5 | WT | Biallelic deletion −1, deletion −5, | none | ga20ox5-6, ga20ox5-5 | R1 | GA20ox5_g |
| 4 | single homo ga20ox5 | 68.27 | 13.8 | WT | Biallelic deletion −2, insertion +1, | none | ga20ox5-8, ga20ox5-7 | R1 | GA20ox5_b |
| 5 | single homo ga20ox5 | 56.89 | 11.3 | WT | Biallelic deletion −5, deletion −1, | none | ga20ox5-6, ga20ox5-5 | R1 | GA20ox5_g |
| 6 | hetero ga20ox3/homo ga20ox5 | 53.7 | 10 | Het insertion +1, | Biallelic insertion +1, insertion +1, | ga20ox3-12 | ga20ox5-11, ga20ox5-10 | R1 | GA20ox3_5_e |
| 7 | homo ga20ox3/hetero ga20ox5 | 53.9 | 9.5 | Biallelic insertion +1, insertion +1, | Het deletion −1, | ga20ox3-8, ga20ox3-7 | ga20ox5-l | R1 | GA20ox3_5_f |
| 8 | homo ga20ox3/hetero ga20ox5 | 56.69 | 10 | Biallelic deletion −2, insertion +1, | Het deletion −2, | ga20ox3-6, ga20ox3-8 | ga20ox5-2 | R1 | GA20ox3_5_f |
| 9 | homo ga20ox3/hetero ga20ox5 | 49.09 | 9.5 | Biallelic insertion +1, deletion −2, | Het deletion −2, | ga20ox3-6, ga20ox3-8 | ga20ox5-2 | R1 | GA20ox3_5_f |
| 10 | homo ga20ox3/hetero ga20ox5 | 54.96 | 10.3 | Biallelic insertion +1, deletion −2, | Het deletion −2, | ga20ox3-6, ga20ox3-8 | ga20ox5-2 | R1 | GA20ox3_5_f |
| 11 | homo ga20ox3/hetero ga20ox5 | 47.13 | 9 | Homozygous insertion +1, | Het deletion −2, | ga20ox3-8 | ga20ox5-2 | R1 | GA20ox3_5_f |
| 12 | hetero ga20ox3/hetero ga20ox5 | 53.31 | 10 | Het insertion +1, | Het deletion −5, | ga20ox3-10 | ga20ox5-6 | R1 | GA20ox3_g |
| 13 | homo ga20ox3/hetero ga20ox5 | 56.57 | 11 | Biallelic insertion +1, insertion +1, | Het insertion +1, | ga20ox3-8, ga20ox3-7 | ga20ox5-3 | R1 | GA20ox3_5_f |

TABLE 5-continued

A list of R1 plants having mutations in GA20 oxidase_3, GA20 oxidase_5, or both genes.

| Plant No. | Plant Genotype | Plant Height (inches) | Internode Length (cm) | GA20ox3 Genotype | GA20ox5 Genotype | ga20ox3 Allele(s) | ga20ox5 Allele(s) | Generation | gRNA |
|---|---|---|---|---|---|---|---|---|---|
| 14 | homo ga20ox3/hetero ga20ox5 | 49.57 | 8.1 | Biallelic insertion +1, insertion +1, | Het insertion +1, | ga20ox3-8, ga20ox3-7 | ga20ox5-3 | R1 | GA20ox3_5_f |
| 15 | homo ga20ox3/hetero ga20ox5 | 53.35 | 9.1 | Biallelic insertion +1, insertion +1, | Het insertion +1, | ga20ox3-8, ga20ox3-7 | ga20ox5-3 | R1 | GA20ox3_5_f |
| 16 | homo ga20ox3/hetero ga20ox5 | 59.41 | 9.6 | Biallelic insertion +1, insertion +1, | Het insertion +1, | ga20ox3-7, ga20ox3-8 | ga20ox5-3 | R1 | GA20ox3_5_f |
| 17 | homo ga20ox3/hetero ga20ox5 | 60.75 | 11 | Biallelic insertion +1, insertion +1, | Het insertion +1, | ga20ox3-7, ga20ox3-8 | ga20ox5-3 | R1 | GA20ox3_5_f |
| 18 | single homo ga20ox5 | 51.54 | 10 | WT | Homozygous deletion −1, | none | ga20ox5-4 | R1 | GA20ox5_a |
| 19 | single homo ga20ox5 | 57.4 | 12.2 | WT | Homozygous deletion −1, | none | ga20ox5-4 | R1 | GA20ox5_a |
| 20 | single homo ga20ox5 | 58.9 | 11.5 | WT | Homozygous deletion −1, | none | ga20ox5-4 | R1 | GA20ox5_a |
| 21 | single homo ga20ox5 | 50.83 | 9 | WT | Homozygous deletion −1, | none | ga20ox5-5 | R1 | GA20ox5_g |
| 22 | single homo ga20ox5 | 55.08 | 10.5 | WT | Homozygous deletion −1, | none | ga20ox5-5 | R1 | GA20ox5_g |
| 23 | single homo ga20ox5 | 54.76 | 10 | WT | Homozygous deletion −1, | none | ga20ox5-5 | R1 | GA20ox5_g |
| 24 | single homo ga20ox5 | 56.54 | 10 | WT | Homozygous deletion −1, | none | ga20ox5-5 | R1 | GA20ox5_g |
| 25 | single homo ga20ox5 | 55.12 | 10.3 | WT | Homozygous deletion −1, | none | ga20ox5-5 | R1 | GA20ox5_g |
| 26 | single homo ga20ox5 | 55.47 | 9 | WT | Homozygous deletion −1, | none | ga20ox5-5 | R1 | GA20ox5_g |
| 27 | single homo ga20ox5 | 61.02 | 10 | WT | Homozygous deletion −1, | none | ga20ox5-5 | R1 | GA20ox5_g |
| 28 | single homo ga20ox5 | 48.62 | 7 | WT | Homozygous deletion −1, | none | ga20ox5-5 | R1 | GA20ox5_g |
| 29 | single homo ga20ox5 | 63.5 | 11.5 | WT | Homozygous deletion −1, | none | ga20ox5-5 | R1 | GA20ox5_g |
| 30 | single homo ga20ox5 | 60.28 | 10.5 | WT | Homozygous deletion −1, | none | ga20ox5-5 | R1 | GA20ox5_g |
| 31 | single homo ga20ox5 | 58.12 | 11.3 | WT | Homozygous deletion −1, | none | ga20ox5-5 | R1 | GA20ox5_g |
| 32 | single homo ga20ox5 | 51.89 | 12 | WT | Homozygous deletion −1, | none | ga20ox5-5 | R1 | GA20ox5_g |
| 33 | single homo ga20ox5 | 70.08 | 14 | WT | Homozygous deletion −3, | none | ga20ox5-9 | R1 | GA20ox5_b |
| 34 | single homo ga20ox5 | 55.55 | 9.8 | WT | Homozygous insertion +1, | none | ga20ox5-10 | R1 | GA20ox3_5_e |
| 35 | not available | 59.57 | 10 | not available | not available | not available | not available | R1 | GA20ox3_d |
| 36 | not available | 67.28 | 13.3 | not available | not available | not available | not available | R1 | GA20ox3_g |
| 37 | not available | 56.54 | 9 | not available | not available | not available | not available | R1 | GA20ox3_d |
| 38 | not available | 63.74 | 11.5 | not available | not available | not available | not available | R1 | GA20ox3_g |
| 39 | single homo ga20ox3 | 65.24 | 10 | Biallelic deletion −1, deletion −1, | WT | ga20ox3-4, ga20ox3-2 | none | R1 | GA20ox3_d |
| 40 | single homo ga20ox3 | 69.49 | 9.5 | Biallelic deletion −1, deletion −1, | WT | ga20ox3-2, ga20ox3-4 | none | R1 | GA20ox3_d |
| 41 | single homo ga20ox3 | 60.12 | 9 | Biallelic deletion −1, deletion −3, | WT | ga20ox3-5, ga20ox3-2 | none | R1 | GA20ox3_d |
| 42 | single homo ga20ox3 | 53.74 | 10 | Biallelic deletion −1, insertion +1, | WT | ga20ox3-10, ga20ox3-9 | none | R1 | GA20ox3_g |
| 43 | single homo ga20ox3 | 58.43 | 9.8 | Biallelic deletion −13, deletion −1, | WT | ga20ox3-1, ga20ox3-2 | none | R1 | GA20ox3_d |
| 44 | single homo ga20ox3 | 57.28 | 11.5 | Biallelic deletion −2, insertion +1, | WT | ga20ox3-8, ga20ox3-6 | none | R1 | GA20ox3_5_f |
| 45 | single homo ga20ox3 | 56.26 | 11.5 | Biallelic insertion +1, deletion −2, | WT | ga20ox3-8, ga20ox3-6 | none | R1 | GA20ox3_5_f |
| 46 | single homo ga20ox3 | 59.8 | 10.8 | Biallelic insertion +1, deletion −2, | WT | ga20ox3-8, ga20ox3-6 | none | R1 | GA20ox3_5_f |

TABLE 5-continued

A list of R1 plants having mutations in GA20 oxidase_3, GA20 oxidase_5, or both genes.

| Plant No. | Plant Genotype | Plant Height (inches) | Internode Length (cm) | GA20ox3 Genotype | GA20ox5 Genotype | ga20ox3 Allele(s) | ga20ox5 Allele(s) | Gene-ration | gRNA |
|---|---|---|---|---|---|---|---|---|---|
| 47 | single hetero ga20ox3 | 54.45 | 11 | Het insertion +1, | WT | ga20ox3-8 | none | R1 | GA20ox3_5_f |
| 48 | single homo ga20ox3 | 52.68 | 9.5 | Homozygous deletion −1, | WT | ga20ox3-2 | none | R1 | GA20ox3_d |
| 49 | single homo ga20ox3 | 64.17 | 12 | Homozygous deletion −1, | WT | ga20ox3-2 | none | R1 | GA20ox3_d |
| 50 | single homo ga20ox3 | 56.97 | 11 | Homozygous deletion −1, | WT | ga20ox3-9 | none | R1 | GA20ox3_g |
| 51 | single homo ga20ox3 | 43.19 | 12.5 | Homozygous deletion −1, | WT | ga20ox3-9 | none | R1 | GA20ox3_g |
| 52 | single homo ga20ox3 | 58.94 | 11.3 | Homozygous deletion −1, | WT | ga20ox3-9 | none | R1 | GA20ox3_g |
| 53 | single homo ga20ox3 | 61.65 | 13 | Homozygous insertion +1, | WT | ga20ox3-8 | none | R1 | GA20ox3_5_f |
| 54 | single homo ga20ox3 | 60.91 | 11.5 | Homozygous insertion +1, | WT | ga20ox3-10 | none | R1 | GA20ox3_g |

TABLE 6

A list of R2 plants having edited alleles in GA20 oxidase_3, GA20 oxidase_5, or both genes. Plant No. 45 and 46 are considered outliers and not included for generating average plant height data shown in Table 7.

| Plant No. | Plant Genotype | Plant Height (inches) | GA20ox3 Genotype | GA20ox5 Genotype | ga20ox3 Allele(s) | ga20ox5 Allele | Generation | gRNA |
|---|---|---|---|---|---|---|---|---|
| 1 | homo ga20ox3/hetero ga20ox5 | 45 | Biallelic +1 insertion | Heterozygous −1 deletion | ga20ox3-7, ga20ox3-8 | ga20ox5-l | R2 | GA2ox3_5_f |
| 2 | homo ga20ox3/hetero ga20ox5 | 45.2 | homozygous +1 insertion | Heterozygous −1 deletion | ga20ox3-8 | ga20ox5-l | R2 | GA2ox3_5_f |
| 3 | homo ga20ox3/hetero ga20ox5 | 45 | Biallelic −2 deletion, +1 insertion | Heterozygous −2 deletion | ga20ox3-6, ga20ox3-8 | ga20ox5-2 | R2 | GA2ox3_5_f |
| 4 | homo ga20ox3/hetero ga20ox5 | 42.8 | homozygous +1 insertion | Heterozygous −2 deletion | ga20ox3-8 | ga20ox5-2 | R2 | GA2ox3_5_f |
| 5 | homo ga20ox3/hetero ga20ox5 | 45.2 | homozygous +1 insertion | Heterozygous −2 deletion | ga20ox3-8 | ga20ox5-2 | R2 | GA2ox3_5_f |
| 6 | homo ga20ox3/hetero ga20ox5 | 48.8 | homozygous +1 insertion | Heterozygous −2 deletion | ga20ox3-8 | ga20ox5-2 | R2 | GA2ox3_5_f |
| 7 | homo ga20ox3/hetero ga20ox5 | 51.8 | homozygous +1 insertion | Heterozygous −2 deletion | ga20ox3-8 | ga20ox5-2 | R2 | GA2ox3_5_f |
| 8 | homo ga20ox3/hetero ga20ox5 | 45.4 | homozygous +1 insertion | Heterozygous −2 deletion | ga20ox3-8 | ga20ox5-2 | R2 | GA2ox3_5_f |
| 9 | homo ga20ox3/hetero ga20ox5 | 47 | Homozygous −2 deletion | Heterozygous −2 deletion | ga20ox3-6 | ga20ox5-2 | R2 | GA2ox3_5_f |
| 10 | homo ga20ox3/hetero ga20ox5 | 49.8 | Homozygous −2 deletion | Heterozygous −2 deletion | ga20ox3-6 | ga20ox5-2 | R2 | GA2ox3_5_f |
| 11 | single homo ga20ox5 | 52.4 | WT | Homozygous −1 deletion | none | ga20ox5-4 | R2 | GA2ox5_a |
| 12 | single homo ga20ox5 | 39.2 | WT | Homozygous −1 deletion | none | ga20ox5-4 | R2 | GA2ox5_a |
| 13 | single homo ga20ox5 | 53 | WT | Homozygous −1 deletion | none | ga20ox5-4 | R2 | GA2ox5_a |
| 14 | single homo ga20ox5 | 54 | WT | Homozygous −1 deletion | none | ga20ox5-4 | R2 | GA2ox5_a |
| 15 | single homo ga20ox5 | 53.8 | WT | Homozygous −1 deletion | none | ga20ox5-4 | R2 | GA2ox5_a |
| 16 | single homo ga20ox5 | 53.4 | WT | Homozygous −1 deletion | none | ga20ox5-4 | R2 | GA2ox5_a |
| 17 | Double homo | 45 | Biallelic +1 insertion | Homozygous +1 insertion | ga20ox3-7, ga20ox3-8 | ga20ox5-3 | R2 | GA2ox3_5_f |
| 18 | Double homo | 37 | homozygous +1 insertion | Homozygous −2 deletion | ga20ox3-8 | ga20ox5-2 | R2 | GA2ox3_5_f |
| 19 | Double homo | 39.2 | homozygous +1 insertion | Homozygous −2 deletion | ga20ox3-8 | ga20ox5-2 | R2 | GA2ox3_5_f |
| 20 | Double homo | 39.8 | homozygous +1 insertion | Homozygous −2 deletion | ga20ox3-8 | ga20ox5-2 | R2 | GA2ox3_5_f |
| 21 | Double homo | 40.8 | homozygous +1 insertion | Homozygous −2 deletion | ga20ox3-8 | ga20ox5-2 | R2 | GA2ox3_5_f |
| 22 | Double homo | 40.8 | homozygous +1 insertion | Homozygous −2 deletion | ga20ox3-8 | ga20ox5-2 | R2 | GA2ox3_5_f |

TABLE 6-continued

A list of R2 plants having edited alleles in GA20 oxidase_3, GA20 oxidase_5, or both genes. Plant No. 45 and 46 are considered outliers and not included for generating average plant height data shown in Table 7.

| Plant No. | Plant Genotype | Plant Height (inches) | GA20ox3 Genotype | GA20ox5 Genotype | ga20ox3 Allele(s) | ga20ox5 Allele | Generation | gRNA |
|---|---|---|---|---|---|---|---|---|
| 23 | Double homo | 41 | homozygous +1 insertion | Homozygous −2 deletion | ga20ox3-8 | ga20ox5-2 | R2 | GA2ox3_5_f |
| 24 | Double homo | 41.4 | homozygous +1 insertion | Homozygous −2 deletion | ga20ox3-8 | ga20ox5-2 | R2 | GA2ox3_5_f |
| 25 | Double homo | 41.8 | homozygous +1 insertion | Homozygous −2 deletion | ga20ox3-8 | ga20ox5-2 | R2 | GA2ox3_5_f |
| 26 | Double homo | 42 | homozygous +1 insertion | Homozygous −2 deletion | ga20ox3-8 | ga20ox5-2 | R2 | GA2ox3_5_f |
| 27 | Double homo | 42 | homozygous +1 insertion | Homozygous −2 deletion | ga20ox3-8 | ga20ox5-2 | R2 | GA2ox3_5_f |
| 28 | Double homo | 42.4 | homozygous +1 insertion | Homozygous −2 deletion | ga20ox3-8 | ga20ox5-2 | R2 | GA2ox3_5_f |
| 29 | Double homo | 43 | homozygous +1 insertion | Homozygous −2 deletion | ga20ox3-8 | ga20ox5-2 | R2 | GA2ox3_5_f |
| 30 | Double homo | 43.8 | homozygous +1 insertion | Homozygous −2 deletion | ga20ox3-8 | ga20ox5-2 | R2 | GA2ox3_5_f |
| 31 | Double homo | 46.2 | homozygous +1 insertion | Homozygous −2 deletion | ga20ox3-8 | ga20ox5-2 | R2 | GA2ox3_5_f |
| 32 | single homo ga20ox3 | 62 | Homozygous −1 deletion | WT | ga20ox3-9 | none | R2 | GA2ox3_g |
| 33 | single homo ga20ox3 | 39 | Homozygous −1 deletion | WT | ga20ox3-9 | none | R2 | GA2ox3_g |
| 34 | single homo ga20ox3 | 51 | Biallelic −2 deletion, +1 insertion | WT | ga20ox3-6, ga20ox3-8 | none | R2 | GA2ox3_5_f |
| 35 | single homo ga20ox3 | 52.8 | homozygous +1 insertion | WT | ga20ox3-8 | none | R2 | GA2ox3_5_f |
| 36 | single homo ga20ox3 | 59.4 | homozygous +1 insertion | WT | ga20ox3-8 | none | R2 | GA2ox3_5_f |
| 37 | single homo ga20ox3 | 46 | homozygous +1 insertion | WT | ga20ox3-8 | none | R2 | GA2ox3_5_f |
| 38 | single homo ga20ox3 | 52.8 | homozygous +1 insertion | WT | ga20ox3-8 | none | R2 | GA2ox3_5_f |
| 39 | single homo ga20ox3 | 51.4 | Homozygous −2 deletion | WT | ga20ox3-6 | none | R2 | GA2ox3_5_f |
| 40 | SUP_Ox3&Ox5 | 43.6 | WT | WT | None | none | n/a | none |
| 41 | SUP_Ox3&Ox5 | 43.8 | WT | WT | None | none | n/a | none |
| 42 | SUP_Ox3&Ox5 | 42.2 | WT | WT | None | none | n/a | none |
| 43 | WT | 56.4 | WT | WT | None | none | n/a | none |
| 44 | WT | 58.8 | WT | WT | None | none | n/a | none |
| 45 | Double homo | 61.8 | Biallelic −2 deletion, +1 insertion | Homozygous −2 deletion | ga20ox3-6 | ga20ox5-2 | R2 | GA2ox3_5_f |
| 46 | Double homo | 61.8 | Biallelic +1 insertion | Homozygous −1 deletion | ga20ox3-7, ga20ox3-8 | ga20ox5-1 | R2 | GA2ox3_5_f |

TABLE 7

R2/R3 stage plant height differences between greenhouse-grown inbred gene-edited plants and reference control plants.

| Plant Genotype | Avg. Plant Height (inches) | Std. Dev | # of Plants | % Reduction |
|---|---|---|---|---|
| WT | 57.6 | 1.7 | 2 | 0 |
| Homo_ox3/WT_Ox5 | 51.8 | 7.2 | 8 | 10.1% |
| WT_Ox3/Homo_ox5 | 51.0 | 5.8 | 6 | 11.5% |
| Homo_ox3/Het_ox5 | 46.6 | 2.7 | 10 | 19.1% |
| Homo_ox3/Homo_ox5 | 41.7 | 2.3 | 17 | 27.5% |
| SUP_Ox3&Ox5 | 43.2 | 6.6 | 3 | 25.0% |

Example 3. Editing Both GA20 Oxidase_3 and GA20 Oxidase_5 Reduces Active GA Levels in the Plant R2 plants having edited alleles in GA20 oxidase_3, GA20 oxidase_5, or both genes were tested in the field along with transgenic inbred corn plants having an artificial microRNA suppression construct targeting the GA20 oxidase_3 and GA20 oxidase_5 genes for suppression (SUP_GA20Ox3&Ox5 ("SUP_Ox3&Ox5")). Various physiological traits were measured including plant height to ear node at R3, plant height to uppermost ligule, ear height, ear length, ear diameter, kernels/ear, kernels/unit area, single kernel weight, stalk diameter, and grain yield estimate. Plants containing homozygous mutant alleles of both GA20 oxidase_3 and GA20 oxidase_5 genes (i.e., double homozygous ga20ox3/ga20ox5 mutants) showed semi-dwarf phenotypes with altered plant architecture. Homozygous single ga20ox3 mutants and homozygous single ga20ox5 mutants showed slightly taller plant height than double homozygous ga20ox3/ga20ox5 mutants. Table 8 shows key traits with percent delta relative to wild type control plants without edited allele (i.e., percent difference compared to control).

In addition, top collared leaf at V8 was collected to measure the level of a panel of Gibberellic acid hormones through standard biochemical assays. Data indicate that at V8 growth stage, top collared leaf tissues of plants with both GA20ox3 and GA20ox5 edits have significantly lower levels of GA20, GA4 and GA1, but higher levels of GA53 compared to the wild type (control). Changes in GA hormone levels observed in tissues of plants with GA20ox3 and GA20ox5 edits were similar to those observed in transgenic SUP_Ox3&Ox5 plants (Table 9).

TABLE 8

Editing GA20 oxidase 3, GA20 oxidase 5, or both genes impacts various physiological traits (shown as average percent difference relative to a wild-type control).

| Trait | Percent_delta relative to WT control: Double homozygous ga20ox3/ga20ox5 (Plant #18 through 31 in Table 6) | Homozygous single ga20ox5 (plant #11 to 16 in Table 6) | Homozygous single ga20ox3 (plant #32 and 33 in Table 6) |
|---|---|---|---|
| Plant Height to Ear Node R3 | −46.12 | −16.24 | −22.55 |
| Plant Height to Uppermost Ligulated Leaf R3 | −30.39 | −4.49 | −8.6 |
| Stalk Diameter Ear Minus Four R3 | −6.21 | −11.01 | −3.37 |
| Days to 50% Visible Silk R1 | −2.48 | −2.48 | −2.48 |
| Ear Diameter (imaging) R6 | −0.4 | −0.48 | −1.72 |
| Ear Length (imaging) R6 | −5.83 | −1.31 | −4.56 |
| Grain Yield Estimate R6 | −12.2 | −17.62 | −16.55 |
| Kernels per Ear R6 | −2.62 | −5.14 | −9.03 |
| Kernels per unit area | −10.59 | −7.08 | −11.15 |
| Single Kernel Weight R6 | −1.59 | −11.32 | −6.29 |

TABLE 9

Editing GA20 oxidase_3, GA20 oxidase_5, or both genes impacts GA hormonal levels (shown as Average Delta, i.e., difference in pmol GA/gram of tissue and (p-value), relative to a wild-type control). Average pmol GA/gram of tissue for wild-type hormonal levels also shown.

| Growth stage | Leaf type | Hormone type | Wild-type (average) | Homozygous single ga20ox3 (Average Delta) | Homozygous single ga20ox5 (Average Delta) | Double homozygous ga20ox3/ga20ox5 (Average Delta) | SUP_Ox3&Ox5 (Average Delta) |
|---|---|---|---|---|---|---|---|
| V8 | Leaf - top collared | GA12-pmole/g | 0.065 | 0.0250 (0.517) | 0.0007 (0.985) | 0.1382 (0.002) | 0.1726 (1.91E−4) |
| V8 | Leaf - top collared | GA1-pmole/g | 2.726 | 0.3236 (0.355) | 0.0984 (0.776) | −1.8405 (5.64E−5) | −1.4112 (7.41E−4) |
| V8 | Leaf - top collared | GA20-pmole/g | 2.025 | 0.6085 (0.017) | 0.6311 (0.014) | −1.8525 (4.85E−7) | −1.8446 (5.13E−7) |
| V8 | Leaf - top collared | GA34-pmole/g | 2.665 | −0.2339 (0.191) | −0.1940 (0.275) | 0.3424 (0.061) | 0.2456 (0.170) |
| V8 | Leaf - top collared | GA3-pmole/g | 0.200 | 0.1747 (0.006) | 0.2062 (0.002) | −0.0586 (0.312) | −0.03487 (0.544) |
| V8 | Leaf - top collared | GA4-pmole/g | 0.270 | −0.0734 (0.455) | 0.0169 (0.863) | −0.1473 (0.144) | −0.0842 (0.393) |
| V8 | Leaf - top collared | GA53-pmole/g | 0.355 | −0.0291 (0.893) | 0.1493 (0.492) | 0.9521 (3.77E−4) | 1.0875 (1.03E−4) |
| V8 | Leaf - top collared | GA8-pmole/g | 0.067 | 0.0066 (0.857) | −0.0063 (0.863) | −0.0065 (0.860) | 0.0393 (0.292) |
| V8 | Leaf - top collared | GA9-pmole/g | 1.894 | −1.0053 (0.034) | −0.5852 (0.201) | 2.5123 (1.48E−5) | 1.9821 (2.29E−4) |

Having described the present disclosure in detail, it will be apparent that modifications, variations, and equivalent embodiments are possible without departing from the spirit and scope of the present disclosure as described herein and in the appended claims. Furthermore, it should be appreciated that all examples in the present disclosure are provided as non-limiting examples.

What is claimed is:

1. A modified corn plant comprising a mutant allele of a GA20 oxidase_3gene at an endogenous GA20 oxidase_3 locus, wherein a wild-type allele of the GA20 oxidase_3gene encodes a GA20 oxidase_3 protein comprising an amino acid sequence that is at least 95% identical to SEQ ID NO: 9, and a mutant allele of a GA20 oxidase_5 gene at an endogenous GA20 oxidase_5 locus, wherein a wild-type allele of the GA20 oxidase_5 gene encodes a GA20oxidase_5 protein comprising an amino acid sequence that is at least 95% identical to SEQ ID NO: 15, wherein said modified corn plant is homozygous for the mutant allele of the GA20oxidase_3 gene and homozygous for the mutant allele of the GA20 oxidase_5 gene, wherein said modified corn plant:

(a) has a 20% to 50% reduction in plant height relative to an unmodified control plant; and (b) has an ear with no significant off-types, wherein said ear has:

(i) a number of kernels per ear that is at least 90% of the number of kernels per ear of the unmodified control plant; or (ii) an average single kernel weight per ear that is at least 90% of the average single kernel weight per ear of the unmodified control plant.

2. The modified corn plant of claim 1, wherein said mutant allele of the GA20 oxidase_3 gene comprises a mutation in a sequence region selected from the group consisting of a promoter, 5' UTR, first exon, first intron, second exon, second intron, third exon, 3' UTR, terminator, and any combination thereof.

3. The modified corn plant of claim 1, wherein said mutant allele of the GA20 oxidase_3 gene comprises a mutation selected from the group consisting of a substitution, a deletion, an insertion, a duplication, and an inversion of one or more nucleotides relative to a wild-type allele of the GA20 oxidase_3 gene.

4. The modified corn plant of claim 1, wherein said mutant allele of the GA20 oxidase_5 gene comprises a mutation in a sequence region selected from the group consisting of a promoter, 5' UTR, first exon, first intron, second exon, second intron, third exon, 3' UTR, terminator, and any combination thereof.

5. The modified corn plant of claim 1, wherein said mutant allele of the GA20 oxidase_5 gene comprises a mutation selected from the group consisting of a substitution, a deletion, an insertion, a duplication, and an inversion of one or more nucleotides relative to a wild-type allele of the GA20 oxidase_5 gene.

6. The modified corn plant of claim 1, wherein said mutant allele of the GA20 oxidase_3 gene, said mutant allele of the GA20 oxidase_5 gene, or both comprises one or more mutations in the first exon of the corresponding gene.

7. The modified corn plant of claim 1, wherein said mutant allele of the GA20 oxidase_3 gene, said mutant allele of the GA20 oxidase_5 gene, or both comprises one or more mutations in the second exon of the corresponding gene.

8. The modified corn plant of claim 1, wherein said mutant allele of the GA20 oxidase_3 gene comprises a sequence selected from the group consisting of SEQ ID NOs: 170 to 193 or 206 to 217.

9. The modified corn plant of claim 1, wherein said mutant allele of the GA20 oxidase_3 gene comprises a mutation identified by one or more of SEQ ID NOs: 182 to 193 relative to the corresponding reference sequence in SEQ ID NOs: 194 to 205.

10. The modified corn plant of claim 1, wherein said mutant allele of the GA20 oxidase_5 gene comprises a sequence selected from the group consisting of SEQ ID NOs: 218 to 239 or 251 to 261.

11. The modified corn plant of claim 1, wherein said mutant allele of the GA20 oxidase_5 gene comprises a mutation identified by one or more of SEQ ID NOs: 229 to 239 relative to the corresponding reference sequence in SEQ ID NOs: 240 to 250.

12. The modified corn plant of claim 1, wherein said modified corn plant has improved lodging resistance relative to the unmodified control plant.

13. The modified corn plant of claim 1, wherein said mutant allele of the GA20 oxidase_3 gene comprises one or more mutation types selected from the group consisting of a nonsense mutation, a missense mutation, a frameshift mutation, a splice-site mutation, and any combination thereof.

14. The modified corn plant of claim 1, wherein said mutant allele of the GA20 oxidase_3 gene results in one or more of the following: a GA20 oxidase_3 protein truncation, a non-translatable GA20 oxidase_3 gene transcript, a non-functional GA20 oxidase_3 protein, a premature stop codon in the GA20 oxidase_3 gene, and any combination thereof.

15. The modified corn plant of claim 1, wherein said mutant allele of the GA20 oxidase_5 gene comprises one or more mutation types selected from the group consisting of a nonsense mutation, a missense mutation, a frameshift mutation, a splice-site mutation, and any combination thereof.

16. The modified corn plant of claim 1, wherein said mutant allele of the GA20 oxidase_5 gene results in one or more of the following: a GA20 oxidase_5 protein truncation, a non-translatable GA20 oxidase_5 gene transcript, a non-functional GA20 oxidase_5 protein, a premature stop codon in the GA20 oxidase_5 gene, and any combination thereof.

17. The modified corn plant of claim 1, wherein the stalk or stem diameter of said modified corn plant at one or more stem internodes is at least 5% greater than the stalk or stem diameter at the same one or more internodes of the unmodified control plant.

18. The modified corn plant of claim 1, wherein the stalk or stem diameter of said modified corn plant at one or more of the first, second, third, and/or fourth internode below the ear is at least 5% greater than the same internode of the unmodified control plant.

19. The modified corn plant of claim 1, wherein the level of one or more active GAs in at least one internode tissue of the stem or stalk of said modified corn plant is at least 5% lower than the same internode tissue of the unmodified control plant.

20. The modified corn plant of claim 1, wherein the level of one or more active GAs in at least one internode tissue of the stem or stalk of said modified corn plant is lower than the same internode tissue of the unmodified control plant.

21. The modified corn plant of claim 1, wherein said modified corn plant comprises one or more traits, relative to the unmodified control plant, selected from the group consisting of improved lodging resistance, reduced green snap, deeper roots, earlier canopy closure, higher stomatal conductance, lower ear height, increased foliar water content, improved drought tolerance, improved nitrogen use efficiency, reduced anthocyanin content and area in leaves under normal or nitrogen-limiting or water-limiting stress conditions.

22. The modified corn plant of claim 1, wherein the mutant allele of the GA20 oxidase_3 gene and the mutant allele of the GA20 oxidase_5 gene are generated using an RNA-guided endonuclease and a guide RNA (gRNA) molecule, and wherein the gRNA molecule comprises a sequence that is at least 90% identical or complementary to one or more of SEQ ID NOs: 138 to 167.

23. A plant part of the modified corn plant of claim 1.

24. The plant part of claim 23, wherein said plant part is a meristem, a leaf, a stem, a node, a root, a flower, a floral organ structure, a seed, a fruit, a propagule, or any portion thereof.

25. The plant part of claim 23, wherein the said plant part is a seed.

* * * * *